(12) United States Patent
Gerg et al.

(10) Patent No.: US 11,618,790 B2
(45) Date of Patent: Apr. 4, 2023

(54) POLYPEPTIDE-POLYNUCLEOTIDE-COMPLEX AND ITS USE IN TARGETED EFFECTOR MOIETY DELIVERY

(71) Applicant: Hoffmann-La Roche Inc., Little Falls, NJ (US)

(72) Inventors: Michael Gerg, Munich (DE); Dieter Heindl, Paehl (DE); Gerhard Niederfellner, Oberhausen (DE); Wolfgang Schaefer, Mannheim (DE); Michael Schraeml, Penzberg (DE); Michael Tacke, Munich (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 432 days.

(21) Appl. No.: 16/704,781

(22) Filed: Dec. 5, 2019

(65) Prior Publication Data

US 2020/0207874 A1 Jul. 2, 2020

Related U.S. Application Data

(63) Continuation of application No. 13/924,233, filed on Jun. 21, 2013, now abandoned, which is a continuation of application No. PCT/EP2011/073631, filed on Dec. 21, 2011.

(30) Foreign Application Priority Data

Dec. 23, 2010 (EP) .................................... 10196688

(51) Int. Cl.
| | | |
|---|---|---|
| *C07K 16/46* | (2006.01) | |
| *C07K 16/18* | (2006.01) | |
| *C07K 16/00* | (2006.01) | |
| *C07K 16/28* | (2006.01) | |
| *C07K 16/32* | (2006.01) | |
| *G01N 33/573* | (2006.01) | |
| *G01N 33/68* | (2006.01) | |
| *A61K 47/68* | (2017.01) | |

(52) U.S. Cl.
CPC .......... *C07K 16/46* (2013.01); *A61K 47/6889* (2017.08); *C07K 16/00* (2013.01); *C07K 16/18* (2013.01); *C07K 16/2863* (2013.01); *C07K 16/32* (2013.01); *G01N 33/573* (2013.01); *G01N 33/6863* (2013.01); *C07K 2317/24* (2013.01); *C07K 2317/30* (2013.01); *C07K 2317/34* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,153,190 A | 10/1964 | Spalding |
| 3,531,581 A | 9/1970 | Chesemore |
| 3,569,619 A | 3/1971 | Simjian |
| 3,773,919 A | 11/1973 | Boswell |
| 3,896,111 A | 7/1975 | Kupchan |
| 4,120,649 A | 10/1978 | Schechter |
| 4,137,230 A | 1/1979 | Hashimoto |
| 4,150,149 A | 4/1979 | Wolfsen |
| 4,151,042 A | 4/1979 | Asai |
| 4,248,870 A | 2/1981 | Miyashita |
| 4,256,746 A | 3/1981 | Miyashita |
| 4,260,608 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,315,929 A | 2/1982 | Freedman |
| 4,317,821 A | 3/1982 | Miyashita |
| 4,322,348 A | 3/1982 | Asai |
| 4,331,598 A | 5/1982 | Hasegawa |
| RE30,985 E | 6/1982 | Cartaya |
| 4,361,544 A | 11/1982 | Goldenberg |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,419,446 A | 12/1983 | Howley et al. |
| 4,424,219 A | 1/1984 | Hashimoto |
| 4,444,744 A | 4/1984 | Goldenberg |
| 4,450,254 A | 5/1984 | Isley |
| 4,560,655 A | 12/1985 | Baker |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Adams, G.P. et al. (1993). "Highly specific in vivo tumor targeting by monovalent and divalent forms of 741F8 anti-c-erbB-2 single-chain Fv," Cancer Res. 53:4026-4034.

(Continued)

*Primary Examiner* — Brad Duffy
(74) *Attorney, Agent, or Firm* — Morrison & Foerster LLP

(57) ABSTRACT

Herein is reported a polypeptide-polynucleotide-complex as therapeutic agent and its use as tool for the targeted delivery of an effector moiety. The polynucleotide part of the complex is essentially resistant to proteolytic and enzymatic degradation in vivo. Additionally the polypeptide part specifically binds to a compound or structure such as a tissue or organ, a process or a disease. Thus, one aspect as reported herein is a polypeptide-polynucleotide-complex comprising a) a polypeptide specifically binding to a target and conjugated to a first member of a binding pair, b) a polynucleotide linker conjugated at its first terminus to the second member of the binding pair, and c) an effector moiety conjugated to a polynucleotide that is complementary to at least a part of the polynucleotide linker.

11 Claims, 24 Drawing Sheets

Figure 1:
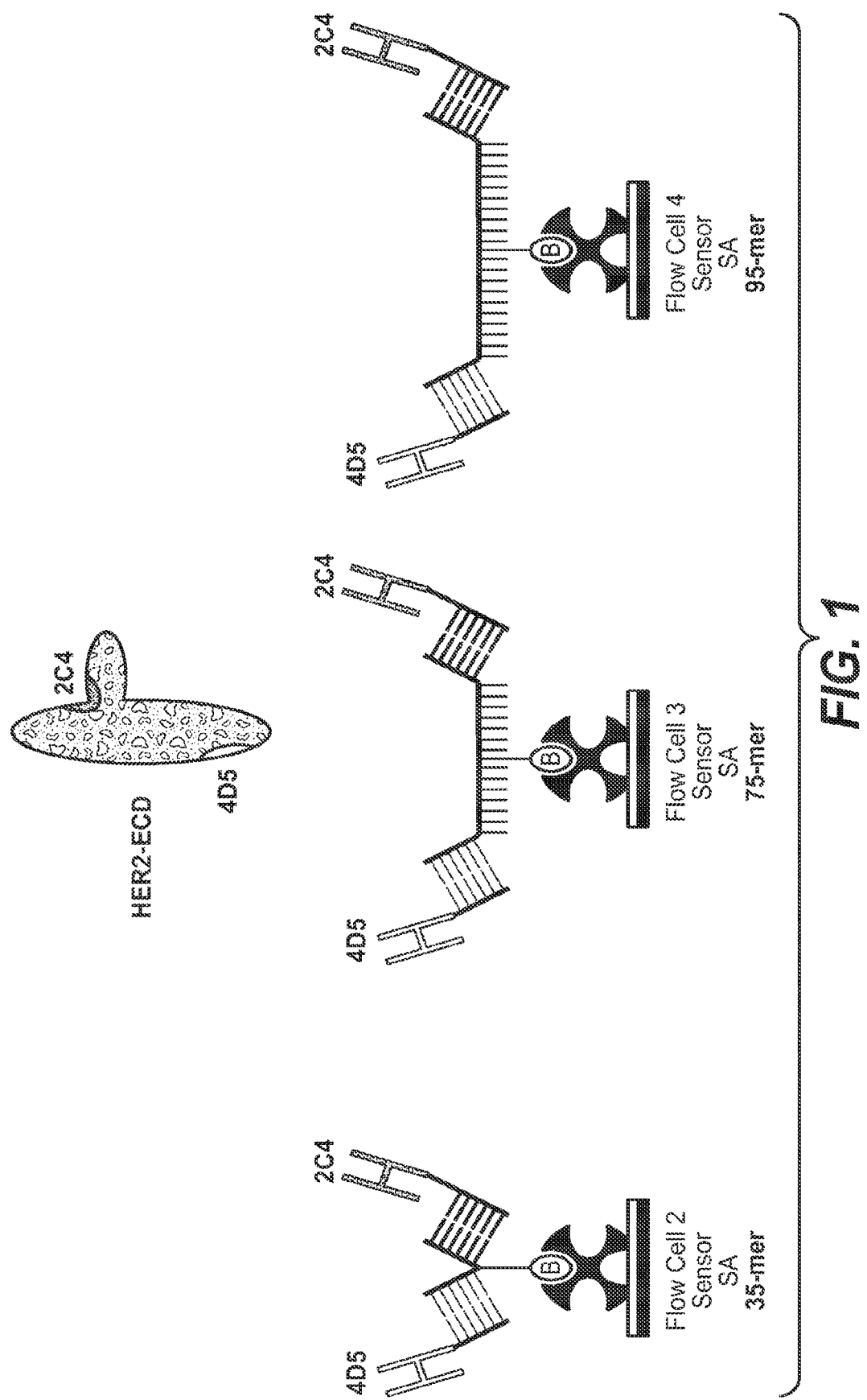

Specification includes a Sequence Listing.

(56) References Cited

U.S. PATENT DOCUMENTS

| | | |
|---|---|---|
| 4,601,978 A | 7/1986 | Karla |
| 4,657,866 A | 4/1987 | Kumar |
| 4,665,077 A | 5/1987 | Stringfellow |
| 4,737,456 A | 4/1988 | Weng |
| 4,767,704 A | 8/1988 | Cleveland |
| 4,816,567 A | 3/1989 | Cabilly |
| 4,927,762 A | 5/1990 | Darfler |
| 4,948,882 A | 8/1990 | Ruth |
| 4,965,199 A | 10/1990 | Capon et al. |
| 4,975,278 A | 12/1990 | Senter |
| 5,053,394 A | 10/1991 | Ellestad |
| 5,114,721 A | 5/1992 | Cohen |
| 5,122,469 A | 6/1992 | Mather et al. |
| 5,143,844 A | 9/1992 | Abrahmsen |
| 5,202,238 A | 4/1993 | Fell, Jr. |
| 5,204,244 A | 4/1993 | Fell |
| 5,208,020 A | 5/1993 | Chari |
| 5,264,365 A | 11/1993 | Georgiou |
| 5,362,852 A | 11/1994 | Geoghegan |
| 5,416,064 A | 5/1995 | Chari |
| 5,451,463 A | 9/1995 | Nelson |
| 5,500,362 A | 3/1996 | Robinson |
| 5,508,192 A | 4/1996 | Georgiou |
| 5,519,142 A | 5/1996 | Hoess |
| 5,532,142 A | 7/1996 | Johnston |
| 5,541,313 A | 7/1996 | Ruth |
| 5,571,894 A | 11/1996 | Wels |
| 5,574,141 A | 11/1996 | Seliger |
| 5,585,481 A | 12/1996 | Arnold, Jr. |
| 5,587,458 A | 12/1996 | King |
| 5,591,828 A | 1/1997 | Bosslet |
| 5,624,821 A | 4/1997 | Winter |
| 5,635,483 A | 6/1997 | Pettit |
| 5,635,602 A | 6/1997 | Cantor |
| 5,639,635 A | 6/1997 | Joly |
| 5,641,870 A | 6/1997 | Rinderknecht |
| 5,648,020 A | 7/1997 | Speer |
| 5,648,237 A | 7/1997 | Carter |
| 5,663,149 A | 9/1997 | Pettit |
| 5,712,374 A | 1/1998 | Kuntsmann |
| 5,714,586 A | 2/1998 | Kunstmann |
| 5,731,168 A | 3/1998 | Carter |
| 5,733,523 A | 3/1998 | Kuijpers |
| 5,739,113 A | 4/1998 | Lee |
| 5,739,116 A | 4/1998 | Hamann |
| 5,747,654 A | 5/1998 | Pastan |
| 5,767,285 A | 6/1998 | Hamann |
| 5,770,701 A | 6/1998 | Mcgahren |
| 5,770,710 A | 6/1998 | Mcgahren |
| 5,773,001 A | 6/1998 | Hamann |
| 5,780,588 A | 7/1998 | Pettit |
| 5,789,199 A | 8/1998 | Pettit et al. |
| 5,798,229 A | 8/1998 | Strittmatter et al. |
| 5,817,786 A | 10/1998 | Ruth |
| 5,821,333 A | 10/1998 | Carter |
| 5,821,337 A | 10/1998 | Carter |
| 5,824,483 A | 10/1998 | Houston, Jr. |
| 5,840,523 A | 11/1998 | Simmons et al. |
| 5,849,879 A | 12/1998 | Nguyen |
| 5,869,046 A | 2/1999 | Presta et al. |
| 5,877,296 A | 3/1999 | Hamann |
| 5,885,793 A | 3/1999 | Griffiths |
| 5,932,448 A | 8/1999 | Tso |
| 5,959,083 A | 9/1999 | Bosslet |
| 5,959,177 A | 9/1999 | Hein et al. |
| 6,027,888 A | 2/2000 | Georgiou |
| 6,040,498 A | 3/2000 | Stomp et al. |
| 6,083,715 A | 7/2000 | Georgiou |
| 6,136,564 A | 10/2000 | Kopetzki |
| 6,153,190 A | 11/2000 | Young |
| 6,166,185 A | 12/2000 | Davis |
| 6,171,586 B1 | 1/2001 | Lam |
| 6,194,551 B1 | 2/2001 | Idusogie |
| 6,239,259 B1 | 5/2001 | Davis |
| 6,248,516 B1 | 6/2001 | Winter et al. |
| 6,267,958 B1 | 7/2001 | Andya |
| 6,350,860 B1 | 2/2002 | Buyse |
| 6,417,429 B1 | 7/2002 | Hein et al. |
| 6,420,548 B1 | 7/2002 | Vezina et al. |
| 6,511,663 B1 | 1/2003 | King |
| 6,531,581 B1 | 3/2003 | Nardone |
| 6,534,628 B1 | 3/2003 | Nilsson |
| 6,558,672 B1 | 5/2003 | Pastan |
| 6,586,207 B2 | 7/2003 | Tirrell |
| 6,602,684 B1 | 8/2003 | Umana et al. |
| 6,630,579 B2 | 10/2003 | Chari |
| 6,660,843 B1 | 12/2003 | Feige |
| 6,833,441 B2 | 12/2004 | Wang |
| 6,835,809 B1 | 12/2004 | Liu |
| 6,878,515 B1 | 4/2005 | Landegren |
| 6,878,575 B2 | 4/2005 | Yoo |
| 6,897,044 B1 | 5/2005 | Braslawsky |
| 6,919,426 B2 | 7/2005 | Boone |
| 6,946,292 B2 | 9/2005 | Kanda |
| 6,982,321 B2 | 1/2006 | Winter |
| 7,041,440 B2 | 5/2006 | Mikoshiba |
| 7,125,978 B1 | 10/2006 | Vezina et al. |
| 7,129,330 B1 | 10/2006 | Little |
| 7,355,008 B2 | 4/2008 | Stavenhagen |
| 7,381,408 B2 | 6/2008 | Mezo |
| 7,498,298 B2 | 3/2009 | Doronina |
| 7,507,796 B2 | 3/2009 | Little |
| 7,642,228 B2 | 1/2010 | Carter |
| 7,651,688 B2 | 1/2010 | Hanai |
| 7,666,622 B2 | 2/2010 | Sharma |
| 7,695,936 B2 | 4/2010 | Carter |
| 7,919,257 B2 | 4/2011 | Hoogenboom |
| 7,928,072 B2 | 4/2011 | Scaria |
| 7,942,042 B2 | 5/2011 | Kawakita |
| 8,007,813 B2 | 8/2011 | Walczak |
| 8,062,635 B2 | 11/2011 | Hattori |
| 8,216,805 B2 | 7/2012 | Carter |
| 8,227,577 B2 | 7/2012 | Klein |
| 8,242,247 B2 | 8/2012 | Klein |
| 8,268,314 B2 | 9/2012 | Baehner |
| 8,304,713 B2 | 11/2012 | Pradel |
| 8,309,300 B2 | 11/2012 | Junutula |
| 8,796,424 B2 | 8/2014 | Croasdale |
| 8,871,912 B2 | 10/2014 | Davis |
| 10,106,612 B2 | 10/2018 | Fenn |
| 2002/0027751 A1 | 3/2002 | Shimazawa |
| 2002/0051986 A1 | 5/2002 | Baez |
| 2002/0155537 A1 | 10/2002 | Carter |
| 2003/0104045 A1 | 6/2003 | Virtanen |
| 2003/0124129 A1 | 7/2003 | Oliner |
| 2003/0152987 A1 | 8/2003 | Cohen |
| 2003/0170230 A1 | 9/2003 | Caterer |
| 2003/0176352 A1 | 9/2003 | Min |
| 2003/0195156 A1 | 10/2003 | Min |
| 2003/0219817 A1 | 11/2003 | Zhu |
| 2003/0219827 A1 | 11/2003 | Comb |
| 2003/0229023 A1 | 12/2003 | Oliner |
| 2003/0236193 A1 | 12/2003 | Oliner |
| 2004/0018557 A1 | 1/2004 | Qu |
| 2004/0033561 A1 | 2/2004 | Okeefe et al. |
| 2004/0038339 A1 | 2/2004 | Kufer |
| 2004/0214988 A1 | 10/2004 | Tirrell |
| 2004/0220388 A1 | 11/2004 | Mertens |
| 2004/0224372 A1 | 11/2004 | Li |
| 2005/0054048 A1 | 3/2005 | Grasso |
| 2005/0064509 A1 | 3/2005 | Bradbury |
| 2005/0079170 A1 | 4/2005 | Le |
| 2005/0100543 A1 | 5/2005 | Hansen |
| 2005/0152894 A1 | 7/2005 | Krummen |
| 2005/0163782 A1 | 7/2005 | Glaser |
| 2005/0169933 A1 | 8/2005 | Steeves |
| 2005/0186208 A1 | 8/2005 | Fyfe et al. |
| 2005/0214833 A1 | 9/2005 | Carter |
| 2005/0238649 A1 | 10/2005 | Doronina |
| 2005/0249722 A1 | 11/2005 | Beliard |
| 2005/0260186 A1 | 11/2005 | Bookbinder et al. |
| 2006/0008845 A1 | 1/2006 | Kondejewski |
| 2006/0063921 A1 | 3/2006 | Moulder |
| 2006/0104968 A1 | 5/2006 | Bookbinder et al. |

(56) References Cited

U.S. PATENT DOCUMENTS

| | | |
|---|---|---|
| 2006/0122370 A1 | 6/2006 | Oliner |
| 2006/0134709 A1 | 6/2006 | Stavenhagen |
| 2006/0160184 A1 | 7/2006 | Hoognboom et al. |
| 2006/0199207 A1 | 9/2006 | Matysiak |
| 2006/0280747 A1 | 12/2006 | Fuh et al. |
| 2007/0014794 A1 | 1/2007 | Carter |
| 2007/0071675 A1 | 3/2007 | Wu |
| 2007/0071742 A1 | 3/2007 | Fang |
| 2007/0141065 A1 | 6/2007 | Fuh et al. |
| 2007/0178552 A1 | 8/2007 | Arathoon |
| 2007/0196274 A1 | 8/2007 | Sun |
| 2007/0269369 A1 | 11/2007 | Gegg |
| 2007/0274985 A1 | 11/2007 | Dubel |
| 2007/0274998 A1 | 11/2007 | Utku |
| 2007/0287170 A1 | 12/2007 | Davis |
| 2008/0044834 A1 | 2/2008 | Heyduk |
| 2008/0063641 A1 | 3/2008 | Huang |
| 2008/0075712 A1 | 3/2008 | Hattori |
| 2008/0131883 A1 | 6/2008 | Adams |
| 2008/0187954 A1 | 8/2008 | Kallmeier |
| 2008/0280778 A1 | 11/2008 | Urdea |
| 2008/0312103 A1 | 12/2008 | Nemoto |
| 2009/0023811 A1 | 1/2009 | Biadatti |
| 2009/0087432 A1 | 4/2009 | Sliwkowski |
| 2009/0117105 A1 | 5/2009 | Hu |
| 2009/0137782 A1 | 5/2009 | Old |
| 2009/0155275 A1 | 6/2009 | Wu |
| 2009/0162359 A1 | 6/2009 | Klein |
| 2009/0162360 A1 | 6/2009 | Klein |
| 2009/0175851 A1 | 7/2009 | Klein |
| 2009/0194692 A1 | 8/2009 | Kobaru |
| 2009/0232811 A1 | 9/2009 | Klein |
| 2010/0021943 A1 | 1/2010 | An |
| 2010/0026617 A1 | 2/2010 | Su |
| 2010/0062436 A1 | 3/2010 | Jarosch |
| 2010/0081792 A1 | 4/2010 | Grant |
| 2010/0081796 A1 | 4/2010 | Brinkmann |
| 2010/0111967 A1 | 5/2010 | Baehner |
| 2010/0254989 A1 | 10/2010 | Bossenmaier |
| 2010/0256338 A1 | 10/2010 | Brinkmann |
| 2010/0256339 A1 | 10/2010 | Bossenmaier |
| 2010/0256340 A1 | 10/2010 | Brinkmann |
| 2010/0266617 A1 | 10/2010 | Carven |
| 2010/0316645 A1 | 12/2010 | Imhof-jung |
| 2010/0322934 A1 | 12/2010 | Imhof-jung |
| 2010/0322935 A1 | 12/2010 | Schanzer |
| 2011/0028695 A1 | 2/2011 | Revets |
| 2011/0054151 A1 | 3/2011 | Lazar |
| 2011/0243966 A1 | 10/2011 | Farrington |
| 2012/0149879 A1 | 6/2012 | Brinkmann |
| 2012/0164726 A1 | 6/2012 | Klein |
| 2012/0184718 A1 | 7/2012 | Bruenker |
| 2012/0225071 A1 | 9/2012 | Klein |
| 2012/0237506 A1 | 9/2012 | Bossenmaier |
| 2012/0237507 A1 | 9/2012 | Bossenmaier |
| 2012/0302737 A1 | 11/2012 | Christensen |
| 2012/0321627 A1 | 12/2012 | Baehner |
| 2013/0022601 A1 | 1/2013 | Brinkmann |
| 2013/0058937 A1 | 3/2013 | Auer |
| 2013/0060011 A1 | 3/2013 | Bruenker |
| 2013/0078249 A1 | 3/2013 | Ast |
| 2013/0156772 A1 | 6/2013 | Bossenmaier |
| 2013/0266568 A1 | 10/2013 | Brinkmann |
| 2013/0267686 A1 | 10/2013 | Brinkmann |
| 2013/0273054 A1 | 10/2013 | Bossenmaier |
| 2013/0288267 A1 | 10/2013 | Gerg |
| 2013/0344094 A1 | 12/2013 | Gerg |
| 2014/0249296 A1 | 9/2014 | Ploegh |
| 2014/0294810 A1 | 10/2014 | Lowman |
| 2015/0004166 A1 | 1/2015 | Baehner |
| 2015/0030598 A1 | 1/2015 | Croasdale |
| 2015/0133638 A1 | 5/2015 | Wranik |
| 2015/0166670 A1 | 6/2015 | Castoldi |
| 2015/0232541 A1 | 8/2015 | Fenn |
| 2015/0232560 A1 | 8/2015 | Heindl |
| 2015/0232561 A1 | 8/2015 | Fenn |
| 2015/0291704 A1 | 10/2015 | Beck |
| 2016/0002356 A1 | 1/2016 | Christensen |
| 2016/0194410 A1 | 7/2016 | Gallusser |
| 2017/0081404 A1 | 3/2017 | Finney |
| 2017/0275380 A1 | 9/2017 | Gerg |
| 2017/0275381 A1 | 9/2017 | Gerg |
| 2019/0002570 A1 | 1/2019 | Fenn |

FOREIGN PATENT DOCUMENTS

| | | |
|---|---|---|
| CN | 1232039 A | 10/1999 |
| CN | 1603345 A | 4/2005 |
| CN | 10137671 A | 9/2007 |
| CN | 101037671 A | 9/2007 |
| CN | 101052653 A | 10/2007 |
| CN | 101065151 A | 10/2007 |
| CN | 101205255 A | 6/2008 |
| CN | 101218251 A | 7/2008 |
| CN | 101355966 A | 1/2009 |
| EP | 0061888 A2 | 10/1982 |
| EP | 0307434 B1 | 3/1989 |
| EP | 0313219 A2 | 4/1989 |
| EP | 0339217 B1 | 11/1989 |
| EP | 0340109 A2 | 11/1989 |
| EP | 0404097 A2 | 12/1990 |
| EP | 0423839 A2 | 4/1991 |
| EP | 0425235 A2 | 5/1991 |
| EP | 0502812 A1 | 9/1992 |
| EP | 0523978 A1 | 1/1993 |
| EP | 0618192 A1 | 10/1994 |
| EP | 0637593 A1 | 2/1995 |
| EP | 0786468 A2 | 7/1997 |
| EP | 0307434 B2 | 7/1998 |
| EP | 0292128 A1 | 11/1998 |
| EP | 1074563 A1 | 2/2001 |
| EP | 1184665 A1 | 3/2002 |
| EP | 1186613 A1 | 3/2002 |
| EP | 1391213 A1 | 2/2004 |
| EP | 1431298 A1 | 6/2004 |
| EP | 1538221 A1 | 6/2005 |
| EP | 1870459 A1 | 12/2007 |
| EP | 2050764 A1 | 4/2009 |
| EP | 2443154 B1 | 4/2012 |
| JP | H08245698 A | 9/1996 |
| JP | H09087296 A | 3/1997 |
| JP | 2000135095 A | 5/2000 |
| JP | 2007531513 A | 11/2007 |
| JP | 2008518605 A | 6/2008 |
| JP | 2008531049 A | 8/2008 |
| JP | H07501698 A | 8/2008 |
| JP | 2014525904 A | 10/2014 |
| JP | 5766296 B2 | 8/2015 |
| RU | 2005124281 A | 1/2006 |
| RU | 2352583 C2 | 4/2006 |
| RU | 2433831 C2 | 11/2011 |
| WO | WO198700195 A1 | 1/1987 |
| WO | WO198902439 A1 | 3/1989 |
| WO | WO198902931 A1 | 4/1989 |
| WO | WO198912642 A1 | 12/1989 |
| WO | WO199003430 A1 | 4/1990 |
| WO | WO199008156 A1 | 7/1990 |
| WO | WO199008187 A1 | 7/1990 |
| WO | WO199011294 A1 | 10/1990 |
| WO | WO199101133 A1 | 2/1991 |
| WO | WO199106305 A1 | 5/1991 |
| WO | WO199201047 A1 | 1/1992 |
| WO | WO199204053 A1 | 3/1992 |
| WO | WO199211388 A1 | 7/1992 |
| WO | WO199215682 A1 | 9/1992 |
| WO | WO199301161 A1 | 1/1993 |
| WO | WO199305060 A1 | 3/1993 |
| WO | WO199306217 A1 | 4/1993 |
| WO | WO199311161 A1 | 6/1993 |
| WO | WO199311162 A1 | 6/1993 |
| WO | WO199316185 A2 | 8/1993 |
| WO | WO199316185 A3 | 9/1993 |
| WO | WO199321232 A1 | 10/1993 |
| WO | WO199404550 A1 | 3/1994 |

(56) References Cited

FOREIGN PATENT DOCUMENTS

| | | |
|---|---|---|
| WO | WO199409131 A1 | 4/1994 |
| WO | WO199410202 A1 | 5/1994 |
| WO | WO199410308 A1 | 5/1994 |
| WO | WO199411026 A3 | 8/1994 |
| WO | WO199429350 A2 | 12/1994 |
| WO | WO199429350 A3 | 2/1995 |
| WO | WO199505399 A1 | 2/1995 |
| WO | WO199509917 A1 | 4/1995 |
| WO | WO199517886 A1 | 7/1995 |
| WO | WO199627011 A1 | 9/1996 |
| WO | WO199627612 A1 | 9/1996 |
| WO | WO199701580 A1 | 1/1997 |
| WO | WO199705156 A1 | 2/1997 |
| WO | WO1997014719 A1 | 4/1997 |
| WO | WO199728267 A1 | 8/1997 |
| WO | WO199743451 A1 | 11/1997 |
| WO | WO199833914 A1 | 8/1998 |
| WO | WO199845331 A2 | 10/1998 |
| WO | WO199845332 A2 | 10/1998 |
| WO | WO199848032 A2 | 10/1998 |
| WO | WO1998050431 A2 | 11/1998 |
| WO | WO1998050431 A3 | 11/1998 |
| WO | WO199845331 A3 | 12/1998 |
| WO | WO199845332 A3 | 12/1998 |
| WO | WO199848032 A3 | 1/1999 |
| WO | WO199906587 A2 | 2/1999 |
| WO | WO199906587 A3 | 7/1999 |
| WO | WO199937791 A1 | 7/1999 |
| WO | WO199954342 A1 | 10/1999 |
| WO | WO199966951 A2 | 12/1999 |
| WO | WO200024770 A2 | 5/2000 |
| WO | WO200029004 A1 | 5/2000 |
| WO | WO199966951 A3 | 6/2000 |
| WO | WO200035956 A1 | 6/2000 |
| WO | WO200024770 A3 | 9/2000 |
| WO | WO200061739 A1 | 10/2000 |
| WO | WO200067744 A1 | 11/2000 |
| WO | WO200100245 A2 | 1/2001 |
| WO | WO200116352 A1 | 3/2001 |
| WO | WO2001042505 A2 | 6/2001 |
| WO | WO2001042505 A3 | 6/2001 |
| WO | WO200100245 A3 | 10/2001 |
| WO | WO200177342 A1 | 10/2001 |
| WO | WO200190192 A2 | 11/2001 |
| WO | WO200202781 A1 | 1/2002 |
| WO | WO200218643 A2 | 3/2002 |
| WO | WO2002051870 A2 | 7/2002 |
| WO | WO2002072141 A2 | 9/2002 |
| WO | WO2002088172 A2 | 11/2002 |
| WO | WO2002092620 A2 | 11/2002 |
| WO | WO200190192 A3 | 1/2003 |
| WO | WO2003002609 A2 | 1/2003 |
| WO | WO2002088172 A3 | 2/2003 |
| WO | WO2003012069 A2 | 2/2003 |
| WO | WO2003019145 A2 | 3/2003 |
| WO | WO2002051870 A3 | 4/2003 |
| WO | WO2003030833 A2 | 4/2003 |
| WO | WO2003031589 A2 | 4/2003 |
| WO | WO2003035694 A2 | 5/2003 |
| WO | WO2003035835 A2 | 5/2003 |
| WO | WO2003055993 A1 | 7/2003 |
| WO | WO2003057134 A2 | 7/2003 |
| WO | WO2002092620 A3 | 8/2003 |
| WO | WO2003002609 A3 | 8/2003 |
| WO | WO2003019145 A3 | 8/2003 |
| WO | WO2003066660 A2 | 8/2003 |
| WO | WO200218643 A3 | 9/2003 |
| WO | WO2003073238 A2 | 9/2003 |
| WO | WO2003035694 A3 | 10/2003 |
| WO | WO2003035835 A3 | 10/2003 |
| WO | WO2003073238 A3 | 10/2003 |
| WO | WO2003012069 A3 | 11/2003 |
| WO | WO2003097105 A1 | 11/2003 |
| WO | WO2003104249 A1 | 12/2003 |
| WO | WO2003106501 A1 | 12/2003 |
| WO | WO2003057134 A3 | 4/2004 |
| WO | WO2004032961 A1 | 4/2004 |
| WO | WO2004058298 A1 | 7/2004 |
| WO | WO2004062602 A2 | 7/2004 |
| WO | WO2004065417 A2 | 8/2004 |
| WO | WO2004065540 A2 | 8/2004 |
| WO | WO2004072117 A2 | 8/2004 |
| WO | WO2004081051 A1 | 9/2004 |
| WO | WO2003030833 A3 | 10/2004 |
| WO | WO2004092215 A2 | 10/2004 |
| WO | WO2003066660 A3 | 12/2004 |
| WO | WO2004062602 A3 | 12/2004 |
| WO | WO2004065417 A3 | 12/2004 |
| WO | WO2004072117 A3 | 1/2005 |
| WO | WO2005000900 A1 | 1/2005 |
| WO | WO2005001025 A2 | 1/2005 |
| WO | WO2005001025 A3 | 1/2005 |
| WO | WO2005004809 A2 | 1/2005 |
| WO | WO2005005635 A2 | 1/2005 |
| WO | WO2005011735 A1 | 2/2005 |
| WO | WO2004065540 A3 | 3/2005 |
| WO | WO2005027966 A2 | 3/2005 |
| WO | WO2004092215 A3 | 4/2005 |
| WO | WO2005035572 A2 | 4/2005 |
| WO | WO2005035727 A2 | 4/2005 |
| WO | WO2005035753 A1 | 4/2005 |
| WO | WO2005044853 A2 | 5/2005 |
| WO | WO2005044859 A2 | 5/2005 |
| WO | WO2005047334 A1 | 5/2005 |
| WO | WO2005051976 A2 | 6/2005 |
| WO | WO2005059509 A2 | 6/2005 |
| WO | WO2005035727 A3 | 7/2005 |
| WO | WO2005063816 A2 | 7/2005 |
| WO | WO2005005635 A3 | 8/2005 |
| WO | WO2005044859 A3 | 8/2005 |
| WO | WO2005063816 A3 | 8/2005 |
| WO | WO2005074417 A2 | 8/2005 |
| WO | WO2005074524 A2 | 8/2005 |
| WO | WO2005075514 A2 | 8/2005 |
| WO | WO2005027966 A3 | 9/2005 |
| WO | WO2005051976 A3 | 9/2005 |
| WO | WO2005117973 A2 | 12/2005 |
| WO | WO2005044853 A3 | 1/2006 |
| WO | WO2005004809 A3 | 2/2006 |
| WO | WO2005075514 A3 | 3/2006 |
| WO | WO2005117973 A3 | 3/2006 |
| WO | WO2006028956 A2 | 3/2006 |
| WO | WO2006031370 A2 | 3/2006 |
| WO | WO2006034488 A2 | 3/2006 |
| WO | WO2005074417 A3 | 4/2006 |
| WO | WO2006044908 A2 | 4/2006 |
| WO | WO2006045049 A1 | 4/2006 |
| WO | WO2006068953 A2 | 6/2006 |
| WO | WO2006028956 A3 | 8/2006 |
| WO | WO2006044908 A3 | 8/2006 |
| WO | WO2006082515 A2 | 8/2006 |
| WO | WO2006089364 A1 | 8/2006 |
| WO | WO2006091209 A2 | 8/2006 |
| WO | WO2006034488 A3 | 9/2006 |
| WO | WO2006093794 A1 | 9/2006 |
| WO | WO2006091209 A3 | 10/2006 |
| WO | WO2006103100 A2 | 10/2006 |
| WO | WO2006113665 A2 | 10/2006 |
| WO | WO2006031370 A3 | 11/2006 |
| WO | WO2006114700 A2 | 11/2006 |
| WO | WO2006116260 A2 | 11/2006 |
| WO | WO2006103100 A3 | 12/2006 |
| WO | WO2006137932 A2 | 12/2006 |
| WO | WO2005035572 A3 | 1/2007 |
| WO | WO2006116260 A3 | 2/2007 |
| WO | WO2005074524 A3 | 3/2007 |
| WO | WO2007024715 A2 | 3/2007 |
| WO | WO2007031875 A2 | 3/2007 |
| WO | WO2006114700 A3 | 4/2007 |
| WO | WO2007038658 A2 | 4/2007 |
| WO | WO2007044887 A2 | 4/2007 |
| WO | WO2007048037 A2 | 4/2007 |
| WO | WO2007059816 A1 | 5/2007 |
| WO | WO2006082515 A3 | 6/2007 |

(56) References Cited

FOREIGN PATENT DOCUMENTS

| | | |
|---|---|---|
| WO | WO2007068895 A1 | 6/2007 |
| WO | WO2007069092 A2 | 6/2007 |
| WO | WO2007048037 A3 | 7/2007 |
| WO | WO2007084181 A2 | 7/2007 |
| WO | WO2006068953 A3 | 8/2007 |
| WO | WO2007089445 A2 | 8/2007 |
| WO | WO2007095338 A2 | 8/2007 |
| WO | WO2006137932 A3 | 9/2007 |
| WO | WO2007108013 A2 | 9/2007 |
| WO | WO2007109254 A2 | 9/2007 |
| WO | WO2007038658 A3 | 10/2007 |
| WO | WO2007110205 A2 | 10/2007 |
| WO | WO2005059509 A3 | 11/2007 |
| WO | WO2008005828 A2 | 1/2008 |
| WO | WO2008012543 A1 | 1/2008 |
| WO | WO2007031875 A3 | 2/2008 |
| WO | WO2007110205 A3 | 2/2008 |
| WO | WO2008017963 A2 | 2/2008 |
| WO | WO2007108013 A3 | 3/2008 |
| WO | WO2007069092 A3 | 4/2008 |
| WO | WO2007089445 A3 | 4/2008 |
| WO | WO2007095338 A3 | 4/2008 |
| WO | WO2008048970 A2 | 4/2008 |
| WO | WO2008005828 A3 | 6/2008 |
| WO | WO2008077077 A2 | 6/2008 |
| WO | WO2008077546 A1 | 7/2008 |
| WO | WO2007084181 A3 | 8/2008 |
| WO | WO2008048970 A3 | 8/2008 |
| WO | WO2008077077 A3 | 8/2008 |
| WO | WO2008100624 A2 | 8/2008 |
| WO | WO2007024715 A3 | 10/2008 |
| WO | WO2007109254 A3 | 10/2008 |
| WO | WO2008017963 A3 | 11/2008 |
| WO | WO2008132568 A2 | 11/2008 |
| WO | WO2008143954 A2 | 11/2008 |
| WO | WO2008132568 A3 | 12/2008 |
| WO | WO2008157379 A2 | 12/2008 |
| WO | WO2008100624 A3 | 1/2009 |
| WO | WO2009007124 A1 | 1/2009 |
| WO | WO2008157379 A3 | 2/2009 |
| WO | WO2009018386 A1 | 2/2009 |
| WO | WO2009021745 A1 | 2/2009 |
| WO | WO2009021754 A2 | 2/2009 |
| WO | WO2009023843 A1 | 2/2009 |
| WO | WO2008143954 A3 | 3/2009 |
| WO | WO2009030780 A2 | 3/2009 |
| WO | WO2009032782 A2 | 3/2009 |
| WO | WO2009037659 A2 | 3/2009 |
| WO | WO2009037659 A3 | 3/2009 |
| WO | WO2006113665 A3 | 4/2009 |
| WO | WO2007044887 A3 | 4/2009 |
| WO | WO2009030780 A3 | 4/2009 |
| WO | WO2009032782 A3 | 5/2009 |
| WO | WO2009059278 A1 | 5/2009 |
| WO | WO2009021754 A3 | 6/2009 |
| WO | WO2009072812 A2 | 6/2009 |
| WO | WO2009080251 A1 | 7/2009 |
| WO | WO2009080252 A1 | 7/2009 |
| WO | WO2009080253 A1 | 7/2009 |
| WO | WO2009080254 A1 | 7/2009 |
| WO | WO2009072812 A3 | 8/2009 |
| WO | WO2009105671 A2 | 8/2009 |
| WO | WO2009105671 A3 | 10/2009 |
| WO | WO2009126944 A1 | 10/2009 |
| WO | WO2008157379 A8 | 1/2010 |
| WO | WO2010034441 A1 | 4/2010 |
| WO | WO2010040508 A1 | 4/2010 |
| WO | WO2010045193 A1 | 4/2010 |
| WO | WO2010065882 A1 | 6/2010 |
| WO | WO2010069532 A1 | 6/2010 |
| WO | WO2010087994 A2 | 8/2010 |
| WO | WO2010099536 A2 | 9/2010 |
| WO | WO2010099536 A3 | 10/2010 |
| WO | WO2010112193 A1 | 10/2010 |
| WO | WO2010112194 A1 | 10/2010 |
| WO | WO2010115552 A1 | 10/2010 |
| WO | WO2010115589 A1 | 10/2010 |
| WO | WO2010118169 A2 | 10/2010 |
| WO | WO2010136172 A1 | 12/2010 |
| WO | WO2010145792 A1 | 12/2010 |
| WO | WO2010145793 A1 | 12/2010 |
| WO | WO2010040508 A8 | 2/2011 |
| WO | WO2010087994 A3 | 2/2011 |
| WO | WO2010118169 A3 | 3/2011 |
| WO | WO2011028952 A1 | 3/2011 |
| WO | WO2011034605 A2 | 3/2011 |
| WO | WO2010040508 A9 | 4/2011 |
| WO | WO2011034605 A3 | 8/2011 |
| WO | WO2010115589 A8 | 10/2011 |
| WO | WO2010145792 A8 | 10/2011 |
| WO | WO2011133886 A2 | 10/2011 |
| WO | WO2011133886 A3 | 12/2011 |
| WO | WO2012025525 A1 | 3/2012 |
| WO | WO2012025530 A1 | 3/2012 |
| WO | WO2012073985 A1 | 6/2012 |
| WO | WO2012085069 A2 | 6/2012 |
| WO | WO2012085111 A1 | 6/2012 |
| WO | WO2012085113 A1 | 6/2012 |
| WO | WO2012085069 A3 | 8/2012 |
| WO | WO2012116927 A1 | 9/2012 |
| WO | WO2013003555 A1 | 1/2013 |
| WO | WO2013006544 A1 | 1/2013 |
| WO | WO2013026833 A1 | 2/2013 |
| WO | WO2013092716 A1 | 6/2013 |
| WO | WO2013006544 A8 | 8/2013 |
| WO | WO2013119966 A2 | 8/2013 |
| WO | WO2013119966 A3 | 10/2013 |
| WO | WO2013174873 A1 | 11/2013 |
| WO | WO2014001326 A1 | 1/2014 |

OTHER PUBLICATIONS

Aggarwal, S. et al. (Jan. 22, 2008). "Fibroblast Activation Protein Peptide Substrates Identified from Human Collagen I Derived Gelatin Cleavage Sites," Biochemistry 47(3):1076-1086.

Amsberry, K.L. et al. (1990) "The Lactonizatin of 2'-Hydroxyhydrocinnamic Acid Amides: A Potential Prodrug For Amines," J. Org. Chem. 55:5867-5877.

An, F. et al. (2008). "Targeted Drug Delivery to Mesothelioma Cells Using Functionally Selected Internalizing Human Single-Chain Antibodies," Mol. Cancer Ther. 7:569-578.

Anonymous. (1997). "Production in yeasts of stable antibody fragments," Expert Opinion on Therapeutic Patents 7(2):179-183.

Anthony, R.M. et al. (2008). "A Recombinant IgG Fc that Recapitulates the Antiinflammatory Activity of IVIG," Science, 320(5874):373-376.

Antos, J.M. et al. (Jun. 5, 2009). "A Straight Path to Circular Proteins," JBC 284(23):16028-16036.

Arie, J-P. et al. (Jan. 1, 2001). "Chaperone Function of FkpA, A Heat Shock Prolyl Isomerase, in the Periplasm of *Escherichia coli*," Molecular Micorbiology 39(1):199-210.

Armour, K.L. et al. (1999). "Recombinant Human IgG Molecules Lacking Fcγ Receptor I Binding and Monocyte Triggering Activities," Eur. J. Immunol. 29:2613-2624.

Arndt, K.M. et al. (1998) "Factors Influencing the Dimer to Monomer Transition of an Antibody Single-Chain Fv Fragment," Biochemistry 15;37(37):12918-12926.

Arndt, K.M. et al. (Sep. 7, 2001). "Helix-Stabilized Fv (hsFv) Antibody Fragments: Substituting the Constant Domains of a Fab Fragment for a Heterodimeric Coiled-Coil Domain," J. Mol. Biology 312(1):221-228.

Atwell, S. et al. (1997). "Stable Heterodimers From Remodeling The Domain Interface Of A Homodimer Using A Phage Display Library," J. Mol. Biol. 270 (1):26-35.

Ausubel, F.M. et al. (1995). Short Protocols in Molecular Biology, Greene Publishing and Wiley Interscience, New York, New York, (Table of Contents), 22 pages.

Avgeris, M. et al. (May 2010). "Kallikrein-Related Peptidase Genes as Promising Biomarkers for Prognosis and Monitoring of Human Malignancies," Biol. Chem 391(5):505-511.

(56) References Cited

OTHER PUBLICATIONS

Bachman. (1987). "Derivations and Genotypes of Some Mutant Derivatives of *Esherichia coli* K-12," Chapter 72 in *Escherichia coli* and *Samonella typimurium* Cellular and Molecular Biology, vol. 2, American Society for Microbiology, Washington D.C., pp. 1190-1219.

Backer, M.V. et al. (2002). "Molecular Vehicles for Targeted Drug Delivery," Bioconjugate Chem. 13:462-467.

Baldwin, R.W. et al. (1986). "Monoclonal Antibodies in Cancer Treatment," Lancet 60:603-606.

Bao, W. et al. (Jul. 2010). "HER2-Mediated Upregulation of MMP-1 is Involved in Gastric Cancer Cell Invasion," Arch Biochem Biophys 499(1-2):49-55.

Barbin, Karin et al., "Influence of Variable N-Glycosylation on the Cytolytic Potential of Chimeric CD19 Antibodies," J. Immunother. (Mar./Apr. 2006); 29(2):122-133.

Barnes, D. et al. (Mar. 1, 1980). "Methods for Growth of Cultured Cells In Serum-Free Medium," Anal. Biochem. 102(2):255-270.

Barnes, L.M. et al. "Advances in Animal Cell Recombinant Protein Production: GS-NS0 Expression System," Cytotechnology 32:109-123 (2000).

Barnes, L.M. et al. "Characterization of the Stability of Recombinant Protein Production in the GS-NS0 Expression System," Biotech. Bioeng. 73:261-270 (2001).

Bass, S. et al. (1990). "Hormone Phage: An Enrichment Method for Variant Proteins With Altered Binding Properties," Proteins 8:309-314.

Behrens, C. et al. (1990). "Synthesis of Achiral Linker Reagents for Direct Labelling of Oligonucleotides on Solid Supports," Nucleosides & Nucleotides 18:291-305.

Bera, T.K. et al. (Aug. 21, 1998). "A Bivalent Disulfide-Stabilized Fv With Improved Antigen Binding to erbB2," J. Mol. Biol. 281(3):475-483.

Bird, R.E. et al. (Apr. 28, 1989)."Single-Chain Antigen-Binding Proteins," Science 244(4903):409, Erratum.

Bird, R.E. et al. (Oct. 21, 1988). "Single-chain antigen-binding proteins," Science 242(4877):423-426.

Boado, R.J. et al. (Feb. 15, 2010). "IgG-Single Chain Fv Fusion Protein Therapeutic for Alzheimer's Disease Expression in CHO Cells and Pharmacokinetics and Brain Delivery in the Rhesus Monkey," Biotechnology and Bioengineering 105(3):627-635.

Boerner, P. et al. (Jul. 1, 1991). "Production of Antigen-Specific Human Monoclonal Antibodies From in Vitro-Primed Human Splenocytes," J. Immunol. 147(1):86-95.

Bolscher, J.G.M. et al. (Aug. 2011; e-published on Apr. 27, 2011). "Sortase A as a Tool for High-Yield Histatin Cyclization," The FASEB Journal 25(8):2650-2658.

Booy, E.P. et al. (Mar.-Apr. 2006, e-pub. Mar. 24, 2006). "Monoclonal and Bispecific Antibodies as Novel Therapeutics," Arch. Immunol. Ther. Exp. 54:85-101.

Bordusa, F. (2004). In Highlights in Bioorganic Chemistry, Schmuck, C. and Wennemers, H., (eds.), Wiley VCH, Weinheim, pp. 389-403.

Borgström, P. et al. (1996). "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," Cancer Research 56:4032-4039.

Bos, E.S. et al. (2004). "In Vitro Evaluation of DNA-DNA Hybridization As A Two-Step Approach In Radioimmunotherapy Of Cancer," Cancer Res. 54:32479-3486.

Bothmann, H. et al., (Jun. 2, 2000). "The Periplasmic *Escherichia coli* Peptidylprolyl cis,trans-Isomerase FkpA," The Journal of Biological Chemistry 275(22):17100-17105.

Brekke, O.H. et al. (1994). "Structure-Function Relationships of Human IgG," The Immunologist 2:125-130.

Brennan, M. et al. (Jul. 5, 1985). "Preparation of Bispecific Antibodies by Chemical Recombination of Monoclonal Immunoglobulin G1 Fragments," Science 229:81-83.

Briggs, J.J. et al. (Jan. 2010). "Cystatin E/M Suppresses Legumain Activity and Invasion of Human Melanoma," BMC Cancer 10(17):1-13.

Brinkmann, U. (Apr. 30, 2010). "Disulfide-Stabilized Fv Fragments," Chapter 14 in Antibody Engineering, Kontermaan et al. eds., vol. 2, Springer-Verlag, Berlin Heidelberg, Germany, pp. 181-189.

Brinkmann, U. et al. (1993). "A Recombinant Immunotoxin Containing a Disulfide-Stabilized FvFragment," PNAS 90(16):7538-7542.

Brorson, K. et al. (1994). "Mutational Analysis of Avidity and Fine Specificity of Anti-Levan Antibodies," J. Immunol. 163:6694-6701.

Bruck, C. et al. (1986). "Purification Of Mouse Monoclonal Antibodies From Ascitic Fluid by DEAE Affi-Gel Blue Chromatography," Methods In Enzymology 121:587-596.

Brummell, D.A. et al. (1993). "Probing the Combining Site of an Anti-Carbohydrate Antibody by Saturation-Mutagenesis: Role of the Heavy-Chain CDR3 Residues," Biochemistry 32(4):1180-1187.

Brunhouse, R. et al. "Isotypes of IgG: Comparison of the Primary Structure of Three Pairs of Isotypes which Differ In Their Ability to Activate Complement," J. Mol. Immunol. 16:907-917 (1997).

Brüggemann et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Budtschanow, J.J. et al. "System of Humoral Immunity Antibodies (Theme 2)," Guidance Manual for General Immunology, Twer (2008) p. 3, English Translation, 3 pages, (5 pages, both English Equivalent and Russian Reference.).

Burgess et al., "Possible Dissociation Of The Heparin-Binding And Mitogenic Activities Of Heparin-Binding (Acidic Fibroblast) Growth Factor-1 From Its Receptor-Binding Activities By Site-Directed Mutagenesis Of A Single Lysine Residue," J. Cell Biol. 111:2129-2138, (1990).

Burks, E.A. et al. (1997). "In Vitro Scanning Saturation Mutagenesis of an Antibody Binding Pocket," PNAS 94(2):412-417.

Burton, D.R. (1985). "Immunoglobulin G: Functional Sites," Molec. Immunol. 22(3):161-206.

Burton, D.R. et al. "The C1q Receptor Site on Immunoglobulin," Nature 288:338-344 (Nov. 27, 1980).

Caldas, C. et al. (May 2003). "Humanization Of The Anti-CD-18 Antibody 6.7: An Unexptected Effect Of A Framework Residue In Binding To Antigen," Mol. Immunol. 39(15):941-952.

Cao, Y. et al. (2003). "Bispecific Antibody Conjugates in Therapeutics," Advanced Drug Delivery Reviews 55:171-197.

Capel, P.J. et al. (Feb. 1994). "Heterogeneity of Human IgG Fc receptors," Immunomethods 4(1):25-34.

Carlsson, J. et al. (Sep. 1, 1978). "Protein Thiolation and Reversible Protein-Protein Conjugation. N-Succinimidyl 3-(2-pyridyldithio)Propionate, a New Heterobifunctional Reagent," Biochem. J. 173:723-737.

Carmichael, J. et al. (1987). "Evaluation of a Tetrazolium-Based Semiautomated Colorimetric Assay: Assessment of Chemosensitivity Testing," Cancer Res. 47:936-942.

Caron, P.C. et al. (Oct. 1, 1992). "Engineering Humanized Dimeric Forms of IgG Are More Effective Antibodies," J. Exp Med. 176:1191-1195.

Carro, E. et al. (2002, e-pub. Nov. 4, 2002). "Serum Insulin-Like Growth Factor I Regulates Brain Amyloid-Levels," Nature Medicine 8(12):1390-1397.

Carter, P. (2001). "Bispecific Human IgG by Design," Immunol. Methods 248:7-15.

Carter, P. et al. (Feb. 1992). "High Level *Escherichia coli* Expression and Production of a Bivalent Humanized Antibody Fragment," BioTechnology 10:163-167.

Carter, P. et al. (May 1992). "Humanization of An Anti-p185HER2 Antibody For Human Cancer Therapy," Proc. Natl. Acad. Sci. USA 89:4285-4289.

Carter, P.J. (2006). "Potent Antibody Therapeutics by Design," Nature Reviews Immunology 6:343-357.

Chames, P. et al. (2009). "Bispecific Antibodies for Cancer Therapy", Current Opinion in Drug Discovery & Development 12(2):276-283.

Chan, A.C. et al. (2010). "Therapeutic Antibodies for Autoimmunity and Inflammation," Nature Reviews 10(5):301-316.

(56) References Cited

OTHER PUBLICATIONS

Chan, L.A. et al. (2004). "Variable Region Domain Exchange in Human IgGs Promotes Antibody Complex Formation with Accompanying Structural Changes and Altered Effector Functions," Molecular Immunology 41:(5)527-538.
Chang, H.-C. et al. (Nov. 1994). "A General Method for Facilitating Heterodimeric Pairing Between Two Proteins: Application to Expression of a and p T-cell Receptor Extracellular Segments," Proc. Natl'l Acad. Sci. 91:11408-11412.
Chari, R.V.J. et al. (Jan. 1, 1992). "Immunoconjugates Containing Noveal maytansinoids: Promissing Anticancer Drugs," Cancer Res. 52:127-131.
Charlton, K.A. (2003)."Expression and Isolation of Recombinant Antibody Fragments in E. coli," Chapter 14 in Methods in Molecular Biology, LO, B.K.C. (ed.), Humana Press, Totowa, NJ, 248:245-254.
Chaudri, Z.N. et al. (1999). "Dual Specificity Antibodies Using A Double-Stranded Oligonucleotide Bridge," FEBS Letters 450:23-26.
Chen, J. et al. (Jul. 9, 1999). "Chaperone Activity of DsbC*," The Journal of Biological Chemistry 274(28):19601-19605.
Chen, L. et al. (2016, e-published on Aug. 18, 2016). "Improved Variants of SrtA for Site-Specific Conjugation on Antibodies and Proteins with High Efficiency," Scientific Reports 6:31899, pp. 1-12.
Chen, Y. et al. (Nov. 5, 1999). "Selection and Analysis of an Optimized Anti-VEGF Antibody: Crystal Structure of an Affinity-Matured Fab in Complex With Antigen," J. Mol. Biol. 293(4):865-881.
Cheong et al. (1990). "Affinity Enhancement of Bispecific Antibody Against Two Different Epitopes in the Same Antigen," Biochem. Biophys. Res. Commun. 173:795-800.
Chernaia, V.I. (Sep.-Oct. 1998). "[Cathepsin L from human brain tumor. Purification and contents]." Ukr Biokhim Zh. 70(5):97-103. (English Translation of Abstract.) (Article in Russian).
Chien, N.C. et al. (Jul. 1989) "Significant Structural and Functional Change Of An Antigen-Binding Site By A Distant Amino Acid Substitution: Proposal Of A Structural Mechanism," Proc. Natl. Acad. Sci. USA 86(14):5532-5536.
Chin, J.W. et al. (2002). "Addition of p-azido-L-phenylalanine to the Genetic Code of *Escherichia coli*", J. Am. Chem. Soc. 124(31):9026-9027.
Chin, J.W. et al. (2002). "In vivo Photocrosslinking With Unnatural Amino Acid Mutagenesis,", ChemBioChem 3(11):1135-1137.
Chin, J.W. et al. (Aug. 20, 2002). "Addition of a Photocrosslinking Amino Acid to the Genetic Code of *Escherichia coli*," Proc. Natl. Acad. Sci. U.S.A. 99(17):11020-11024.
Chitnis, M.M. et al. (Oct. 15, 2008). "The Type 1 Insulin-Like Growth Factor Receptor Pathway," Clin. Cancer Res. 14(20):6364-6370.
Chothia, C. et al. (Aug. 20, 1987). "Canonical Structures for the Hypervariable Regions of Immunoglobulins," J. Mol. Biol. 196(4):901-917.
Chow, K.M. et al. (Jun. 30, 2000). "Studies on the Subsite Specificity of Rat Nardilysin (N-Arginine Dibasic Convertase)," J. Biol. Chem. 275(26):19545-19551.
Chung, D.-E. et al. (Oct. 1, 2006). "Development of a Novel Albumin-Binding Prodrug That is Cleaved by Urokinase-Type-Plasminogen Activator (uPA)," Bioorg Med Chem Lett. 16(19):5157-5163.
Clackson, T. et al. (1991). "Making Antibody Fragments Using Phage Display Libraries," Nature 352:624-628.
Clancy, K.W. et al. (2010). "Sortase Transpeptidases: Insights Into Mechanism, Substrate Specificity, and Inhibition," Biopolymers 94(4):385-396.
Clynes, R. et al. (Jan. 1998). "Fc Receptors are Required in Passive and Active Immunity to Melanoma," Proc. Natl. Acad. Sci. U.S.A. 95:652-656.
Cocca, B.A. et al. (1999). "Tandem Affinity Tags for the Purification of Bivalent Anti-DNA Single-Chain Fv Expressed in *Escherichia coli*," Protein Expression and Purification 17: 290-298.
Cocuzza, A.J. (1989). "A Phosphoramidite Reagent for Automated Solid Phase Synthesis of 5'-biotinylated Oligonucleotides," Tetrahedron Letters 30:6287-6290.
Cohen, S.N. et al. (Aug. 1972). "Nonchromosomal Antibiotic Resistance in Bacteria: Genetic Transformation of *Escherichia coli* by R-Factor DNA," Proc. Natl. Acad. Sci. USA 69(8):2110-2114.
Cole, S.P.C. et al. (1985). "THE EBV-Hybridoma Technique and its Application to Human Lung Cancer," Monoclonal Antibodies and Cancer Therapy, Alan R. Liss, Inc., New York, New York, pp. 77-96.
Coleman, P.M., "Effects of Aminio Acid Sequence Changes On Antibody-Antigen Interactions," Res. Immunology. 145:33-36 (1994).
Coloma, M.J. et al. (Feb. 1997). "Design and Production of Novel Tetravalent Bispecific Antibodies" Nature Biotech 15(2):159-163.
Cordingley, M.G. et al. (1990). "Substrate Requirements of Human Rhinovirus 3C Protease for Peptide Cleavage in vitro," J. Biol. Chem. 265(16):9062-9065.
Cortesio, C.L. et al. (Mar. 10, 2008). "Calpain 2 and PTP1B Function in a Novel Pathway With Src to Regulate Invadopodia Dynamics and Breast Cancer Cell Invasion," J. Cell Biol. 180(5):957-971.
Cowburn, D. et al. , (1995). "Enhanced Affinities and Specificities Of Consolidated Ligands For the Src Homology (SH) 3 and SH2 Domains Of Abelson Protein-Tyrosine Kianse," J. Biol. Chem. 270(45):26738-36741.
Coxon, A. et al. (Apr. 2008). "Combined Treatment of Angiopoietin and VEGF Pathway Antagonists Enhances Antitumor Activity in Preclinical Models of Colon Carcinoma," 99th AACR Annual Meeting, Abstract #1113, 2 pages.
Crawford, H.C. et al. (Jun. 2002). "Matrix Metalloproteinase-7 is Expressed By Pancreatic Cancer Precursors and Regulates Acinar-To-Ductal Metaplasia in Exocrine Pancreas," J. Clin. Invest. 109(11):1437-1444.
CRC Handbook Of Chemistry and Physic (2010-2011). "Section 9: Molecular Structure ans Spectroscopy," Haynes et al. 91st Edition, Boca Raton: CRC Press, 9-1 to 9-119.
Cudic, M. et al. (Aug. 2009). "Extracellular Proteases as Targets for Drug Development," Curr. Protein Pept Sci 10(4):297-307.
Cullen, S.P. et al. (Apr. 2010). "Granzymes in Cancer and Immunity," Cell Death Differ 17(4):616-623.
Dall'Acqua, W. et al. (1998). "Contribution of Domain Interface Residues to the Stability of Antibody CH3 Domain Homodimers", Biochemistry37:9266-9273.
Davies, J. et al. (Aug. 2001). "Expression of GnTIII in a Recombinant Anti-CD20 CHO Production Cell Line Expression of Antibodies With Altered Glycoforms Leads to an Increase in ADCC Through Higher Affinity for FC gamma RIII," Biotechnol. Bioeng. 74(4):288-294.
Davies, J. et al. (Feb. 21, 1994). "'Camelising' Human Antibody Fragments: NMR Studies on VH Domains," FEBS Letters 339(3):285-290.
Davis, J.H. et al. (2010, e-pub. Feb. 4, 2010). "SEEDbodies: Fusion Proteins Based on Strand-Exchange Engineered Domain (Seed) CH3 Heterodimers in an Fc Analogue Platform for Asymmetric Binders or Immunofusions and Bispecific Antibodies," Protein Engineering Design & Selection 23(4):195-202.
Daëron, M. (1997). "Fc receptor biology," Ann. Rev. Immunol. 15:203-234.
De Graaf, A.J. et al. (2009)."Nonnatural Amino Acids for Site Specific Protein Conjugation," Bioconjug. Chem. 20:1281-1295.
De Haas, M. et al. (Oct. 1995). "Fcy Receptors of Phagocytes," J. Lab. Clin. Med. 126(4):330-341.
De Kruif, J. et al. (1996). "Leucine Zipper Dimerized Bivalent and Bispecific SCFV Antibodies from a Phage Display Library," Abst. 308, Immunotechnology 2: 298-299.
De Kruif, J. et al. (1996). "Leucine Zipper Dimerized Bivalent and Bispecific scFv Antibodies From A Semi-Sythetic Antibody Phage Display Library," The Journal of Biological Chemistry, 271(13):7630-7634.
Dervan, P.B. (2001). "Molecular Recognition of DNA by Small Molecules," Bioorg. Med. Chem. 9:2215-2235.

(56) References Cited

OTHER PUBLICATIONS

Deyev, S.M. et al. (2008). "Multivalency: The Hallmark of Antibodies Ased for Optimization of Tumor Targeting by Design," Bioessays 30(9):904-918.

Deyev, S.M. et al. (2009) "Modem Technologies For Creating Synthetic Antibodies For Clinical Application," Acta Nature 1:32-50.

Dimmock, N.J. et al. (2004). "Valency of Antibody Binding to Virions and its Determination by Surface Plasmon Resonance," Rev. Med. Virol.14:123-135.

Ding, H. et al. (2007). "Gold Nanorods Coated with Multilayer Polyelectrolyte as Contrast Agents for Multimodal Imaging," J. Phys. Chem. C 111:12552-12557.

Donaldson, J.M. et al. (Nov. 15, 2009). "Design and Development of Masked Therapeutic Antibodies to Limit Off-Target Effects: Application to Anti-EGFR Antibodies," Cancer Biology & Therapy 8(22):2145-2150.

Dong, H. et al. (2011). "Stable IgG-like Bispecific Antibodies Directed toward the Type I Insulin-like Growth Factor Receptor Demonstrate Enhanced Ligand Blockade and Anti-tumor Activity," The Journal of Biological Chemistry 286(6):4703-4717.

Dooley, H. et al. (2006, e-pub. Jul. 22, 2005). "Antibody Repertoire Development in Cartilaginous Fish," Dev. Comp. Immunol. 30:43-56.

Doronina, S.O. et al. (Jul. 2003). "Development of Potent Monoclonal Antibody Auristatin Conjugates for Cancer Therapy," Nat. Biotechnol. 21(7):778-784.

Dubowchik, G.M. et al. (2002). "Doxorubicin Immunoconjugates Containing Bivalent, Lysosomally-Cleavable Dipeptide Linkages," Bioorganic & Medicinal ChemistryLetters 12:1529-1532.

Dufner, P. et al. (2006). "Harnessing Phage and Ribosome Display for Antibody Optimization," Trends Biotechol. 24(11):523-529.

Durocher, Y. et al. , (2002). "High-Level and High-Throughput Recombinant Protein Production by Transient Transfection of Suspension-Growing Human 293-EBNA1 Cells," Nucleic Acids Research 30(2 e9):9 pages.

Eaton, D.L. et al. (Dec. 30, 1986). "Construction and Characterization of an Active Factor VIII Variant Lacking the Central One-Third of the Molecule," Biochemistry 25(26):8343-8347.

Edelman, G.M. et al. (1969). "The Covalent Structure of an Entire γG Immunoglobulin Molecule," Proc. Natl. Acad. Sci. USA 63:78-85.

Ellman, J. et al. (1991). "Biosynthetic Method for Introducing Unnatural Amino Acids Site-Specifically into Proteins," Meth. Enzym. 202:301-336.

Els Conrath, K. et al. (Mar. 9, 2001). "Camel Single-Domain Antibodies as Modular Building Units in Bispecific and Bivalent Antibody Constructs," Journal of Biological Chemistry 276(19):7346-7350.

Eulberg, D. et al. (2003). "Spiegelmers: Biostable Aptamers," Chembiochem 4:979-983.

Extended European Search Report dated Aug. 5, 2013, for European Patent Application No. 10817575.3, eleven pages.

Fischer, N. et al. (2007). "Bispecific Antibodies: Molecules that Enable Novel Therapeutic Strategies," Pathobiology 74:3-14.

Flatman, S. et al. (2007, e-pub. Dec. 11, 2006). "Process Analytics for Purification of Monoclonal Antibodies," J. Chromatogr. B. 848:79-87.

Fraker, P.J. et al. (Feb. 28, 1978). "Protein and Cell Membrane Iodinations With a Sparingly Soluble Chloroamide, 1,3,4,6-Tetrachloro-3a,6a-Diphenylglycoluril," Biochem. Biophys. Res. Commun. 80(4):849-857.

Francois, C. et al. (1993). "Construction of a Bispecific Antibody Reacting with the a- and ~-Chains of the Human IL-2 Receptor," The Journal of Immunology150(10):4610-4619.

Franklin, M.C. et al. (2004). "Insights Into ErbB Signaling From The Structure Of The ErbB2-Pertuzumab Complex," Cancer Cell 5(4):317-328.

Frese, M.-A. et al. (2009). "Formylglycine aldehyde Tag—protein engineering through a novel post-translational modification," ChemBioChem 10:425-427.

Friend, P.J. et al. (1999). "Phase I Study of an Engineered Aglycosylated Humanized CD3 Antibody in Renal Transplant Rejection," Transplantation 68(11):1632-1637.

Gadgil, H.S. et al. (2006). "Identification of Cysteinylation of a Free Cysteine in the Fab Region of a Recombinant Monoclonal IgG1 Antibody Using lys-C Limited Proteolysis Coupled With LC/MS Analysis," Analytical biochem. 2006: 355:185-174.

Galamb, O. et al. (2008). "Inflammation, Adenoma and Cancer: Objective Classification of Colon Biopsy Specimens With Gene Expression Signature," Dis Markers 25(1):1-16.

Galfrè, G. et al. (1981). "Preparation of Monoclonal Antibodies: Strategies and Procedures," Methods in Enzymology 73:3-46.

Gautier, A. et al. (2008). "An Engineered Protein Tag for Multiprotein Labeling in Living Cells," Chem. Biol. 15:128-136.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Geisse, S. et al. "Eukaryotic Expression Systems: A Comparison," Protein Expr. Purif. 8(3):271-282 (Nov. 1996).

Geoghegan, K. F. et al. (1992). "Site-Directed Conjugation of Nonpeptide Groups to Peptides and Proteins via Periodate Oxidation of a 2-Amino Alcohol. Application to Modification at N-Terminal Serine," Bioconjugate Chem. 3(2):138-146.

Gerngross, T.U. (Nov. 2004). "Advances in the Production of Human Therapeutic Proteins in Yeasts and Filamentous Fungi," Nature Biotechnology 22(11):1409-1414.

Gerspach, J. et al. (2006). "Target-Selective Activation of a TNF Prodrug by Urokinase-Type Plasminogen Activator (uPA) Mediated Proteolytic Processing at the Cell Surface," Cancer Immunol. Immunother 55:1590-1600.

Giusti, A.M. et al. (May 1987). "Somatic Diversification Of S107 From An Antiphosphocholine To An Anti-DNA Autoantibody Is Due To A Single Base Change In Its Heavy Chain Variable Region," Proc. Natl. Acad. Sci. USA 84(9):2926-2930.

Gold, D.V. et al. (2008). "A Novel Bispecific, Trivalent Antibody Construct for Targeting Pancreatic Carcinoma," Cancer Res. 68(12):4819-4826.

Goldenberg, D. et al. (2012). "Bi-Specific Antibodies that Bind Specific Target Tissue and Targeted Conjugates," Derwent Information Ltd.12 pages.

Goldenberg, D.M. et al. (Jan. 2008). "Multifunctional Antibodies by the Dock-and-Lock Method for Improved Cancer Imaging and Therapy by Pretargeting," J. Nuc. Med. 49(1):158-163.

Goodman, J.W. et al. (1994). "Immunoglobulin Proteins," Chapter 6 in Basic And Clinical Immunology, Eighth Edition, Appleton & Lange: Norwalk, Conneticut, pp. 66-79.

Graham, F.L. et al. (Apr. 1973). "A New Technique for the Assay of Infectivity of Human Adenovirus 5 DNA," Virology 52(2):456-467.

Graham, F.L. et al. (1977). "Characteristics of a Human Cell Line Transformed by DNA from Human Adenovirus Type 5," J. Gen Virol. 36:59-74.

Greenwood, J. et al. (May 1993). "Structural Motifs Involved in Human IgG Antibody Effector Functions," Eur. J. Immunology 23(5):1098-1104.

Grote, M. et al. (2012). "BispecificAntibody Derivatives Based On Full-Length IgG Formats," Methods Mol. Biol. 901:247-263.

Gruber, M. et al. (1994). "Efficient Tumor Cell Lysis Mediated by a Bispecific Single Chain Antibody Expressed in *Escherichia coli*," J. Immunol. 152:5368-5374.

Grönwall C. et al. (Jun. 2008). "Generation of Affibody Ligands Binding lnterleukin-2 Receptor α/CD25," Biotechnol. Appl. Biochem. 50(Pt. 2):97-112.

Guss, B. et al. (Jul. 1986). "Structure of the IgG-Binding Regions of Streptococcal Protein G," EMBO J. 5(7):1567-1575.

Guyer, R.L. et al. (Aug. 1976). "Immunoglobulin Binding By Mouse Intestinal Epithelial Cell Receptors," J. Immunol. 117(2):587-593.

Gussow, D. et al. (1991). "Humanization Of Monoclonal Antibodies," Methods in Enzymology 203:99-121.

(56) References Cited

OTHER PUBLICATIONS

Hackenberger, P.R. et al. (2008). "Chemoselective Ligation and Modification Strategies for Peptides and Proteins," Angew. Chem. Int. Ed. 47:10030-10074.
Ham, R.G. et al. (1979). "Media and Growth Requirements," Meth. Enzymol. 58:44-93.
Hamers-Casterman, C. et al. (Jun. 3, 1993). "Naturally Occurring Antibodies Devoid of Light Chains," Nature 363:446-448.
Hara, H. et al. (1996) "Overproduction of Penicillin-Binding Protein 7 Suppresses Thermosensitive Growth Defect at Low Osmolarity due to an spr Mutation of *Escherichia coli*," Microhial Drug Resistance 2(1):63-72.
Harlow, E. et al. (1988). Structure of the Antibody-Antigen Complex, Antibodies: A Laboratory Manual, Cold Spring Harbor Laboratory Press, NY, Chapter 3, pp. 23-26.
Hartog, H. et al. (Aug. 23, 2007). "The Insulin-Like Growth Factor 1 Receptor in Cancer: Old Focus, New Future," European Journal of Cancer, Pergamon Press, Oxford, GB, 43(13):1895-1904.
Hatfield, K.J. et al. (2005). "Antiangiogenic Therapy in Acute Myelogenous Leukemia: Targeting of Vascular Endothelial Growth Factor and Interleukin 8 as Possible Antileukemic Strategies," Curr. Cancer Drug Targets 5(4):229-248.
Hauser, N.C. et al. (2006, e-pub. Sep. 20, 2006). "Utilising The Left-Helical Conformation Of L-DNA For Analysing Different Marker Types On A Single Universal Microarray Platform," Nucl. Acids Res. 34(8):5101-5111.
Hayashi, G. et al. (2005). "Application of L-DNA as a Molecular Tag," Nucl. Acids Symp. Ser. 49:261-262.
Hayden, M.S. et al. (1997). "Antibody Engineering," Current Opinion in Immunology 9(2):201-212.
Heitner, T. et al. (2001). "Selction Of Cell Binding and Internalizing Epidermal Growth Factor Receeptor Antibodies From A Phage Display Library," Journal Of Immunological Methods 248:17-30.
Henry, L.R. et al. (Mar. 15, 2007). "Clinical Implications of Fibroblast Activation Protein in Patients With Colon Cancer," Clin Cancer Res. 13(6):1736-1741.
Herberman, R.B. (1979). "Immunodiagnosis of Cancer", in The Clinical Biochemistry of Cancer, Fleisher, M et al., American Association of Clinical Chemists, Washington, D.C. pp. 347-364.
Hey, T. et al. (2005). "Artificial, Non-Antibody Binding Proteins for Pharmaceutical and Industrial Applications," Trends Biotechnol. 23:514-522.
Hezareh et al. (2001). "Effector function activities of a panel of mutants of a broadly neutralizing antibody against human immunodeficiency virus type 1" J. Virol. 75: 12161-12168.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.
Hollander, N.. (Mar. 2009). "Bispecific Antibodies for Cancer Therapy," Immunotherapy 1(2):211-222.
Holliger, P. et al. (Jul. 1993). "Diabodies": Small Bivalent and Bispecific Antibody Fragments, Proc. Natl. Acad. Sci. USA 90:6444-6448.
Holliger, P. et al. (Sep. 2005) "Engineered Antibody Fragments and The Rise Of Single Domains," Nat. Biotechnol. 23(9):1126-1136.
Holt, L. et al. (Nov. 2003) "Domain Antibodies: Proteins For Therapy," TRENDS in Biotechnology 21(11):484-490.
Hoogenboom, H.R. et al. (1992). "By-Passing Immunisation. Human Antibodies From Synthetic Repertoires of Germline VH Gene Segments Rearranged in Vitro," J. Mol. Biol. 227:381-388.
Hoppe, H.-J. et al. (1994). "A Parallel Three Stranded Alpha-Helical Bundle at the Nucleation Site of Collagen Triple-Helix Formation," FEBS Lett. 344:191-195.
Huber, R. et al. (1976). "Crystallographic Structure Studies of an IgG Molecule and an Fc Fragment," Nature, 264:415-420.
Hudson, P.J. et al. (Jan. 2003). "Engineered Antibodies," Nat. Med. 9(1):129-134.
Hust, M. et al. (Mar. 8, 2007). "Single Chain Fab (scFab) Fragment," BMC Biotechnology 7(14):1-15.
Huston, J.R. et al. (Aug. 1988). "Protein engineering of antibody binding sites: recovery of specific activity in an anti-digoxin single-chain Fv analogue produced in *Escherichia coli*," Proc. Natl. Acad. Sci. U.S.A. 85(16)5879-5883.
Huston, J.S. et al. (1993). "Medical Applications of Single-Chain Antibodies," Intern. Rev. Immunol. 10(2-3):195-217.
Ibragimova, G.T. et al. (Oct. 1999)."Stability of the β-Sheet of the WW Domain: A Molecular Dynamics Simulation Study," Biophysical Journal 77:2191-2198.
Idusogie, E.E. et al. (2000). "Mapping of the C1q Binding Site on Rituxan, a Chimeric Antibody With a Human IgGI Fc," J. Imrmmol. 164:4178-4184.
Ilangovan, U. et al. (2001). "Structure of Sortase, The Transpeptidase That Anchors Proteins to the Cell Wall of *Staphylococcus aureus*," Proc. Natl. Acad. Sci. U.S.A. 98(11):6056-6061.
International Preliminary Report on Patentability for PCT/EP2011/054505, dated Oct. 2, 2012, filed on Mar. 24, 2011, eight pages.
International Preliminary Report on Patentability dated Aug. 12, 2014, for PCT Patent Application No. PCT/US2013/025365, filed on Feb. 8, 2013, ten pages.
International Search Report for PCT/EP2011/054505 dated Jun. 28, 2011, filed on Mar. 24, 2011, seven pages.
International Search Report dated Mar. 6, 2012 in Application No. PCT/EP201 I/073633, 6 pages.
International Search Report dated Aug. 13, 2013, for PCT Patent Application No. PCT/EP2013/063259, filed on Jun. 25, 2013, six pages.
International Search Report dated Aug. 5, 2014, for PCT Patent Application No. PCT/EP2013/063258, filed on Jun. 25, 2013, seven pages.
International Search Report dated Aug. 6, 2013, for PCT Application No. PCT/US2013/025365, filed Feb. 8, 2013, six pages.
International Search Report dated Aug. 6, 2013, PCT Patent Application No. PCT/EP2013/063260, filed on Jun. 25, 2013, seven pages.
International Search Report dated Dec. 6, 2011, for PCT Patent Application No. PCT/EP2011/064468 filed on Aug. 23, 2011, seven pages.
International Search Report dated Dec. 6, 2011, for PCT Patent Application No. PCT/EP2011/064476 filed on Aug. 23, 2011, seven pages.
International Search Report dated Jun. 15, 2011 for PCT Patent Application No. PCT/US2010/002546 filed on Sep. 16, 2010, five pages.
International Search Report dated Nov. 4, 2013, for PCT Application No. PCTEP2013/068910, filed on Sep. 12, 2013, five pages.
Iyer, R.P. et al. (1990). "Abasic Oligodeoxyribonucleoside Phosphorothioates: Synthesis and Evaluation as Anti-HIV-1 Agents," Nucleic Acids Research 18:2855-2859.
Jackman, J. et al. (Jul. 2, 2010). "Development of a Two-part Strategy to Identify a Therapeutic Human Bispedfic Antibody That Inhibits IgE Receptor Signaling," The Journal of Biological Chemistry 285(27):20850-20859.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.
Janeway, C.A. (Oct. 1989). "Immunotherapy by peptides?" Nature, 341:482-483.
Jang, Y.-J. et al. (1998). "The Structural Basis for DNA Binding by an Anti-DNA Autoantibody," Mol. Immunol. 35(18):1207-1217.
Jarvius, M. et al. , (2007). "In Situ Detection of Phosphorylated Platelet-derived Growth Factor Receptor~ Using a Generalized Proximity Ligation Method," Molecular & Cellular Proteomis 6(9):1500-1509.
Jefferis, R. et al. (Jun. 1998). "IgG-Fc-Mediated Effector Functions: Molecular Definition of Interaction Sites for Effector Ligands and the Role of Glycosylation," Immunol. Rev. 163:59-76.

(56) References Cited

OTHER PUBLICATIONS

Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.

Jendreyko, N. et al. (2006). "Simultaneous, Phenotypic Knockout of VEGF-R2 and Tie-2 With an Intradiabody Enhances Antiangiogenic Effects In Vivo," Therapieoptimierung and Risikostratifizierung, Scripps Research Institute, 218:143-151.

Jia, L. et al. (Jun. 29, 2010). "A Novel Trifunctional IgG-Like Bispecific Antibody to Inhibit HIV-1 Infection and Enhance Lysis of HIV by Targeting Activation of Complement," Virology Journal 7(142):1-4.

Jiang, X.-R. et al. (2011). "Advances in the Assessment and Control of the Effector Functions of Therapeutic Antibodies," Nat. Rev. Drug Discov., 10(2):101-111.

Johnson, G. et al. (2003). "The Kabat Database and a Bioinformatics Example," Chapter 2 in Methods in Molecular Biology, Lo, B.K.C, Humana Press, Totawa, N.J., 248:11-25.

Johnson, G. et al. "Kabat Database and Its Applications: 30 Years After The First Variability Plot," Nucleic Acids Res. 28:214-218 (2000).

Johnson, S. et al. (1991)."Construction of Single-Chain Fv Derivatives Monoclonal Antibodies and their Production in *Escherichia coli*," Methods Enzymol. 203:88-98.

Joly, J.C. et al. (Mar. 1998). "Overexpression of *Escherichia coli* Oxidoreductases Increases Recombinant Insulinlike Growth Factor-I Accumulation," Proc. Natl. Acad. Sci. USA 95:2773-2777.

Jones, P. et al. (May 29, 1986) "Replacing The Complementarity-Determining Regions In A Human Antibody With Those From A Mouse," Nature 321:522-525.

Kabat, E.A. et al. (1991). Sequences of Proteins of Immunological Interest (Table of Contents and Introduction), 5th edition, Bethesda, MD: Public Health Service, NIH, vol. 1.

Kabat, E.A. et al. (Jul. 1975). "Evolutionary and Structural Influences on Light Chain Constant (CL) Region of Human and Mouse Immunoglobulins," Proc. Natl. Acad. Sci. USA 72(7):2785-2788.

Karadag, A. et al. (Apr. 2006). "ADAM-9 (MDC-9/meltrin-γ), A Member of the a Disintegrin and Metalloproteinase Family, Regulates Myeloma-Cell-lnduced Interleukin-6 Production in Osteoblasts by Direct Interaction With the αvβ5 Integrin," Blood 107(8):3271-3278.

Kaufman, R.J. (2000). "Overview of Vector Design for Mammalian Gene Expression," Molecular Biotechnology 16:151-160.

Kazama, Y. et al. (1995). "Hepsin, A Putative Membrane-Associated Serine Protease, Activates Human Factor VII and Initiates a Pathway of Blood Coagulation on the Cell Surface Leading to Thrombin Formation," JBC 270:66-72.

Kim, J-K. et al. (1994). "Localization of the Site of the Murine IgGI Molecule That is Involved in Binding to the Murine Intestinal Fc Receptor," Eur. J. Immunol. 24:2429-2434.

Kim, J.K. et al. (1993). "Inhibition of Vascular Endothelial Growth Factor-Induced Angiogenesis Suppresses Tumour Growth In Vivo," Nature 362:841-844.

Kindt, T.J. et al. (2007). "Antigens and Antibodies," in Chapter 4 of Kuby Immunology, 6th ed., W.H. Freeman and Co., N.Y, pp. 91, 14 pages.

King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.

Klein, C. et al. (2012). "Progress in Overcoming the Chain Association Issue in Bispecific Heterodimeric IgG Antibodies," mAbs 4(6):653-663.

Kleinschmidt, M. et al. , (Mar. 21, 2003). "Design of a Modular Immunotoxin Connected by Polyionic Adapter Peptides," J. Mol. Biol. 327(2):445-452.

Klonisch, T. et al. (1996). "Enhancement In Antigen Binding By A Combination Of Synergy and Antibody Capture," Immunology 89:165-171.

Klonisch, T. et al. (1996). "Relative Location Of Epitopes Involved In Synergistric Antibody Binding Using Human Chorionic Gonadotropin As A Model," Eur. J. Immunol. 26:1987-1905.

Kobayashi, H. et al. (1998). "Similarities in the Biodistribution of Iodine-Labeled Anti-Tac Single-Chain Disulfide-Stabilized Fv Fragment and Anti-Tac Disulfide-Stabilized Fv Fragment," Nuclear Medicine & Biology 25:387-393.

Kobayashi, H. et al. (1999). "Tryptophan H33 Plays an Important Role in Pyrimidine (6-4) Pyrimidone Photoproduct Binding by a High-Affinity Antibody," Protein Engineering 12(10):879-844.

Kodukula, K. et al. (Mar. 5, 1991). "Biosynthesis of Phosphatidylinositol Glycan-Anchored Membrane Proteins. Design of a Simple Protein Substrate to Characterize the Enzyme that Cleaves the COOH-Terminal Signal Peptide," The Journal of Biological Chemistry 266(7):4464-4470.

Kontermann, R.E. et al. (Mar.-Apr. 2012, e-pub. Mar. 1, 2012). "Dual Targeting Strategies With Strategies With Bispecific Antibodies," MAbs. 4(2):182-197.

Kostelny, S.A. et al. (Mar. 1, 1992). "Formation of a Bispecific Antibody By The Use of Leucine Zippers," J. Immunol. 148(5):1547-1553.

Kratz, F. et al. (2006). "Prodrugs of Anthracyclines in Cancer Chemotherapy," Current Medicinal Chemistry 13(5):477-523.

Krugmann, S. et al. (1997). "Structural Requirements for Assembly of Dimeric IgA Probed by Site-Directed Mutagenesis of J Chain and a Cysteine Residue of the α-Chain CH2 Domain," The Journal of Immunology 159:244-249.

Kuijpers, W.H.A. et al. (1993). "Specifica Recognition Of Antibody-Oligonucleotide Conjugates By Radiolabeled Antisense Nucleotides: A Novel Approach For Two-Step Radioimmunotherapy Of Cancer," Bioconjug. Chem. 4:94-102.

Kumar, S. et al. (Nov. 10, 2000). "Molecular Cloning and Expression of the Fabs of Human Autoantibodies in *Escherichia coli*," J. Biol. Chem. 275(45):35129-35136.

Kunik, V. et al. (2012, e-pub. Jun. 6, 2012). "Paratome: An Online tool For Systematic Identification of Antigen-Binding Regions in Antibodies Based on Sequence or Structure," Nucleic Acids Research 40:W521-W524.

Lamkanfi, M. et al. (Jan. 2009). "Inflammasomes: Guardians of Cytosolic Sanctity," Immunol. Rev. 227(1):95-105.

Landschulz, W.H. et al. (1988). "The Leucine Zipper: A Hypothetical Structure Common to a New Class of DNA Binding Proteins," Science 240:1759-1764.

Lazar et al., "Transforming Growth Factor A: Mutation Of Aspartic Acid 47 and Leucine 48 Results In Different Biological Activities," Mol. Cell. Biol. 8:1247-1252, (1988).

Ledbetter, J.A. et al. (1990). "CD28 Ligation in T-Cell Activation: Evidence for Two Signal Transduction Pathways," Blood, 75(7):1531-1539.

Lederman, S. et al. (1991). A Single Amino Acid Substitution in a Common African Allele of the CD4 Molecule Ablates Binding of the Monoclonal Antibody, OKT4, Molecular Immunology 28(11):1171-1181.

Lee, H.-S. et al. (1999). "Generation And Characterization of A Novel Single-Gene-Encoded Single-Chain Immunoglobulin Molecule With Antigen Binding Activity and Effector Functions," Mol Immunol. 36(1):61-71.

Lee, K.N. et al. (Jun. 16, 2009). "Using Substrate Specificity of Antiplasmin-Cleaving Enzyme for Fibroblast Activation Protein Inhibitor Design," Biochemistry 48(23):5149-5158.

Lee, S.-H. et al. (2010). "Humanization of an Agonistic Anti-Death Receptor 4 Single Chain Variable Fragment Antibody and Avidity-Mediated Enhancement of its Cell Death-Inducing Activity," Molecular Immunology47: 816-824.

Leeman, M.F. et al. (2002). "The Structure, Regulation, and Function of Human Matrix Metalloproteinase-13," Crit. Rev Biochem Mol. Biol. 37(3):149-166.

Levary, D.A. et al. (2011). "Protein-Protein Fusion Catalyzed by Sortase A," PLOS One 6:e18342.1-e18342.6. Supplementary material, eight pages.

Levary, D.A. et al. (2011). "Protein-Protein Fusion Catalyzed by Sortase A," PLOS One 6:e18342.1-e18342.6.

(56) References Cited

OTHER PUBLICATIONS

Li, H. et al. (Feb. 2006; e-published on Jan. 22, 2006). "Optimization of Humanized IgGs in Glycoengineered Pichia pastoris," Nature Biotechnology 24(2):210-215.
Liang, W.-C. et al. (2006). "Cross-Species Vascular Endothelial Growth Factor (VEGF)-blocking Antibodies Completely Inhibit the Growth of Human Tumor Xenografts and Measure the Contribution of Stromal VEGF," Journal of Biological Chemistry 281(2):951-961.
Lifely, M.R. et al. (Dec. 1995). "Glycosylation and Biological Activity of CAMPATH-1H Expressed in Different Cell Lines and Grown Under Different Culture Conditions," Glycobiology 5(8):813-822.
Lin, C. (Jan. 2009), "Mirror Image DNA Nanostructures for Chiral Supramolecular Assemblies," Nano Lett. 9:433-436, 8 pages.
Lin, M.C. et al. (1975). "Structure-Function Relationships in Glucagon: Properties of Highly Purified des-his-, monoiodo-, and [Des-Asn28, Thr29](homoserine lactone27)-glucagon," Biochemistry USA 14:1559-1563.
Lindmark, R. et al. (1983). "Binding of Immunoglobulins to Protein A and Immunoglobulin Levels in Mammalian Sera," J. Immunol. Meth. 62:1-13.
Liotta, L.A. et al. (Mar. 6, 1980). "Metastatic Potential Correlates With Enzymatic Degradation of Basement Membrane Collagen," Nature 284(5751) 67-68.
Liu, B. et al. (2004). "Mapping Tumor Epitope Space by Direct Selection of Single-Chain Fv Antibody Libraries on Prostate Cancer Cells," Cancer Res. 64:704-710.
Liu, B. et al. (2002). "Towards Proteome-Wide Production Of Monoclonal Antibody By Phage Display," J. Mol. Biol. 315:1063-1073.
Liu, C. et al. (Aug. 1996). "Eradication of Large Colon Tumor Xenografts by Targeted Delivery of Maytansinoids," Proc. Natl. Acad. Sci. USA 93:8618-8623.
Liu, F.-Y. et al. (2005). "Clinical and imaging diagnosis of primary hepatic lymphoma," J First Mil Med. Univ, 25(10):1290-1292, three pages. (Translation of the Abstract Only.).
Liu, H. et al. (Jul. 2008). "Heterogeneity of Monoclonal Antibodies," Journal of Pharmaceutical Sciences 97(7):2426-2447.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lopez-Otin, C. et al. (Apr. 2010). "The Regulatory Crosstalk Between Kinases and Proteases in Cancer," Nat. Rev. Cancer 10(4):278-292.
Love, T.W. et al. (1989). "Recombinant Antibodies Possessing Novel Effector Eunctions," Methods in Enzymology 178:515-527.
Lu, D. et al. (2004, e-pub. Apr. 22, 2004). "The Effect Of Variable Domain Orientation And Arrangement on the Antigen-Binding Activity of a Recombinant Human Bispecific Diabody," Biochem. Biophys. Res. Commun. 318(2):507-513.
Lu, D. et al. (Jan. 23, 2004). "Simultaneous Blockage of Both the Epidermal Growth Factor Receptor And the Insulin-Like Growth Factor Receptor Signaling Pathways in Cancer Cells With a Fully Human Recombinant Bispecific Antibody" J. Biol. Chem. 279(4):2856-2865.
Lu, D. et al. (2002). "Fab-scFv Fusion Protein: an Efficient Approach to Production of Bispecific Antibody Fragments" J. Immunol Methods 267(2):213-226.
Lu, D. et al. (May 20, 2005). "A Fully Human Recombinant IgG-Like Bispecific Antibody to Both the Epidermal growth Factor Receptor and the Insulin-Like Growth Factor Receptor for Enhanced Antitumor Activity," The Journal of Biological Chemistry 280(20):19665-19672.
Lu, X. et al. (Aug. 2009). "ADAMTS1 and MMP1 proteolytically engage EGF-like ligands in an osteolytic signaling cascade for bone metastasis," Genes Dev. 23(16):1882-1894.

Lukas, T.J. et al. "Inhibition of C1-Mediated Immune Hemolysis By Monomeric and Dimeric Peptides From The Second Constant Domain of Human immunoglobulin G," J. Immunol. 127(6):2555-2560 (Dec. 1981).
Lund, J. et al. (Jan. 1995). "Oligosaccharide-Protein Interactions in IgG can Modulate Recognition by FcGamma Receptors," FASEB 9:115-119.
MacCallum, R.M. et al. (1996). "Antibody-Antigen Interactions: Contact Analysis and Binding Site Topography," J. Mol. Biol. 262:732-745.
Machida, S. et al. (2008). "Module Assembly for Protein-Surface Recognition: Geranylgeranyltransferase I Bivalent Inhibitors for Simultaneous Targeting ofInterior and Exterior Protein Surfaces," Chem. Eur. J.14:1392-1401.
Madej, M.P. et al. (2012). "Engineering of an Anti-Epidermal Growth Factor Receptor Antibody to Single Chain Format and Labeling by Sortase A-Mediated Protein Ligation", Biotechnology and Bioengineering109(6):1461-1470.
Makrides, S.C. "Components Of Vectors For Gene Transfer And Expression In Mammalian Cells," Protein Expr. Purif 17(2):183-202 (Nov. 1999).
Malmborg, A.-C. et al. (1995). "BIAcore as a Tool in Antibody Engineering," J. Immunol. Methods 183:7-13.
Mamoune, A. et al. (Aug. 2003). "Calpain-2 as a Target For Limiting Prostate Cancer Invasion," Cancer Res. 63(15):4632-4640.
Mandler, R. et al. (2000). "Immunoconjugates of Geldananlycin and Anti-HER2 Monoclonal Antibodies Antiproliferative Activity on Human Breast Carcinoma Cell Lines," J. Nat. Cancer Inst. 92(19):1573-1581.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002). "Modifications in Synthesis Strategy Improve the Yield and Efficacy of Geldanamycin-Herceptin Immunoconjugates," Bioconjugate Chem. 13:786-791.
Mann, M. et al. (2003). "Proteomic Analysis of Post-Translational Modifications," Biochemistry 21:255-261.
Mao, H. et al. (2004). "Sortase-Mediated Protein Ligation: A New Method for Protein Engineering," J. Am. Chem. Soc. 126:2670-2671.
Mariuzza, R.A. et al. (1987). "The Structural Basis Of Antigen-Antibody Recognition," Annu. Rev. Biophys. Biophys. Chem. 16:139-159.
Marks, J.D. et al. (1991). "By-Passing Immunization. Human Antibodies From V-Gene Libraries Displayed on Phage," J. Mol. Biol. 222:581-597.
Marvin, J.S. et al. (2006). "Bispecific Antibodies for Dual-Modality Cancer Therapy: Killing Two Signaling Cascades With One Stone," Curr. Opin. Drug Discov. Devl. 9:184-193.
Marvin, J.S. et al. (Jun. 2005). "Recombinant Approaches to IgG-Like Bispecific Antibodies," Acta Pharmacol. Sin. 26(6):649-658.
Mason, J.M. et al. (2004). "Coiled Coil Domains: Stability, Specificity, and Biological Implications," ChemBioChem 5:170-176.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals N.Y. Acad. Sci. 383:44-68.
Matrisian, L.M.. (Oct. 1999)."Cancer Biology: Extracellular Proteinases in Malignancy," Curr. Biol. 9(20):R776-R778.
McCarron, P.A. et al. (2005). "Antibody Conjugates and Therapeutic Strategies," Mol. Interventions 5:368-380.
McKeen, C.M. et al. (2003)."Synthesis of Fluorophore and Quencher Monomers for Use in Scorpion Primers and Nucleic Acid Structural Probes," Organic & Biomol. Chem. 1:2267-2275.
McLean, G.R. et al. "A Point Mutation in the CH3 Domain of Human IgG3 Inhibits Antibody Secretion Without Affecting Antigen Specificity," Molecular Immunology, 42:1111-1119.
Meares, C.F. et al. (2003). "Molecular Tools For Targeted Imaging and Therapy Of Cancer," J. Mol. Recognit. 16:255-259.

(56) References Cited

OTHER PUBLICATIONS

Meissner, P. et al. (2001). "Transient Gene Expression: Recombinant Protein Production with Suspension-Adapted HEK293-EBNA Cells," Biotechnology and Bioengineering 75:197-203.
Melnyk, O. et al. (1996). "Vascular Endothelial Growth Factor Promotes Tumor Dissemination by a Mechanism Distinct from Its Effect on Primary Tumor Growth," Cancer Research 56:921-924.
Merchant, A. M. et al. (Jul. 1998). "An Efficient Route To Human Bispecific IgG," Nature Biotechnology 16:677-681.
Meyer, A. et al. "Oligonucleotide Sequential Bis-Conjugation Via Click-Oxime and Click-Huisgen Procedures," Journal of Organic Chemistry 75:3927-3930.
Michaelson, J.S. et al. (Mar. 2009, e-pub. Mar. 11, 2009). "Anti-Tumor Activity of Stability-Engineered IgG-Like Bispecific Antibodies Targeting TRAIL-R2 and LTβR," MAbs 1(2):128-141.
Miller, K. et al. (2003). "Design, Construction, and In Vitro Analyses of Multivalent Antibodies," J. Immunol. 170:4854-4861.
Milstein, C. et al. (Oct. 6, 1983). "Hybrid Hybridomas and Their Use In Immunohistochemistry," Nature 305:537-540.
Mimura, Y. et al. (Dec. 7, 2001). "Role of Oligosaccharide Residues of IgG1-Fc in FcγRIIb Binding," The Journal of Biological Chemistry 276(49): 45539-45547.
Minn, A.J. et al. (Jul. 2005). "Genes That Mediate Breast Cancer Metastasis to Lung," Nature 436(7050):518-524, 15 pages.
Mirny, L. et al. (2001). "Protein Folding Theory: From Lattice to All-Atom Models," Annu. Rev. Biophys. Biomol. Struct., 30:361-396.
Mizukami, Y. et al. (2005). "Induction of Interleukin-8 Preserves the Angiogenic Response in HIF-1α-Deficient Colon Cancer Cells," Nature Med. 11:992-997.
Morgan, A. et al. "The N-Terminal End Of The CH2 Domain Of Chimeric Human IgGI Anti-HLA-DR Is Necessary For C1q, FcγRI and FcγRIII Binding," Immunology 86(2):319-324 (Oct. 1995).
Morimoto, K. et al. (1992). "Single-Step Purification of F(AB')2 Fragments of Mouse Monoclonal Antibodies KImmunoglobulins G1) By Hydrophobic Interaction High Performance Liquid Chromatography Using TSKgel Phenyl-5PW," J. Biochem. Biophys. Method 24:107-117.
Morocho, A.M. et al. "Novel Biotin Phosphoramidites With Super-Long Tethering Arms," Nucleosides, Nucleotides & Nucleic Acids 22 (2003) 1439-1441.
Morrison, S.L. (Apr. 28, 1994). "Success in Specification," Nature 368:812-813.
Morrison, S.L. (Nov. 2007). "Two Heads are Better Than One," Nature Biotechnology 25(11):1233-1234.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. et al. (Jan. 1, 1998). "Variable Region Domain Exchange Influences the Functional Properties of IgG," Journal of Immunology, American Association of Immunologists 160:2802-2808.
Mukhopadhyay, S. et al. (2010) "Matrix Metalloproteinase-12 is a Therapeutic Target for Asthma in Children and Young Adults," J. Allergy Clin Immunol. 126:70-76.
Muller, L. et al. (Dec. 15, 2000). "Processing and Sorting of the Prohormone Convertase 2 Propeptide," J. Biol. Chem. 275(50):39213-39222.
Murakami, M.S. et al. (1995). "Cell Cycle Regulation, Oncogenes, and Antineoplastic Drugs," Chapter 1 in The Molecular Basis of Cancer, W.B. Saunders Company, Philadelphia, pp. 3-17.
Muyldermans, S. et al. (Apr. 2001). "Recognition Of Antigens By Single-Domain Antibody Fragments: The Superfluous Luxury Of Paired Domains," Trends Biochem. Sci. 26(4):230-235.
Möhlmann, S. et al. (2011). "In Vitro Sortagging of an Antibody Fab Fragment: Overcoming Unproductive Reactions of Sortase with Water and Lysine Side Chains", Chembiochem: A European Journal of Chemical Biology 12(11):1774-1780.

Müller, D. et al. (2007). "Bispecific Antibodies," Chapter 2 in Handbook of Therapeutic Antibodies, Dubel, S. ed., Wiley-VCH Verlag GmbH & Company KGaA, Weinheim, pp. 345-378.
Müller, D. et al. (2007). "Recombinant Bispecific Antibodies for Cellular Cancer Immunotherapy," Current Opinion in Molecular Therapeutics 9:319-326.
Müller, K.M. et al. (1998). "A Dimeric Bispecific Miniantibody Combines Two Specificities with Avidity," FEBS Lett. 432:45-49.
Müller, K.M. et al. (1998). "The First Constant Domain (CH1 and CL) of an Antibody Used as Heterodimerization Domain for Bispecific Miniantibodies," FEBS Letters 422:259-264.
Nagy, A. et al. (Jan. 18, 2000). "Stability of Cytotoxic Luteinizing Hormone-Releasing Hormone Conjugate (AN-152) Containing Doxorubicin 14-O-Hemiglutarate in Mouse and Human Serum in Vitro: Implications for the Design of Preclinical Studies," Proc. Nat'l. Acad. Sci. 97(2):829-834.
Natsume, A. et al. (Sep. 1, 2006). "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," Journal of Biochemistry 140(3):359-368.
Nelson, P.S., et al., "Oligonucleotide Labeling Methods. 3. Direct Labeling of Oligonucleotides Employing a Novel, Non-Nucleosidic, 2-aminobutyl-1,3-Propanediol Backbone," Nucleic Acids Research 20:6253-6259, (1992).
Neri, D. et al. (1995). "High-Affinity Antigen Binding by Chelating Recombinant Antibodies (CRAbs)," J. Mol. Biol. 246:367-373.
Netzel-Arnett, S. et al. (Jun. 29, 1993). "Comparative Sequence Specificities of Human 72- and 92-kDa Gelatinases (type IV collagenases) and PUMP (matrilysin)," Biochemistry 32(25):6427-6432.
Netzel-Arnett, S. et al. (Apr. 15, 1991). "Sequence Specificities of Human Fibroblast and Neutrophil Collagenases," J. Biol. Chem. 266(11):6747-6755.
Neuberger, M.S. et al. (Mar. 21, 1985). "A Hapten-Specific Chimaeric IgE Antibody With Human Physiological Effector Function," Nature 314:268-270.
Nicolaou, K.C. et al. (1994). "Calicheamicin θ : A Rationally Designed Molecule with Extremely Potent and Selective DNA Cleaving Properties and Apoptosis Inducing Activity," Angew. Chem. Intl. Ed. Engl. 33(2):183-186.
Niculesu-Duvaz, I. et al. (1997). "Antibody-Directed Enzyme Prodrug Therapy (ADEPT): A Review," Adv. Drug Del. Rev. 26:151-172.
Nielsen, U.B. et al. (2002). "Therapeutic Efficacy of Anti-ErbB2 Immunoliposomes Targeted by a Phage Antibody Selected for Cellular Endocytosis," Biochim. Biophys. Acta 1591:109-118.
Nieri, P. et al. (Feb. 1, 2009). "Antibodies for Therapeutic Uses and the Evolution of Biotechniques," Current Med. Chem. 16(6):753-779.
Nilsson, B. et al. (1987). "A Synthetic IgG-Binding Domain Based on Staphylococcal Protein A," Prot. Eng. 1:107-133.
Niwa, R. et al. (2005). "IgG Subclass-Independent Improvement of Antibody-Dependent Cellular Cytotoxicity by Fucose Removal From Asn297-Linked Oligosaccharides," J. Immunol. Methods 306:151-160.
Nord, K. et al. (1995). "A Combinatorial Library of an α-Helical Bacterial Receptor Domain," Prot. Eng. 8:601-608.
Nord. K. et al. (1997). "Binding Proteins Selected From Combinatorial Libraries of an α-Helical Bacterial Receptor Domain," Nat. Biotech. 15:772-777.
Norderhaug, L. et al. "Versatile Vectors For Transient and Stable Expression Of Recombinant Antibody Molecules In Mammalian Cells," J. Immunol. Methods 204(1):77-87 (May 12, 1997).
Noren, C.J. et al. (Apr. 14, 1989). "A General Method for Site-Specific Incorporation of Unnatural Amino Acids into Proteins," Science 244:182-188.
Novellino, L. et al. "A Listing of Human Tumor Antigens Recognized by T Cells: Mar. 2004 Update," Cancer Immunol. Immunother. 54:187-207.
Novotný, J. et al. (1985). "Structural Invariants of Antigen Binding: Comparison of Immunoglobulin VL-VH and VL-VL Domain Dimmers," Proc. Natl. Acad. Sci. USA, 82:4592-4596.

(56) References Cited

OTHER PUBLICATIONS

Obrist, R. et al. (1983). "Monocyte Chemotaxis Mediated By Formyl-Methionyl-Leucyl-Phenylalanine Conjugated With Monoclonal Antibodies Against Human Ovarian Carcinoma," Int. J. Immunopharmacol. 5(4):307-314.

Obrist, R. et al. (1988). "Chemotactic Monoclonal Antibody Conjugates: A Comparison Of Four Different f-Met-Peptide-Conjugates," Biochem. Biophys. Res. Commun. 155(3):1139-1144.

Obrist, R. et al. (1991). "Acute and Subacute Toxicity Of Chemotactic Conjugates Between Monoclonal Antibody and fMet-Leu_Phe In Humans: A Phase I Clinical Trial," Cancer Immunol. Immunother. 32:406-408.

Offner, H. et al. (Jan. 1991). "T cell receptor peptide therapy triggers autoregulation of experimental encephalomyelitis," Science, 251(4992):430-432.

Ohno, S. et al. "Antigen-Binding Specificities Of Antibodies Are Primarily Determined By Seven Residues Of VH," Proc. Natl. Acad. Sci. USA 82:2945-2949, (May 1985).

Oliner, J. et al. (2004). Suppression of Angiogenesis and Tumor Growth by Selective Inhibition of Angiopoietin-2, Cancer Cell 6:507-516.

Orcutt, K.D. et al. (Apr. 2010, e-pub. Dec. 17, 2009). "A Modular IgG-scFv Bispecific Antibody Topology," Protein Engineering, Design & Selection 23(4):221-228.

Orlandi et al. "Cloning Immunoglobulin Variable Domains for Expression by the Polymerase Chain Reaction," Proc. Natl. Acad. Sci. USA 86:3833-3837, (May 1989).

Otrock, Z.K. et al. "Vascular Endothelial Growth Factor Family of Ligands and Receptors: Review," Blood Cells, Molecules, and Diseases38:258-268.

O'Shea, E.K. et al. (1993). "Peptide 'Velcro': Design of a Heterodimeric Coiled Coil," Current Biology 3(10):658-667.

Pace, C.N. et al. (1995). "How to Measure and Predict the Molar Absorption Coefficient of a Protein," Protein Science 4:2411-2423.

Pack, P. et al. (Feb. 18, 1992). "Miniantibodies: Use of Amphipathic Helices to Produce Functional, Flexibly Linked Dimeric FV Fragments with High Avidity in *Escherichia coli*," Biochem. 31(6):1579-1584.

Pack, P. et al. (Feb. 10, 1995). "Tetravalent Miniantibodies with High Avidity Assembling in *Escherichia coli*," J. Mol. Biol.246(1):28-34.

Pakula, A.A. et al. (1989). "Genetic Analysis of Protein Stability and Function," Annu. Rev. Genet. 23:289-310.

Pan, Q. et al. (Jan. 2007). "Blocking Neuropilin-1 Function Has an Additive Effect with nti-VEGF to Inhibit Tumor Growth," Cancer Cell 11:53-67.

Park, J.W. et al. (2001). "Tumor Targeting Using Anti-Her2 Immunoliposomes," Journal Of Controlled Release 74:95-113.

Parmiani, G. et al. (2007).. "Unique Human Tumor Antigens: Immunobiology and Use in Clinical Trials," J. Immunol. 178:1975-1979.

Pettit, G.R. (1997). "The Dolastatins," Progress in the Chemistry of Organic Natural Products, Springer-Verlag, New York, 70:1-79.

Pettit, G.R. et al. (1998). "Antineoplastic Agents 360. Synthesis and Cancer Cell Growth Inhibitory Studies of Dolastatin 15 Structural Modifications," Anti-Cancer Drug Design 13:47-66.

Pettit, G.R. et al. (Jul.-Aug. 1981). "Marine Animal Biosynthetic Constituents for Cancer Chemotherapy," J. Nat. Prod. 44:482-485.

Pettit, R.K. et al. (Nov. 1998). "Specific Activities of Dolastatin 10 and Peptide Derivatives Against Cryptococcus neoformans," Antimicrobial Agents and Chemotherapy 42(11):2961-2965.

Pirollo, K.F. et al. (Jan. 2006). "Tumor-Targeting Nanoimmunoliposomes Complex For Shrot Interfering RNA Delivery," Human Gene Therapy 17:117-124.

Pleass, R.J. et al. "Identification of Residues in the CH2/CH3 Domain Interface of IgA Essential for Interaction With the Human fcα Receptor (Fcα R) CD89," The Journal of Biology Chemistry 274(33):23508-23514.

Plückthun, A. (1994). "Antibodies from *Escherichia coli*," in Chapter 11 The Pharmacology of Monoclonal Antibodies, vol. 113, Rosenburg and Moore eds., SpringerVerlag, New York, pp. 269-315.

Plückthun, A. et al. (Jun. 1997). "New Protein Engineering Approaches to Multivalent and Bispecific Antibody Fragments," Immunotechnology 3:83-105.

Pon, R.T. (1991). "A Long Chain Biotin Phosphoramidite Reagent for the Automated Synthesis of 5'-Biotinylated Oligonucleotides," Tetrahedron Letters 32:1715-1718.

Poncet, J. (1999). "The Dolastatins, A Family of Promising Antineoplastic Agents," Curr. Pharm. Des. 5:139-162.

Popp, M.W.-L. et al. (2011). "Making and Breaking Peptide Bonds: Protein Engineering Using Sortase," Angewandte Chemie, 50(22):5024-5032.

Portolano, S. et al. (Feb. 1, 1993). "Lack of Promiscuity in Autoantigen-Specific H and L Chain Combinations as Revealed by Human H And L Chain 'Roulette'," The Journal of Immunology 150(3):880-887.

Poul, M.-A. et al. "Selection Of Tumor-Specific Internalizing Human Antibodies From Phage Libraries," J. Mol. Biol. 301:1149-1161.

PreScission Protease, GE Healthcare Catalogue No. 27-0843-01, located at http://www.gelifesciences.com/webapp/wcs/stores/servlet/productByld/en/GELifeScience, last visited on Jul. 10, 2013, one page.

Presta, L.G. (1992). "Antibody Engineering," Current Opinion in Structural Biology 2:593-596.

Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.

Presta, L.G. et al. (Sep. 1, 1993). "Humanization of an Antibody Directed Against IgE," J. Immunol. 151(5):2623-2632.

Proba, K. et al. (1995). "Functional Antibody Single-chain Fragments From The Cytoplasm of *Escherichia coli* Influence of Thioredoxin Reductase (trxb)," Gene 159(2):203-207.

Proft, T. (2010). "Sortase-Mediated Protein Ligation: An Emerging Biotechnology Tool for Protein Modification and Immobilisation," Biotechnol Lett.32: 1-10.

Prokhorenko, I.A. et al. (1995). "Incorpration Of A Pyrene Nucleoside Analogue Into Synthetic Oligodeoxynucleotides Using A Nucleoside-Like Synthon," Bioorganic & Medicinal Chemistry Letters 5:2081-2084.

Putnam, W.C. et al. (2005). "Synthesis and Evaluation of RNA Transesterification Efficiency Using Stereospecific Serinol-Terpyridine Conjugates," Nucleosides, Nucleotides & Nucleic Acids 24:1309-1323.

Raag, R. et al. (Jan. 1995). "Single-chain Fvs," The FASEB Journal 9:73-80.

Radaev, S. et al. (May 11, 2001). "Recognition of IgG by Fcγ Receptor," The Journal of Biological Chemistry 276(19):16478-16483.

Rajagopal, V. et al. (1997). "A Form of Anti-Tac(Fv) Which is Both Single-chain and Disulfide Stabilized Comparison with its single-chain and Disulfide-stabilized Homologs," Protein Engineering 10(12):1453-1459.

Raju, T.S. (Apr. 2003). "Glycosylation Variations with Expression Systems and Their Impact on Biological Activity of Therapeutic Immunoglobulins," BioProcess International 1(4): 44-53.

Ramm, K. et al. (2000). "The Periplasmic *Escherichia coli* Peptidylprolyl cis,Trans-Isomerase FkpA," The Journal of Biological Chemistry 275(22):17106-17113.

Ramzaeva, N. et al. (2000). "Oligonucleotides Fuctionalized by Fluorescein and Rhodamine Dyes: Michael Addition of Methyl Acrylate to 2'-Deoxypseudouridine," Helv. Chim. Acta 83:1108-1126.

Ravetch, J.V. et al. (1991). "Fc Receptors," Annu. Rev. Immunol. 9:457-492.

Rawlings, N.D. (2009, e-pub. Nov. 2, 2009). "A Large and Accurate Collection of Peptidase Cleavages in the MEROPS Database," Database (Oxford), pp. 1-14.

(56) References Cited

OTHER PUBLICATIONS

Reiter, Y. et al. (1994). "Cytotoxic and antitumor activity of a recombinant immunotoxin composed of disulfide-stabilized anti-Tac Fv fragment and truncated Pseudomonas exotoxin," International Journal of Cancer 58:142-149.
Reiter, Y. et al. (Feb. 1, 1996). "Antibody Engineering of Recombinant Fv Immunotoxins for Improved Targeting of Cancer: Disulfide-Stabilized Fv Immunotoxins," Clin. Cancer Res. 2(2):245-252.
Reiter, Y. et al. (1994). "Antitumor activity and pharmacokinetics in mice of a recombinant immunotoxin containing a disulfide-stabilized Fv fragment," Cancer Research 54:2714-2718.
Reiter, Y. et al. (1994). "Improved binding and antitumor activity of a recombinant anti-erbB2 immunotoxin by disulfide stabilization of the Fv fragment," JBC 269:18327-18331.
Reiter, Y. et al. (1994). "Stabilization of the Fv Fragments in Recombinant Immunotoxins by Disulfide Bonds Engineered Into Conserved Framework Regions," Biochemistry 33:5451-5449.
Reiter, Y. et al. (1995). "Construction of a functional disulfide-stabilized TCR Fv indicates that antibody and TCR Fv frameworks are very similar in structure," Immunity 2:281-287.
Reiter, Y. et al. (Dec. 1995). "Disulfide Stabilization Of Antibody Fv: Computer Predictions and Experimental Evaluation," Protein Eng. 8(12):1323-1331.
Reiter, Y. et al. (May 1994). "Engineering Interchain Disulfide Bonds Into Conserved Framework Regions of Fv Fragments: Improved Biochemical Characteristics of Recombinant Immunotoxins Containing Disulfide-Stabilized Fv," Protein Eng. 7(5):697-704.
Reiter, Y. et al. (Oct. 1996). "Engineering Antibody Fv Fragments for Cancer Detection and Therapy: Disulfide-Stabilized Fv Fragments," Nature Biotechnology 14:1239-1245.
Remacle, A.G. et al. (Jul. 25, 2008). "Substrate Cleavage Analysis of Furin and Related Proprotein Convertases," Journal of Biological Chemistry 283(30):20897-20906.
Ren, H. et al. (2009). "A Biocompatible Condensation Reaction for the Labeling of Terminal Cysteine Residues on Proteins," Angew. Chem. Int. Ed. 48:9658-9662.
Ren, Y. et al. (2005). "Macrophage Migration Inhibitory Factor Stimulates Angiogenic Factor Expression and Correlates With Differentiation and Lymph Node Status in Patients With Esophageal Squamous Cell Carcinoma," Ann. Surg. 242:55-63.
Rheinnecker, M. et al. (1996). "Multivalent Antibody Fragments with High Functional Affinity for a Tumor-Associated Carbohydrate Antigen," The Journal of Immunology 157:2989-2997.
Ridgway, J.B.B. et al. (1996). "'Knobs-Into-Holes' Engineering of Antibody CH3 Domains for Heavy Chain Heterodimerization," Protein Engineering 9(7):617-621.
Riechmann, L. et al. (Mar. 24, 1988). "Reshaping Human Antibodies for Therapy," Nature 332:323-327.
Robinson-Mosher, A. et al. (Nov. 2014). "Designing Cell-Targeted Therapeutic Proteins Reveals The Interplay Between Domain Connectivity and Cell Binding," Biophysical Journal 107:2456-2466.
Rodrigues, M.L. et al. (Apr. 1995). "Synthesis and 3-Lactamase-Mediated Activation Of A Cephalosporine-Taxol Prodrug," Chem. Biol. 2:223-227.
Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," Nucleic Acids Research 17:7643-7651.
Roitt A. et al. (2000). "Multispecific Antibodies Comprising Full Length Antibodies and Single Chain Fab Fragments," Immunology, English Translation, Moscow:Mir, pp. 388-389.
Roitt, A. et al. (2000), "Immunology" English Translation by McElroy Translation Company, Moscow "Mir" p. 110-111, eight pages.
Rossi, E.A. et al. (2006). "Multivalent Anti-CD20/Anti-CD22 Bispecific Antibody Fusion Proteins Made by the DNL Method Show Potent Lymphoma Cytotoxicity," Blood, American Society of Hematology 8:11, Abstract No. 2495, pp. 707A.
Routier, F.H. et al. (1997). "The Glycosylation Pattern of a Humanized IgGI Antibody (D1.3) Expressed in CHO Cells," Glycoconjugate Journal 14:201-207.
Roux, K.H. et al. (1998). "Comparisons of the Ability of Human IgG3 Hinge Mutants, IgM, IgE, and IgA2, to Form Small Immune Complexes: A Role for Flexibility and Geometry," J. Immunol. 161:4083-4090.
Rowland, G.F. et al. (1986). "Drug Localisation And Growth Inhibition Studies of Vindesine-Monoclonal Anti-CEA Conjugates in a Human Tumour Xenograft," Cancer Immunol. Immunother. 21:183-187.
Ruppert, C. et al. (1997). "Protease Levels in Breast, Ovary and Other Gynecological Tumor Tissues: Prognostic Importance in Breast Cancer," Cancer Detect. Prev. 21(5):452-459.
Ruppert, S. et al. (Mar. 11, 1993). "Cloning and Expression of Human TAFII250: a TBP-Associated Factor Implicated in Cell-Cycle Regulation," Nature 362:175-179.
Sakamoto, T. et al. (2010, e-pub. Nov. 11, 2010). "Enzyme-Mediated Site-Specific Antibody-Protein Modification Using a ZZ Domain as a Linker," BioConjugate Chem. 21:2227-2233.
Salfeld, J.G. (Dec. 2007). "Isotype Selection in Antibody Engineering," Nat. Biotechnol. 25(12):1369-1372.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 29 pages, (Table of Contents only).
Santos, A.D. et al. (Oct. 1999) "Generation and Characterization of a Single Gene-Encoded Single-Chain-tetravalent Antitumor Antibody" Clinical Cancer Research 5(10 Suppl):3118s-3123s.
Schaefer, W. et al. (Jul. 5, 2011, e-pub. Jun. 20, 2011). "Immunoglobulin Domain Crossover as a Generic Approach for the Production of Bispecific IgG Antibodies," Proc. Natl. Acad. Sci. U.S.A. 108(27):11187-11192.
Schirrmann, T. et al. (Jan./Feb. 2010). "Oligomeric Forms of Single Chain Immunoglobulin (scigG)," Landes Bioscience 2(1):73-76.
Schmidt, M. et al. (1999). "Suppression of Metastasis Formation by a Recombinant Single Chain Antibody-Toxin Targeted to Full-length and Oncogenic Variant EGF Receptors," Oncogene 18:1711-1721.
Schmiedl, A. et al. "Effects of Unpaired Cysteines on Yield, Solubility and Activity of Different Recombinant Antibody Constructs Expressed in E. coli," Journal of Immunological Methods 242:101-114.
Schmiedl, A. et al. (Oct. 2000). "Expression of a Bispecific dsFv-dsFv' Antibody Fragment in Escherichia coli," Protein Engineering 13(10):725-734.
Schoonjans, R. et al. (2000). "Fab Chains As An Efficient Heterodimerization Scaffold For The Production of Recombinant Bispecific and Trispecific Antibody Derivatives," Journal of Immunology 165:7050-7057.
Schoonjans, R. et al. (2000). "Efficient Heterodimerization of Recombinant Bi- and Trispecific Antibodies" Bioseparation 9(3):179-183.
Schouten, A. et al. (1996). "The C-Terminal KDEL Sequence Increases the Expression Level of a Single-Chain Antibody Designed to be Targeted to Both the Cytosol and the Secretory Pathway in Transgenic Tobacco," Plant Molecular Biology 30:781-793.
Schröder, E. et al. (1965). "Formation of Peptide Bond," in The Peptides: Methods of Peptide Synthesis,Academic Press Inc., 111 Fifth Avenue, New York, New York 10003, 1:76-136.
Schwartz, G.P. et al. (Sep. 1987). "A Superactive Insulin: (B10-aspartic acid]insulin(human)," Proc. Natl. Acad. Sci. USA 84:6408-6411.
Scott, C.J. et al. (Nov. 2010). "Biologic Protease Inhibitors as Novel Therapeutic Agents," Biochimie 92(11):1681-1688.
Seela, F. (1987). "Oligodeoxyribonucleotides Containing 1,3-Propanediol as Nucleoside Substitute," Nucleic Acids Research 15:3113-3129.
Sensi, M. et al. (2006). "Unique Tumor Antigens: Evidence for Immune Control of Genome Integrity and Immunogenic Targets forT Cell-Mediated Patient-Specific Immunotherapy," Clin. Cancer Res. 12:5023-5032.

(56) References Cited

OTHER PUBLICATIONS

Senter, P.D. (2009), "Potent antibody drug conjugates for cancer therapy," Current Opinion in Chemical Biology 13:235-244.
Seo, J. et al. (Jan. 2004)."Post-Translational Modifications and Their Biological Functions: Proteomic Analysis and Systematic Approaches," Biochemistry and Molecular Biology 37(1):35-44.
Shabat, D. et al. (Jun. 2001). "In Vivo Activity In A Catalytic Antibody-Prodrug System: Antibody Catalyzed Etoposide Prodrug Activation For Selective Chemotherapy," Proc. Natl. Acad. Sci. USA 98(13):7258-753.
Shabat, D/ et al. (Jun. 1999). "Multiple Event Activation Of A Generic Prodrug Trigger by Antibody Catalysis," Proc. Natl. Acad. Sci. USA 96:6925-6930.
Shechter, Y. et al. (1976). "Selective Chemical Cleavage of Tryptophanyl Peptide Bonds by Oxidative Chlorination With N-Chlorosuccinimide," Biochemistry 15(23):5071-5075.
Shen, J. et al. (Apr. 21, 2006, e-pub. Feb. 15, 2006). "Single Variable Domain-IgG Fusion: A Novel Recombinant Approach to Fc Domain-Containing Bispecific Antibodies," J. of Biological Chemistry 281(16):10706-10714.
Shen, J. et al. (2007, e-pub. Oct. 26, 2006). "Single Variable Domain Antibody as a Versatile Building Block for the Construction of IgG-like Bispecific Antibodies," Journal of Immunological Methods 318:65-74.
Sheriff, S. et al. (1996). "Redefining the Minimal Antigen-Binding Fragment," Nature Struct. Biol. 3(9):733-736.
Shi, Z.-D. et al. (2002).. "A Stereospecific Synthesis of L-Deoxyribose, L-Ribose and L-Ribosides," Tetrahed. 58:3287-3296.
Shields, R.L. et al. (Jul. 26, 2002, e-pub. May 1, 2002). "Lack of Fucose on Human IgGI N-Linked Oligosaccharide Improves Binding to Human FcγRIII and Antibody-dependent Cellular Toxicity," J. Biol. Chem. 277:26733-26740.
Shields, R.L. et al. (Mar. 2, 2001). "High Resolution Mapping of the Binding Site on Human IgGI for FcγRI, FcγII. FcγIII, and FcRn and Design of IgGI Variants With Improved Binding to the FcγR," J. Biol.Chem. 276(9):6591-6604.
Shinkawa, Toyohide et al., "The Absence Of Fucose But Not The Presence Of Galactose Or Bisecting N-Acetylglucosamine Of Human IgG1 Complex-Type Oligosaccharides Shows The Critical Role Of Enhancing Antibody-Dependent Cellular Cytotoxicity," Journal of Biological Chemistry, (Jan. 31, 2003); 278(5):3466-3473.
Siebenlist, U. et al. (Jun. 1980). "E. coli RNA Polymerase Interacts Homologously With Two Different Promoters," Cell 20(2):269-281.
Silva, J.A. et al. (1998). "Synthesis of a New Phosphoramidite Nucleoside Biotinylated For the Preparation Ligonucleotide Multibiotinilados," Biotecnologia Aplicada 15:154-158.(English Abstract Only.).
Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2): 133-147.
Simon, T. et al. (1990) "Antibody Domain Mutants Demonstrate Autonomy of the Antigen Binding Site," The EMBO Journal 9(4):1051-1056.
Sims, M.J. et al. (Aug. 15, 1993). "A Humanized CD18 Antibody Can Block Function Without Cell Destruction," J. Immunol. 151:2296-2308.
Singer, M. et al. (1998). "Genes and Genomes," Moscoer, MIR 1:63-64.
Smith-Gill, S.J. et al. (Dec. 15, 1987). "Contributions of Immunoglobulin Heavy and Light Chain to Antibody Specificity for Lysozyme and Two Haptens," J. Immunol. 139(12):4135-4144.
Sondermann, P. et al. "The 3.2-A Crystal Structure of the Human IgGI Fc Fragment-FcγRIII Complex," Nature, 406:267-273.
Song, M.-K. et al. (2000). "Light Chain of Natural Anibody Plays a Dominant Role in Protein Antigen Binding," Biochem. Biophys. Res. Comm. 268(2):390-394.
Steiner, D.F.. (1991). "The Biosynthesis of Biologically Active Peptides: A Perspective," Chapter 1 in Peptide Biosynthesis and Processing, Fricker ed., CRC Press, Boca Raton, FL, pp. 1-15.

Stella, V.J. et al. (1985). "Prodrugs: A Chemical Approach to Targeted Drug Delivery," in Directed Drug Delivery, pp. 247-267.
Stetler-Stevenson, W.G. et al. (1994-1995). "Progelatinase A Activation During Tumor Cell Invasion," Invasion Metastasis 14(1-6):259-268.
Stevenson, G.T. et al. (Mar. 1989). "A Chimeric Antibody With Dual Fc Regions (bisFabFc) Prepared by Manipulations at the IgG Hinge," Anti-cancer Drug Des.3(4):219-230.
Stites, D.P. et al. (1994). "Immunoglobulin Protiens," Chapter 6 in Basic Clinical Immunology, 8th Edition, Appleton & Lange, Norwalk, CT, pp. 71-79.
Stork, R. et al. (Nov. 2007, e-pub. Nov. 3, 2007). "A Novel Tri-Functional Antibody Fusion Protein with Improved Pharmacokinetic Properties Generated by Fusing a Bispecific Single-Chain Diabody With an Albumin-Binding Domain From Streptococcal Protein G," Protein Eng. Des. Sel. 20(11):569-576.
Strijbis, K. et al. (Jun. 2012, e-published on Mar. 23, 2012). "Protein Ligation in Living Cells Using Sortase" Traffic 13(6):780-789.
Strop, P. et al. (2012). "Generating Bispecific Human IgGI and IgG2 Antibodies from Any Antibody Pair," Journal of Molecular Biology 420(3):204-219.
Su, S.-H. et al. (1997). "Novel Non-Nucleosidic Phosphoramidites for Oligonucleotide Modification and Labeling," Bioorganic & Medicinal Chemistry Letters 7:1639-1644.
Sunbul, M. et al. "Site Specific Protein Labeling by Enzymatic Posttranslational Modification," Org. Biomol. Chem. 7:3361-3371.
Swee. L.K. et al. (2013). "Sortase-Mediated Modification of αDEC205 Affords Optimization of Antigen Presentation and Immunization Against a Set of Viral Epitopes," PNAS 110(4):1428-1433.
Syrigos, K. et al. (1999). "Antibody Directed Enzyme Prodrug Therapy (ADEPT): A Review of the Experimental and Clinical Considerations," Anticancer Research 19:605-614.
Ta, H.T. et al. (Aug. 5, 2011). "Enzymatic Single-Chain Antibody Tagging A Universal Approach to Targeted Molecular Imaging and Cell Homing in Cardiovascular Disease," Circulation Research 109(4):365-373.
Taki, M., et al. (2004). "Transglutaminase-Mediated N- and C-Terminal Fluorescein Labeling of a Protein Can Support the Native Activity of the Modified Protein," Prot. Eng. Des. Sel. 17:119-126.
Tao, M.-H. et al. (Apr. 1991). "The Differential Ability of Human IgG1 and IgG4 to Activate Complement is Determined by the COOH-terminal Sequence of the CH2 Domain," J. Exp. Med 173:1025-1028.
Taylor, E.V. et al. (2009). "Native Chemical Ligation: SemiSynthesis Of Post-Translationally Modified Proteins and Biological Probes," Nucl. Acids Mol. Biol. 22:65-96.
Theisen, P. et al. (1992). "Fluorescent Dye Phosphoramidite Labelling of Oligonucleotides," Nucleic Acids Symposium Series 27(Nineteenth Symposium on Nucleic Acids Chemistry pp. 99-100.
Thie, H. et al. (Jul. 22, 2009). "Multimerization Domains for Antibody Phage Display and Antibody Production," New Biotech. 26(6):314-321.
Thies, M.J.W. et al. (1999). "Folding and Association of the Antibody Domain CH3: Prolyl Isomerization Proceeds Dimerization," J. Mol. Biol., 293:67-79.
Thommesen, J.E. et al. "Lysine 322 In The Human IgG3 C(H)2 Domain Is Crucial For Antibody Dependent Complement Activation," Mol. Immunol. 37(16):995-1004 (Nov. 2000).
Thorpe, (1985). "Antibody Carriers Of Cytotoxic Agents In Cancer Therapy: A Review," in Monoclonal Antibodies '84: Biological And Clinical Applications, Pincheraet al. (eds.), pp. 475-506.
Ton-That, H. et al. (1999). "Purification and Characterization of Sortase, the Transpeptidase That Cleaves Surface Proteins of *Staphylococcus aureus* at the LPXTG Motif," Proc. Natl. Acad. Sci. U.S.A., 96(22):12424-12429.
Torgov, M.Y. et al. (2005; e-published on Apr. 27, 2005). "Generation of an Intensely Potent Anthracycline by a Monoclonal Antibody-β-Galactosidase Conjugate," Bioconjugate Chem. 16:717-721.
Torres, M. et al. (2005). "Variable-Region-Identical Antibodies Differing in Isotype Demonstrate Differences in Fine Specificity and Idiotype", The Journal of Immunology, 174:2132.

(56) References Cited

OTHER PUBLICATIONS

Tripathi, M. et al. (2008). "Laminin-332 is a Substrate for Hepsin, a Protease Associated with Prostate Cancer Progression," JBC 283:30576-30584.
Tso, J.Y. et al. (1995). "Preparation of a Bispecific F(ab')2 Targeted to the Human II-2 Receptor," J. Hematotherapy 4:389-394.
Tsukiji, S. et al. (2009). "Sortase-Mediated Ligation: A Gift from Gram-Positive Bacteria to Protein Engineering", Chembiochem, 10(5):787-798.
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
Urata, H. et al. (1992). "Synthesis and Properties of Mirror-Image DNA," Nucl. Acids Res. 20:3325-3332.
Urlaub, G. et al. (Jul. 1980). "Isolation of Chinese hamster cell mutants deficient in dihydrofolate reductase activity," Proc. Natl. Acad. Sci. USA 77(7):4216-4220.
Vallbohmer, D. et al. (2005). "Molecular Determinants of Cetuximab Efficacy," J. Clin. Oncol. 23:3536-3544.
Van Dijk, M.A. et al. (2001). "Human Antibodies as Next Generation Therapeutics," Curr. Opin. Pharmacol 5:368-374.
Van Spriel, A.B. et al. (Aug. 2000). "Immunotherapeutic Perspective for Bispecific Antibodies," Immunology Today 21(8):391-397.
Van't Veer, L.J. et al. (Jan. 2002). "Gene Expression Profiling Predicts Clinical Outcome of Breast Cancer," Nature 415(6871):530-536.
Vazquez-Ortiz, G. et al. (Jun. 30, 2005). "Overexpression of Cathepsin F, Matrix Metalloproteinases 11 and 12 in Cervical Cancer," BMC Cancer 5:68.
Velasco, G. et al. (Oct. 28, 1994). "Human Cathepsin O. Molecular Cloning From a Breast Carcinoma, Production of the Active Enzyme in *Escherichia coli*, and Expression Analysis in Human Tissues," J. Biol Chem 269(43):27136-27142.
Verhoeyen, M. et al. (Mar. 25, 1988). "Reshaping Human Antibodies: Grafting an Antilysozyme Activity," Science 239:1534-1536.
Veveris-Lowe, T.L. et al. (2007). "Seminal Fluid Characterization for Male Fertility and Prostate Cancer: Kallikrein-Related Serine Proteases and whole Proteome Approaches," Semin Thromb Hemost. 33(1):87-99.
Vijayalakshmi, M.A. (1998). "Antibody Purification Methods" Applied Biochemistry and Biotechnology 75:93-102.
Vitetta, E.S. et al. (Nov. 20, 1987). "Redesigning Nature's Poisons to Create Anti-tumor Reagents," Science 238:1098-1104.
Vu, H. et al. "Synthesis of Cholesteryl Supports and Phosphoramidites Containing a Novel Peptidyl Linker for Automated Synthesis of Triple-Helix Forming Oligonucleotides," in Nucleic Acids Symposium Series 29 (Second International Symposium on Nucleic Acids Chemistry), pp. 19-20.
Wagner, K. et al. (Nov. 25, 2014). "Bispecific Antibody Generated with Sortase and Click Chemistry has Broad Antiinfluenza Virus Activity," Proc. Natl. Acad. Sci. USA 111(47):16820-16825.
Walker, L.M. et al. (Jun. 5, 2009, e-pub. Apr. 16, 2009). "Efficient Recovery of High-Affinity Antibodies From a Single-Chain Fab Yeast Display Library," J. Mol. Biol. 389(2):365-375.
Walker, P.A. et al. (1994). "Efficient and Rapid Affinity Purification of Proteins Using Recombinant Fusion Proteases," Bio/Technology 12:601-605.
Wang, C.C.-Y. et al. (2003). "Site-Specific Fluorescent Labeling of DNA Using Staudinger Ligation," Bioconjugate Chemistry 14:697-701.
Wang, L. et al. (2002). "Expanding the Genetic Code," Chem. Commun (Camb.), 7:1-11.
Ward et al. (Oct. 1, 1989). "Binding Activities of a Repertoire of Single Immunoglobulin Variable Domains Secreted From *Escherichia coli*," Nature 341:544-546.
Ward, E.S. et al. (1995). "The Effector Functions of Immunoglobulins: Implications for Therapy," Ther. Immunol., 2:77-94.
Warren, R.S. et al. (1995). "Regulation by Vascular Endothelial Growth Factor of Human Colon Cancer Tumorigenesis in a Mouse Model of Experimental Liver Metastasis," J. Clin. Invest. 95:1789-1797.
Webber, K.O. et al. (1995). "Preparation and Characterization of a Disulfide-Stabilized Fv Fragment of the Anti-Tac Antibody: Comparison With its Single-Chain Analog," Molecular Immunology 32:249-258.
Werner, R.G. et al. "Appropriate Mammalian Expression Systems For Biopharmaceuticals," Arzneimittelforschung 48:870-880 (Aug. 1998).
Wielockx, B. et al. (Apr.-Jun. 2004). "Matrilysin (matrix metalloproteinase-7): A New Promising Drug Target in Cancer and Inflammation?," Cytokine Growth Factor Rev. 15(2-3):111-115.
Willems, A. et al. (2003) "Optimizing Expression and Purification from Cell Culture Medium of Trispecific Recombinant Antibody Derivatives," Journal of Chromatography B 786:161-176.
Williams, B.A.R. et al. (2009). "Creating Protein Affinity Reagents by Combining Peptide Ligands on Synthetic DNA Scaffolds," J. Am. Chem. Soc. 131:17233-17241.
Williams, K.P. et al. (Oct. 1997). "Bioactive and Nuclease-Resistant L-DNA Liqand Of Vasopressin," Proc. Natl. Acad. Sci. USA 94:11285-11290.
Wilman, D.E. (1986). "Prodrugs in Cancer Chemotherapy" Biochemical Society Transactions, 615th Meeting Belfast, 14:376-382.
Witte, M.D. et al. (Jul. 24, 2012). "Preparation of Unnatural N-to-N and C-to-C Protein Fusions", Proceedings of the National Academy of Sciences of the United States of America 109(30):11993-11998.
Wojczewski, C. et al. (1999). "Fluorescent Oligonucleotides—Versatile Tools as Probes and Primers for DNA and RNA Analysis," Synlett 10:1667-1678.
Woof, J.M. et al. (2004). "Human Antibody-FC Receptor Interactions Illuminated By Crystal Structures," Nat. Rev. Immunol. 4:1-11.
Woyke, T. et al. (Dec. 2001). "In Vitro Activities and Postantifungal Effects of the Potent Dolastatin 10 Derivative Auristatin PHE," Antimicrob. Agents and Chemother. 45(12):3580-3584.
Wranik, B.J. et al. (Dec. 21, 2012). "LUZ-Y, A Novel Platform for the Mammalian Cell Production of Full-Length IgG-bispecific Antibodies," The Journal of Biological Chemistry 287(52):43331-43339.
Wright, A. et al. (Jan. 1997). "Effect of Glycosylation on Antibody Function: Implications for Genetics Engineering," Trends Biotechnol. 15:26-32.
Wright, C.M. et al. (Aug. 2010). "ADAM28: A Potential Oncogene Involved In Asbestos-Related Lung Adenocarcinomas," Genes Chromosomes Cancer 49(8);688-698.
Wright, M.J. et al. (2007). "Phage Display of Chelating Recombinant Antibody Libraries," Molecular Immunology 44:2860-2869.
Written Opinion (Second) of the International Searching Authority dated Jul. 11, 2014, for PCT Patent Application No. PCT/EP2013/063259, filed on Jun. 25, 2013, seven pages.
Written Opinion dated Aug. 6, 2013, for PCT Application No. PCT/US2013/025365, filed Feb. 8, 2013, nine pages.
Written Opinion of the International Searching Authority dated Aug. 13, 2013, for PCT Patent Application No. PCT/EP2013/063259, filed on Jun. 25, 2013, six pages.
Written Opinion of the International Searching Authority dated Aug. 5, 2014, for PCT Patent Application No. PCT/EP2013/063258, filed on Jun. 25, 2013, seven pages.
Written Opinion of the International Searching Authority dated Aug. 6, 2013, PCT Patent Application No. PCT/EP2013/063260, filed on Jun. 25, 2013, eight pages.
Written Opinion of the International Searching Authority dated Dec. 6, 2011, for PCT Patent Application No. PCT/EP2011/064468 filed on Aug. 23, 2011, four pages.
Written Opinion of the International Searching Authority dated Dec. 6, 2011, for PCT Patent Application No. PCT/EP2011/064476 filed on Aug. 23, 2011, four pages.
Written Opinion of the International Searching Authority dated Jun. 15, 2011 for PCT Patent Application No. PCT/US2010/002546 filed on Sep. 16, 2010, seven pages.

(56) References Cited

OTHER PUBLICATIONS

Written Opinion of the International Searching Authority dated Nov. 4, 2013, for PCT Application No. PCT/EP2013/068910, filed on Sep. 12, 2013, six pages.

Wu, C. et al. (Nov. 2007; e-pub. Oct. 14, 2007). "Simultaneous Targeting of Multiple Disease Mediators by a Dual-Variable-Domain Immunoglobulin," Nat. Biotechnol. 25(11):1290-1297.

Xie, Z. et al. (2005). "A New Format of Bispecific Antibody: Highly Efficient Heterodimerization, Expression and Tumor Cell Lysis," J. of Immunol. Methods 296:95-101.

Xu, J.L. et al. (Jul. 2000). "Diversity in the eCDR3 Region of VH is Sufficient for Most Antibody Specificities," Immunity 13:37-45.

Yamaguchi, Y. et al. (1995). "Proteolytic Fragmentation With High Specificity of Mouse Immunoglobulin G," Journal of Immunological Methods 181:259-267.

Yaniv, M.. (May 6, 1982). "Enhancing Elements for Activation of Eukaryotic Promoters," Nature 297:17-18.

Yazaki, P.J. et al. (2004). "Expression of Recombinant Antibodies in Mammalian Cell Lines," Chapter 15 in Methods in Molecular Biology, LO, B.K.C. (ed.), Humana Press, Totowa, NJ, 248:255-268.

Zapata, G. et al. (1995). "Engineering Linear F(ab')2 Fragments for Efficient Production in *Escherichia coli* and Enhanced Antiproliferative Activity," Protein Eng. 8(10):1057-1062.

Zeidler, R. et al. (1999). "Simultaneous Activation of T Cells and Accessory Cells By a New Class of Intact Bispecific Antibody Results In Efficient Tumor Cell Killing," Journal of Immunology 163:1246-1252.

Zhan, Z.-Y. J. et al. "Alternative Heterocycles for DNA Recognition: a 3-Pyrazole/Pyrrole Pair Specifies for G.C Base Pairs," Bioorg. Med. Chem. 8:2467-2474.

Zhu, Z. et al. (1997). "Remodeling Domain Interfaces to Enhance Heterodimer Formation," Protein Science 6:781-788.

Zuo, Z. et al. (2000). "An Efficient Route to the Production of an IgG-Like Bispecific Antibody," Protein Engineering 13(5):361-367.

| Linker | Analyte | ssFab 1 | ssFab 2 | ka (1/Ms) | kd (1/s) | t1/2 diss (min) | KD (M) | KD (nM) |
|---|---|---|---|---|---|---|---|---|
| T40 | pIGF-1R | 8.1.2 | 1.4.168 | 2,24E+06 | 2,79E-05 | 414 | 1,25E-11 | 0,01 |
| T40 | pIGF-1R | 8.1.2 | - | 1,17E+06 | 2,21E-02 | 0,5 | 1,89E-08 | 19 |
| T40 | pIGF-1R | - | 1.4.168 | 1,96E+06 | 4,19E-03 | 3 | 2,14E-09 | 2 |
| T40 | pINR | 8.1.2 | 1.4.168 | 1,57E+06 | 3,70E-02 | 0,3 | 2,36E-08 | 24 |
| T40 | pINR | 8.1.2 | - | 1,36E+06 | 4,45E-02 | 0,3 | 3,27E-08 | 33 |
| T40 | pINR | - | 1.4.168 | n.i. | n.i. | n.i. | n.i. | n.i. |
| T40 | IGF-1R | 8.1.2 | 1.4.168 | 2,73E+06 | 2,66E-03 | 4,3 | 9,73E-10 | 1 |
| T40 | IGF-1R | 8.1.2 | - | n.i. | n.i. | n.i. | n.i. | n.i. |
| T40 | IGF-1R | - | 1.4.168 | 3,30E+06 | 3,62E-03 | 3 | 1,10E-09 | 1 |
| T0 | pIGF-1R | 8.1.2 | 1.4.168 | 1,75E+06 | 6,01E-05 | 192 | 3,44E-11 | 0,03 |
| T0 | pIGF-1R | 8.1.2 | - | 1,03E+06 | 2,22E-02 | 1 | 2,15E-08 | 22 |
| T0 | pIGF-1R | - | 1.4.168 | 1,12E+06 | 2,91E-03 | 4 | 2,59E-09 | 3 |
| T0 | pINR | 8.1.2 | 1.4.168 | 1,70E+06 | 4,18E-02 | 0,3 | 2,46E-08 | 25 |
| T0 | pINR | 8.1.2 | - | 1,09E+06 | 4,83E-02 | 0,2 | 4,41E-08 | 44 |
| T0 | pINR | - | 1.4.168 | n.d | n.d. | n.d | n.d. | n.d. |
| T0 | IGF-1R | 8.1.2 | 1.4.168 | 1,98E+06 | 2,38E-03 | 5 | 1,20E-09 | 1 |
| T0 | IGF-1R | 8.1.2 | - | n.i. | n.i. | n.i. | n.i. | n.i. |
| T0 | IGF-1R | - | 1.4.168 | 2,41E+06 | 3,26E-03 | 4 | 1,35E-09 | 1 |

FIG. 18

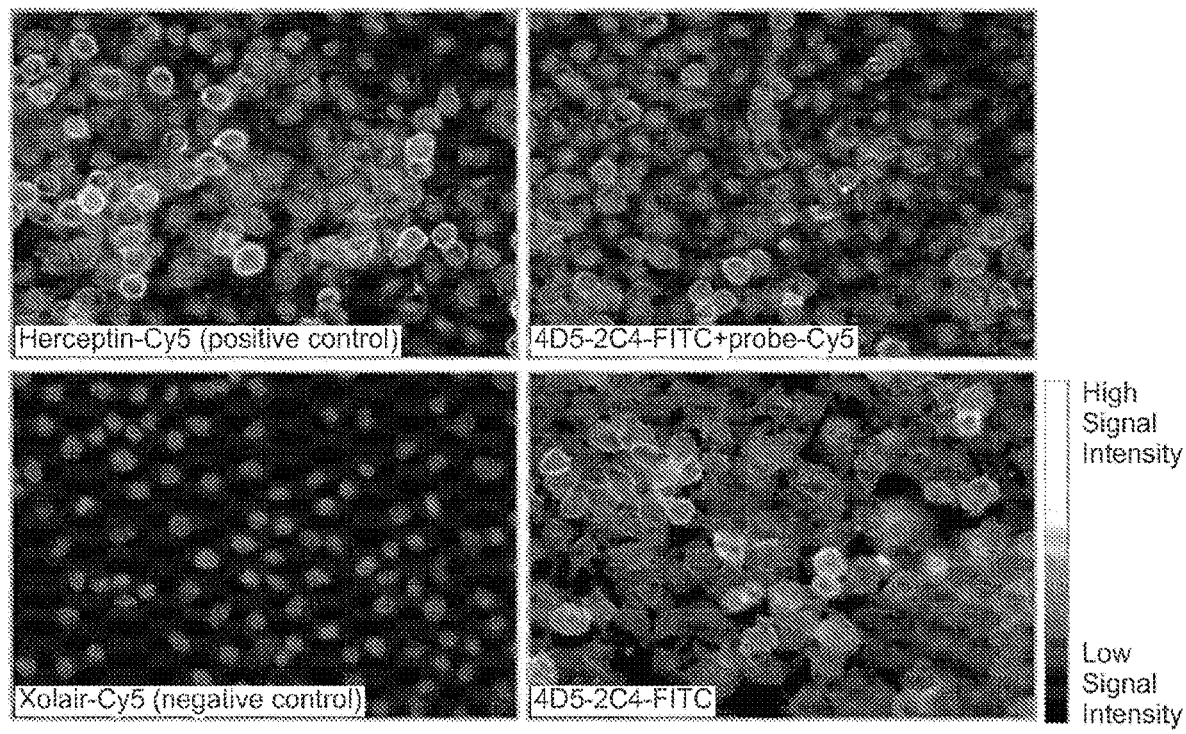
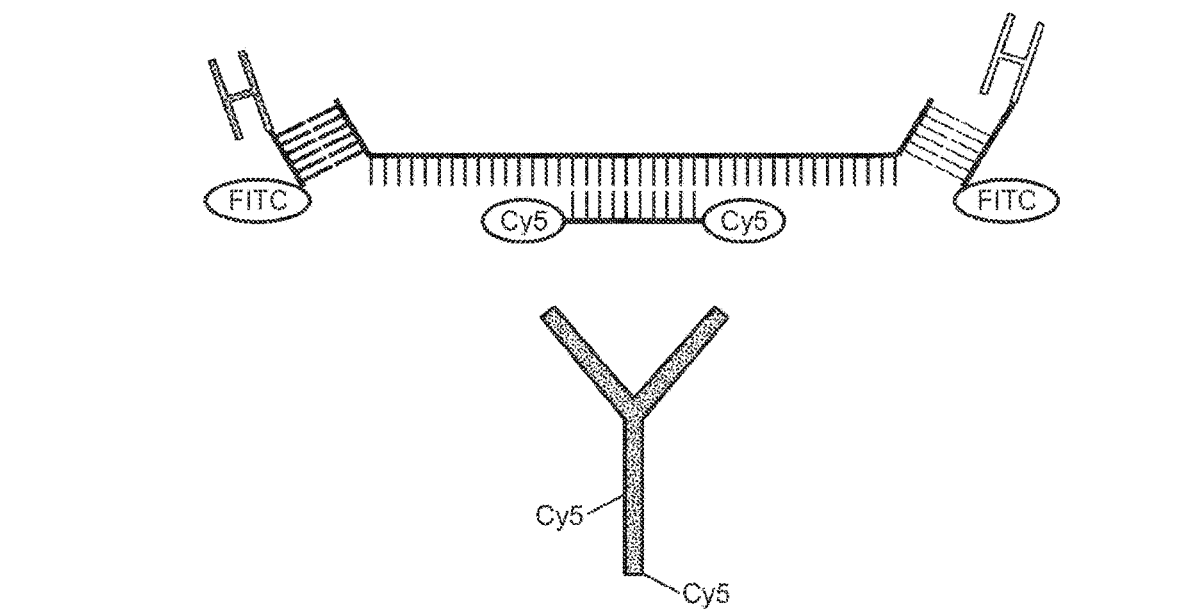
FIG. 22

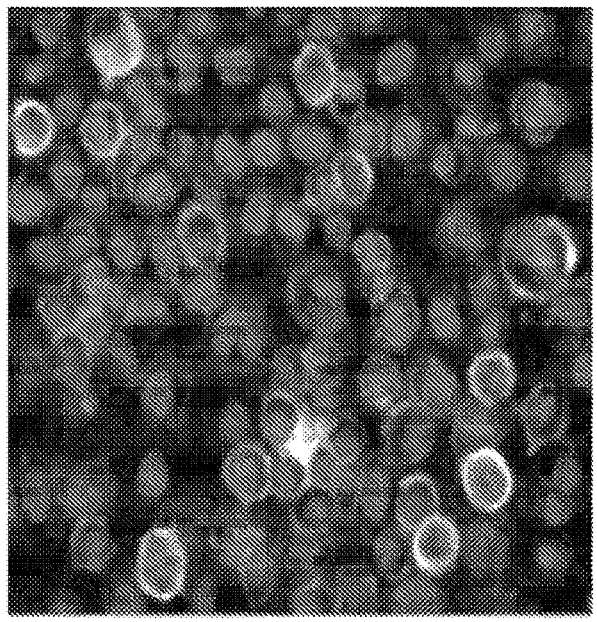 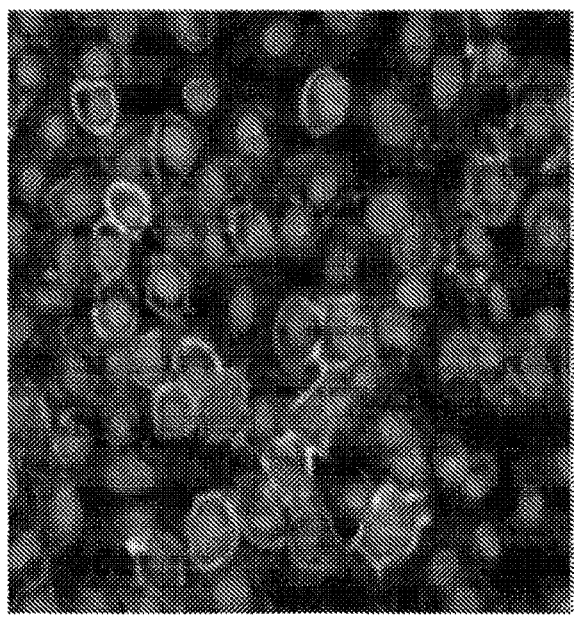
*FIG. 23A*          *FIG. 23B*
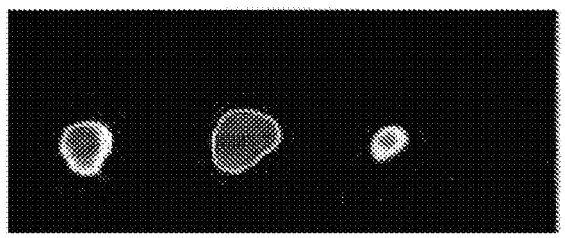 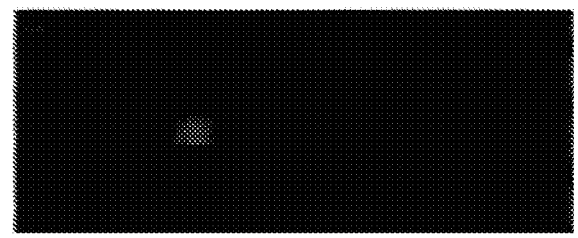
*FIG. 24*

SEQUENCE LISTING

```
<160> NUMBER OF SEQ ID NOS: 77

<210> SEQ ID NO 1
<211> LENGTH: 122
<212> TYPE: PRT
<213> ORGANISM: Artificial Sequence
<220> FEATURE:
<223> OTHER INFORMATION: VH (mAb 1.4.168)

<400> SEQUENCE: 1

Gln Cys Asp Val Lys Leu Val Glu Ser Gly Gly Leu Val Lys Pro
1               5                   10                  15

Gly Gly Ser Leu Lys Leu Ser Cys Ala Ala Ser Gly Phe Thr Phe Ser
            20                  25                  30

Asp Tyr Pro Met Ser Trp Val Arg Gln Thr Pro Glu Lys Arg Leu Glu
        35                  40                  45
```

```
Trp Val Ala Thr Ile Thr Thr Gly Gly Thr Tyr Thr Tyr Pro Asp
 50                  55                  60

Ser Ile Lys Gly Arg Phe Thr Ile Ser Arg Asp Asn Ala Lys Asn Thr
 65                  70                  75                  80

Leu Tyr Leu Gln Met Gly Ser Leu Gln Ser Glu Asp Ala Ala Met Tyr
                 85                  90                  95

Tyr Cys Thr Arg Val Lys Thr Asp Leu Trp Trp Gly Leu Ala Tyr Trp
                100                 105                 110

Gly Gln Gly Thr Leu Val Thr Val Ser Ala
            115                 120

<210> SEQ ID NO 2
<211> LENGTH: 116
<212> TYPE: PRT
<213> ORGANISM: Artificial Sequence
<220> FEATURE:
<223> OTHER INFORMATION: VL (mAb 1.4.168)

<400> SEQUENCE: 2

Gln Leu Val Leu Thr Gln Ser Ser Ser Ala Ser Phe Ser Leu Gly Ala
 1               5                  10                  15

Ser Ala Lys Leu Thr Cys Thr Leu Ser Ser Gln His Ser Thr Tyr Thr
                 20                  25                  30

Ile Glu Trp Tyr Gln Gln Pro Leu Lys Pro Pro Lys Tyr Val Met
             35                  40                  45

Glu Leu Lys Lys Asp Gly Ser His Thr Thr Gly Asp Gly Ile Pro Asp
 50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ser Ile Tyr Ile Cys Gly Val Gly Asp
                 85                  90                  95

Thr Ile Lys Glu Gln Phe Val Tyr Val Phe Gly Gly Thr Lys Val
                100                 105                 110

Thr Val Leu Gly
        115

<210> SEQ ID NO 3
<211> LENGTH: 121
<212> TYPE: PRT
<213> ORGANISM: Artificial Sequence
<220> FEATURE:
<223> OTHER INFORMATION: VH (mAb 8.1.2)

<400> SEQUENCE: 3

Glu Val Gln Leu Gln Gln Ser Gly Pro Ala Leu Val Lys Pro Gly Ala
 1               5                  10                  15

Ser Val Lys Met Ser Cys Lys Ala Ser Gly Phe Thr Phe Thr Ser Tyr
                 20                  25                  30

Val Ile His Trp Val Lys Gln Lys Pro Gly Gln Gly Leu Glu Trp Ile
             35                  40                  45

Gly Tyr Leu Asn Pro Tyr Asn Asp Asn Thr Lys Tyr Asn Glu Lys Phe
 50                  55                  60

Lys Gly Lys Ala Thr Leu Thr Ser Asp Arg Ser Ser Ser Thr Val Tyr
 65                  70                  75                  80

Met Glu Phe Ser Ser Leu Thr Ser Glu Asp Ser Ala Val Tyr Phe Cys
                 85                  90                  95
```

```
Ala Arg Arg Gly Ile Tyr Ala Tyr Asp His Tyr Phe Asp Tyr Trp Gly
            100                 105                 110

Gln Gly Thr Ser Leu Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: VL (mAb 8.1.2)

<400> SEQUENCE: 4

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Val Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Leu Thr
                85                  90                  95

Phe Gly Ala Gly Thr Lys Leu Glu Leu Lys
            100                 105

<210> SEQ ID NO 5
<211> LENGTH: 17
<212> TYPE: DNA
<213> ORGANISM: Artificial Sequence
<220> FEATURE:
<223> OTHER INFORMATION: 17mer ssDNA (covalently bound with 5' end to
      Fab' )

<400> SEQUENCE: 5
agttctatcg tcgtcca                                                    17

<210> SEQ ID NO 6
<211> LENGTH: 19
<212> TYPE: DNA
<213> ORGANISM: Artificial Sequence
<220> FEATURE:
<223> OTHER INFORMATION: 19mer ssDNA (covalently bound with 3' end to
      Fab' )

<400> SEQUENCE: 6
agtctattaa tgcttctgc                                                  19

<210> SEQ ID NO 7
<211> LENGTH: 19
<212> TYPE: DNA
<213> ORGANISM: Artificial Sequence
<220> FEATURE:
<223> OTHER INFORMATION: complementary 19mer ssDNA (used as part of a
      linker)

<400> SEQUENCE: 7
gcagaagcat taatagact                                                  19
```

```
<210> SEQ ID NO 8
<211> LENGTH: 17
<212> TYPE: DNA
<213> ORGANISM: Artificial Sequence
<220> FEATURE:
<223> OTHER INFORMATION: complementary 17mer ssDNA (used as part of a
      linker)

<400> SEQUENCE: 8
tggacgacga tagaact                                                    17

<210> SEQ ID NO 9
<211> LENGTH: 33
<212> TYPE: PRT
<213> ORGANISM: Artificial Sequence
<220> FEATURE:
<223> OTHER INFORMATION: fragment
<220> FEATURE:
<221> NAME/KEY: MISC_FEATURE
<222> LOCATION: (16)..(17)
<223> OTHER INFORMATION: beta-alanine

<400> SEQUENCE: 9

Glu Arg Ala Glu Gln Gln Arg Ile Arg Ala Glu Arg Glu Lys Glu Xaa
1               5                   10                  15

Xaa Ser Leu Lys Asp Arg Ile Glu Lys Arg Arg Arg Ala Glu Arg Ala
            20                  25                  30

Glu

<210> SEQ ID NO 10
<211> LENGTH: 31
<212> TYPE: PRT
<213> ORGANISM: Artificial Sequence
<220> FEATURE:
<223> OTHER INFORMATION: fragment
<220> FEATURE:
<221> NAME/KEY: MISC_FEATURE
<222> LOCATION: (15)..(16)
<223> OTHER INFORMATION: amino-trioxa-octanoic-acid

<400> SEQUENCE: 10

Leu Lys Asp Arg Ile Glu Arg Arg Arg Ala Glu Arg Ala Glu Xaa Xaa
1               5                   10                  15

Glu Arg Ala Glu Gln Gln Arg Ile Arg Ala Glu Arg Glu Lys Glu
            20                  25                  30

<210> SEQ ID NO 11
<211> LENGTH: 27
<212> TYPE: PRT
<213> ORGANISM: Artificial Sequence
<220> FEATURE:
<223> OTHER INFORMATION: IGF-1R (1340-1366)

<400> SEQUENCE: 11

Phe Asp Glu Arg Gln Pro Tyr Ala His Met Asn Gly Gly Arg Lys Asn
1               5                   10                  15

Glu Arg Ala Leu Pro Leu Pro Gln Ser Ser Thr
            20                  25

<210> SEQ ID NO 12
<211> LENGTH: 27
<212> TYPE: PRT
<213> ORGANISM: Artificial Sequence
<220> FEATURE:
<223> OTHER INFORMATION: hInsR(1355-1382)
```

-continued

```
<400> SEQUENCE: 12

Tyr Glu Glu His Ile Pro Tyr Thr His Met Asn Gly Gly Lys Lys Asn
1               5                   10                  15

Gly Arg Ile Leu Thr Leu Pro Arg Ser Asn Pro
            20                  25

<210> SEQ ID NO 13
<211> LENGTH: 35
<212> TYPE: DNA
<213> ORGANISM: Artificial Sequence
<220> FEATURE:
<223> OTHER INFORMATION: 35-mer polynucleotide linker
<220> FEATURE:
<221> NAME/KEY: misc_feature
<222> LOCATION: (1)..(35)
<223> OTHER INFORMATION: n is a, c, g, or t

<400> SEQUENCE: 13
nnnnnnnnnn nnnnnnnnnn nnnnnnnnnn nnnnn                           35

<210> SEQ ID NO 14
<211> LENGTH: 75
<212> TYPE: DNA
<213> ORGANISM: Artificial Sequence
<220> FEATURE:
<223> OTHER INFORMATION: 75-mer polynucleotide linker
<220> FEATURE:
<221> NAME/KEY: misc_feature
<222> LOCATION: (1)..(75)
<223> OTHER INFORMATION: n is a, c, g, or t

<400> SEQUENCE: 14
nnnnnnnnnn nnnnnnnnnn nnnnnnnnnn nnnnnnnnnn nnnnnnnnnn nnnnnnnnnn    60
nnnnnnnnnn nnnnn                                                     75

<210> SEQ ID NO 15
<211> LENGTH: 95
<212> TYPE: DNA
<213> ORGANISM: Artificial Sequence
<220> FEATURE:
<223> OTHER INFORMATION: 95-mer polynucleotide linker
<220> FEATURE:
<221> NAME/KEY: misc_feature
<222> LOCATION: (1)..(95)
<223> OTHER INFORMATION: n is a, c, g, or t

<400> SEQUENCE: 15
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnn                               95

<210> SEQ ID NO 16
<211> LENGTH: 218
<212> TYPE: PRT
<213> ORGANISM: Artificial Sequence
<220> FEATURE:
<223> OTHER INFORMATION: 4D5 Fab' heavy chain amino acid sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val
210                 215

<210> SEQ ID NO 17
<211> LENGTH: 214
<212> TYPE: PRT
<213> ORGANISM: Artificial Sequence
<220> FEATURE:
<223> OTHER INFORMATION: 4D5 Fab' light chain amino acid sequence

<400> SEQUENCE: 17

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
                130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

```
Tyr Ser Cys Gln Val Thr His Glu Gly Ser Thr Val Glu Lys Thr Val
            195                 200                 205

Ala Pro Thr Glu Cys Ser
    210

<210> SEQ ID NO 18
<211> LENGTH: 217
<212> TYPE: PRT
<213> ORGANISM: Artificial Sequence
<220> FEATURE:
<223> OTHER INFORMATION: 2C4 Fab' heavy chain amino acid sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215

<210> SEQ ID NO 19
<211> LENGTH: 212
<212> TYPE: PRT
<213> ORGANISM: Artificial Sequence
<220> FEATURE:
<223> OTHER INFORMATION: 2C4 Fab' light chain amino acid sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 20
<211> LENGTH: 645
<212> TYPE: PRT
<213> ORGANISM: Artificial Sequence
<220> FEATURE:
<223> OTHER INFORMATION: HER2 ECD fragment

<400> SEQUENCE: 20

Met Glu Leu Ala Ala Leu Cys Arg Trp Gly Leu Leu Leu Ala Leu Leu
  1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
             35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205
```

-continued

```
Ser Glu Asp Cys Gln Ser Leu Thr Arg Thr Val Cys Ala Gly Gly Cys
210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
            245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
            325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
            405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
            485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
            565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
610                 615                 620
```

Pro Cys Pro Ile Asn Cys Thr His Ser Cys Val Asp Leu Asp Asp Lys
625                 630                 635                 640

Gly Cys Pro Ala Glu
            645

<210> SEQ ID NO 21
<211> LENGTH: 24
<212> TYPE: DNA
<213> ORGANISM: Artificial Sequence
<220> FEATURE:
<223> OTHER INFORMATION: fragment
<220> FEATURE:
<221> NAME/KEY: misc_feature
<223> OTHER INFORMATION: X = propylene-phosphate introduced via
      phosphoramidite C3 (3-(4,4'-dimethoxytrityloxy)propyl-1-[(2-
      cyanoethyl)-(N,N-diisopropyl)]-phosphoramidite
<220> FEATURE:
<221> NAME/KEY: misc_feature
<223> OTHER INFORMATION: Y = 5'-amino-modifier C6 introduced via
      (6-(4-monomethoxytritylamino)hexyl-(2-cyanoethyl)-(N,N-
      diisopropyl)-phosphoramidite
<220> FEATURE:
<221> NAME/KEY: misc_feature
<223> OTHER INFORMATION: Z = 4[N-maleinimidomethyl]cyclohexane-1-carboxy
      introduced via Sulfosuccinimidyl 4-[N-maleimidomethyl]cyclohexane-
      1-carboxylate
<220> FEATURE:
<221> NAME/KEY: misc_feature
<222> LOCATION: (20)..(24)
<223> OTHER INFORMATION: n is a, c, g, or t

<400> SEQUENCE: 21
agtctattaa tgcttctgcn nnnn                                          24

<210> SEQ ID NO 22
<211> LENGTH: 22
<212> TYPE: DNA
<213> ORGANISM: Artificial Sequence
<220> FEATURE:
<223> OTHER INFORMATION: fragment
<220> FEATURE:
<221> NAME/KEY: misc_feature
<223> OTHER INFORMATION: X = propylene-phosphate introduced via
      Phosphoramidite C3 (3-(4,4'-Dimethoxytrityloxy)propyl-1-[(2-
      cyanoethyl)-(N,N-diisopropyl)]-phosphoramidite
<220> FEATURE:
<221> NAME/KEY: misc_feature
<223> OTHER INFORMATION: Y = 5'-Amino-Modifier C6 introduced via
      (6-(4-Monomethoxytritylamino)hexyl-(2-cyanoethyl)-(N,N-
      diisopropyl)-phosphoramidite
<220> FEATURE:
<221> NAME/KEY: misc_feature
<223> OTHER INFORMATION: Z = 4[N-maleinimidomethyl]cyclohexane-1-carboxy
      introduced via Sulfosuccinimidyl 4-[N-maleimidomethyl]cyclohexane-
      1-carboxylate
<220> FEATURE:
<221> NAME/KEY: misc_feature
<222> LOCATION: (1)..(5)
<223> OTHER INFORMATION: n is a, c, g, or t

<400> SEQUENCE: 22
nnnnnagttc tatcgtcgtc ca                                            22

<210> SEQ ID NO 23
<211> LENGTH: 36
<212> TYPE: DNA
<213> ORGANISM: Artificial Sequence
<220> FEATURE:
<223> OTHER INFORMATION: biotinylated ssDNA linker 1
<220> FEATURE:
<221> NAME/KEY: misc_feature
<223> OTHER INFORMATION: n=biotin dT

```
<220> FEATURE:
<221> NAME/KEY: misc_feature
<222> LOCATION: (20)..(20)
<223> OTHER INFORMATION: n is a, c, g, or t

<400> SEQUENCE: 23
gcagaagcat taatagactn ggacgacgat agaact                                    36

<210> SEQ ID NO 24
<211> LENGTH: 46
<212> TYPE: DNA
<213> ORGANISM: Artificial Sequence
<220> FEATURE:
<223> OTHER INFORMATION: biotinylated ssDNA linker 2
<220> FEATURE:
<221> NAME/KEY: misc_feature
<223> OTHER INFORMATION: n=biotin dT
<220> FEATURE:
<221> NAME/KEY: misc_feature
<222> LOCATION: (25)..(25)
<223> OTHER INFORMATION: n is a, c, g, or t

<400> SEQUENCE: 24
gcagaagcat taatagactt ttttnttttt ggacgacgat agaact                         46

<210> SEQ ID NO 25
<211> LENGTH: 66
<212> TYPE: DNA
<213> ORGANISM: Artificial Sequence
<220> FEATURE:
<223> OTHER INFORMATION: biotinylated ssDNA linker 3
<220> FEATURE:
<221> NAME/KEY: misc_feature
<223> OTHER INFORMATION: n=biotin dT
<220> FEATURE:
<221> NAME/KEY: misc_feature
<222> LOCATION: (35)..(35)
<223> OTHER INFORMATION: n is a, c, g, or t

<400> SEQUENCE: 25
gcagaagcat taatagactt ttttttttt ttttnttttt ttttttttt ggacgacgat            60 agaact                                                                     66

<210> SEQ ID NO 26
<211> LENGTH: 120
<212> TYPE: PRT
<213> ORGANISM: Artificial Sequence
<220> FEATURE:
<223> OTHER INFORMATION: anti-HER2 antibody 4D5 heavy chain variable
      domain

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 27
<211> LENGTH: 10
<212> TYPE: PRT
<213> ORGANISM: Artificial Sequence
<220> FEATURE:
<223> OTHER INFORMATION: VH CDR1

<400> SEQUENCE: 27

Gly Phe Asn Ile Lys Asp Thr Tyr Ile His
1               5                   10

<210> SEQ ID NO 28
<211> LENGTH: 17
<212> TYPE: PRT
<213> ORGANISM: Artificial Sequence
<220> FEATURE:
<223> OTHER INFORMATION: VH CDR2

<400> SEQUENCE: 28

Arg Ile Tyr Pro Thr Asn Gly Tyr Thr Arg Tyr Ala Asp Ser Val Lys
1               5                   10                  15

Gly

<210> SEQ ID NO 29
<211> LENGTH: 11
<212> TYPE: PRT
<213> ORGANISM: Artificial Sequence
<220> FEATURE:
<223> OTHER INFORMATION: VH CDR3

<400> SEQUENCE: 29

Trp Gly Gly Asp Gly Phe Tyr Ala Met Asp Tyr
1               5                   10

<210> SEQ ID NO 30
<211> LENGTH: 109
<212> TYPE: PRT
<213> ORGANISM: Artificial Sequence
<220> FEATURE:
<223> OTHER INFORMATION: anti-HER2 antibody 4D5 heavy light variable
      domain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

```
<210> SEQ ID NO 31
<211> LENGTH: 12
<212> TYPE: PRT
<213> ORGANISM: Artificial Sequence
<220> FEATURE:
<223> OTHER INFORMATION: VL CDR1

<400> SEQUENCE: 31

Arg Ala Ser Gln Asp Val Asn Thr Ala Val Ala Trp
1               5                   10

<210> SEQ ID NO 32
<211> LENGTH: 7
<212> TYPE: PRT
<213> ORGANISM: Artificial Sequence
<220> FEATURE:
<223> OTHER INFORMATION: VL CDR2

<400> SEQUENCE: 32

Ser Ala Ser Phe Leu Tyr Ser
1               5

<210> SEQ ID NO 33
<211> LENGTH: 9
<212> TYPE: PRT
<213> ORGANISM: Artificial Sequence
<220> FEATURE:
<223> OTHER INFORMATION: VL CDR3

<400> SEQUENCE: 33

Gln Gln His Tyr Thr Thr Pro Pro Thr
1               5

<210> SEQ ID NO 34
<211> LENGTH: 119
<212> TYPE: PRT
<213> ORGANISM: Artificial Sequence
<220> FEATURE:
<223> OTHER INFORMATION: anti-HER2 antibody 2C4 heavy chain variable
      domain

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 35
<211> LENGTH: 10
<212> TYPE: PRT
<213> ORGANISM: Artificial Sequence
```

<220> FEATURE:
<223> OTHER INFORMATION: VH CDR1

<400> SEQUENCE: 35

Gly Phe Thr Phe Thr Asp Tyr Thr Met Asp
1               5                   10

<210> SEQ ID NO 36
<211> LENGTH: 17
<212> TYPE: PRT
<213> ORGANISM: Artificial Sequence
<220> FEATURE:
<223> OTHER INFORMATION: VH CDR2

<400> SEQUENCE: 36

Asp Val Asn Pro Asn Ser Gly Gly Ser Ile Tyr Asn Gln Arg Phe Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: VH CDR3

<400> SEQUENCE: 37

Asn Leu Gly Pro Ser Phe Tyr Phe Asp Tyr
1               5                   10

<210> SEQ ID NO 38
<211> LENGTH: 107
<212> TYPE: PRT
<213> ORGANISM: Artificial Sequence
<220> FEATURE:
<223> OTHER INFORMATION: anti-HER2 antibody 2C4 light chain variable
      domain

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 39
<211> LENGTH: 11
<212> TYPE: PRT
<213> ORGANISM: Artificial Sequence
<220> FEATURE:
<223> OTHER INFORMATION: VL CDR1

```
<400> SEQUENCE: 39

Lys Ala Ser Gln Asp Val Ser Ile Gly Val Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: VL CDR2

<400> SEQUENCE: 40

Ser Ala Ser Tyr Arg Tyr Thr
1               5

<210> SEQ ID NO 41
<211> LENGTH: 9
<212> TYPE: PRT
<213> ORGANISM: Artificial Sequence
<220> FEATURE:
<223> OTHER INFORMATION: VL CDR3

<400> SEQUENCE: 41

Gln Gln Tyr Tyr Ile Tyr Pro Tyr Thr
1               5

<210> SEQ ID NO 42
<211> LENGTH: 24
<212> TYPE: DNA
<213> ORGANISM: Artificial Sequence
<220> FEATURE:
<223> OTHER INFORMATION: amino modified polynucleotide linker precursors
<220> FEATURE:
<221> NAME/KEY: misc_feature
<223> OTHER INFORMATION: X= Fluorescein
     Y=C7Aminolinker
     Z=C3 spacer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (21)..(24)
<223> OTHER INFORMATION: n is a, c, g, or t

<400> SEQUENCE: 42
nagtctatta atgcttctgc nnnn                                      24

<210> SEQ ID NO 43
<211> LENGTH: 24
<212> TYPE: DNA
<213> ORGANISM: Artificial Sequence
<220> FEATURE:
<223> OTHER INFORMATION: amino modified polynucleotide linker precursors
<220> FEATURE:
<221> NAME/KEY: misc_feature
<223> OTHER INFORMATION: X=Cy5
     Y=C7Aminolinker
     Z=C3 spacer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (21)..(24)
<223> OTHER INFORMATION: n is a, c, g, or t
```

```
<400> SEQUENCE: 43
nagtctatta atgcttctgc nnnn                                              24

<210> SEQ ID NO 44
<211> LENGTH: 22
<212> TYPE: DNA
<213> ORGANISM: Artificial Sequence
<220> FEATURE:
<223> OTHER INFORMATION: amino modified polynucleotide linker precursors
<220> FEATURE:
<221> NAME/KEY: misc_feature
<223> OTHER INFORMATION: X=Aminolinker
      Y= Fluorescein
      Z=C3 spacer
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 44
nnnnagttct atcgtcgtcc an                                                22

<210> SEQ ID NO 45
<211> LENGTH: 24
<212> TYPE: DNA
<213> ORGANISM: Artificial Sequence
<220> FEATURE:
<223> OTHER INFORMATION: amino modified L-polynucleotide linker
      precursors
<220> FEATURE:
<221> NAME/KEY: misc_feature
<223> OTHER INFORMATION: X=Fluorescein
      Y= C7Aminolinker
      Z=C3 spacer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (21)..(24)
<223> OTHER INFORMATION: n is a, c, g, or t

<400> SEQUENCE: 45
nagtctatta atgcttctgc nnnn                                              24

<210> SEQ ID NO 46
<211> LENGTH: 22
<212> TYPE: DNA
<213> ORGANISM: Artificial Sequence
<220> FEATURE:
<223> OTHER INFORMATION: amino modified L-polynucleotide linker
      precursors
<220> FEATURE:
<221> NAME/KEY: misc_feature
<223> OTHER INFORMATION: X= Aminolinker
      Y=  Fluorescein
      Z=C3 spacer
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
```

```
<400> SEQUENCE: 46
nnnnagttct atcgtcgtcc an                                           22

<210> SEQ ID NO 47
<211> LENGTH: 36
<212> TYPE: DNA
<213> ORGANISM: Artificial Sequence
<220> FEATURE:
<223> OTHER INFORMATION: ssDNA linker 1

<400> SEQUENCE: 47
gcagaagcat taatagactt ggacgacgat agaact                            36

<210> SEQ ID NO 48
<211> LENGTH: 76
<212> TYPE: DNA
<213> ORGANISM: Artificial Sequence
<220> FEATURE:
<223> OTHER INFORMATION: ssDNA linker 2

<400> SEQUENCE: 48
gcagaagcat taatagactt tttttttttt tttttttttt tttttttttt tttttttttt  60
ggacgacgat agaact                                                  76

<210> SEQ ID NO 49
<211> LENGTH: 37
<212> TYPE: DNA
<213> ORGANISM: Artificial Sequence
<220> FEATURE:
<223> OTHER INFORMATION: biotinylated ss-L-DNA linker 3
<220> FEATURE:
<221> NAME/KEY: misc_feature
<223> OTHER INFORMATION: n=biotin dT
<220> FEATURE:
<221> NAME/KEY: misc_feature
<222> LOCATION: (20)..(20)
<223> OTHER INFORMATION: n is a, c, g, or t

<400> SEQUENCE: 49
gcagaagcat taatagactn tggacgacga tagaact                           37

<210> SEQ ID NO 50
<211> LENGTH: 47
<212> TYPE: DNA
<213> ORGANISM: Artificial Sequence
<220> FEATURE:
<223> OTHER INFORMATION: biotinylated ss-L-DNA linker 4
<220> FEATURE:
<221> NAME/KEY: misc_feature
<223> OTHER INFORMATION: n=biotin dT
<220> FEATURE:
<221> NAME/KEY: misc_feature
<222> LOCATION: (25)..(25)
<223> OTHER INFORMATION: n is a, c, g, or t

<400> SEQUENCE: 50
gcagaagcat taatagactt ttttnttttt tggacgacga tagaact                47

<210> SEQ ID NO 51
<211> LENGTH: 77
<212> TYPE: DNA
<213> ORGANISM: Artificial Sequence
<220> FEATURE:
<223> OTHER INFORMATION: biotinylated ss-L-DNA linker 5
<220> FEATURE:
<221> NAME/KEY: misc_feature
<223> OTHER INFORMATION: n=biotin dT
```

```
<220> FEATURE:
<221> NAME/KEY: misc_feature
<222> LOCATION: (40)..(40)
<223> OTHER INFORMATION: n is a, c, g, or t

<400> SEQUENCE: 51
gcagaagcat taatagactt tttttttttt tttttttttn tttttttttt      60
tggacgacga tagaact                                          77

<210> SEQ ID NO 52
<211> LENGTH: 97
<212> TYPE: DNA
<213> ORGANISM: Artificial Sequence
<220> FEATURE:
<223> OTHER INFORMATION: biotinylated ss-L-DNA linker 6
<220> FEATURE:
<221> NAME/KEY: misc_feature
<223> OTHER INFORMATION: n=biotin dT
<220> FEATURE:
<221> NAME/KEY: misc_feature
<222> LOCATION: (50)..(50)
<223> OTHER INFORMATION: n is a, c, g, or t

<400> SEQUENCE: 52
gcagaagcat taatagactt tttttttttt tttttttttt tttttttttn tttttttttt   60
tttttttttt tttttttttt tggacgacga tagaact                            97

<210> SEQ ID NO 53
<211> LENGTH: 47
<212> TYPE: DNA
<213> ORGANISM: Artificial Sequence
<220> FEATURE:
<223> OTHER INFORMATION: biotinylated ssDNA linker 7
<220> FEATURE:
<221> NAME/KEY: misc_feature
<223> OTHER INFORMATION: n=biotin dT
<220> FEATURE:
<221> NAME/KEY: misc_feature
<222> LOCATION: (25)..(25)
<223> OTHER INFORMATION: n is a, c, g, or t

<400> SEQUENCE: 53
gcagaagcat taatagactt ttttnttttt tggacgacga tagaact         47

<210> SEQ ID NO 54
<211> LENGTH: 57
<212> TYPE: DNA
<213> ORGANISM: Artificial Sequence
<220> FEATURE:
<223> OTHER INFORMATION: biotinylated ssDNA linker 8
<220> FEATURE:
<221> NAME/KEY: misc_feature
<223> OTHER INFORMATION: n= biotin dT
<220> FEATURE:
<221> NAME/KEY: misc_feature
<222> LOCATION: (30)..(30)
<223> OTHER INFORMATION: n is a, c, g, or t

<400> SEQUENCE: 54
gcagaagcat taatagactt tttttttttn tttttttttt tggacgacga tagaact   57

<210> SEQ ID NO 55
<211> LENGTH: 67
<212> TYPE: DNA
<213> ORGANISM: Artificial Sequence
<220> FEATURE:
<223> OTHER INFORMATION: biotinylated ssDNA linker 9
```

```
<220> FEATURE:
<221> NAME/KEY: misc_feature
<223> OTHER INFORMATION: n= biotin dt
<220> FEATURE:
<221> NAME/KEY: misc_feature
<222> LOCATION: (35)..(35)
<223> OTHER INFORMATION: n is a, c, g, or t

<400> SEQUENCE: 55
gcagaagcat taatagactt tttttttttt ttttntttttt tttttttttt tggacgacga       60
tagaact                                                                  67

<210> SEQ ID NO 56
<211> LENGTH: 76
<212> TYPE: DNA
<213> ORGANISM: Artificial Sequence
<220> FEATURE:
<223> OTHER INFORMATION: biotinylated ssDNA linker 10
<220> FEATURE:
<221> NAME/KEY: misc_feature
<223> OTHER INFORMATION: n=biotin dt
<220> FEATURE:
<221> NAME/KEY: misc_feature
<222> LOCATION: (40)..(40)
<223> OTHER INFORMATION: n is a, c, g, or t

<400> SEQUENCE: 56
gcagaagcat taatagactt tttttttttt tttttttttn tttttttttt tttttttttt       60
ggacgacgat agaact                                                        76

<210> SEQ ID NO 57
<211> LENGTH: 39
<212> TYPE: DNA
<213> ORGANISM: Artificial Sequence
<220> FEATURE:
<223> OTHER INFORMATION: biotinylated ssDNA linker 11
<220> FEATURE:
<221> NAME/KEY: misc_feature
<223> OTHER INFORMATION: n=biotin dt
       s=spacer C18
<220> FEATURE:
<221> NAME/KEY: misc_feature
<222> LOCATION: (21)..(21)
<223> OTHER INFORMATION: n is a, c, g, or t

<400> SEQUENCE: 57
gcagaagcat taatagacts nstggacgac gatagaact                               39

<210> SEQ ID NO 58
<211> LENGTH: 41
<212> TYPE: DNA
<213> ORGANISM: Artificial Sequence
<220> FEATURE:
<223> OTHER INFORMATION: biotinylated ssDNA linker 12
<220> FEATURE:
<221> NAME/KEY: misc_feature
<223> OTHER INFORMATION: n=biotin dt
       s=spacer c18
<220> FEATURE:
<221> NAME/KEY: misc_feature
<222> LOCATION: (22)..(22)
<223> OTHER INFORMATION: n is a, c, g, or t

<400> SEQUENCE: 58
gcagaagcat taatagacts snsstggacg acgatagaac t                            41
```

-continued

```
<210> SEQ ID NO 59
<211> LENGTH: 43
<212> TYPE: DNA
<213> ORGANISM: Artificial Sequence
<220> FEATURE:
<223> OTHER INFORMATION: biotinylated ssDNA linker 13
<220> FEATURE:
<221> NAME/KEY: misc_feature
<223> OTHER INFORMATION: n=biotin dt
      s=spacer c18
<220> FEATURE:
<221> NAME/KEY: misc_feature
<222> LOCATION: (23)..(23)
<223> OTHER INFORMATION: n is a, c, g, or t

<400> SEQUENCE: 59
gcagaagcat taatagacts ssnssstgga cgacgataga act                    43

<210> SEQ ID NO 60
<211> LENGTH: 45
<212> TYPE: DNA
<213> ORGANISM: Artificial Sequence
<220> FEATURE:
<223> OTHER INFORMATION: biotinylated ss-L-DNA linker 14
<220> FEATURE:
<221> NAME/KEY: misc_feature
<223> OTHER INFORMATION: n=biotin dt
      s=spacer c18
<220> FEATURE:
<221> NAME/KEY: misc_feature
<222> LOCATION: (24)..(24)
<223> OTHER INFORMATION: n is a, c, g, or t

<400> SEQUENCE: 60
gcagaagcat taatagacts sssnssssstg gacgacgata gaact                 45

<210> SEQ ID NO 61
<211> LENGTH: 77
<212> TYPE: DNA
<213> ORGANISM: Artificial Sequence
<220> FEATURE:
<223> OTHER INFORMATION: digoxygenylated ss-L-DNA linker 15
<220> FEATURE:
<221> NAME/KEY: misc_feature
<223> OTHER INFORMATION: n=digoxigenin dt
<220> FEATURE:
<221> NAME/KEY: misc_feature
<222> LOCATION: (40)..(40)
<223> OTHER INFORMATION: n is a, c, g, or t

<400> SEQUENCE: 61
gcagaagcat taatagactt tttttttttt tttttttttn tttttttttt tttttttttt    60
tggacgacga tagaact                                                   77

<210> SEQ ID NO 62
<211> LENGTH: 37
<212> TYPE: DNA
<213> ORGANISM: Artificial Sequence
<220> FEATURE:
<223> OTHER INFORMATION: digoxygenylated ss-L-DNA linker 16
<220> FEATURE:
<221> NAME/KEY: misc_feature
<223> OTHER INFORMATION: n=digoxigenin dt
<220> FEATURE:
<221> NAME/KEY: misc_feature
<222> LOCATION: (20)..(20)
<223> OTHER INFORMATION: n is a, c, g, or t

<400> SEQUENCE: 62
gcagaagcat taatagactn tggacgacga tagaact                           37
```

```
<210> SEQ ID NO 63
<211> LENGTH: 37
<212> TYPE: DNA
<213> ORGANISM: Artificial Sequence
<220> FEATURE:
<223> OTHER INFORMATION: biotinylated ss-L-DNA linker 17
<220> FEATURE:
<221> NAME/KEY: misc_feature
<223> OTHER INFORMATION: n=biotin dt
<220> FEATURE:
<221> NAME/KEY: misc_feature
<222> LOCATION: (20)..(20)
<223> OTHER INFORMATION: n is a, c, g, or t

<400> SEQUENCE: 63
gcagaagcat taatagactn tggacgacga tagaact                              37

<210> SEQ ID NO 64
<211> LENGTH: 9
<212> TYPE: PRT
<213> ORGANISM: Artificial Sequence
<220> FEATURE:
<223> OTHER INFORMATION: HA-tag

<400> SEQUENCE: 64

Tyr Pro Tyr Asp Val Pro Asp Tyr Ala
1               5

<210> SEQ ID NO 65
<211> LENGTH: 15
<212> TYPE: PRT
<213> ORGANISM: Artificial Sequence
<220> FEATURE:
<223> OTHER INFORMATION: Avi-tag

<400> SEQUENCE: 65

Gly Leu Asn Asp Ile Phe Glu Ala Gln Lys Ile Glu Trp His Glu
1               5                   10                  15

<210> SEQ ID NO 66
<211> LENGTH: 5
<212> TYPE: PRT
<213> ORGANISM: Artificial Sequence
<220> FEATURE:
<223> OTHER INFORMATION: linker

<400> SEQUENCE: 66

Ser Gly Gly Gly Ser
1               5

<210> SEQ ID NO 67
<211> LENGTH: 3
<212> TYPE: PRT
<213> ORGANISM: Artificial Sequence
<220> FEATURE:
<223> OTHER INFORMATION: fMLP
<220> FEATURE:
<221> NAME/KEY: MISC_FEATURE
<223> OTHER INFORMATION: X=f-met
<220> FEATURE:
<221> NAME/KEY: misc_feature
<222> LOCATION: (1)..(1)
<223> OTHER INFORMATION: Xaa can be any naturally occurring amino acid

<400> SEQUENCE: 67

Xaa Leu Phe
1
```

-continued

```
<210> SEQ ID NO 68
<211> LENGTH: 4
<212> TYPE: PRT
<213> ORGANISM: Artificial Sequence
<220> FEATURE:
<223> OTHER INFORMATION: f-Met-Leu-Phe-o-methyl ester
<220> FEATURE:
<221> NAME/KEY: MISC_FEATURE
<222> LOCATION: (1)..(1)
<223> OTHER INFORMATION: f-met
<220> FEATURE:
<221> NAME/KEY: MISC_FEATURE
<222> LOCATION: (4)..(4)
<223> OTHER INFORMATION: o-methyl ester

<400> SEQUENCE: 68

Xaa Leu Phe Xaa
1

<210> SEQ ID NO 69
<211> LENGTH: 107
<212> TYPE: PRT
<213> ORGANISM: Homo sapiens

<400> SEQUENCE: 69

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 70
<211> LENGTH: 105
<212> TYPE: PRT
<213> ORGANISM: Homo sapiens

<400> SEQUENCE: 70

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 71
<211> LENGTH: 330
<212> TYPE: PRT
<213> ORGANISM: Homo sapiens

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 330
<212> TYPE: PRT
<213> ORGANISM: Homo sapiens
```

-continued

```
<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 73
<211> LENGTH: 330
<212> TYPE: PRT
<213> ORGANISM: Homo sapiens

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 74
<211> LENGTH: 327
<212> TYPE: PRT
<213> ORGANISM: Homo sapiens

<400> SEQUENCE: 74

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

-continued

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 75
<211> LENGTH: 327
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Cys Pro Ala Pro
            100                 105                 110

Glu Phe Glu Gly Gly Pro Ser Val Phe Leu Phe Pro Pro Lys Pro Lys
            115                 120                 125

```
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 76
<211> LENGTH: 23
<212> TYPE: DNA
<213> ORGANISM: Artificial Sequence
<220> FEATURE:
<223> OTHER INFORMATION: detection probe
<220> FEATURE:
<221> NAME/KEY: misc_feature
<223> OTHER INFORMATION: Y = 5'-Amino-Modifier
      Z = 3'-Aminomodifier C6
      Cy5-dye at 5' and 3' terminus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 76
nnatgcgagt accttagagt cnn                                              23

<210> SEQ ID NO 77
<211> LENGTH: 95
<212> TYPE: DNA
<213> ORGANISM: Artificial Sequence
<220> FEATURE:
<223> OTHER INFORMATION: T20-linker

<400> SEQUENCE: 77
gcagaagcat taatagactt tttttttttt tttttttttg actctaaggt actcgcattt       60
tttttttttt tttttttttg gacgacgata gaact                                  95
```

POLYPEPTIDE-POLYNUCLEOTIDE-COMPLEX AND ITS USE IN TARGETED EFFECTOR MOIETY DELIVERY

CROSS REFERENCE TO RELATED APPLICATIONS

This application is a continuation of U.S. patent application Ser. No. 13/924,233, filed on Jun. 21, 2013, which is a continuation of International Application No. PCT/EP2011/073631 having an international filing date of Dec. 21, 2011, the entire contents of which are incorporated herein by reference, and which claims benefit under 35 U.S.C. § 119 to European Patent Application No. 10196688.5 filed Dec. 23, 2010.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392042201SEQLIST.TXT, date recorded: Dec. 4, 2019, size: 57 KB).

Herein is reported a polypeptide-polynucleotide-complex as novel therapeutic agent as well as in vivo imaging agent. Also reported is the use of the complex as tool for the targeted delivery of an effector moiety. The polynucleotide part of the complex is essentially resistant to proteolytic and enzymatic degradation in vivo and supports at the same time a maximum of molecular flexibility. Additionally the polypeptide part specifically binds to a compound or structure such as a tissue or organ.

BACKGROUND OF THE INVENTION

Over the past years, a wide variety of tumor-specific targeting proteins, including antibodies, antibody fragments, and ligands for cell surface receptors have been developed and clinically tested. These targeting molecules have been conjugated to several classes of therapeutic toxins such as small molecule drugs, enzymes, radioisotopes, protein toxins, and other toxins for specific delivery to patients. While these efforts have made meaningful inroads to treat cancers, significant challenges lie ahead to develop more effective toxins, to create more robust and specific delivery systems, and to design therapeutic proteins and protein vectors that avoid a detrimental immune response in humans.

Effective delivery to the site of disease is a prerequisite for high efficacy and low toxicity of any drug substance. It is clear that antibodies can participate in this context by facilitating the transport of a drug cargo within the body and thereby invoking the often cited "magic bullet" concept, as put forward by Ehrlich over a century ago. Conjugation of a drug to an antibody makes it possible to achieve excellent localization of the drug at the desired site within the human body. This increases the effective drug concentration within this target area, thereby optimizing the therapeutic effect of the agent. Furthermore, with targeted delivery, the clinician may be able to lower the dose of the therapeutic agent—something that is particularly relevant if the drug payload has associated toxicities or if it is to be used in the treatment of chronic conditions (see e.g. McCarron, P. A., et al., Mol. Interventions 5 (2005) 368-380).

The generation of bispecific antibodies is e.g. reported in WO 2004/081051. A broad spectrum of bispecific antibody formats has been designed and developed (see e.g. Fischer, N. and Leger, O., Pathobiology 74 (2007) 3-14). Chelating recombinant antibodies (CRAbs) are originally reported by Neri, D., et al. (Neri, D., et al., J. Mol. Biol. 246 (1995) 367-373). Wright, M. J. and Deonarain, M. P. (Molecular Immunology 44 (2007) 2860-2869) reported a phage display library for generation of chelating recombinant antibodies.

Ideally, linkers that connect the payload and the antibody must exhibit excellent plasma stability, yet must relinquish to either enzymatic or chemical (i.e. acidic hydrolysis) degradation within the tumor cell. Numerous immolate linker molecules have been described in the literature are commercially available (see e.g. Amsberry, K. L. and Borchardt, R. T., J. Org. Chem. 55 (1990) 5867-5877; Dubowchik, G. M., et al., Tet. Lett. 38 (1997) 5261-5264; Rodrigues, M. L., et al., Chem. Biol. 2 (1995) 223-227; Shabat, D., et al., Proc. Natl. Acad. Sci. USA 96 (1999) 6925-6930; Shabat, D., et al., Proc. Natl. Acad. Sci. USA 98 (2001) 7528-7533.

In addition, antibodies targeting internalizing tumor epitopes could be exploited to achieve efficient and specific intracellular delivery of chemotherapeutic drugs and/or other tumor modulating agents (see e.g. Liu, B., et al., Cancer Res. 64 (2004) 704-710; Nielsen, U. B., et al., Biochim. Biophys. Acta 1591 (2002) 109-118; Pirollo, K. F., et al., Hum. Gene Ther. 17 (2006) 117-124; Song, E., et al., Nat. Biotechnol. 23 (2005) 709-717; Liu, B., et al., J. Mol. Biol. 315 (2002) 1063-1073).

Targeted drug delivery to mesothelioma cells using functionally selected internalizing human single-chain antibodies is reported by Feng, A., et al., Mol. Cancer Ther. 7 (2008) 569-578. Mapping tumor epitope space by direct selection of single-chain Fv antibody libraries on prostate cancer cells is reported by Liu, B., et al., Cancer Res. 64 (2004) 704-710. Poul, M. A., et al., report the selection of tumor-specific internalizing human antibodies from phage libraries (J. Mol. Biol. 301 (2000) 1149-1161). Nielsen, U. B., et al., report the therapeutic efficacy of anti-ErbB2 immunoliposomes targeted by a phage antibody selected for cellular endocytosis (Biochim. Biophys. Acta 1591 (2002) 109-118). Heitner, T., et al., report selection of cell binding and internalizing epidermal growth factor receptor antibodies from a phage display library (J. Immunol. Meth. 248 (2001) 17-30).

Molecular vehicles for targeted drug delivery are reported by Backer, M. V., et al., Bioconjugate Chem. 13 (2002) 462-467. WO 2010/118169 reports human protein scaffolds with controlled serum pharmacokinetics. Methods and compositions related to peptides and proteins with C-terminal elements cross-reference to related applications is reported in WO 2009/105671. In WO 2007/038658 antibody-drug conjugates and methods of use are reported. Compositions and methods for targeted biological delivery of molecular carriers are reported in WO 2004/062602. In WO 2002/072141 targeted ligands are reported.

In WO 2009/037659 magnetic detection of small entities is reported. Homogeneous analyte detection is reported in WO 2006/137932. In US 2008/0044834 a three-component biosensor for detecting macromolecules and other analytes is reported. The design and synthesis of bispecific reagents is reported in WO 95/05399.

SUMMARY OF THE INVENTION

It has been found that for the targeted delivery of an effector moiety a complex comprising polypeptide and polynucleotide components is especially useful. The effector moiety, the polypeptide component and the polynucleotide component of the complex are non-covalently bound to each other. This allows a modular production of the individual components of the complex. Due to the modular architecture of the complex individual components can be change without the need to change the other components of the complex. This allows for an easy and efficient assembly of a multitude of complex variants e.g. for the provision of a library.

Thus, one aspect as reported herein is a complex comprising
- a) a first polypeptide
  - i) that specifically binds to a first target, and
  - ii) that is conjugated to a first member of a first binding pair,
- b) a second polypeptide
  - i) that specifically binds to a second target, and
  - ii) that is conjugated to a first member of a second binding pair, and
- c) a polynucleotide linker
  - i) that is conjugated to the second member of the first binding pair, and
  - ii) that is conjugated to the second member of the second binding pair.

Another aspect as reported herein is a complex that is an intermediate during the production of the above complex. This complex comprises
- a) a polypeptide
  - i) that specifically binds to a target, and
  - ii) that is conjugated to a first member of a binding pair,
- b) a polynucleotide linker that is conjugated to the second member of the binding pair.

The following are embodiments of all aspects as reported herein.

In one embodiment the complex is a non-covalent complex.

In one embodiment the complex further comprises an effector moiety that is conjugated to a polynucleotide that is complementary to at least a part of the polynucleotide linker.

In one embodiment the complex further comprises a further polypeptide i) that specifically binds to a second target, and ii) that is conjugated to a first member of a second binding pair, and the polynucleotide linker is conjugated to the second member of the second binding pair.

In one embodiment the complex further comprises an effector moiety conjugated to a polynucleotide that is i) complementary to at least a part of the polynucleotide that is conjugated to the first effector moiety and ii) not complementary to the polynucleotide linker.

In one embodiment the first target and/or the second target is/are a cell surface protein.

In one embodiment the polypeptide is a monovalent binding polypeptide. In one embodiment the monovalent binding polypeptide is an antibody or antibody fragment.

In one embodiment the first and second polypeptide bind to the same target and to non-overlapping epitopes thereon.

In one embodiment the polynucleotide linker comprises of from 8 to 1000 nucleotides. In one embodiment the polynucleotide linker comprises of from 10 to 500 nucleotides.

In one embodiment the members of the binding pairs are selected from the group consisting of leucine zipper domain dimers and hybridizing nucleic acid sequences.

In one embodiment the polynucleotide linker is enantiomeric DNA. In one embodiment the enantiomeric DNA is L-DNA. In one embodiment the L-DNA is single stranded L-DNA (ss-L-DNA).

In one embodiment the effector moiety is selected from the group consisting of a binding moiety, a labeling moiety, and a biologically active moiety.

In one embodiment the polynucleotide linker is conjugated to the member of the binding pair at its first or second terminus.

In one embodiment the polynucleotide linker is conjugated to two second members of two binding pairs, whereby the second member of the first binding pair is conjugated to the first terminus of the polynucleotide linker and the second member of the second binding pair is conjugated to the second terminus of the polynucleotide linker.

One aspect as reported herein is a complex as reported herein wherein the first polypeptide is the FAB' fragment of the anti-HER2 antibody 2C4, the second polypeptide is the FAB' fragment of the anti-HER2 antibody 4D5, the members of the binding pairs are each hybridizing nucleic acids, and the polynucleotide linker comprises 60 to 100 L-DNA nucleotides.

In one embodiment the FAB' fragment of the anti-HER2 antibody 2C4 comprises (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 37, and the FAB' fragment of the anti-HER2 antibody 4D5 comprises (a) HVR-H1 comprising the amino acid sequence of SEQ ID NO: 27, (b) HVR-H2 comprising the amino acid sequence of SEQ ID NO: 28, and (c) HVR-H3 comprising the amino acid sequence of SEQ ID NO: 29.

In one embodiment the first and second member of the first binding pair comprise the nucleic acid sequences of SEQ ID NO: 05 and SEQ ID NO: 08, respectively.

In one embodiment the first and second member of the second binding pair comprise the nucleic acid sequences of SEQ ID NO: 06 and SEQ ID NO: 07, respectively.

In one embodiment the FAB' fragment of the anti-HER2 antibody 2C4 comprises (a) HVR-L1 comprising the amino acid sequence of SEQ ID NO: 39, (b) HVR-L2 comprising the amino acid sequence of SEQ ID NO: 40, and (c) HVR-L3 comprising the amino acid sequence of SEQ ID NO: 41, and the FAB' fragment of the anti-HER2 antibody 4D5 comprises (a) HVR-L1 comprising the amino acid sequence of SEQ ID NO: 31, (b) HVR-L2 comprising the amino acid sequence of SEQ ID NO: 32, and (c) HVR-L3 comprising the amino acid sequence of SEQ ID NO: 33.

In one embodiment the FAB' fragment of the anti-HER2 antibody 4D5 comprises a heavy chain variable domain with the amino acid sequence of SEQ ID NO: 26 and/or a light chain variable domain with the amino acid sequence of SEQ ID NO: 30.

In one embodiment the FAB' fragment of the anti-HER2 antibody 2C4 comprises a heavy chain variable domain with the amino acid sequence of SEQ ID NO: 34 and/or a light chain variable domain with the amino acid sequence of SEQ ID NO: 38.

In one embodiment first and/or the second polypeptide of the complex further comprises independently of each other one or more of a CH1 domain of human IgG1 class, or of human IgG2 class, or of human IgG3 class, or of human IgG4 class, and light chain constant domain of human kappa class, or of human lambda class.

Another aspect as reported herein is a method of producing a complex comprising the following components
- a) a first polypeptide
  - i) that specifically binds to a first target, and
  - ii) that is conjugated to a first member of a first binding pair, b) a second polypeptide
   i) that specifically binds to a second target, and
   ii) that is conjugated to a first member of a second binding pair, and
c) a polynucleotide linker
   i) that is conjugated to the second member of the first binding pair, and
   ii) that is conjugated to the second member of the second binding pair, comprising the steps of:
a) synthesizing the first polypeptide that specifically binds to a first target and that is conjugated to a first member of a first binding pair,
b) synthesizing the second polypeptide that specifically binds to a second target and that is conjugated to a first member of a second binding pair,
c) synthesizing the polynucleotide linker that is conjugated to the second member of the first binding pair and that is conjugated to the second member of the second binding pair, and
d) forming the complex by combining the synthesized components.

Also an aspect as reported herein is a method of producing a complex comprising the components
a) a polypeptide
   i) that specifically binds to a target, and
   ii) that is conjugated to a first member of a binding pair,
b) a polynucleotide linker that is conjugated to the second member of the binding pair, and
c) an effector moiety that is conjugated to a polynucleotide that is complementary to at least a part of the polynucleotide linker,
comprising the steps of:
a) synthesizing the polypeptide that specifically binds to a target and that is conjugated to a first member of a binding pair,
b) synthesizing the polynucleotide linker that is conjugated to the second member of the binding pair,
c) synthesizing the effector moiety that is conjugated to a polynucleotide that is complementary to at least a part of the polynucleotide linker, and
d) forming the complex by combining the synthesized components.

Another aspect as reported herein is a pharmaceutical formulation comprising the complex as reported herein and optionally a pharmaceutically acceptable carrier.

A further aspect as reported herein is a complex as reported herein for use as a medicament.

Also an aspect as reported herein is the complex as reported herein for use in treating cancer.

A further aspect as reported herein is the complex as reported herein for use in inhibiting growth of HER2 positive cancer cells.

Another aspect as reported herein is the use of the complex as reported herein in the manufacture of a medicament.

In one embodiment the medicament is for treatment of cancer. In one embodiment the medicament is for inhibiting growth of HER2 positive cancer cells.

An aspect as reported herein is a method of treating an individual having cancer comprising administering to the individual an effective amount of the complex as reported herein.

An aspect as reported herein is a method for inhibiting the growth of HER2 positive cancer cells in an individual comprising administering to the individual an effective amount of the complex as reported herein to inhibit the growth of HER2 positive cancer cells.

An aspect as reported herein is a complex that comprises at least one antibody fragment that binds to human ErbB2 and that blocks ligand activation of an ErbB receptor, as well as a composition comprising the complex and a pharmaceutically acceptable carrier as well as the complex as reported herein further comprising a cytotoxic agent.

Herein is reported a method of treating cancer in an individual, wherein the cancer is characterized by overexpression of the ErbB2 receptor, comprising administering to the individual a therapeutically effective amount of a complex as reported herein wherein the complex comprises an antibody or antibody fragment that binds to ErbB2.

Herein is also reported a method of treating cancer in an individual, wherein the cancer is not characterized by overexpression of the ErbB2 receptor, comprising administering to the individual a therapeutically effective amount of the complex as reported herein wherein the complex comprises an antibody or an antibody fragment that binds to ErbB2 and blocks ligand activation of an ErbB receptor.

In addition, herein is reported a method of treating hormone independent cancer in a human comprising administering to the human a therapeutically effective amount of the complex as reported herein wherein the complex comprises an antibody or an antibody fragment that binds to ErbB2 and blocks ligand activation of an ErbB receptor.

It is further reported herein a method of treating cancer in an individual comprising administering to the individual therapeutically effective amounts of (a) a first complex comprising an antibody or antibody fragment that binds to ErbB2 and inhibits growth of cancer cells which overexpress ErbB2, and (b) a second complex comprising an antibody or an antibody fragment that binds to ErbB2 and blocks ligand activation of an ErbB receptor.

It is also reported herein a method of treating cancer in an individual wherein the cancer is selected from the group consisting of colon, rectal, and colorectal cancer, comprising administering to the individual a therapeutically effective amount of a complex as reported herein comprising an antibody or an antibody fragment that binds to ErbB2 and blocks ligand activation of an ErbB receptor.

DETAILED DESCRIPTION OF THE INVENTION

Herein is reported a complex of the general Formula (A-a':a-S-b:b'-B)-X(n) or(A-a':a-S-b:b'-B):X(n)

wherein A and B each represent a polypeptide that specifically binds to a target wherein A does not interfere with the binding of B, wherein a':a and b:b' each represent a binding pair consisting of a first member (a and b, respectively) and a second member (a' and b', respectively) wherein a' and a do not interfere with the binding of b to b' and vice versa, wherein S is a polynucleotide linker of at least 1 nm in length, wherein X denotes an effector moiety that is bound to at least one of a', a, b, b' or S, wherein n is an integer denoting the number of effector moieties in the complex, wherein - represents a covalent bond, wherein : represents a non-covalent bond, and wherein a-S-b has a length of from 6 nm to 100 nm.

Terms and Expressions as Used Herein

The articles "a" and "an" are used herein to refer to one or to more than one (i.e., to at least one) of the grammatical object of the article. By way of example, "an antibody" means one antibody or more than one antibody.

An "acceptor human framework" is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "affinity" denotes the strength of the sum total of non-covalent interactions between a single binding site of a molecule (e.g. a polypeptide or an antibody) and its binding partner (e.g. a target or an antigen). Unless indicated otherwise, as used herein, "binding affinity" refers to intrinsic binding affinity which reflects a 1:1 interaction between members of a binding pair (e.g. in a polypeptide-polynucleotide-complex, or between a polypeptide and its target, or between an antibody and its antigen). The affinity of a molecule X for its partner Y can generally be represented by the dissociation constant (kD). Affinity can be measured by common methods known in the art, such as surface plasmon resonance and also including those reported herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "caged" denotes that the effector is protected with a protecting group which has a controlled half-life in serum and body fluids. The protecting group can be enzymatically cleaved by endogenous enzymes. The protecting group can be removed, cleaved, degraded, enzymatically digested or metabolized by a second effector which is externally administered by injection or given orally, such as ascorbic acid. The caged effector molecules can be activated by enzymes which are naturally occurring in body fluids. The caged effector moieties can be activated by reducing agents also occurring in body fluids such as ascorbic acid.

The term "effector moiety" denotes any molecule or combination of molecules whose activity it is desired to be delivered (in)to and/or localize at a cell. Effector moieties include, but are not limited to labels, cytotoxins (e.g. *Pseudomonas* exotoxin, ricin, abrin, Diphtheria toxin, and the like), enzymes, growth factors, transcription factors, drugs, radionuclides, ligands, antibodies, liposomes, nanoparticles, viral particles, cytokines, and the like.

The term "HER2" refers to any native HER2 (ErbB2 or p185$^{neu}$) from any vertebrate source, including mammals such as primates (e.g. humans) and rodents (e.g., mice and rats), unless otherwise indicated. The term encompasses "full-length", unprocessed HER2 as well as any form of HER2 that result from processing in the cell. The term also encompasses naturally occurring variants of HER2, e.g., splice variants or allelic variants. Human HER2 protein is reported, for example, in Semba, K., et al., Proc. Natl. Acad. Sci. USA 82 (1985) 6497-6501 and Yamamoto, T., et al., Nature 319 (1986) 230-234 and GenBank accession number X03363. The amino acid sequence of an exemplary HER2 is shown in SEQ ID NO: 20.

The terms "anti-HER2 antibody" and "an antibody that binds to HER2" refer to an antibody that is capable of binding HER2 (ErbB2 or p185$^{neu}$) with sufficient affinity such that the antibody is useful as a diagnostic and/or therapeutic agent in targeting HER2. In one embodiment, the extent of binding of an anti-HER2 antibody to an unrelated, non-HER2 protein is less than about 10% of the binding of the antibody to HER2 as measured, e.g., by a radioimmunoassay (RIA). In certain embodiments, an antibody that binds to HER2 has a dissociation constant (kD) of $10^{-8}$ M or less (in one embodiment of from $10^{-8}$ M to $10^{-13}$ M, in one embodiment of from $10^{-9}$ M to $10^{-13}$ M).

Hudziak, R. M., et al., (Mol. Cell. Biol. 9 (1989) 1165-1172) describe the generation of a panel of anti-HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α (see also U.S. Pat. No. 5,677,171). The anti-HER2 antibodies discussed in Hudziak, R. M., et al. are further characterized in Fendly, B. M., et al. (Cancer Research 50 (1990) 1550-1558), Kotts, C. E., et al. (In Vitro 26 (1990) 59A), Sarup, J. C., et al. (Growth Reg. 1 (1991) 72-82), Shepard, H. M., et al. (J. Clin. Immunol. 11 (1991) 117-127), Kumar, R., et al. (Mol. Cell. Biol. 11 (1991) 979-986), Lewis, G. D., et al. (Cancer Immunol. Immunother. 37 (1993) 255-263), Pietras, R. J., et al. (Oncogene 9 (1994) 1829-1838), Vitetta, E. S., et al. (Cancer Res. 54 (1994) 5301-5309), Sliwkowski, M. X., et al. (J. Biol. Chem. 269 (1994) 14661-14665), Scott, G. K., et al. (J. Biol. Chem. 266 (1991) 14300-14305), D'souza, B., et al. (Proc. Natl. Acad. Sci. USA 91 (1994) 7202-7206), Lewis, G. D., et al. (Cancer Res. 56 (1996) 1457-1465), and Schaefer, G., et al. (Oncogene 15 (1997) 1385-1394).

A recombinant humanized version of the murine anti-HER2 antibody 4D5 (huMAb4D5-8, rhuMab HER2, Trastuzumab or HERCEPTIN®, see U.S. Pat. No. 5,821,337) is clinically active in patients with HER2 overexpressing metastatic breast cancers that have received extensive prior anti-cancer therapy (Baselga, J., et al., J. Clin. Oncol. 14 (1996) 737-744). Humanized anti-HER2 antibodies include huMAb4D5-1, huMAb4D5-2, huMAb4D5-3, huMAb4D5-4, huMAb4D5-5, huMAb4D5-6, huMAb4D5-7, and huMAb4D5-8 (HERCEPTIN®) as described in Table 3 of U.S. Pat. No. 5,821,337 expressly incorporated herein by reference; humanized 520C9 as described in WO 93/21319 and humanized 2C4 antibodies as described in WO 01/000245 expressly incorporated herein by reference.

The anti-HER2 antibody 4D5 comprises a heavy chain variable domain that has the amino acid sequence of SEQ ID NO: 26 which in turn comprises three CDRs determined according to Kabat wherein VH-CDR1 has the amino acid sequence of SEQ ID NO: 27, VH-CDR2 has the amino acid sequence of SEQ ID NO: 28 and VH-CDR3 has the amino acid sequence of SEQ ID NO: 29. The anti-HER2 antibody 4D5 comprises a light chain variable domain that has the amino acid sequence of SEQ ID NO: 30 which in turn comprises three CDRs determined according to Kabat wherein VL-CDR1 has the amino acid sequence of SEQ ID NO: 31, VL-CDR2 has the amino acid sequence of SEQ ID NO: 32 and VL-CDR3 has the amino acid sequence of SEQ ID NO: 33.

Other anti-HER2 antibodies with various properties have been described in Tagliabue, E., et al. (Int. J. Cancer 47 (1991) 933-937), McKenzie, S. J., et al. (Oncogene 4 (1989) 543-548), Maier, L. A., et al. (Cancer Res. 51 (1991) 5361-5369), Bacus, S. S., et al. (Mol. Carcinogen. 3 (1990) 350-362), Stancovski, et al. (Proc. Natl. Acad. Sci. USA 88 (1991) 8691-8695), Bacus, S. S., et al. (Cancer Res. 52 (1992) 2580-2589), Xu, F., et al. (Int. J. Cancer 53 (1993) 401-408, WO 94/00136, Kasprzyk, P. G., et al. (Cancer Res. 52 (1992) 2771-2776), Handcock, M. C., et al. (Cancer Res. 51 (1991) 4575-4580), Shawver, L. K., et al. (Cancer Res. 54 (1994) 1367-1373), Arteaga, C. L., et al. (Cancer Res. 54 (1994) 3758-3765), Harwerth, I. M., et al. (J. Biol. Chem. 267 (1992) 15160-15167), U.S. Pat. No. 5,783,186, and Klapper, L. N., et al. (Oncogene 14 (1997) 2099-2109).

Homology screening has resulted in the identification of two other HER family members: HER3 (U.S. Pat. Nos. 5,183,884, 5,480,968, Kraus, M. H., et al., Proc. Natl. Acad. Sci. USA 86 (1989) 9193-9197) and HER4 (EP 0 599 274, Plowman, G. D., et al., Proc. Natl. Acad. Sci. USA 90 (1993) 1746-1750, Plowman, G. D., et al., Nature 366 (1993) 473-475). Both of these receptors display increased expression on at least some breast cancer cell lines. The HER receptors are generally found in various combinations in cells and heterodimerization is thought to increase the diversity of cellular responses to a variety of HER ligands (Earp, H. S., et al., Breast Cancer Res. Treat. 35 (1995) 115-132).

Epidermal growth factor receptor (EGFR) is bound by six different ligands: epidermal growth factor (EGF), transforming growth factor alpha (TGF-α), amphiregulin, heparin binding epidermal growth factor (HB-EGF), beta-cellulin and epiregulin (Groenen, L. C., et al., Growth Factors 11 (1994) 235-257). A family of heregulin proteins resulting from alternative splicing of a single gene are ligands for HER3 and HER4. The heregulin family includes alpha, beta and gamma heregulins (Holmes, W. E., et al., Science 256 (1992) 1205-1210, U.S. Pat. No. 5,641,869, Schaefer, G., et al., Oncogene 15 (1997) 1385-1394), neu differentiation factors (NDFs), glial growth factors (GGFs), acetylcholine receptor inducing activity (ARIA), and sensory and motor neuron derived factor (SMDF) (see Groenen, L. C., et al., Growth Factors 11 (1994) 235-257, Lemke, G., Mol. Cell. Neurosci. 7 (1996) 247-262, Lee, D. C., et al., Pharm. Rev. 47 (1995) 51-85. Recently three additional HER ligands were identified: neuregulin-2 (NRG-2) which is relied to bind either HER3 or HER4 (Chang, H., et al., Nature 387 (1997) 509-512, Carraway, K. L., et al., Nature 387 (1997) 512-516), neuregulin-3 which binds HER4 (Zhang, D., et al., Proc. Natl. Acad. Sci. USA 94 (1997) 9562-9567), and neuregulin-4 which binds HER4 (Harari, D., et al., Oncogene 18 (1999) 2681-2689). HB-EGF, beta-cellulin and epiregulin also bind to HER4.

While EGF and TGFα do not bind HER2, EGF stimulates EGFR to form a heterodimer with HER2, which results in transphosphorylation of HER2 by EGFR and vice versa in the heterodimer (see Earp, H. S., et al., supra). Likewise, when HER3 is co-expressed with HER2, an active signaling complex is formed and antibodies directed against HER2 are capable of disrupting this complex (Sliwkowski, M. X., et al., J. Biol. Chem. 269 (1994) 14661-14665). Additionally, the affinity of HER3 for heregulin (HRG) is increased to a higher affinity state when co-expressed with HER2 (see also, Levi, A. D., et al., J. Neurosci. 15 (1995) 1329-1340, Morrissey, T. K., et al., Proc. Natl. Acad. Sci. USA 92 (1995) 1431-1435, Lewis, G. D., et al., Cancer Res. 56 (1996) 1457-1465 with respect to the HER2-HER3 protein complex). HER4, like HER3, forms an active signaling complex with HER2 (Carraway, K. L. and Cantley, L. C., Cell 78 (1994) 5-8).

Patent publications related to HER antibodies include U.S. Pat. Nos. 5,677,171, 5,720,937, 5,720,954, 5,725,856, 5,770,195, 5,772,997, 6,165,464, 6,387,371, 6,399,063, US 2002/0192211, U.S. Pat. Nos. 6,015,567, 6,333,169, 4,968, 603, 5,821,337, 6,054,297, 6,407,213, 6,719,971, 6,800,738, US 2004/0236078, U.S. Pat. Nos. 5,648,237, 6,267,958, 6,685,940, 6,821,515, WO 98/17797, U.S. Pat. Nos. 6,127, 526, 6,333,398, 6,797,814, 6,339,142, 6,417,335, 6,489,447, WO 99/31140, US 2003/0147884, US 2003/0170234, US 2005/0002928, U.S. Pat. No. 6,573,043, US 2003/0152987, WO 99/48527, US 2002/0141993, WO 01/000245, US 2003/0086924, US 2004/0013667, WO 00/69460, WO 01/00238, WO 01/15730, U.S. Pat. Nos. 6,627,196, 6,632, 979, WO 01/00244, US 2002/0090662, WO 01/89566, US 2002/0064785, US 2003/0134344, WO 2004/24866, US 2004/0082047, US 2003/0175845, WO 03/087131, US 2003/0228663, WO 2004/008099, US 2004/0106161, WO 2004/048525, US 2004/0258685, U.S. Pat. Nos. 5,985,553, 5,747,261, 4,935,341, 5,401,638, 5,604,107, WO 87/07646, WO 89/10412, WO 91/05264, EP 0 412 116, EP 0 494 135, U.S. Pat. No. 5,824,311, EP 0 444 181, EP 1 006 194, US 2002/0155527, WO 91/02062, U.S. Pat. Nos. 5,571,894, 5,939,531, EP 0 502 812, WO 93/03741, EP 0 554 441, EP 0 656 367, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028,059, WO 96/07321, U.S. Pat. Nos. 5,804,396, 5,846,749, EP 0 711 565, WO 96/16673, U.S. Pat. Nos. 5,783,404, 5,977,322, 6,512,097, WO 97/00271, U.S. Pat. Nos. 6,270,765, 6,395, 272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922, 845, WO 98/18489, WO 98/33914, U.S. Pat. No. 5,994,071, WO 98/45479, U.S. Pat. No. 6,358,682, US 2003/0059790, WO 99/55367, WO 01/20033, US 2002/0076695, WO 00/78347, WO 01/09187, WO 01/21192, WO 01/32155, WO 01/53354, WO 01/56604, WO 01/76630, WO 02/05791, WO 02/11677, U.S. Pat. No. 6,582,919, US 2002/0192652, US 2003/0211530, WO 02/44413, US 2002/ 0142328, U.S. Pat. No. 6,602,670, WO 02/45653, WO 02/055106, US 2003/0152572, US 2003/0165840, WO 02/087619, WO 03/006509, WO 03/012072, WO 03/028638, US 2003/0068318, WO 03/041736, EP 1 357 132, US 2003/0202973, US 2004/0138160, U.S. Pat. Nos. 5,705,157, 6,123,939, EP 0 616 812, US 2003/0103973, US 2003/0108545, U.S. Pat. No. 6,403,630, WO 00/61145, WO 00/61185, U.S. Pat. No. 6,333,348, WO 01/05425, WO 01/64246, US 2003/0022918, US 2002/0051785, U.S. Pat. No. 6,767,541, WO 01/76586, US 2003/0144252, WO 01/87336, US 2002/0031515, WO 01/87334, WO 02/05791, WO 02/09754, US 2003/0157097, US 2002/0076408, WO 02/055106, WO 02/070008, WO 02/089842, WO 03/86467.

In one embodiment the complex as reported herein is a HER dimerization inhibitor and inhibits the heterodimerization of HER2 with EGFR, or HER3, or HER4. In one embodiment the complex is a HER dimerization inhibitor and comprises a fragment of the anti-HER2 antibody 4D5 and/or the anti-HER2 antibody 2C4. Herein the antibody 2C4 and in particular the humanized variant thereof (see WO 01/00245; produced by the hybridoma cell line deposited with the American Type Culture Collection, Manassass, Va., USA under ATCC HB-12697) is an antibody, which binds to a region in the extracellular domain of HER2 (e.g. anyone or more residues in the region from about residue 22 to about residue 584 of HER2, inclusive). Examples of humanized 2C4 antibodies are provided in Example 3 of WO 01/00245 (incorporated herein by reference in its entirety). The humanized anti-HER2 antibody 2C4 is also called Pertuzumab.

Pertuzumab (formerly 2C4) is the first of a new class of agents known as HER dimerization inhibitors (HDIs). Pertuzumab binds to HER2 at its dimerization domain, thereby inhibiting its ability to form active dimer receptor complexes and thus blocking the downstream signal cascade that ultimately results in cell growth and division (see Franklin, M. C., Cancer Cell 5 (2004) 317-328). Pertuzumab is a fully humanized recombinant monoclonal antibody directed against the extracellular domain of HER2. Binding of Pertuzumab to the HER2 on human epithelial cells prevents HER2 from forming complexes with other members of the HER family (including EGFR, HER3, HER4) and probably also HER2 homodimerization. By blocking complex formation, Pertuzumab prevents the growth stimulatory effects and cell survival signals activated by ligands of HER1, HER3 and HER4 (e.g. EGF, TGFα, amphiregulin, and the heregulins). Pertuzumab is a fully humanized recombinant monoclonal antibody based on the human IgG1(K) framework sequences. The structure of Pertuzumab consists of two heavy chains (449 residues) and two light chains (214 residues). Compared to Trastuzumab (Herceptin®), Pertuzumab has 12 amino acid differences in the light chain and 29 amino acid differences in the IgG1 heavy chain.

The anti-HER2 antibody 2C4 comprises a heavy chain variable domain that has the amino acid sequence of SEQ ID NO: 34 which in turn comprises three CDRs determined according to Kabat wherein VH-CDR1 has the amino acid sequence of SEQ ID NO: 35, VH-CDR2 has the amino acid sequence of SEQ ID NO: 36 and VH-CDR3 has the amino acid sequence of SEQ ID NO: 37. The anti-HER2 antibody 2C4 comprises a light chain variable domain that has the amino acid sequence of SEQ ID NO: 38 which in turn comprises three CDRs determined according to Kabat wherein VL-CDR1 has the amino acid sequence of SEQ ID NO: 39, VL-CDR2 has the amino acid sequence of SEQ ID NO: 40 and VL-CDR3 has the amino acid sequence of SEQ ID NO: 41.

Trastuzumab is indicated for the treatment of patients with metastatic breast cancer whose tumors overexpress HER2 or have HER2 gene amplification as monotherapy for the treatment of those patients who have received at least two chemotherapy regimens for their metastatic disease; prior chemotherapy must have included at least an anthracycline and a taxane unless patients are unsuitable for these treatments; hormone receptor positive patients must also have received hormonal therapy, unless patients are unsuitable for these treatments, in combination with paclitaxel for the treatment of those patients who have not received chemotherapy for their metastatic disease and for whom an anthracycline is not suitable, and in combination with docetaxel for the treatment of those patients who have not received chemotherapy for their metastatic disease.

In the art, the treatment of breast cancer patients with Herceptin/Trastuzumab is, for example, recommended and routine for patients having HER2-positive disease. HER2-positive disease is present if a high HER2 (protein) expression level detected by immunohistochemical methods (e.g. HER2 (+++)) or HER2 gene amplification (e.g. a HER2 gene copy number higher than 4 copies of the HER2 gene per tumor cell) or both is found in samples obtained from the patients such as breast tissue biopsies or breast tissue resections or in tissue derived from metastatic sites.

The "epitope 2C4" is the region in the extracellular domain of ErbB2 to which the anti-HER2 antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of ErbB2 (e.g. anyone or more residues in the region from about residue 22 to about residue 584 of ErbB2, inclusive).

The "epitope 4D5" is the region in the extracellular domain of ErbB2 to which the anti-HER2 antibody 4D5 (ATCC CRL 10463) binds. This epitope is close to the transmembrane domain of ErbB2. To screen for antibodies which bind to the 4D5 epitope, a routine cross-blocking assay such as that described in Antibodies. A Laboratory Manual, Cold Spring Harbor Laboratory, Ed Harlow and David Lane (1988), can be performed. Alternatively, epitope mapping can be performed to assess whether the antibody binds to the 4D5 epitope of ErbB2 (e.g. anyone or more residues in the region from about residue 529 to about residue 625, inclusive).

An antibody which "blocks" ligand activation of an ErbB receptor is one which reduces or prevents such activation, wherein the antibody is able to block ligand activation of the ErbB receptor substantially more effectively than monoclonal antibody 4D5, e.g. about as effectively as monoclonal antibodies 7F3 or 2C4 or FAB fragments thereof and especially about as effectively as monoclonal antibody 2C4 or a FAB fragment thereof. For example, the antibody that blocks ligand activation of an ErbB receptor may be one which is about 50-100% more effective than 4D5 at blocking formation of an ErbB hetero-oligomer. Blocking of ligand activation of an ErbB receptor can occur by any means, e.g. by interfering with ligand binding to an ErbB receptor, ErbB complex formation, tyrosine kinase activity of an ErbB receptor in an ErbB complex, and/or phosphorylation of tyrosine kinase residue(s) in or by an ErbB receptor. Examples of antibodies which block ligand activation of an ErbB receptor include monoclonal antibodies 2C4 and 7F3 (which block HRG activation of ErbB2/ErbB3 and ErbB2/ErbB4 hetero-oligomers, and EGF, TGF-α, amphiregulin, HB-EGF and/or epiregulin activation of an EGFR/ErbB2 hetero-oligomer), and L26, L96 and L288 antibodies (Klapper, L. N., et al., Oncogene 14 (1997) 2099-2109), which block EGF and NDF binding to T47D cells which express EGFR, ErbB2, ErbB3 and ErbB4.

An "ErbB hetero-oligomer" denotes a non-covalently associated oligomer comprising at least two different ErbB receptors. Such complexes may form when a cell expressing two or more ErbB receptors is exposed to an ErbB ligand and can be isolated by immunoprecipitation and analyzed by SDS-PAGE as described in Sliwkowski, M. X., et al., J. Biol. Chem. 269 (1994) 14661-14665, for example. Examples of such ErbB hetero-oligomers include EGFR-ErbB2, ErbB2-ErbB3 and ErbB3-ErbB4 complexes. Moreover, the ErbB hetero-oligomer may comprise two or more ErbB2 receptors combined with a different ErbB receptor, such as ErbB3, ErbB4 or EGFR. Other proteins, such as a cytokine receptor subunit (e.g. gp130) may be included in the hetero-oligomer.

By "ligand activation of an ErbB receptor" is meant signal transduction (e.g. that caused by an intracellular kinase domain of an ErbB receptor phosphorylating tyrosine residues in the ErbB receptor or a substrate polypeptide) mediated by ErbB ligand binding to an ErbB hetero-oligomer comprising the ErbB receptor of interest. Generally, this will involve binding of an ErbB ligand to an ErbB hetero-oligomer which activates a kinase domain of one or more of the ErbB receptors in the hetero-oligomer and thereby results in phosphorylation of tyrosine residues in one or more of the ErbB receptors and/or phosphorylation of tyrosine residues in additional substrate polypeptides(s). ErbB receptor activation can be quantified using various tyrosine phosphorylation assays.

The term "antibody" herein is used in the broadest sense and encompasses various antibody structures, including but not limited to monoclonal antibodies and antibody fragments so long as they exhibit the desired antigen-binding activity.

The term "antibody fragment" denotes a fragment of a complete or full length antibody that retains the ability to specifically bind to an antigen. Examples of antibody fragments include but are not limited to Fv, FAB, FAB', FAB'-SH, F(ab')2; diabodies; linear antibodies; single-chain antibody molecules (e.g. scFv). For a review of certain antibody fragments, see Hudson, P. J., et al., Nat. Med. 9 (2003) 129-134. In more detail encompassed within the term "antibody fragment" is (i) a FAB fragment, i.e. a monovalent antibody fragment consisting of the VL, VH, CL and CH1 domains (for discussion of FAB and F(ab')2 fragments comprising salvage receptor binding epitope residues and having increased in vivo half-life, see U.S. Pat. No. 5,869,046), (ii) a F(ab')2 fragment, i.e. a bivalent fragment comprising two FAB fragments linked by a disulfide bridge at the hinge region, (iii) a Fd fragment consisting of the VH and CH1 domains, (iv) a Fv fragment consisting of the VL and VH domains of a single arm of an antibody (see, e.g., Plueckthun, in The Pharmacology of Monoclonal Antibodies, vol. 113, Rosenburg and Moore (eds.), (Springer-Verlag, New York), (1994) pp. 269-315, WO 93/16185, U.S. Pat. Nos. 5,571,894, 5,587,458), (v) a dAb fragment (see e.g. Ward, E. S., et al., Nature 341 (1989) 544-546), which consists of a VH domain, and (vi) an isolated complementarity determining region (CDR). Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv), see e.g., Bird, R. E., et al., Science 242 (1988) 423-426; Huston, J. S., et al., Proc. Natl. Acad. Sci. USA 85 (1988) 5879-5883). These antibody fragments can be obtained using conventional techniques known to those with skill in the art and can be screened for their binding properties in the same manner as are intact antibodies.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamylamines including altretamine, triethylenemelamine, trietylenephosphoramide, triethylenethiophosphoramide and trimethylomelamine; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitroureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-II; 35 topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

An "anti-angiogenic agent" refers to a compound which blocks, or interferes with to some degree, the development of blood vessels. The anti-angiogenic agent may, for instance, be a small molecule or an antibody that binds to a growth factor or growth factor receptor involved in promoting angiogenesis. The anti-angiogenic factor is in one embodiment an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and -P; mullerian-inhibiting substance; mouse gonadotropin-associated peptide; inhibin; activin; vascular endothelial growth factor; integrin; thrombopoietin (TPO); nerve growth factors such as NGF-p; platelet growth factor; transforming growth factors (TGFs) such as TGF-a and TGF-p; insulin-like growth factor-I and -II; erythropoietin (EPO); osteoinductive factors; interferons such as interferon-a, -P, and -y; colony stimulating factors (CSFs) such as macrophage-CSF (M-CSF); granulocyte-macrophage-CSF (GM-CSF); and granulocyte-CSF (GCSF); interleukins (ILs) such as IL-I, IL-la, IL-2, IL-3, IL-4, IL-5, IL-6, IL-7, IL-8, IL-9, IL-IO, IL-II, IL-12; a tumor necrosis factor such as TNF-αt or TNF-P; and other polypeptide factors including LIF and kit ligand (KL). As used herein, the term cytokine includes proteins from natural sources or from recombinant cell culture and biologically active equivalents of the native sequence cytokines.

The term "fMLP" denotes the tripeptide consisting of N-formylmethionine, leucine and phenylalanine. In one embodiment the effector moiety is fMLP or a derivative thereof.

The term "prodrug" refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, Vol. 14, 615th Meeting Belfast (1986) pp. 375-382 and Stella, et al., "Prodrugs: A Chemical Approach to Targeted Drug Delivery", Directed Drug Delivery, Borchardt, et al., (eds.), pp. 247-267, Humana Press (1985). The prodrugs that can be used as effector moiety include, but are not limited to, phosphate-containing prodrugs, thiophosphate-containing prodrugs, sulfate-containing prodrugs, peptide-containing prodrugs, D-amino acid-modified prodrugs, glycosylated prodrugs, b-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described herein.

The term "cytotoxic moiety" refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

An "effective amount" of an agent, e.g., a pharmaceutical formulation, refers to an amount effective, at dosages and for periods of time necessary, to achieve the desired therapeutic or prophylactic result.

The term "Fc region" is used herein to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, Md. (1991).

The term "framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L 1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc region as defined herein. Such an antibody generally comprises two heavy chains and two light chains.

A "human antibody" is an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g. CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (see Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (see Kabat, et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues" or "SDRs," which are residues that contact the antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

An "immunoconjugate" is an antibody or antibody fragment conjugated to one or more non-antibody derived molecules, including but not limited to a member of a binding pair, a nucleic acid, or an effector moiety.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "monoclonal antibody" refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies or monoclonal antibody fragments to be used in the complex as reported herein may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "monovalent binding polypeptide" or "monovalent binding antibody fragment" denotes a molecule that has only a single site or region for binding to its target or antigen. Examples of monovalent binding polypeptides are peptides, peptide mimetics, aptamers, small organic molecules (inhibitors capable of specific binding to a target polypeptide), darpins, ankyrin repeat proteins, Kunitz type domain, single domain antibodies (see: Hey, T., et al., Trends Biotechnol. 23 (2005) 514-522), (natural) ligands of a cell surface receptor, monovalent fragments of full length antibodies, and the like. For example a full length antibody has two bindings sites for its target and is, thus, bivalent, where as a scFv or FAB' antibody fragment has only one binding site for its target and is, thus, monovalent. In case monovalent antibodies or antibody fragments are used as a polypeptide this site is called the paratope.

A "naked antibody" or "naked antibody fragment" refers to an antibody or antibody fragment that is not conjugated to a non-antibody moiety (e.g. a nucleic acid, or a cytotoxic moiety, or radiolabel).

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "polynucleotide" or "nucleic acid sequence" denotes a short, generally single stranded, polynucleotides that comprise at least 8 nucleotides and at most about 1000 nucleotides. In one embodiment a polynucleotide has a length of at least 9, or 10, or 11, or 12, or 15, or 18, or 21, or 24, or 27, or 30 nucleotides. In one embodiment a polynucleotide has a length of no more than 200, or 150, or 100, or 90, or 80, or 70, or 60, or 50, or 45, or 40, or 35, or 30 nucleotides. In a further embodiment a polynucleotide has a length of at least 9, or 10, or 11, or 12, or 15, or 18, or 21, or 24, or 27, or 30 nucleotides and of no more than 200, or 150, or 100, or 90, or 80, or 70, or 60, or 50, or 45, or 40, or 35, or 30 nucleotides.

The term "L-polynucleotide" denotes a nucleic acid that comprises more than 50% L-nucleotides as monomeric building blocks, such as L-DNA. In one embodiment an L-polynucleotide comprises only L-nucleotides. The number of nucleotides of such a L-polynucleotides it is to be understood to range from one L-nucleotide to any number. However, in one embodiment the number or L-nucleotides is at least 10, or 15, or 20, or 25, or 30, or 35, or 40, or 45, or 50, or 55, or 60, or 70, or 80, or 90, or 100 nucleotides. The L-polynucleotides are made of L-A, L-G, L-C, L-U, L-T and combinations thereof, whereby L-A denotes L-ribose-adenine etc. The L-polydeoxynucleotides are made of L-dA, L-dG, L-dC, L-dU, L-dT and combinations thereof, whereby L-dA denotes L-deoxyribose-adenine etc.

The term "polynucleotide linker" denotes a moiety linking two nucleotide sequences together. In one embodiment the polynucleotide linker is a polynucleotide. In one embodiment the polynucleotide linker comprises at least one polynucleotide and at least one non-polynucleotide. The non-polynucleotide can be a polypeptide, a polymer, or a polysaccharide. In one embodiment the polynucleotide linker comprises a polynucleotide of from 10 to 30 nucleotides in length and a linear poly (ethylene glycol).

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

A "polypeptide epitope" denotes the binding site on a polypeptidic target bound by a corresponding monovalent binding polypeptide. It is generally composed of amino acids. The binding polypeptide either binds to a linear epitope, i.e. an epitope consisting of a stretch of 5 to 12 consecutive amino acids, or the binding polypeptide binds to a three-dimensional structure formed by the spatial arrangement of several short stretches of the polypeptidic target. Three-dimensional epitopes recognized by a binding polypeptide, e.g. by the antigen recognition site or paratope of an antibody or antibody fragment, can be thought of as three-dimensional surface features of an antigen molecule. These features fit precisely (in)to the corresponding binding site of the binding polypeptide and thereby binding between the binding polypeptide and its target is facilitated.

The term "specifically binding" denotes that the polypeptide or antibody or antibody fragments binds to its target with an dissociation constant (KD) of $10^{-8}$ M or less, in one embodiment of from $10^{-8}$ M to $10^{-13}$ M, in one embodiment of from $10^{-9}$ M to $10^{-13}$ M. The term is further used to indicate that the polypeptide does not specifically bind to other biomolecules present, i.e. it binds to other biomolecules with a dissociation constant (KD) of $10^{-6}$ M or more, in one embodiment of from $10^{-6}$ M to 1 M.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, complexes as reported herein are used to delay development of a disease or to slow the progression of a disease.

The term "variable region" or "variable domain" refers to the domain of an antibody heavy or light chain that is involved in binding the antibody to its antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, et al., Kuby Immunology, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887, Clarckson, T., et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Polypeptide-Polynucleotide-Complex

Herein is reported a complex for the delivery of one or more effector moieties to a target, whereby the complex comprises at least two components that are connected by a non-covalent interaction, whereby the components are more resistant to proteolytic and enzymatic degradation in vivo than isolated RNA or DNA, especially D-DNA. The complex has a high affinity for its target and has a good solubility.

It has been found that a complex comprising a mixture of polypeptidic and polynucleotidic parts, especially L-polynucleotidic parts, fulfills these requirements and is especially suited for the delivery of an effector moiety in vivo.

The complex as reported herein can e.g. be used to bind an analyte in an immunoassay. If e.g. an analyte has at least two non-overlapping epitopes the complex as reported herein comprises a linker polynucleotide and two polypeptide that specifically bind to the non-overlapping epitopes and it is constructed such that the linker polynucleotide has the optimal length for synergistic binding of the polypeptides specifically binding to these epitopes. This can e.g. be of great utility in a method for the detection of an analyte employing such a complex.

Thus, one aspect as reported herein is the use of a complex as reported herein in the detection of an analyte of interest in a sample. In certain embodiments the detection method used is an enzyme-linked immunosorbent assay (ELISA), a direct, indirect, competitive, or sandwich immunoassay employing any appropriate way of signal detection, e.g. electrochemiluminescense, or the complexes used in immunohistochemistry.

One aspect as reported herein is a polypeptide-polynucleotide-complex of the formula:

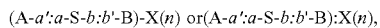

(A-a':a-S-b:b'-B)-X(n) or(A-a':a-S-b:b'-B):X(n), wherein A as well as B is a polypeptide that specifically binds to a target,
wherein a':a as well as b:b' is a binding pair, wherein a' and a and do not interfere with the binding of b to b' and vice versa,
wherein S is a linker polynucleotide,
wherein (: X) denotes an effector moiety bound either covalently or via a binding pair to at least one of a', a, b, b' or S,
wherein (n) is an integer,
wherein - represents a covalent bond, and
wherein : represents a non-covalent bond.

Also reported herein as an aspect is a method for producing a polypeptide-polynucleotide-complex of the formula:

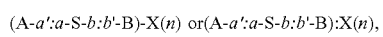
(A-a':a-S-b:b'-B)-X(n) or(A-a':a-S-b:b'-B):X(n), as outlined above comprising the steps of:
a) synthesizing A-a' and b'-B, respectively,
b) synthesizing the linker a-S-b, and
c) forming the complex of the formula,
wherein the effector moiety X is bound to at least one of a', a, b, b' or S in step a), b), or c).

Based on its individual components the complex as reported herein can be obtained according to standard procedures by hybridization between the members of the binding pair conjugated to the individual components of the complex.

In order to obtain a complex with 1:1:1 stoichiometry the complex can be separated by chromatography from other conjugation side-products. This procedure can be facilitated by using a dye labeled binding pair member and/or a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from non-bound components, like a labeled monovalent binder.

One aspect as reported herein is reported a method of producing a polypeptide-polynucleotide-complex comprising the components
a) a polypeptide that specifically binds to a target and that is conjugated to a first member of a binding pair,
b) a polynucleotide linker conjugated at its first terminus to the second member of the binding pair, and
c) an effector moiety conjugated to a polynucleotide that is complementary to at least a part of the polynucleotide linker,
comprising the steps of: a) synthesizing i) the polypeptide specifically binding to a target and conjugated to a first member of a binding pair and ii) an effector moiety conjugated to a polynucleotide that is complementary to at least a part of the polynucleotide linker, respectively, b) synthesizing the polynucleotide linker conjugated at its first terminus to the second member of the binding pair, and c) forming the polypeptide-polynucleotide-complex by hybridizing the synthesized components.

Another aspect as reported herein is a method of producing a polypeptide-polynucleotide-complex comprising the components
a) a first polypeptide that specifically binds to a first target which is conjugated to a first member of a first binding pair,
b) a second polypeptide that specifically binds to a second target which is conjugated to a first member of a second binding pair, and
c) a polynucleotide linker conjugated at its first terminus to the second member of the first binding pair and conjugated at its second terminus to the second member of the second binding pair,
comprising the steps of: a) synthesizing the first polypeptide specifically binding to a first target which is conjugated to a first member of a first binding pair, and the second polypeptide specifically binding to a second target which is conjugated to a first member of a second binding pair, respectively, and b) synthesizing the polynucleotide linker conjugated at its first terminus to the second member of the first binding pair and conjugated at its second terminus to the second member of the second binding pair, and c) forming the polypeptide-polynucleotide-complex by hybridizing the synthesized components.

The complex can additionally contain one or several counter ions Y to equalize the charge. Examples of suitable negatively charged counter ions are halogenides, $OH^-$, carbonate, alkylcarboxylate, e.g. trifluoroacetate, sulphate, hexafluorophosphate and tetrafluoroborate groups. Hexafluorophosphate, trifluoroacetate and tetrafluoroborate groups are especially suited. Other suited positively charged counter ions are monovalent cations such as alkaline metal ions and/or ammonium ions.

A full library of complexes as reported herein can easily be provided, analyzed and a suitable binding agent out of such library can be produced at large scale, as required.

The library refers to a set of complexes as reported herein, wherein each of the polypeptides and the binding pair members are identical and wherein the length of the polynucleotide linker is adjusted to best meet the requirements set out for the binding agent. It is easily possible to first use a polynucleotide linker ladder spanning the whole spectrum of 1 nm to 100 nm and having steps that are about 10 nm apart. The linker length is then again easily further refined around the most appropriate length identified in the first round.

Herein is also reported a method for the selection of a polypeptide-polynucleotide-complex from a library comprising a multitude of complexes with different polynucleotide linker length. In one embodiment of this method several linker molecules with polynucleotide linkers of various lengths are synthesized and used in the formation of a complex as reported herein comprising polynucleotide linkers of variable length and those complexes are selected having an improvement in the $K_{diss}$ of at least 5-fold over the better of the two monovalent polypeptide binders. Selection of a bivalent binding agent with the desired $K_{diss}$ in one embodiment is performed by BIAcore-analysis as disclosed in the Examples.

One aspect as reported herein is a complex comprising
a) a polypeptide that specifically binds to a first target and that is conjugated to a first single stranded L-DNA moiety,
b) a second polypeptide that specifically binds to a second target and that is conjugated to a second single stranded L-DNA moiety, and
c) a linker that comprises at its first (or 3') terminus a first single stranded L-DNA linker moiety that is complementary to the first single stranded L-DNA moiety and that comprises at its second (or 5') terminus a second single stranded L-DNA linker moiety that is complementary to the second single stranded L-DNA moiety.

One aspect as reported herein is a complex comprising
a) an antibody FAB fragment or a scFv that specifically binds to a first target and that is conjugated to a first single stranded L-DNA moiety, b) an antibody FAB fragment or a scFv that specifically binds to a second target and that is conjugated to a second single stranded L-DNA moiety, and
c) a linker that comprises at its first (or 3') terminus a first single stranded L-DNA linker moiety that is complementary to the first single stranded L-DNA moiety and that comprises at its second (or 5') terminus a second single stranded L-DNA linker moiety that is complementary to the second single stranded L-DNA moiety.

The first single stranded L-DNA moiety does not hybridize with the second single stranded L-DNA moiety and does not hybridize with the second single stranded L-DNA linker moiety. In turn, the second single stranded L-DNA moiety does not hybridize with the first single stranded L-DNA moiety and does not hybridize with the first single stranded L-DNA linker moiety.

In the following embodiments of all aspects as presented herein are given: In one embodiment the polypeptide that specifically binds to a target is an antibody or antibody fragment. In one embodiment the antibody fragment is a FAB.

In one embodiment the first and/or second single stranded L-DNA moiety has a length of from 10 to 50 nucleotides. In one embodiment the length is of from 15 to 35 nucleotides. In one embodiment the length is of from 20 to 30 nucleotides.

In one embodiment the linker comprises a first single stranded L-DNA linker moiety, a second single stranded L-DNA linker moiety, and a single stranded docking moiety. In one embodiment the linker further comprises a linear non-nucleotide moiety. In one embodiment the linear non-nucleotide moiety is a polypeptide or a non-ionic polymer. In one embodiment the non-ionic polymer is linear poly (ethylene glycol). In one embodiment the linear poly (ethylene glycol) comprises of from 1 to 100 ethylene glycol units. In one embodiment the linear poly (ethylene glycol) comprises of from 1 to 50 ethylene glycol units. In one embodiment the linear poly (ethylene glycol) comprises of from 1 to 25 ethylene glycol units.

In one embodiment the complex comprises
a) a polypeptide that specifically binds to a first target and that is conjugated to a first single stranded L-DNA moiety,
b) a polypeptide that specifically binds to a second target and that is conjugated to a second single stranded L-DNA moiety, and
c) a linker that comprises at its first (or 3') terminus a first single stranded L-DNA linker moiety that is complementary to the first single stranded L-DNA moiety, that comprises at its second (or 5') terminus a second single stranded L-DNA linker moiety that is complementary to the second single stranded L-DNA moiety, and that comprises a third single stranded L-DNA linker moiety between the first and second single stranded L-DNA moieties.

In one embodiment the linker comprises in 3' to 5' orientation
a first single stranded L-DNA linker moiety that is complementary to the first single stranded L-DNA moiety,
a docking single stranded L-DNA moiety, and
a second single stranded L-DNA linker moiety that is complementary to the second single stranded L-DNA moiety.

The docking single stranded L-DNA moiety does not hybridize with the first single stranded L-DNA moiety or its complementary first single stranded linker moiety and it does not hybridize with the second single stranded L-DNA moiety or its complementary second single stranded L-DNA linker moiety.

In one embodiment the linker comprises in 3' to 5' orientation
a first single stranded L-DNA linker moiety that is complementary to the first single stranded L-DNA moiety,
a linear non-nucleotide moiety,
a docking single stranded L-DNA moiety, and
a second single stranded L-DNA linker moiety that is complementary to the second single stranded L-DNA moiety.

In one embodiment the linker comprises in 3' to 5' orientation
a first single stranded L-DNA linker moiety that is complementary to the first single stranded L-DNA moiety,
a docking single stranded L-DNA moiety,
a non-nucleotide moiety, and
a second single stranded L-DNA linker moiety that is complementary to the second single stranded L-DNA moiety.

In one embodiment the linker comprises in 3' to 5' orientation
a first single stranded L-DNA linker moiety that is complementary to the first single stranded L-DNA moiety,
a non-nucleotide moiety,
a docking single stranded L-DNA moiety, and
a second single stranded L-DNA linker moiety that is complementary to the second single stranded L-DNA moiety.

In one embodiment the linker comprises in 3' to 5' orientation
a first single stranded L-DNA linker moiety that is complementary to the first single stranded L-DNA moiety,
a first non-nucleotide moiety,
a docking single stranded L-DNA moiety,
a second non-nucleotide moiety,
a second single stranded L-DNA linker moiety that is complementary to the second single stranded L-DNA moiety.

In one embodiment the first non-nucleotide moiety and the second non-nucleotide moiety are the same or different. In one embodiment the linear non-nucleotide moiety is a polypeptide or a non-ionic polymer. In one embodiment the non-ionic polymer is linear poly (ethylene glycol). In one embodiment the linear poly (ethylene glycol) comprises of from 1 to 100 ethylene glycol units. In one embodiment the linear poly (ethylene glycol) comprises of from 1 to 50 ethylene glycol units. In one embodiment the linear poly (ethylene glycol) comprises of from 1 to 25 ethylene glycol units.

The Polypeptide Component

Monoclonal antibody techniques allow for the production of specifically binding agents in the form of specifically binding monoclonal antibodies or fragments thereof. For creating monoclonal antibodies, or fragments thereof, techniques such as immunizing mice, rabbits, hamsters, or any other mammal with a polypeptide, i.e. the target of the antibody, or/and nucleic acid encoding the polypeptide can be used. Alternatively monoclonal antibodies, or fragments thereof, can be obtained by the use of phage libraries of scFv (single chain variable region), specifically human scFv (see e.g. U.S. Pat. No. 5,885,793, WO 92/01047, WO 99/06587).

In one embodiment the polypeptide that specifically binds to a target is a monovalent antibody fragment. In one embodiment the monovalent antibody fragment is derived from a monoclonal antibody.

Monovalent antibody fragments include, but are not limited to FAB, FAB'-SH, single domain antibody, F(ab')2, Fv, and scFv fragments. Thus, in one embodiment the monovalent antibody fragment is selected from the group comprising FAB, FAB'-SH, single domain antibody, F(ab')2, Fv, and scFv fragments.

In one embodiment at least one of the polypeptides of the complex as reported herein is a single domain antibody, or a FAB-fragment, or a FAB'-fragment of a monoclonal antibody.

In one embodiment both of the polypeptides of the complex as reported herein are independently of each other a single domain antibody, or a FAB-fragment, or a FAB'-fragment of a monoclonal antibody.

In one embodiment both of the polypeptides of the complex as reported herein are single domain antibodies, or FAB-fragments, or FAB'-fragments.

In one embodiment the targets or epitopes specifically bound by the polypeptides or monovalent binding polypeptides do not overlap.

Diabodies are antibody fragments with two antigen-binding sites that may be bivalent or bispecific (see e.g. EP 0 404 097, WO 93/01161, Hudson, P. J., et al., Nat. Med. 9 (2003) 129-134, and Holliger, P., et al., Proc. Natl. Acad. Sci. USA 90 (1993) 6444-6448). Triabodies and tetrabodies are also described in Hudson, P. J., et al., Nat. Med. 9 (2003) 129-134.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; U.S. Pat. No. 6,248,516).

An Fv is a minimum antibody fragment that contains a complete antigen-binding site and is devoid of constant region. For a review of scFv, see, e.g., Plueckthun, in The Pharmacology of Monoclonal Antibodies, vol. 113, Rosenburg and Moore (eds.), (Springer-Verlag, New York, 1994), pp. 269-315, WO 93/16185, U.S. Pat. Nos. 5,571,894, 5,587,458. Generally, six hyper variable regions (HVRs) confer antigen-binding specificity to an antibody. However, even a single variable domain (or half of an Fv comprising only three HVRs specific for an antigen) has the ability to recognize and bind its antigen.

In one embodiment the monovalent antibody fragments is a two-chain Fv species consisting of a dimer of one heavy- and one light-chain variable domain in tight, non-covalent association.

In one embodiment the monovalent antibody fragments is a single-chain Fv (scFv) species consisting of one heavy-chain and one light-chain variable domain covalently linked by a flexible peptide linker.

A FAB fragment of an antibody contains the heavy-chain and light-chain variable domains as well as the constant domain of the light chain and the first constant domain (CH1) of the heavy chain.

A FAB' fragments differ from a FAB fragment by the addition of a few residues at the carboxy terminus of the heavy chain CH1 domain including one or more cysteines from the antibody hinge region.

FAB'-SH denotes a FAB' in which the cysteine residue(s) of the constant domains bear a free thiol group.

Various techniques have been developed for the production of antibody fragments. Traditionally, antibody fragments can be obtained via proteolytic digestion of full length antibodies (see, e.g., Morimoto, K., et al., J. Biochem. Biophys. Meth. 24 (1992) 107-117, Brennan, M., et al., Science 229 (1985) 81-83). For example, papain digestion of full length antibodies results in two identical antigen-binding fragments, called "FAB" fragments, each with a single antigen-binding site, and a residual "Fc" fragment, whose name reflects its ability to crystallize readily. For a review of certain antibody fragments, see Hudson, P. J., et al., Nat. Med. 9 (2003) 129-134.

Antibody fragments can also be produced directly by recombinant means. FAB, Fv and scFv antibody fragments can all be expressed in and secreted from e.g. *E. coli*, thus, allowing the facile production of large amounts of these fragments. Antibody fragments can be isolated from antibody phage libraries according to standard procedures. Alternatively, FAB'-SH fragments can be directly recovered from *E. coli*. (Carter, P., et al., Bio/Technology 10 (1992) 163-167). Mammalian cell systems can be also used to express and, if desired, secrete antibody fragments.

In one embodiment the polypeptide that specifically binds to an antigen is a single-domain antibody. In a certain embodiment a single-domain antibody is a human single-domain antibody (see, e.g., U.S. Pat. No. 6,248,516). In one embodiment a single-domain antibody consists of all or a portion of the heavy chain variable domain of an antibody.

A single-domain antibody is a single polypeptide chain comprising all or a portion of the heavy chain variable domain or all or a portion of the light chain variable domain of an antibody.

In certain embodiments, the polypeptide binds to its target with a dissociation constant (KD) of $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M).

In one embodiment in which the polypeptide is an antibody or an antibody fragment, the dissociation constant is determined by a radiolabeled antigen binding assay (RIA) performed with the FAB fragment of the antibody and its antigen as described by the following assay.

Solution binding affinity of FABs for antigen is measured by equilibrating FAB with a minimal concentration of ($^{125}$I)-labeled antigen in the presence of a titration series of unlabeled antigen, then capturing bound antigen with an anti-FAB antibody-coated plate (see, e.g., Chen, Y., et al., J. Mol. Biol. 293 (1999) 865-881). To establish conditions for the assay, MICROTITER® multi-well plates (Thermo Scientific) are coated overnight with 5 μg/ml of a capturing anti-FAB antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a FAB of interest (e.g., consistent with assessment of the anti-VEGF antibody, FAB-12, in Presta, L. G., et al., Cancer Res. 57 (1997) 4593-4599). The FAB of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each FAB that give less than or equal to 20% of maximal binding are chosen for use in competitive binding assays.

According to another embodiment, the dissociation constant is determined using surface plasmon resonance assays using a BIACORE®-2000 or a BIACORE®-3000 or a BIACORE® A-100 (BIAcore, Inc., Piscataway, N.J.) at 25° C. with immobilized antigen CM5 chips at ~10 response units (RU).

Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions.

Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of FAB (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (KD) is calculated as the ratio koff/kon (see e.g. Chen, Y., et al., J. Mol. Biol. 293 (1999) 865-881). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (FAB form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In case, two binding molecules recognize two independent binding sites, a cooperative binding event can be generated, which can be in dependence of the polynucleotide linker length.

A cooperative binding effect is physically characterized in that the free Gibbs binding energies $\Delta G°_1$ and $\Delta G°_2$ summarize to $\Delta G°_{coop}$: $\Delta G°_1 + \Delta G°_2 = \Delta G°_{coop}$.

According to the Gibbs Equation $\Delta G°_{coop} = -RT \ln K_{Dcoop}$, $\Delta G°_{coop}$ forms the product from the affinities $K_{D1}$ and $K_{D2}$.

Enhancement of the free Gibbs binding energy by cooperativity dramatically increases binding affinity ($K_{Dcoop}$) and binding specificity.

Binding specificity is further increased, when the addressed binding sites are independently located on two different target molecules, which e.g. might be co-localized on the surface of a tumor cell.

The polypeptide specifically binding to a target likely carries one or more free OH, COOH, $NH_2$ and/or SH groups, which could potentially react with certain coupling reagents. To avoid (side-)reactions during the conjugation reaction one of the coupling chemistries as given in the following Table 1 can be chosen.

Table 1 provides an overview over reactive groups for covalently binding the polypeptides to the respective member of a binding pair as well as for covalently binding the linker to the respective members of a binding pair.

TABLE 1

| reactive site within the first polypeptide | first reactive site of the linker L | second reactive site of the linker | reactive site within the second polypeptide |
|---|---|---|---|
| $ONH_2$ (aminoxy) | C(H)=O (aldehyde) | —C≡C (alkyne) or triphenylphosphin carboxylic ester | $N_3$ (azide) |
| C(H)=O (aldehyde) | $ONH_2$ (aminoxy) | $N_3$ (azide) | —C≡C (alkyne) or triphenylphosphin carboxylic ester |
| ONH2 (aminoxy) | C(H)=O (aldehyde) | Diene | Dienophile |
| C(H)=O (aldehyde) | $ONH_2$ (aminoxy) | Dienophile | Diene |
| Dien | Dienophile | $N_3$ (azide) | —C≡C (alkyne) or triphenylphosphin carboxylic ester |
| Dienophile | Diene | $N_3$ (azide) | —C≡C (alkyne) or triphenylphosphin carboxylic ester |
| Dienophile | Diene | —C≡C (alkyne) or triphenylphosphin carboxylic ester | N3 (azide) |
| Dien | Dienophile | —C≡C (alkyne) or triphenylphosphin carboxylic ester | $N_3$ (azide) |

The above bi-orthogonal coupling chemistries are especially appropriate for the conjugation of the monovalent binding polypeptides. If the two binding partners are not carrying certain reactive functional groups, e.g. in the case of combination of two aptamers there is more freedom in selection of the reactive sites. Therefore in addition or in combination with the pairs of corresponding reactive sites given in the above table, amino/active ester (e.g. NHS ester), and SH/SH or SH/maleinimido can be used for orthogonal coupling.

The monovalent binding polypeptide may also be a synthetic peptide or peptide mimic. In case a polypeptide is chemically synthesized, amino acids with orthogonal chemical reactivity can be incorporated during such synthesis (see e.g. de Graaf, A. J., et al., Bioconjug. Chem. 20 (2009) 1281-1295). Since a great variety of orthogonal functional groups is at stake and can be introduced into a synthetic peptide, conjugation of such peptide to a linker is standard chemistry.

The Polynucleotide Component

The complex as reported herein comprises a (polynucleotide) linker. The linker can either be covalently bound to the polypeptide(s) or the (polynucleotide) linker and the polypeptide(s) can be bound to each other by a specific binding pair.

When (polynucleotide) linkers of different length are used resulting complex constructs with different distances in between the first and second polypeptide specifically binding to a target can be obtained. This allows for optimal distance and/or flexibility.

The term polynucleotide is to be understood broadly and includes DNA and RNA as well as analogs and modifications thereof.

In one embodiment the polynucleotide linker is composed of a mixture of different types of monomers as long as more than 20% of the monomers are nucleosides. In one embodiment the polynucleotide linker is composed of a mixture of different types of monomers as long as more than 30% of the monomers are nucleosides. In one embodiment the polynucleotide linker is composed of a mixture of different types of monomers as long as more than 40% of the monomers are nucleosides. In one embodiment the polynucleotide linker is composed of a mixture of different types of monomers as long as more than 50% of the monomers are nucleosides.

For example, the linker can be composed exclusively of nucleosides or it can be a mixture of nucleosides and amino acids, and/or sugar residues, and/or diols, and/or phospho-sugar units, and/or non-ionic polymer building blocks.

An oligonucleotide may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are 5-substituted pyrimidines (like 5-methyl-dC, aminoallyl-dU or -dC, 5-(aminoethyl-3-acrylimido)-dU, 5-propinyl-dU or -dC), 5-halogenated-dU or -dC, N-substituted pyrimidines (like N4-ethyl-dC), N-substituted purines (like N6-ethyl-dA, N2-ethyl-dG), 8-substituted purines (like 8-[6-amino]-hex-1-yl]-8-amino-dG or -dA), 8-halogenated-dA or -dG, 8-alkyl-dG or -dA, and 2-substituted-dA (like 2-amino-dA).

An oligonucleotide may contain a nucleotide or a nucleoside analog. I.e. the naturally occurring nucleobases can be exchanged by using nucleobase analogs like 5-nitroindol-D-riboside, 3-nitro-pyrrole-D-riboside, deoxyinosine (dI), deoxyxanthosine (dX), 7-deaza-dG, -dA, -dI or -dX, 7-deaza-8-aza-dG, -dA, -dI or -dX, 8-aza-dA, -dG, -dI or -dX, D-Formycin, pseudo-dU, pseudo-iso-dC, 4-thio-dT, 6-thio-dG, 2-thio-dT, iso-dG, 5-methyl-iso-dC, N8-linked-8-aza-7-deaza-dA, 5,6-dihydro-5-aza-dC, etheno-dA, or pyrollo-dC. As obvious to the skilled artisan, the nucleobase in the complementary strand has to be selected in such manner that duplex formation is specific. If, for example, 5-methyl-iso-dC is used in one strand (e.g. (a)) iso-dG has to be in the complementary strand (e.g. (a')).

In one embodiment the oligonucleotide backbone of the linker is modified to contain substituted sugar residues, sugar analogs, modifications in the inter-nucleoside phosphate moiety, and/or is a PNA (having a backbone without phosphate and d-ribose).

An oligonucleotide may for example contain a nucleotide with a substituted deoxy ribose like 2'-methoxy-, 2'-fluoro-, 2'-methylseleno-, 2'-allyloxy-, 4'-methyl-dN (wherein N is a nucleobase, e.g., A, G, C, T or U).

Sugar analogs are for example xylose, 2',4'-bridged ribose like (2'-0, 4'-C methylene) (oligomer known as LNA), or (2'-0, 4'-C ethylene) (oligomer known as ENA), L-ribose, L-D-ribose, hexitol (oligomer known as HNA), cyclohexenyl (oligomer known as CeNA), altritol (oligomer known as ANA), a tricyclic ribose analog where C3' and C5' atoms are connected by an ethylene bridge that is fused to a cyclopropane ring (oligomer known as tricyclo DNA), glycerin (oligomer known as GNA), glucopyranose (oligomer known as Homo DNA), carbaribose (with a cyclopentane instead of a tetrahydrofurane subunit), hydroxymethyl-morpholine (oligomers known as morpholino DNA).

A great number of modification of the inter-nucleosidic phosphate moiety are also known not to interfere with hybridization properties and such backbone modifications can also be combined with substituted nucleotides or nucleotide analogs. Examples are phosphorthioate, phosphordithioate, phosphoramidate and methylphosphonate oligonucleotides.

The above mentioned modified nucleotides, nucleotide analogs as well as polynucleotide backbone modifications can be combined as desired in a polynucleotide comprised in the complex as reported herein.

The (polynucleotide) linker has a length of from 1 nm to 100 nm. In one embodiment the (polynucleotide) linker has a length of from 4 nm to 80 nm. In one embodiment the (polynucleotide) linker has a length of from 5 nm to 50 nm or of from 6 nm to 40 nm. In one embodimente the (polynucleotide) linker has a length of 10 nm or longer or of 15 nm or longer. In one embodiment the (polynucleotide) linker has a length between 10 nm and 50 nm.

In one embodiment the members of a binding pair conjugated to the (polynucleotide) linker have a length of at least 2.5 nm each.

The length of the (polynucleotide) linker can be calculated by using known bond distances and bond angles of components which are chemically similar to the entities. Such bond distances are summarized for some molecules in standard text books (see e.g. CRC Handbook of Chemistry and Physics 91st edition 2010-2011 section 9).

In the calculation of a spacer or a linker length the following approximations apply: a) for calculating lengths of non-nucleosidic entities an average bond length of 130 pm with an bond angle of 180° independently of the nature of the linked atoms is used, b) one nucleotide in a single strand is calculated with 500 pm, and c) one nucleotide in a double strand is calculated with 330 pm.

The value of 130 pm is based on calculation of the distance of the two terminal carbon atoms of a C(sp3)-C(sp3)-C(sp3) chain with a bond angle of 109°28' and a distance of 153 pm between two C(sp3) which is approx. 250 pm which translates with an assumed bond angle of 180° and bond distance between two C(Sp3) with 125 pm. Taking in account that heteroatoms like P and S and sp2 and sp1 C atoms could also be part of the linker the value 130 pm is taken. If the linker comprises a cyclic structure like cycloalkyl or aryl the distance is calculated in analogous manner by counting the number of the bonds of the cyclic structure which are part of the overall chain of atoms which are defining the distance.

The length of the (polynucleotide) linker in a complex as reported herein can be varied as desired. In order to easily make available linkers of variable length, i.e. a library, it is suitable to have a simple synthetic access to the different linkers of such library. A combinatorial solid phase synthesis of the linker is suited. Since linkers have to be synthesized up to a length of about 100 nm, the synthesis strategy is chosen in such a manner that the monomeric synthetic building blocks are assembled during solid phase synthesis with high efficiency. The synthesis of deoxy oligonucleotides based on the assembly of phosphoramidite as monomeric building blocks meet this requirement. In such a linker monomeric units within a linker are linked in each case via a phosphate or phosphate analog moiety.

The (polynucleotide) linker can contain as in one embodiment free positively or/and negatively charged groups of polyfunctional amino-carboxylic acids, e.g. amino, carboxylate or phosphate. For example the charge carriers can be derived from trifunctional aminocarboxylic acids which contain a) an amino group and two carboxylate groups, or b) two amino groups and one carboxylate group. Examples of such trifunctional aminocarboxylic acids are lysine, ornithine, hydroxylysine, α,β-diamino propionic acid, arginine, aspartic acid and glutamic acid, carboxy glutamic acid and symmetric trifunctional carboxylic acids like those described in EP 0 618 192 or U.S. Pat. No. 5,519,142. Alternatively one of the carboxylate groups in the trifunctional aminocarboxylic acids of a) can be replaced by a phosphate, sulphonate or sulphate group. An example of such a trifunctional amino acid is phosphoserine.

The (polynucleotide) linker can also contain as in one embodiment uncharged hydrophilic groups. Suited examples of uncharged hydrophilic groups are ethylene oxide or poly (ethylene oxide) groups comprising especially at least three building blocks, such as ethylene oxide, sulphoxide, sulphone, carboxylic acid amide, carboxylic acid ester, phosphonic acid amide, phosphonic acid ester, phosphoric acid amide, phosphoric acid ester, sulphonic acid amide, sulphonic acid ester, sulphuric acid amide and sulphuric acid ester groups. The amide groups are in one embodiment primary amide groups, especially carboxylic acid amide residues in amino acid side groups, e.g. of the amino acids asparagine and glutamine. The esters are especially derived from hydrophilic alcohols, in particular C1-C3 alcohols, or diols, or triols.

Enantiomeric L-DNA is known for its orthogonal hybridization behavior, its nuclease resistance, and for ease of synthesis of polynucleotides of variable length.

In one embodiment all polynucleotides in the complex are enantiomeric L-DNA or L-RNA. In one embodiment all polynucleotides in the complex are enantiomeric L-DNA.

Enantiomeric, single stranded L-DNA (ss-L-DNA) combines high molecular flexibility and stability in body fluids. When single stranded L-DNA is used as a linker between two or more independent binding molecules, these binding molecules can get adjusted to virtually any binding angle and binding distance, which are just dependent from the ss-L-DNA linker length.

In one embodiment the (polynucleotide) linker is synthesized in segments that can hybridize with each other.

In this case the linker can be formed by hybridization of the segments with one another. The resulting linker construct comprises oligonucleotide duplex portions.

In case the linker is constructed that way the sequence of the hybridizable polynucleotide entity forming the duplex is chosen in such a manner that no hybridization or interference with the binding pair nucleic acids can occur.

In one embodiment the polynucleotide linker is synthesized in ss-L-DNA segments, e.g. A and B, which can hybridize with each other.

In this case the polynucleotide linker can be build up by the hybridization of the segments with one another. Therefore, the linker length can be self-adjusted to the distance between two binding sites simply by sequential application of the concatemer forming building blocks, i.e. A and B as exemplified. The linker is characterized in that the nucleic acid termini of the established linker hybridize with lower melting point temperature (i.e. TM1) to the ss-L-DNA labeled binding molecules than the inter-concatemeric melting point temperature (i.e. TM2, thus with TM2>TM1). To analyze the final length of the full length linker, the obtained complex is incubated at a third temperature (i.e. TM3) that is above the first melting point temperature but below the second melting point temperature (i.e. TM3>TM1 and TM3<TM2). The temperature-eluted linker can be analyzed by standard methods e.g. using ethidiumbromide stained agarose gel. The linker length can also be calculated, because the length of each concatemer is known. The individual concatemers can be labeled in one embodiment.

The duplex portions can rigidize the oligonucleotide linker. This can be used to reduce the linker mobility and flexibility.

In one embodiment one or more L-DNA oligonucleotides are hybridized to the oligonucleotide L-DNA linker.

In this embodiment the oligonucleotide linker is rigidized via L-DNA duplex formation.

In one embodiment an L-DNA/poly (ethylene glycol) hybrid is used as (oligonucleotide) linker.

In one embodiment an L-DNA/D-DNA/poly (ethylene glycol) hybrid is used as (oligonucleotide) linker.

In one embodiment an L-DNA/D-DNA/poly (ethylene glycol)/polypeptide hybrid is used as (oligonucleotide) linker.

In one embodiment one or more L-DNA oligonucleotides are hybridized to the L-DNA/poly (ethylene glycol) hybrid (oligonucleotide) linker.

In one embodiment one or more L-DNA oligonucleotides, which are covalently coupled to a poly (ethylene glycol) molecule of varying length, are hybridized to the oligonucleotide L-DNA poly (ethylene glycol) hybrid (oligonucleotide) linker.

In one embodiment an L-DNA/D-DNA hybrid is used as (oligonucleotide) linker.

In one embodiment an L-DNA/D-DNA hybrid is used as (oligonucleotide) linker, wherein one or more D-DNA oligonucleotides are hybridized to the oligonucleotide D-DNA portion of the (oligonucleotide) linker to form double stranded D-DNA.

In one embodiment an L-DNA/D-DNA hybrid is used as linker, wherein one or more L-DNA oligonucleotides are hybridized to the oligonucleotide L-DNA portion of the (oligonucleotide) linker to form double stranded L-DNA.

The formation of double stranded, i.e. helical, DNA-duplexes can be used to modify or adjust the in vivo half-life of the complex making it available for the enzymatic action of nucleases.

A simple way to build the (polynucleotide) linker is to use standard D or L nucleoside phosphoramidite building blocks.

In one embodiment a single strand stretch of dT is used.

This is advantageous, because dT does not require carrying a base protecting group.

Hybridization can be used in order to vary the (polynucleotide) linker length (distance between the binding pair members at the termini of the polynucleotide linker) and the flexibility of the spacer, because the double strand length is reduced compared to the single strand and the double strand is more rigid than a single strand.

For hybridization in one embodiment oligonucleotides modified with a functional moiety are used.

The oligonucleotide used for hybridization can have one or two terminal extensions not hybridizing with the linker and/or is branched internally. Such terminal extensions that are not hybridizing with the linker (and not interfering with the members of the binding pairs) can be used for further hybridization events.

In one embodiment an oligonucleotide hybridizing with a terminal extension is oligonucleotide comprising an effector moiety.

This labeled oligonucleotide again may comprise terminal extensions or being branched in order to allow for further hybridization, thereby a polynucleotide aggregate or dendrimer can be obtained. A poly-oligonucleic acid dendrimer is especially used in order to produce a polylabel, or in order to get a high local concentration of an effector moiety.

Modified nucleotides which do not interfere with the hybridization of polynucleotides can be incorporated into those polynucleotides. Suited modified nucleotides are C5-substituted pyrimidines or C7-substituted 7-deaza purines. Polynucleotides can be modified internally or at the 5' or 3' terminus with non-nucleotidic entities which are used for the introduction of the effector moiety.

In one embodiment such non-nucleotidic entities are located within the (polynucleotide) linker between the two binding pair members conjugated to its ends.

Many different non-nucleotidic building blocks for construction of a polynucleotide are known in literature and a great variety is commercially available. For the introduction of an effector moiety either non-nucleosidic bifunctional building blocks or non-nucleosidic trifunctional building blocks can either be used as CPG for terminal labeling or as phosphoramidite for internal labeling (see e.g. Wojczewski, C., et al., Synlett 10 (1999) 1667-1678).

Bifunctional spacer building blocks in one embodiment are non-nucleosidic components. For example, such linkers are C2-C18 alkyl, alkenyl, alkinyl carbon chains, whereas the alkyl, alkenyl, alkinyl chains may be interrupted by additional ethyleneoxy and/or amide moieties or quarternized cationic amine moieties in order to increase hydrophilicity of the linker. Cyclic moieties like C5-C6-cycloalkyl, C4N-, C5N-, C4O-, C5O-heterocycloalkyl, phenyl which are optionally substituted with one or two C1-C6 alkyl groups can also be used as non-nucleosidic bifunctional linkers. Suited bifunctional building blocks comprise C3-C6 alkyl moieties and tri- to hexa-ethylene glycol chains. Tables 2a and 2b show some examples of nucleotidic bifunctional spacer building blocks with different hydrophilicity, different rigidity and different charges. One oxygen atom is connected to an acid labile protecting group preferably dimethoxytrityl and the other is part of a phosphoramidite.

TABLE 2a

| Non-nucleotidic bifunctional spacer building blocks | Reference |
|---|---|
|  | Seela, F., Nucleic Acids Research 15 (1987) 3113-3129. |
| 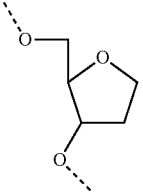 | Iyer, R.P., Nucleic Acids Research 18 (1990) 2855-2859. |
| 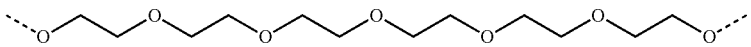 | WO 89/02931 A1 |
| 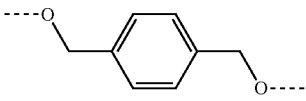 | EP 1 538 221 |
| 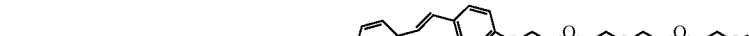 | US 2004/224372 |
| 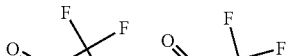 | WO 2007/069092 |

TABLE 2b

| Bifunctional non-nucleosidic modifierIntroduction of building blocks | | Reference |
|---|---|---|
| 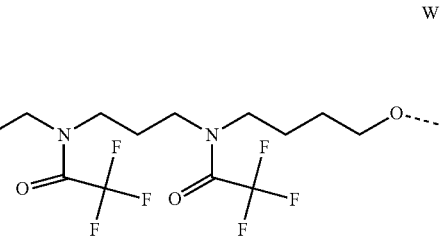 |  | Pon, R.T., Tetrahedron Letters 32 (1991) 1715-1718. |
| |  | Theisen, P., et al., Nucleic Acids Symposium Series 27 (Nineteenth Symposium on Nucleic Acids Chemistry (1992)) 99-100. EP 0 292 128 |

TABLE 2b-continued

| Bifunctional non-nucleosidic modifier | Introduction of building blocks | Reference |
|---|---|---|
| [structure: -O-(CH2)6-] | [structure: -S-S-(CH2)6-O-CH3] | EP 0 523 978 |
| [structure: -O-(CH2)3-] | [structure: alkyne ≡] | Meyer, A., et al., Journal of Organic Chemistry 75 (2010) 3927-3930. |
| [structure: -O-cyclohexyl-NH-C(O)-C(O)-NH-(CH2)3-O-(CH2)2-O-(CH2)2-O-(CH2)3-] | [structure: -NH-C(O)-label] | Morocho, A.M., et al., Nucleosides, Nucleotides & Nucleic Acids 22 (2003) 1439-1441. |
| [structure: -O-CH2-phenyl-] | [structure: -NH-C(O)-label] | Cocuzza, A., Tetrahedron Letters 30 (1989) 6287-6290. |

Therefore trifunctional building blocks allow for positioning of a functional moiety to any location within a polynucleotide. Trifunctional building blocks are also a prerequisite for synthesis using solid supports, e.g. controlled pore glass (CPG), which are used for 3' terminal labeling of polynucleotides. In this case, the trifunctional linkers is connected to a functional moiety or a—if necessary—a protected functional moiety via an C2-C18 alkyl, alkenyl, alkinyl carbon chains, whereas the alkyl, alkenyl, alkinyl chains may be interrupted by additional ethyleneoxy and/or amide moieties in order to increase hydrophilicity of the linker and comprises a hydroxyl group which is attached via a cleavable spacer to a solid phase and a hydroxyl group which is protected with an acid labile protecting group. After removal of this protecting group a hydroxyl group is liberated that could thereafter react with a phosphoramidite.

Trifunctional building blocks may be non-nucleosidic or nucleosidic.

Non-nucleosidic trifunctional building blocks are C2-C18 alkyl, alkenyl, alkinyl carbon chains, whereas the alkyl, alkenyl, alkinyl are optionally interrupted by additional ethyleneoxy and/or amide moieties in order to increase hydrophilicity of the linker. Other trifunctional building blocks are cyclic groups like C5-C6-cycloalkyl, C4N-, C5N-, C40-, C50-heterocycloalkyl, phenyl which are optionally substituted with one or two C1-C6 alkyl groups. Cyclic and acyclic groups may be substituted with one (C1-C18)alkyl-O-PG group, whereas the C1-C18 alkyl comprises (Ethyleneoxy)n, (Amide)m moieties with n and m independently from each other=0-6 and PG is an acid labile protecting group. Preferred trifunctional building blocks are C3-C6 alkyl, cycloalkyl, C50-heterocycloalkyl moieties optionally comprising one amide bond and substituted with a C1-C6 alkyl O-PG group, wherein PG is an acid labile protecting group, preferably monomethoxytrityl, dimethoxytrityl, pixyl, xanthyl most preferred dimethoxytrityl.

Non-limiting, yet suited examples for non-nucleosidic trifunctional building blocks are e.g. summarized in Table 3.

TABLE 3

| Trifunctional | introduction of | Reference |
|---|---|---|
| [structure: branched -O-CH2-CH(-)-CH2-O- with pentyl chain] | [structure: -NH-C(O)-label] | Nelson, P.S., et al., Nucleic Acids Research 20 (1992) 6253-6259. |
| | [structure: -N(H)-C(=S)-N(H)-label] | EP 0 313 219; U.S. Pat. No. 5,585,481; U.S. Pat. No. 5,451,463; EP 0 786 468; WO 92/11388, WO 89/02439 |

TABLE 3-continued

| Trifunctional | introduction of | Reference |
|---|---|---|
| 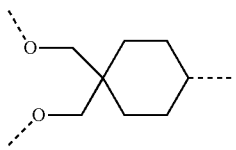 | 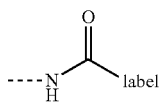 | Su, Sheng-Hui, et al., Bioorganic & Medicinal Chemistry Letters 7 (1997) 1639-1644. WO 97/43451 |
| | 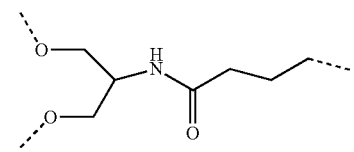 | |
| 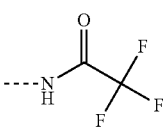 | 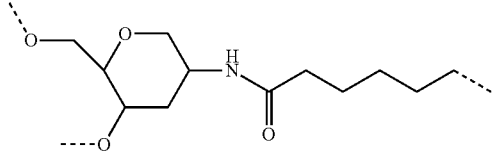 | Putnam, W.C. and Bashkin, J.K., Nucleosides, Nucleotides & Nucleic Acids 24 (2005) 1309-1323. US 2005/214833, EP 1 186 613 |
| | 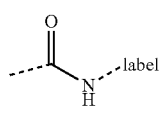 | |
| 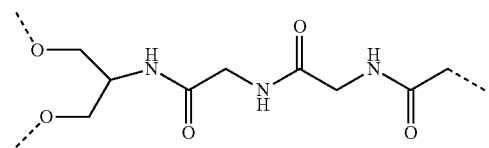 | 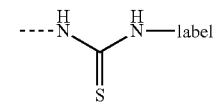 | EP 1 431 298 |
| | 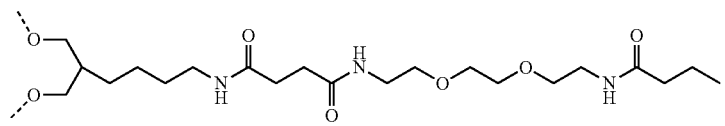 | |
| 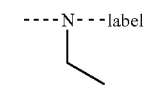 | 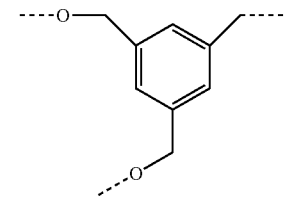 | WO 94/04550 Huynh Vu, et al., Nucleic Acids Symposium Series (1993) 29 (Second International Symposium on Nucleic Acids Chemistry) 19-20. |
| 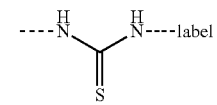 | | WO 2003/019145 |
| | | Behrens, C. and Dahl, O., Nucleosides & Nucleotides 18 (1999) 291-305. WO 97/05156 |

TABLE 3-continued

| Trifunctional | introduction of | Reference |
|---|---|---|
| (structure) | (structure) label | Prokhorenko, I.A., et al., Bioorganic & Medicinal Chemistry Letters 5 (1995) 2081-2084. WO 2003/104249 |
| (structure) | (structure) label | U.S. Pat. No. 5,849,879 |

Nucleosidic trifunctional building blocks are used for internal labeling whenever it is necessary not to influence the polynucleotide hybridization properties compared to a non-modified polynucleotide. Therefore nucleosidic building blocks comprise a base or a base analog which is still capable of hybridizing with a complementary base. The general formula of a labeling compound for labeling a nucleic acid sequence of one or more of a, a', b, b' or S comprised in a complex as reported herein is given in Formula II.

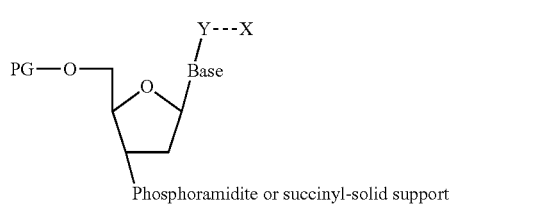

Formula II

Phosphoramidite or succinyl-solid support wherein PG is an acid labile protecting group, especially monomethoxytrityl, dimethoxytrityl, pixyl, xanthyl, especially dimethoxytrityl, wherein Y is C2-C18 alkyl, alkenyl alkinyl, wherein the alkyl, alkenyl, alkinyl may comprise ethyleneoxy and/or amide moieties, wherein Y preferably is C4-C18 alkyl, alkenyl or alkinyl and contains one amide moiety and wherein X is a functional moiety.

Specific positions of the base may be chosen for such substitution to minimize the influence on hybridization properties. Therefore the following positions are especially suited for substitution: a) with natural bases: uracil substituted at C5, cytosine substituted at C5 or at N4, adenine substituted at C8 or at N6, and guanine substituted at C8 or at N2, and b) with base analogs: 7-deaza-A and 7-deaza-G substituted at C7, 7-deaza-8-aza-A and 7-deaza-8-aza-G substituted at C7, 7-deaza-aza-2-amino-A substituted at C7, pseudouridine substituted at N1 and formycin substituted at N2.

TABLE 4

| Trifunctional nucleosidic | introduction of | Reference |
|---|---|---|
| (structure) | (structure) label | Roget, A., et al., Nucleic Acids Research 17 (1989) 7643-7651. WO 89/12642, WO 90/08156, WO 93/05060 |

TABLE 4-continued

| Trifunctional nucleosidic | introduction of | Reference |
|---|---|---|
| | amide (–NH–C(=O)–) label | Silva, J.A., et al., Biotecnologia Aplicada 15 (1998)1154-158. |
| | sulfonamide (–NH–S(=O)$_2$–) Label | U.S. Pat. No. 6,531,581 EP 0 423 839 |
| | amide (–NH–C(=O)–) label | U.S. Pat. No. 4,948,882; U.S. Pat. No. 5,541,313; U.S. Pat. No. 5,817,786 |
| | tertiary amine (–N(Et)–) label | WO 2001/042505 |
| | amide (–NH–C(=O)–) label | McKeen, C.M., et al., Organic & Biomol. Chem. 1 (2003) 2267-2275. |

TABLE 4-continued

| Trifunctional nucleosidic | introduction of | Reference |
|---|---|---|
| (structure: 7-alkynyl-7-deaza-2'-deoxyadenosine derivative with 4-NH$_2$, propargyl group, and protected 5'- and 3'-hydroxyl groups) | H–N–C(=S)–N(H)–label | Ramzaeva, N., et al Helv. Chim. Acta 83 (2000) 1108-1126. |

In Table 4 the terminal oxygen atom of bifunctional moiety or one of the terminal oxygen atoms of a trifunctional moiety are part of a phosphoramidite that is not shown in full detail but obvious to the skilled artisan. The second terminal oxygen atom of trifunctional building block is protected with an acid labile protecting group PG, as defined for Formula II above.

Post-synthetic modification is another strategy for introducing a covalently bound functional moiety into a linker. In this approach an amino group is introduced by using bifunctional or trifunctional building blocks during solid phase synthesis.

After cleavage from the support and purification of the amino modified linker the linker is reacted with an activated ester of a functional moiety or with a bifunctional reagent wherein one functional group is an active ester. Especially suited active esters are NHS ester or pentafluor phenyl esters.

Post-synthetic modification is especially useful for introducing a functional moiety which is not stable during solid phase synthesis and deprotection. Examples are modification with triphenylphosphincarboxymethyl ester for Staudinger ligation (Wang, Charles C.-Y., et al., Bioconjugate Chemistry 14 (2003) 697-701), modification with digoxigenin or for introducing a maleinimido group using commercial available sulfo SMCC.

The Binding Pair Component

In one embodiment each member of a binding pair is of/has a molecular weight of 10 kDa or less. In one embodiment the molecular weight of each member of a binding pair is 8 kDa, or 7 kDa, or 6 kDa, or 5 kDa, or 4 kDa or less.

The dissociation constant, i.e. the binding affinity, for (within) a binding pair is at least $10^{-8}$ M (=$10^{-8}$ mol/l=$10^8$ 1/mol). The members of both binding pairs in the complex as reported herein are different. The difference between the binding pairs a:a' and b:b' is e.g. acknowledged if the dissociation constant for the reciprocal binding, e.g. binding of a as well as a' to b or b', is 10 times the dissociation constant of the pair a:a' or more.

In one embodiment dissociation constant for the reciprocal binding, i.e. binding of a as well as a' to b or b', respectively, is 20 times the dissociation constant of the pair a:a' or more. In one embodiment the dissociation constant is 50 times the dissociation constant within the pair a:a' or more. In one embodiment the reciprocal (cross-reactive) binding dissociation constant is 100 times or more the dissociation constant within a binding pair.

In one embodiment the members of the binding pairs are selected from the group consisting of leucine zipper domain dimers and hybridizing nucleic acid sequences.

In one embodiment both binding pairs are leucine zipper domain dimers.

In one embodiment both binding pairs are hybridizing nucleic acid sequences. In one embodiment all binding pair members are L-DNA sequences. In one embodiment both binding pairs are hybridizing L-DNAs.

In one embodiment both member of the binding pairs represent leucine zipper domains.

The term "leucine zipper domain" denotes a dimerization domain characterized by the presence of a leucine residue at every seventh residue in a stretch of approximately 35 residues. Leucine zipper domains are peptides that promote oligomerization of the proteins in which they are found. Leucine zippers were originally identified in several DNA-binding proteins (Landschulz, W. H., et al., Science 240 (1988) 1759-1764). Among the known leucine zippers are naturally occurring peptides and derivatives thereof that dimerize or trimerize. Examples of leucine zipper domains suitable for producing soluble multimeric proteins are those reported in WO 94/10308, and the leucine zipper derived from lung surfactant protein D (SPD) as reported in Hoppe, H. J., et al., FEBS Lett. 344 (1994) 191-195.

Leucine zipper domains form dimers (binding pairs) held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

If leucine zipper domains form the first binding pair and the second binding pair, both leucine zipper sequences are different, i.e. the members of the first binding pair do not bind to the members of the second binding pair. Leucine zipper domains may be isolated from natural proteins known to contain such domains, such as transcription factors. One leucine zipper domain may e.g. come from the transcription factor fos and a second one from the transcription factor jun. Leucine zipper domains may also be designed and synthesized artificially, using standard techniques for synthesis and design known in the art.

In one embodiment both binding pairs are hybridizing nucleic acid sequences.

Thus, the members of each binding pair, i.e. a and a' as well as b and b', hybridize to one another, respectively. The nucleic acid sequences comprised in the first binding pair on the one hand and in the second binding pair on the other hand are different, i.e. do not hybridize with each other.

In one embodiment the binding pairs are both hybridizing nucleic acid pairs, wherein the hybridizing nucleic acid sequences of the different binding pairs do not hybridize with one another.

With other words the nucleic acids of the first binding pair hybridize to each other but do not bind to any of the nucleic acids of the second binding pair or interfere with their hybridization and vice versa. Hybridization kinetics and hybridization specificity can easily be monitored by melting point analyses. Specific hybridization of a binding pair and non-interference is acknowledged, if the melting temperature for the binding pair as compared to any possible combination with other binding pairs or combination of binding pair members is at least 20° C. higher.

The nucleic acid sequences forming a binding pair may comprise in principle any naturally occurring nucleobase or an analogue thereto and may have in principle a modified or a non-modified backbone as described above provided it is capable of forming a stable duplex via multiple base pairing. Stable denotes that the melting temperature of the duplex is higher than 30° C., especially higher than 37° C.

The double strand is in one embodiment consisting of two fully complementary single stranded polynucleotides.

However mismatches or insertions are possible as long as the stability at 37° C. is given.

A nucleic acid duplex can be further stabilized by interstrand crosslinking. Several appropriate cross-linking methods are known, e.g. methods using psoralen or based on thionucleosides.

The nucleic acid sequences representing the members of a binding pair in one embodiment consist of from 12 to 50 nucleotides. In one embodiment such nucleic acid sequences consist of from 15 to 35 nucleotides.

RNAses are ubiquitous and special care has to be taken to avoid unwanted digestion of RNA-based binding pairs and/or linker sequences. While RNA-based binding pairs and/or linkers can be used, binding pairs and/or linkers based on DNA are especially suited.

Appropriate hybridizing nucleic acid sequences can easily be designed to provide for more than two pairs of orthogonal complementary polynucleotides, allowing for an easy generation and use of more than two binding pairs. Another advantage of using hybridizing nucleic acid sequences in a complex as reported herein is that modifications can be easily introduced. Modified building blocks are commercially available which e.g. allow for an easy synthesis of a polynucleotide comprising a functional moiety. Such functional moiety can be easily introduced at any desired position and in any of the members of the first and/or second binding pair and/or the polynucleotide linker, provided they all represent a polynucleotide.

The (polynucleotide) linker comprising members of bindings pairs at its termini can be provided for and synthesize as a single polynucleotide. The polypeptides specifically binding to a target can each be coupled to hybridizing nucleic acid sequences, i.e. members of binding pairs. The length of the (polynucleotide) linker can easily be varied in any desired manner.

Depending on the biochemical nature of the polypeptide that specifically binds to a target different strategies for the conjugation to the member of a binding pair are at hand. In case the polypeptide is naturally occurring or recombinantly produced and between 50 to 500 amino acid residues in length, standard procedures as reported in text books can be easily followed by the skilled artisan (see e.g. Hackenberger, C. P. R., and Schwarzer, D., Angew. Chem. Int. Ed. 47 (2008) 10030-10074).

In one embodiment for the conjugation the reaction of a maleinimido moiety with a cysteine residue within the polypeptide is used.

This is an especially suited coupling chemistry in case e.g. a FAB or FAB'-fragment of an antibody is used a monovalent binding polypeptide.

In one embodiment coupling of a member of a binding pair to the C-terminal end of the polypeptide is performed.

C-terminal modification of a protein, e.g. of a FAB-fragment can e.g. be performed as described (Sunbul, M. and Yin, J., Org. Biomol. Chem. 7 (2009) 3361-3371).

In general site specific reaction and covalent coupling of a binding pair member to a monovalent binding polypeptide is based on transforming a natural amino acid into an amino acid with a reactivity which is orthogonal to the reactivity of the other functional groups present in a polypeptide.

For example, a specific cysteine within a rare sequence context can be enzymatically converted in an aldehyde (see e.g. Frese, M-A. and Dierks, T., ChemBioChem 10 (2009) 425-427). It is also possible to obtain a desired amino acid modification by utilizing the specific enzymatic reactivity of certain enzymes with a natural amino acid in a given sequence context (see e.g.: Taki, M., et al., Prot. Eng. Des. Sel. 17 (2004) 119-126, Gautier, A., et al., Chem. Biol. 15 (2008) 128-136; Bordusa, F., in Highlights in Bioorganic Chemistry (2004), Schmuck, C. and Wennemers, H., (eds.), Wiley VCH, Weinheim, pp. 389-403).

Site specific reaction and covalent coupling of a binding pair member to a monovalent binding polypeptide can also be achieved by the selective reaction of terminal amino acids with appropriate modifying reagents.

The reactivity of an N-terminal cysteine with benzonitrils (see Ren, H., et al., Angew. Chem. Int. Ed. 48 (2009) 9658-9662) can be used to achieve a site-specific covalent coupling.

Native chemical ligation can also rely on C-terminal cysteine residues (Taylor, E., et al., Nucl. Acids Mol. Biol. 22 (2009) 65-96).

EP 1 074 563 reports a conjugation method which is based on the faster reaction of a cysteine within a stretch of negatively charged amino acids with a cysteine located in a stretch of positively charged amino acids.

The Effector Component

The effector moiety can be selected from the group consisting of a binding moiety, a labeling moiety, a biologically active moiety, and a reactive moiety. If more than one effector moiety is present in the complex, each such effector moiety can in each case be independently a binding moiety, a labeling moiety, a biologically active moiety, or a reactive moiety. The binding moiety will be selected to have no interference with each of the binding pairs.

In one embodiment the effector moiety is selected from the group consisting of a binding moiety, a labeling moiety, and a biologically active moiety.

In one embodiment the effector moiety is a binding moiety.

Examples of binding moieties are the members of a bioaffine binding pair which can specifically interact with each other. Suitable bioaffine binding pairs are hapten or antigen and antibody; biotin or biotin analogues such as aminobiotin, iminobiotin or desthiobiotin and avidin or streptavidin; sugar and lectin, polynucleotide and complementary polynucleotide, receptor and ligand, e.g., steroid hormone receptor and steroid hormone; and the pair of an 104-aa fragment of bovine ribonuclease A (known as S-protein) and a 15-aa fragment of bovine ribonuclease A (known as S-peptide).

In one embodiment the effector moiety is a binding moiety and is covalently bound to at least one of the components of the complex.

In one embodiment the smaller partner of a bioaffine binding pair, e.g. biotin or an analogue thereto, a receptor ligand, a hapten or a polynucleotide is covalently bound to at least one of the polynucleotides comprised in the complex as reported herein.

In one embodiment the effector moiety is a binding moiety selected from hapten, biotin or biotin analogues such as aminobiotin, iminobiotin or desthiobiotin; polynucleotide and steroid hormone.

In one embodiment the effector moiety is a labeling group.

The labeling group can be selected from any known detectable group.

In one embodiment the labeling group is selected from dyes like luminescent labeling groups such as chemiluminescent groups e.g. acridinium esters or dioxetanes or fluorescent dyes e.g. fluorescein, coumarin, rhodamine, oxazine, resorufin, cyanine and derivatives thereof, luminescent metal complexes such as ruthenium or europium complexes, enzymes as used for CEDIA (Cloned Enzyme Donor Immunoassay, e.g. EP 0 061 888), microparticles or nanoparticles e.g. latex particles or metal sols, and radioisotopes.

In one embodiment the labeling group is a luminescent metal complex and the compound has a structure of the general formula (I):

$$[M(L_1L_2L_3)]n\text{-}Y\text{-}XmA \quad (I)$$

in which M is a divalent or trivalent metal cation selected from rare earth or transition metal ions, $L_1$, $L_2$ and $L_3$ are the same or different and denote ligands with at least two nitrogen-containing heterocycles in which $L_1$, $L_2$ and $L_3$ are bound to the metal cation via nitrogen atoms, X is a reactive functional group which is covalently bound to at least one of the ligands $L_1$, $L_2$ and $L_3$ via a linker Y, n is an integer from 1 to 10, especially 1 to 4, m is 1 or 2, or especially 1 and A denotes the counter ion which may be required to equalize the charge.

The metal complex is in one embodiment a luminescent metal complex i.e. a metal complex which undergoes a detectable luminescence reaction after appropriate excitation.

The luminescence reaction can for example be detected by fluorescence or by electrochemiluminescense measurement. The metal cation in this complex is for example a transition metal or a rare earth metal.

The metal is in one embodiment ruthenium, osmium, rhenium, iridium, rhodium, platinum, indium, palladium, molybdenum, technetium, copper, chromium or tungsten. Ruthenium, iridium, rhenium, chromium and osmium are especially suited. Ruthenium is most suited.

Gold nanorods (GNRs) can also be used as labeling moiety in the complexes as reported herein. The nanorods can have a length of from 10 to 100 nm, inclusive, and including all integers there between.

In one embodiment, the GNRs have an average length of from 70-75 nm.

The GNRs can have a diameter of from 5 to 45 nm inclusive, and including all integers there between.

In one embodiment, the GNRs have an average diameter of 25-30 nm. The GNRs can be pure gold, or may be from 90% to 99%, inclusive, including all integers there between, pure gold.

In various embodiments, the GNRs may contain up to 1% silver on their surfaces, and may contain cetyltrimethylammonium bromide (CTAB).

In this regard, GNRs can be made by any suitable method. For example, electrochemical synthesis in solution, membrane templating, photochemical synthesis, microwave synthesis, and seed mediated growth are all suitable and non-limiting examples of methods of making the GNRs.

In one embodiment, the gold nanorods are made using the seed-mediated growth method in cetyltrimethylammonium bromide (CTAB).

In order to form complexes of the gold nanorods and the RNA polynucleotides, the surfaces of the gold nanorods can be functionalized so as impart a positive zeta potential suitable for electrostatically complexing the GNRs with DNA or RNA polynucleotides. Any suitable method of creating a positive zeta potential on the gold nanorods may be used. For example, the surfaces of the gold nanorods can be functionalized with bifunctional molecules, such as thiolated-PEG-NH2 or thiolated-PEG-COOH.

In one embodiment, the surface functionalization is achieved by coating the CTAB-coated gold nanorods first with the anionic polyelectrolyte poly (3,4-ethylenedioxythi-6-phene)/poly (styrene sulfate) (PEDT/PSS), then with the cationic polyelectrolyte poly (diallyl dimethyl ammonium chloride) (PDDAC).

This results in gold nanorods with a cationic surface charge (positive zeta potential), and also masks the CTAB layer (see, e.g., Ding, H., et al., J. Phys. Chem. C 111 (2007) 12552-12557).

The positively charged gold nanorods are electrostatically complexed to the DNA polynucleotides using electrostatic interactions.

The formation of nanoplexes can be confirmed from an observed red-shift in localized longitudinal plasmon resonance peak of the gold nanorods, as well as from restricted electrophoretic mobility of the nanoplexes using gel electrophoresis.

In one embodiment the effector moiety X is a therapeutically active substance.

Therapeutically active substances have different ways in which they are effective, e.g. in inhibiting cancer, damaging the DNA template by alkylation, by cross-linking, or by double-strand cleavage of DNA. Other therapeutically active substances can block RNA synthesis by intercalation. Some agents are spindle poisons, such as vinca alkaloids, or anti-metabolites that inhibit enzyme activity, or hormonal and anti-hormonal agents. The effector moiety may be selected from alkylating agents, antimetabolites, antitumor antibiotics, vinca alkaloids, epipodophyllotoxins, nitrosoureas, hormonal and anti-hormonal agents, and toxins.

Suited alkylating agents are cyclophosphamide, chlorambucil, busulfan, melphalan, thiotepa, ifosfamide, or nitrogen mustard.

Suited antimetabolites are methotrexate, 5-Fluorouracil, cytosine arabinoside, 6-thioguanine, 6-mercaptopurin.

Suited antitumor antibiotics are doxorubicin, daunorubicin, idorubicin, nimitoxantron, dactinomycin, bleomycin, mitomycin, and plicamycin.

Suited spindle poisons are maytansine and maytansinoids, vinca alkaloids and epipodophyllotoxins may be exemplified by vincristin, vinblastin, vindestin, Etoposide, Teniposide.

Furthermore, suited taxane agents may be exemplified by Paclitaxel, Docetaxel, SB-T-1214.

Suited nitrosoureas are carmustine, lomustine, semustine, streptozocin.

Suited hormonal and anti-hormonal agents are adrenocorticoids, estrogens, anti-estrogens, progestins, aromatase inhibitors, androgens, anti-androgens.

Suited random synthetic agents are dacarbazine, hexamethylmelamine, hydroxyurea, mitotane, procarbazine, cisplatin, carboplatin.

Suited monocytes chemotactic factors are f-Met-Leu-Phe (fMLP), f-Met-Leu-Phe-o-methyl ester, formyl-norleucylphenylalanine, formyl-methionyl-phenylalanine.

Suited NK cell attracting factors are IL-12, IL-15, IL-18, IL-2, and CCL5, the FC portion of an antibody.

The effector moiety can be bound either covalently or via an additional binding pair to at least one of the components of the complex. The effector moiety can be comprised for one to several (n) times in the complex as reported herein, whereby (n) is an integer and 0 or 1 or more than one. In one embodiment (n) is between 1 and 1,000,000. In one embodiment (n) is between 1,000 and 300,000. In one embodiment (n) is 1 to 50. In one embodiment (n) is 1 to 10, or 1 to 5. In one embodiment (n) is 1 or 2 For covalent binding of the effector moiety to at least one of the components in the complex any appropriate coupling chemistry can be used. It is also possible to incorporate a functional moiety by use of appropriate building blocks when synthesizing the members of the first and/or second binding pair and/or the (polynucleotide) linker, especially in the members of the binding pairs conjugated to the polypeptide or the (polynucleotide) linker.

Conjugation methods resulting in linkages which are substantially (or nearly) non-immunogenic are especially suited. Therefore, peptide- (i.e. amide-), sulfide-, (sterically hindered), disulfide-, hydrazone-, or ether linkage are especially suited.

These linkages are nearly non-immunogenic and show reasonable stability within serum (see e.g. Senter, P. D., Curr. Opin. Chem. Biol. 13 (2009) 235-244; WO 2009/059278; WO 95/17886).

In one embodiment the effector moiety is bound to the (polynucleotide) linker of the complex as reported herein.

In one embodiment the effector moiety is covalently bound to a member of a binding pair conjugated to the polypeptide or the (polynucleotide) linker of the complex as reported herein.

If an effector moiety is located within a hybridizing polynucleotide it is especially suited to bind it to a modified nucleotide or is attached to the internucleosidic P atom (see e.g. WO 2007/059816).

Bifunctional building blocks (as described above) can be used to connect an effector moiety or a—if necessary—a protected effector moiety to a phosphoramidite group for attaching the building block at the 5'-end (regular synthesis) or at the 3'-end (inverted synthesis) to the terminal hydroxyl group of a growing polynucleotide chain.

Trifunctional building blocks (as described above) can be used to connect (i) a effector moiety or a—if necessary—a protected effector moiety, (ii) a phosphoramidite group for coupling the reporter or the effector moiety or a—if necessary—a protected effector moiety, during the polynucleotide synthesis to a hydroxyl group of the growing polynucleotide chain and (iii) a hydroxyl group which is protected with an acid labile protecting group especially with a dimethoxytrityl protecting group. After removal of this acid labile protecting group a hydroxyl group is liberated which can react with further phosphoramidites.

The effector moiety is bound in one embodiment to at least one of the members of the first and/or second binding pair or to the polynucleotide linker via an additional third binding pair. In one embodiment the third binding pair is a pair of hybridizing nucleic acid sequences. The members of the third binding pair do not interfere with the binding of the members of the other binding pairs to each other.

The additional binding pair to which an effector moiety can be bound is especially a leucine zipper domain or a hybridizing nucleic acid. In case the effector moiety is bound to at least one of the members of the first and/or second binding pair or the (polynucleotide) linker via an additional binding pair member, the binding pair member to which the effector moiety is bound and the first and second binding pairs members, respectively, all are selected to have different specificity. The members of the first and second binding pair and the binding pair to which the effector moiety is bound each bind to (e.g. hybridize with) their respective partner without interfering with the binding of any of the other binding pairs.

In one embodiment the complementary nucleic acids of the binding pairs and/or the (polynucleotide) linker is made at least partly of L-DNA, or L-RNA, or LNA, or iso-C nucleic acid, or iso-G nucleic acid, or any combination thereof. In one embodiment the (polynucleotide) linker is made at least to 50% of L-DNA, or L-RNA, or LNA, or iso-C nucleic acid, or iso-G nucleic acid, or any combination thereof. In one embodiment the (polynucleotide) linker is an L-polynucleotide (a spiegelmer). In one embodiment the L-polynucleotide is L-DNA.

In one embodiment the (polynucleotide) linker is DNA. In one embodiment the (polynucleotide) linker is the L-stereoisomer of DNA also known as beta-L-DNA or L-DNA or mirror image DNA.

This stereoisomeric DNA features advantages like orthogonal hybridization behavior, which means that a duplex is formed only between two complementary single strands of L-DNA but no duplex is formed between a single strands of L-DNA and the complementary D-DNA strand, nuclease resistance and ease of synthesis even of a long linker. The ease of synthesis and variability in spacer length are important for providing a linker library. (Polynucleotide) Linkers of variable length are useful in identifying complexes as reported herein having a polynucleotide linker of optimal length, thus, providing for the optimal distance between two polypeptide specifically binding a target.

In one embodiment the complex is a non-covalent complex. In one embodiment the non-covalent complex is formed via binding pairs.

In some embodiments, the effector moiety is a therapeutic drug.

For instance, the effector moiety can be a therapeutic radionuclide, hormone, cytokine, interferon, antibody or antibody fragment, nucleic acid aptamer, enzyme, polypeptide, toxin, cytotoxin, a chemotherapeutic agent, or a radiation sensitizer.

One aspect as reported herein is a method of using the complex as reported herein.

For example, herein is reported a method of killing a cell, wherein a complex as reported herein is administered to the cell in an amount sufficient to kill the cell.

In one embodiment, the cell is a cancer cell.

Herein is also reported a method of retarding or stopping the growth of a cancer cell in a mammal, wherein a complex as reported herein is administered to the mammal in an amount sufficient to retard or stop growth of the cancer cell.

In one embodiment the method is a method for inhibiting the growth or proliferation of a cancer cell.

In one embodiment the polypeptide specifically binding to a target is specifically binding to a cell surface molecule of a cell. In one embodiment the cell surface molecule is specifically present on cancer cells.

In one embodiment the first and second polypeptide specifically binding to a target are independently from each other selected from the group consisting of an antibody, an antibody fragment, a single-chain variable region antibody, a small peptidic molecule, a cyclic polypeptide, a peptidomimetic, and an aptamer.

In one embodiment the first and the second polypeptide specifically binding to a target are monovalent binding polypeptides.

In one embodiment the cell surface molecule to which the polypeptide is specifically binding is selected from the group consisting of pIgR, pIgR stalk, an apolipoprotein (e.g., apolipoprotein A1, A2, A3, A4, A5, B, C1, C2, C3, C4, D, and/or E), a cytokine receptor, a Toll- or Toll-like receptor, a receptor tyrosine kinase, a scavenger receptor, a GPI-linked protein, a glycolipid, a glycosphingolipid, a ceramide, a cerebroside, transferrin receptor, transferrin bound to transferrin receptor, apo-transferrin bound to transferrin receptor, vitamin B12 receptor, FcRn, members of the PGDF and VEGF receptor families (e.g., Fit-1, Flk-1, Flt-4), aquaporin, high density lipoprotein binding proteins (e.g., ATP binding cassette protein-1, scavenger receptor-BI), a cadherin (e.g., E-cadherin, N-cadherin, P-cadherin, R-cadherin, K-cadherin, and/or OB-cadherin), and low density lipoprotein receptor.

In one embodiment the target of the polypeptide of the complex as reported herein is selected from the group comprising the leukocyte markers, CD2, CD3, CD4, CD5, CD6, CD7, CD8, CD11a,b,c, CD13, CD14, CD18, CD19, CD20, CD22, CD23, CD27, CD28, CD29, CD30, CD40, CD44, CD45 and isoforms, CDw52 (Campath antigen), CD56, CD58, CD69, CD72, CTLA-4, LFA-1, TCR, her2-neu, mucin, CEA and endosialin CMV glycoproteins B, H, and gCIII, HIV-1 envelope glycoproteins, RSV envelope glycoproteins, HSV envelope glycoproteins, HPV envelope glycoproteins, Hepatitis family surface antigens. To achieve efficient, targeted delivery of the effector moiety to cells, a polypeptide specifically binding to a target directly on the surface of cells can be used.

In one embodiment the polypeptide is an antibody fragment. In one embodiment the antibody fragment is from an internalizing antibody that specifically binds to a cell surface molecule.

The conjugation of an effector moiety to a complex as reported herein allows for specific localization of the effector moiety at the desired site on a cell. The localization increases the effective concentration of the effector moiety on the target cell and thereby optimizes the effect of the effector moiety. Furthermore, the complex can be administered at a lower dose compare to a non-targeted effector moiety. This can be particularly relevant if the effector moiety has associated toxicities or if it is to be used in the treatment of chronic diseases.

L-DNA is a useful nucleotide in the formation of complexes as reported herein. L-DNA does not, by itself, hybridize to the naturally occurring form of DNA (D-DNA) or RNA. Since L-DNA is not a natural substrate for many enzymes, the stability of an L-DNA in vivo can be greater than that of D-DNA. L-DNA duplexes have the same physical characteristics in terms of solubility, duplex stability and selectivity as D-DNA but form a left-helical double-helix. It is to be understood that the L-polynucleotide as used herein may also comprise some D-polynucleotides.

Due to the chemical nature of the L-polynucleotides these are not metabolized so that the pharmacokinetics underlying the use of L-nucleotides is not or at least not to such an extend affected by DNA specific degradation processes. In view of the increased stability of the L-polynucleotides the in vivo half-life of the complex as reported herein in a mammal is, thus, factually unlimited. Of particular importance is the fact that the L-polynucleotides are not nephrotoxic.

In one embodiment the mammal is selected from humans, monkeys, dogs, cats, horses, rats, or mice. In one embodiment the polynucleotide linker comprises D-DNA and L-DNA nucleotides, i.e. the polynucleotide linker is a mixture of D-DNA and L-DNA.

With this linker it is possible to engineer the half-life of the polynucleotide linker, i.e. the in vivo half-life of the oligonucleotide linker can be tailor made and adjusted to the intended application of the complex.

Each of the polynucleotides present in the complex as reported herein can comprise one or more effector moieties. Effector moieties allow the use of the complex as reported herein in the treatment of a disease. The effector moieties can be used e.g. for carrier purposes, i.e. the delivery of an effector function, and/or modulation of pharmacokinetic behavior, and/or modulation of the physico-chemical properties.

In one embodiment the effector moiety is selected from lipophilic moieties, peptides, proteins, carbohydrates and liposomes.

In one embodiment the polynucleotide is an L-polynucleotide.

The L-poly (deoxy) nucleotides can be present either as single- or as double-stranded polynucleotide. Typically, the L-poly (deoxy) nucleotide is present as single-stranded nucleic acid, which may form (defined) secondary structures and also tertiary structures. In such secondary structures also double-stranded stretches can be present. The L-poly (deoxy) nucleotide, however, can also be present at least partly as double-stranded molecule in the meaning that two strands, which are complementary to each other, are hybridized. The L-polynucleotide(s) can also be modified. The modification can be related to the individual nucleotides of the polynucleotide.

In order to avoid secondary structure formation 2,4-Dihydroxy-5-methylpyrimidin (T) can be used as nucleobase in one embodiment.

The L-polynucleotides in the complex as reported herein are in one embodiment susceptible to "self-hybridization".

Thus, the L-polynucleotides are more readily able to hybridize with complementary L-polynucleotide sequences but do not form a stable duplex with natural DNA or RNA.

In one embodiment, the nucleotides in the L-DNA segment have a conformation of 1'S, 3' R, and 4'S.

In one embodiment, the L-DNA polynucleotide linker is conjugated through hybridization of the members of the binding pairs at its termini with the polypeptide(s) of the complex.

In one embodiment the polynucleotide linker has a length of at least 1 nm. In one embodiment the polynucleotide linker has a length of from 6 nm to 100 nm. In one embodiment the polynucleotide linker has a length of at least 70 nucleotides.

The polynucleotide linker may also comprise a tag sequence. The tag sequence may be selected from commonly used protein recognition tags such as YPYDVPDYA (HA-Tag, SEQ ID NO: 64) or GLNDIFEAQKIEWHE (Avi-Tag, SEQ ID NO: 65).

Thus, in one embodiment of the methods as reported herein, the complex as reported herein not comprising an effector moiety is administered first and allowed to bind to its target(s) and afterwards the effector moiety conjugated to a polynucleotide complementary to at least a part of the (polynucleotide) linker is administered. Thereby the effector moiety is co-located to the complex bound to its target by hybridizing to the complex as reported herein in situ.

It is to be understood that the complex as reported herein is not limited to any specific nucleic acid sequence, or any polypeptide specifically binding to a target, or to specific cell types, or to specific conditions, or to specific methods, etc., as such may vary and the numerous modifications and variations therein will be apparent to those skilled in the art.

In one embodiment of the methods as reported herein the complex binds to the cell surface of a tumor cell and locally enriches to a high density or high local concentration of the effector moiety.

In one embodiment the effector moiety is labeled ss-L-DNA, which is administered simultaneously or subsequently to the initial target association of the complex.

The labeled ss-L-DNA effector moiety hybridizes to ss-L-DNA (oligonucleotide) linker of the complex.

The target bound complex is used to activate the innate immune response, namely to attract cytotoxic lymphocytes, also called natural killer cells (NK cells). NK cells play a major role in the rejection of tumors and cells infected by viruses. They kill cells by releasing small cytoplasmic granules of proteins called perforin and granzyme that cause the target cell to die by apoptosis.

In one embodiment the complex as reported herein is used to attract NK cells into close proximity of the bound complex. In one embodiment ss-L-DNA conjugated to a cytokine is used as effector moiety.

This cytokine labeled effector moiety can be used to attract NK cells. Cytokines involved in NK activation include IL-12, IL-15, IL-18, IL-2, and CCL5.

In one embodiment ss-L-DNA conjugated to an Fc portion of an antibody is used as effector moiety.

NK cells, along with macrophages and several other cell types, express the Fc receptor (FcR) molecule (FC-gamma-RIII=CD16), an activating biochemical receptor that binds the Fc portion of antibodies. This allows NK cells to target cells against which a humoral response has been mobilized and to lyse cells through antibody-dependent cellular cytotoxicity (ADCC).

In one embodiment, one or more or a combination of ss-L-DNA conjugated to one or more Fc parts is/are used as effector moieties.

In this embodiment the complex can be used to modulate the ADCC and/or the complement activation (CDC).

In one embodiment this complex is used in a method to screen engineered Fc compartments for their efficacy in engaging ADCC and CDC.

In one embodiment the complex is used to inhibit seminal fluid phosphatase.

In this embodiment the complex can be used to avoid NK cell inactivation.

In one embodiment the polypeptide specifically binding to a target, such as an antibody or antibody fragment specifically binding to a cell surface molecule, is conjugated to a ligand for a target receptor or large molecule that is more easily engulfed by the endocytotic mechanisms of a cell in order to increase the uptake of the complex into the cell presenting the target.

The target bound complex can then be internalized by endocytosis and the effector moiety released inside the cell.

The polypeptide specifically binding to a target is in one embodiment an antibody fragment.

The term "single-chain variable region fragment" or "scFv" denotes a variable, antigen-binding region of a single antibody light chain and single antibody heavy chain linked together by a covalent linkage having a length sufficient to allow the light and heavy chain portions to form an antigen binding site. Such a linker may be as short as a covalent bond. Especially suited linkers comprise of from 2 to 50 amino acid residues, and especially of from 5 to 25 amino acid residues.

Other antibody fragments are diabodies, first described by Holliger, P., et al. (PNAS (USA) 90 (1993) 6444-6448)). These may be constructed using heavy and light chains of an antibody, as well as by using individual CDR regions of an antibody. Typically, diabodies comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites.

An Fv antibody fragment contains a complete antigen-binding site which includes a VL domain and a VH domain held together by non-covalent interactions. Fv fragments also include constructs in which the VH and VL domains are cross-linked through glutaraldehyde, intermolecular disulfide bonds, or other linkers. The variable domains of the heavy and light chains can be fused together to form a single chain variable fragment (scFv), which retains the original specificity of the parent antibody. Single chain Fv (scFv) dimers, first described by Gruber, M., et al., J. Immunol. 152 (1994) 5368-5374, may be constructed using heavy and light chains of an antibody, as well as by using individual CDR regions of an antibody. Many techniques known in the art can be used to prepare the specific binding constructs suitable in the complex as reported herein (see e.g., US 2007/0196274, US 2005/0163782).

Bispecific antibodies can be generated by chemical cross-linking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. A suitable short linker is SGGGS (SEQ ID NO: 66) but other linkers can be used. Thus, two fragments assemble into a dimeric molecule. Further reduction of the linker length to zero to two amino acid residues can generate trimeric (triabodies) or tetrameric (tetrabodies) molecules.

In one embodiment the polypeptide specifically binding to a target, e.g. an antibody specifically binding to a cell surface receptor, can be linked to a ligand for a target receptor or large molecule that is more easily engulfed by the cell's endocytotic mechanisms.

In this embodiment the complex can be used to increase the uptake of the complex into the cell presenting the target. The target bound complex can then be internalized by endocytosis and the effector moiety released by acid hydrolysis or enzymatic activity when the endocytotic vesicle fuses with lysosomes.

The complexes as reported herein can be used to deliver the effector moiety intracellularly and extracellularly. The complex can be used to recognize cancer cells in situ making them attractive candidates for the development of targeted therapeutics.

When the non-covalent association of a component to another component (or to a particle or capsule) is desired, appropriate associative interactions that may be employed include, but are not limited to, antibody-antigen, receptor-hormone, avidin-biotin pairs, streptavidin-biotin, metal-chelate, small molecule/polynucleotide (see, e.g., Dervan, P. B., Bioorg. Med. Chem. 9 (2001) 2215-2235; Zahn, Z. Y. and Dervan, P. B., Bioorg. Med. Chem. 8 (2000) 2467-2474); polynucleotide/complementary polynucleotide (e.g., dimeric and trimeric helices), aptamer/small molecule, aptamer/polypeptide, coiled-coil, and polynucleotide/polypeptide (e.g. zinc finger, helix-tum-helix, leucine zipper, and helix-loop-helix motifs that bind to DNA sequences).

The complex as reported herein can be used to deliver a variety of effector moieties such as cytotoxic drugs including therapeutic drugs, components emitting radiation, molecules of plants, fungal, or bacterial origin, biological proteins, and mixtures thereof to a cell. The cytotoxic drug, e.g., can be an intracellularly acting cytotoxic drug, such as short-range radiation emitters, including, for example, short-range, high-energy α-emitters.

In one embodiment the effector moiety is a liposome encapsulating a drug (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the cell, and the like.

In one embodiment the effector moiety can comprise a radiosensitizer that enhances the cytotoxic effect of ionizing radiation (e.g., such as might be produced by $^{60}$Co or an X-ray source) on a cell.

In one embodiment the effector moiety is selected from monocytes chemotactic factors, or f-Met-Leu-Phe (fMLP), or f-Met-Leu-Phe-o-methyl ester, or formyl-norleucyl-phenylalanine, or formyl-methionyl-phenylalanine, or derivatives thereof.

In one embodiment the effector moiety is a reactive group.

The reactive group can be selected from any known reactive group, like Amino, Sulfhydryl, Carboxylate, Hydroxyl, Azido, Alkinyl or Alkenyl.

In one embodiment the reactive group is selected from Maleinimido, Succinimidyl, Dithiopyridyl, Nitrophenylester, Hexafluorophenylester.

If the mode of action depends on creating on a target a high local concentration of an effector like in the case of fMLP as effector moiety, the L-DNA nature of the linker entities allows specific hybridization with a second L-DNA oligonucleotide modified with the same or a different effector moiety.

The number of effector moieties which are bound to the second L-DNA has to be limited in order that there is no response induced by the single effector modified L-DNA. If desired, the second L-DNA compromises a further site which is capable of specifically hybridizing with a third L-DNA oligonucleotide modified with the same or a different effector moiety. Since it is easy to select many different sequences which form specifically a duplex in the presence of other duplexes a multimeric complex can be built up easily.

Multimeric complexes can be built up by using oligonucleotides with overlapping sequences to form a linear multimeric complex or by using branched oligonucleotides, wherein the branches are capable of hybridizing with a third oligonucleotide which results in formation of dendritic, multimeric complexes.

In one embodiment the effector moiety is an alpha emitter, i.e. a radioactive isotope that emits alpha particles. Suitable alpha emitters include, but are not limited to Bi, $^{213}$Bi, $^{211}$At, and the like.

The effector moiety can also comprise a ligand, an epitope tag, or an antibody.

Enzymatically active toxins and fragments thereof can be selected from diphtheria toxin A fragment, non-binding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), Morodica *charantia* inhibitor, curcin, crotin, *Saponaria officinalis* inhibitor, gelonin, mitogillin, restrictocin, phenomycin, and enomycin.

In one embodiment one or more L-DNA oligonucleotides, modified with a high density of caged effector moieties are hybridized to the L-DNA linker.

Cancer cells differ from normal cells in a variety of ways, one of which is the molecular composition of the cell surface. The altered surface chemistry allows cancer cells to respond efficiently to external signals for growth and survival and to interact directly with a variety of host tissue elements to migrate, enter the circulation, extravasate, and become colonized at a distant site. Besides serving as markers for malignant cells, tumor cell surface molecules are valuable targets for therapy due to their relatively easy accessibility to targeting molecules administered to the bloodstream or extracellular space (Feng, A., et al., Mol. Cancer Ther. 7 (2008) 569-578).

Contemplated tumor specific antigens include, but are not limited, to CEA, CD20, HER1, HER2/neu, HER3, HER4, PSCA, PSMA, CA-125, CA-19-9, c-Met, MUC1, RCAS1, Ep-CAM, Melan-A/MART1, RHA-MM, VEGF, EGFR, integrins, ED-B of fibronectin, ChL6, Lym-1, CD1b, CD3, CD5, CD14, CD20, CD22, CD33, CD52, CD56, TAO-72, interleukin-2 receptor (IL-2R), ferritin, neural cell adhesion molecule (NCAM), melanoma-associated antigen, ganglioside Gm, EOF receptor, tenascin, c-Met (HGFR).

In one embodiment the antibody is specifically binding to a post-translationally modified target on a cell surface receptor. In one embodiment the post-translationally target is modified by phosphorylation or glycosylation.

In one embodiment the first polypeptide and the second polypeptide bind to the same or an overlapping epitope.

It has been found that a posttranslationally modified target polypeptide can be detected by a complex consisting of two monovalent polypeptides specifically binding to a target that are linked to each other via a polynucleotide linker, wherein the first polypeptide binds to a polypeptide epitope of the target, the second polypeptide binds to a posttranslational polypeptide modification, wherein each monovalent binder has a Kdiss in the range of $10^{-2}$/sec to $10^{-3}$/sec, and wherein the complex has a Kdiss of $10^{-4}$/sec or less.

Different types of covalent amino acid modifications are known. The posttranslational modifications reported e.g. by Mann and Jensen (2003) and by Seo and Lee (2004) are herewith included by reference (Mann, M. and Jensen, O. N., Biochemistry 21 (2003) 255-261; Seo, J. and Lee, K.-J., Biochemistry and Molecular Biology 37/1 (2004) 35-44).

In one embodiment the posttranslational modification is selected from the group consisting of acetylation, phosphorylation, acylation, methylation, glycosylation, ubiquitinylation, sumoylation, sulfatation and nitration.

Acetylation (+42 Da molecular weight change) is a rather stable secondary modification. Examples are the acetylation which is found on the N-termini of many proteins or the acetylation on lysine or serine residues. Usually acetylation of a lysine residue is found at one or more well-defined position(s) within a polypeptide chain, while other lysine residues are acetylated less frequently or not at all.

Phosphorylation and de-phosphorylation (the net balance of which may be referred to as phosphorylation status) of a protein is known to be one of the key elements in regulating a proteins biological activity. A low percentage of phosphorylated amino acid residues may already be sufficient to trigger a certain biological activity.

Phosphorylation results in a mass increase of 80 Da (molecular weight increase). The amino acids tyrosine (Y), serine (S), threonine (T), histidine (H), and aspartic acid (D) can be phosphorylated. The more complex the biological function of a polypeptide is the more complex the corresponding pattern of possible sites of phosphorylation is. This is especially known and true for membrane-bound receptors, especially the so-called receptor tyrosine kinases (RTKs). As the nomenclature already suggests, at least part of the intracellular signaling of the RTKs is mediated by the phosphorylation status of certain tyrosine of the intracellular domain of such RTKs.

Polypeptides may be acylated by farnesyl, myristoyl or palmitoyl groups. Acylation usually occurs on the side chain of a cysteine residue.

Methylation as a secondary modification occurs via the side chain of a lysine residue. It has been shown that the binding properties of regulatory proteins that are able to bind to a nucleic acid can e.g. be modulated via methylation.

Glycosylation is a common secondary modification. It has a major influence on protein-protein interactions, on solubilization of proteins, their stability, also. Two different types of glycosylation are known: the N-linked (via the amino acid N (asparagine)) side chains and the O-linked side chains (via serine (S) or threonine (T)). Many different polysaccharides (linear or with branched side chains), some containing sugar derivatives like O-Glc-NAc, have been identified.

Ubiquitinylation and sumoylation, respectively, are known to influence the half-life of proteins in the circulation. Ubiquitinylation may serve as a destruction signal, resulting in cleavage and/or removal of ubiquitinylated polypeptides.

Sulfatation via a tyrosine residue (Y) appears to be important in the modulation of protein-protein (cell-cell) interaction as well as in protein ligand-interaction.

Nitration of tyrosine residues (Y) appears to be a hallmark of oxidative damage as e.g. in inflammatory processes.

The L-deoxynucleoside phosphoramidite units L-dT, L-dC, L-dA and L-dG can be prepared according to the literature (see e.g. Urata, H., et al., Nucl. Acids Res. 20 (1992) 3325-3332; Shi, Z. D., et al., Tetrahed. 58 (2002) 3287-3296). The L-deoxyribose derivative can be synthesized from L-arabinose through 8 steps. The L-deoxynucleosides can be obtained by a glycosylation of appropriate nucleobase derivatives with the L-deoxyribose derivative. After derivatization to nucleoside phosphoramidites, they can be incorporated into oligodeoxynucleosides by a solid phase DNA synthesis method. The oligomer can be purified by reverse phase HPLC and poly acrylamide gel electrophoresis (PAGE).

L-DNA can be synthesized like DNA in large scales by using standard synthesis protocols.

For expression and purification of scFv antibody fragments the scFv encoding nucleic acid can be cloned into an expression and/or secretion vector, such as pUC119mycHis, which would result in the addition of a c-myc epitope tag and hexahistidine tag at the C-terminus of the scFv. To create the (scFv')$_2$ dimer for immunohistochemistry (Adams, G. P., et al., Cancer Res. 53 (1993) 4026-4034), the c-myc epitope tag can be genetically removed from pUC119mycHis, and a free cysteine can be introduced at the C-terminus of the scFv preceding the hexahistidine tag. scFv or (scFv')$_2$ dimer protein can be harvested from the bacterial periplasm and purified by immobilized metal affinity chromatography and gel filtration (Nielsen, U. B., et al., Biochim. Biophys. Acta 1591 (2002) 109-118).

Alternatively scFvs can be produced by introducing the structural genes encoding scFvs an expression vector imparting a c-myc and a hexahistidine tag at the C-terminus (Liu, B., et al., Cancer Res. 64 (2004) 704-710). To produce soluble (scFv)$_2$, a second vector can be used to impart a cysteine and a hexahistidine tag at the C-terminus. Following IPTG induction, antibody fragments can be purified from bacterial periplasmic space on nitrilotriacetic acid-nickel beads. For FACS and immunohistochemistry studies, scFvs can be biotinylated using EZ-Link Sulfo-NHS-LC-Biotin (Pierce) according to the manufacturer's instructions.

For dissociation constant (KD) determination the a cell line expressing the respective target surface molecule can be grown to 90% confluency in suitable medium such as RPMI 1640 supplemented with 10% FCS. The cells can be harvested by brief digestion with trypsin (0.2%) in 2 mmol/l EDTA/PBS.

Biotinylated scFvs can be incubated with $10^5$ cells for 4 h at 4° C. in PBS/0.25% bovine serum albumin. Bound scFvs can be detected by streptavidin-phycoerythrin and analyzed by FACS. Data can be curve fitted and KD values can be calculated using GraphPad Prism (Graph-Pad Software).

For immunohistochemistry tissue sections from frozen and/or paraffin-embedded blocks can be used. For immunohistochemical analysis, tissue sections can be incubated with purified dimeric scFv (e.g. 50 µg/ml in 2% milk/PBS) at 4° C. for four hours, washed with PBS, incubated with an anti-(His)6 antibody diluted 1:400 (Santa Cruz Biotechnology), followed by biotinylated anti-anti-(His)6 antibody antibody diluted 1:400 (Vector Lab) and horseradish peroxidase-conjugated streptavidin diluted 1:400 (Sigma). Binding can be detected using diaminobenzidine as the substrate (Sigma).

Alternatively frozen sections of test and control tissues can be stained with biotinylated scFvs (250 nmol/l) at room temperature for one hour. A scFv that does not bind to the test cell lines by FACS can be used as a control for all experiments. Bound scFvs can be detected by streptavidin-horseradish peroxidase using 3,3'-diaminobenzidine substrate. The stained tissues can be counter-stained with hematoxylin, dried in 70%, 95% and 100% ethanol, mounted and analyzed.

Specifically see US 2003/0152987 concerning immunohistochemistry (IHC) and fluorescence in situ hybridization (FISH) for detecting HER2 overexpression and amplification (incorporated herein by reference).

For the determination of internalization the following procedure can be used. For fluorescence microscopy experiments, cells can be grown to about 80% confluency in 24-well plates and co-incubated with non-targeted or targeted complexes labeled with 1,1'-dioctadecyl-3,3,3',3'-tetramethylindocarbocyanine-5,5'-disulfonic acid for four hours at 37° C. The cells can be washed with PBS and examined with a Nikon Eclipse TE300 fluorescence microscope. For FACS analysis, cells can be incubated with 1,1'-dioctadecyl-3,3,3',3'-tetramethylindocarbocyanine-5,5'-disulfonic acid-labeled complexes at 37° C. for two hours, removed from the dish by trypsin digestion, exposed to glycine buffer (pH 2.8; 150 mmol/l NaCl) at room temperature for 5 min. to remove surface-bound liposomes, and analyzed by FACS (LSRII; BD Biosciences). Mean fluorescence intensity values can be used to calculate the percentage of internalized liposomes (resistant to glycine treatment) over total cell associated liposomes (before glycine treatment).

For a growth inhibition and internalization assays cancer cells at about 30%-80% confluence can be incubated with various concentrations of affinity-purified complex at 37° C. for 72 h in medium containing 1% FCS. Growth status can be assessed using the tetrazolium salt 3-(4,5-dimethylthizaol-2-yl)-2,5-diphenyltetrazolium bromide assay (Promega), and the $IC_{50}$ can be calculated using KaleidaGraph 3.5 (Synergy Software). For internalization assays, the complex can be biotinylated with sulfo-NHS-LC-biotin (Pierce) and incubated with target cells at 37° C. for various amounts of time. Cells can be washed with 100 mM glycine buffer (pH 2.8), fixed with 2% formaldehyde, permeabilized with ice-cold 100% methanol, and incubated with streptavidin-FITC. The stained cells can be first examined with an Axiophot fluorescence microscope (Zeiss) and further studied with a Leica TCS NT confocal laser fluorescence microscope (Leica).

For toxicity determination cells can be plated at 6,000 per well in 96-well plates and incubated with a complex as reported herein at varying concentrations (0-10 µg/ml) for two hours at 37° C. After removal of the complex, the cells can be washed once with RPMI 1640 supplemented with 10% FCS and incubated for an additional 70 h at 37° C. The cell viability can be assayed using Cell Counting Kit-8 (Dojindo) according to the manufacturer's instructions. The data can be expressed as the percent of viable cells compared with that of untreated control cells.

For in vitro cytotoxicity determination cancer cells can be seeded in 96-well plates (6,000 cells per well for e.g. PC3 and Du-145 cells or 10,000 cells per well for e.g. LNCaP cells) and incubated with the complex as reported herein (0-10 µg/ml) for 4 h at 37° C. Cells can be washed twice with supplemented RPMI 1640 to remove drugs and incubated with fresh medium for an additional 72 h at 37° C. Cell viabilities can be assayed using the 3-(4,5-dimethylthiazol-2-yl)-2,5-diphenyltetrazolium bromide staining (Carmichael, J., et al., Cancer Res. 47 (1987) 936-942), and the results can be read at 570 nm using a microtiter plate reader (SpectraMax 190, Molecular Devices). The cell viability can be determined using the Cell counting kit-8 (Dojindo) according to the manufacturer's instructions.

For an assay of intracellular delivery the following method can be used. To assess intracellular complex delivery, the complex can be added to cells along with 1 µg/ml of purified (His)6-tagged scFv, incubated at 37° C. for 30 min, and washed three times with saline containing 1 mM EDTA to remove cell surface-bound complexes that failed to internalize. Uptake of the complex can be determined by microfluorimetry with a Gemini microfluorometer (Molecular Devices) and by an inverted fluorescence microscope (Nikon).

Recombinant Methods and Compositions

Generally polypeptides such as antibody fragments or members of a binding pair may be produced using recombinant methods and compositions, e.g., as described in U.S. Pat. No. 4,816,567.

In one embodiment isolated nucleic acid encoding each polypeptide of the complex as reported herein is provided.

Such nucleic acid may encode an amino acid sequence comprising the VL and/or an amino acid sequence comprising the VH of an antibody (e.g., the light and/or heavy chains of the antibody) and/or an amino acid sequence of a member of a binding pair.

In one embodiment a host cell comprising such nucleic acid is provided. In one embodiment a host cell is provided that comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment the host cell is a eukaryotic cell, e.g. a Chinese Hamster Ovary (CHO) cell or lymphoid cell (e.g., Y0, NS0, Sp20 cell). For expression of antibody fragments and polypeptides in bacteria, see, e.g., U.S. Pat. Nos. 5,648,237, 5,789,199, and 5,840,523, Charlton, Methods in Molecular Biology, Vol. 248, B. K. C. Lo, (ed.), Humana Press, Totowa, N.J., (2004) pp. 245-254. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors (see Gemgross, T. U., Nat. Biotech. 22 (2003) 1409-1414), and Li, H., et al., Nat. Biotech. 24 (2006) 210-215).

Plant cell cultures can also be utilized as hosts (see, e.g., U.S. Pat. Nos. 5,959,177, 6,040,498, 6,420,548, 7,125,978, and 6,417,429).

Vertebrate cells may also be used as hosts. For example, mammalian cell lines that are adapted to grow in suspension may be useful. Other examples of useful mammalian host cell lines are monkey kidney CV1 line transformed by SV40 (COS-7), human embryonic kidney line (HEK 293), baby hamster kidney cells (BHK), mouse sertoli cells (TM4 cells as described, e.g., in Mather, J. P., Biol. Reprod. 23 (1980) 243-252), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells, as described, e.g., in Mather, J. P., et al., Annals N.Y. Acad. Sci. 383 (1982) 44-68, MRC 5 cells, and FS4 cells. Other useful mammalian host cell lines include Chinese hamster ovary (CHO) cells, including DHFR$^-$ CHO cells (Urlaub, G., et al., Proc. Natl. Acad. Sci. USA 77 (1980) 4216-4220), and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

The host cells used to produce the polypeptides of the complex as reported herein can be cultured in a variety of media. Commercially available media such as Ham's F10 (Sigma), Minimal Essential Medium ((MEM), (Sigma), RPMI-I640 (Sigma), and Dulbecco's Modified Eagle's Medium ((DMEM), Sigma) are suitable for culturing the host cells. In addition, any of the media described in Ham, R. G., et al., Meth. Enzymol. 58 (1979) 44-93, Barnes, D., et al., Anal. Biochem. 102 (1980) 255-270, U.S. Pat. Nos. 4,767,704, 4,657,866, 4,927,762, 4,560,655, 5,122,469, WO 90/03430, WO 87/00195, and U.S. Re 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic components usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the polypeptide can be produced intracellularly, in the periplasmic space, or directly secreted into the medium. If the polypeptide is produced intracellularly, as a first step, the particulate debris, either host cells or lysed fragments, is removed, for example, by centrifugation or ultrafiltration. For example, Carter, P., et al., Bio/Technology 10 (1992) 163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. The polypeptide composition prepared from the cells can be purified using, for example, hydroxylapatite chromatography, gel electrophoresis, dialysis, and affinity chromatography, with affinity chromatography being the preferred purification technique for antibodies. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark, R., et al., J. Immunol. Meth. 62 (1983) 1-13). Protein G is recommended for all mouse isotypes and for human γ3 (Guss, B., et al., EMBO J. 5 (1986) 1567-1575). The matrix to which the affinity ligand is attached is most often agarose, but other matrices are available. Mechanically stable matrices such as controlled pore glass or poly (styrene divinyl) benzene allow for faster flow rates and shorter processing times than can be achieved with agarose. Where the antibody comprises a CH3 domain, the Bakerbond ABX™ resin (J.T. Baker, Phillipsburg, N.J., USA) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a poly aspartic acid column), chromatofocusing, SDS-PAGE, and ammonium sulfate precipitation are also available depending on the antibody to be recovered.

Following any preliminary purification step(s), the mixture comprising the polypeptide of interest and contaminants may be subjected to low pH hydrophobic interaction chromatography using an elution buffer at a pH between about 2.5-4.5, especially performed at low salt concentrations (e.g., from about 0-0.25 M salt).

The complex and its individual components as reported herein can be isolated and purified as desired. Unwanted components of a reaction mixture in which the complex is formed are e.g. polypeptides and polynucleotides that did not end up in the desired complex but constitute its building blocks. In one embodiment the complex is purified to greater than 80% purity as determined by analytical size exclusion chromatography. In some embodiments, the complex is purified to greater than 90%, 95%, 98%, or 99% purity by weight as determined by analytical size exclusion chromatography, respectively. Purity can alternatively e.g. be easily determined by SDS-PAGE under reducing or non-reducing conditions using, for example, Coomassie blue or silver stain in protein detection. In case purity is assessed on the complex level, size exclusion chromatography can be applied to separate the complex from side products and the OD at 260 nm is monitored to assess its purity.

Immunoconjugates

Herein are also provided complexes in which at least one of the polypeptides that specifically binds to a target or the linker is further conjugated to one or more effector moieties, e.g. cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment the effector moiety is a drug, including but not limited to a maytansinoid (see U.S. Pat. Nos. 5,208,020, 5,416,064, EP 0 425 235), an auristatin such as monomethylauristatin drug moieties DE and DF (MMAE and MMAF, see U.S. Pat. Nos. 5,635,483, 5,780,588, 7,498, 298), a dolastatin, a calicheamicin or derivative thereof (see U.S. Pat. Nos. 5,712,374, 5,714,586, 5,739,116, 5,767,285, 5,770,701, 5,770,710, 5,773,001, 5,877,296, Hinman, L. M., et al., Cancer Res. 53 (1993) 3336-3342, Lode, H. N., et al., Cancer Res. 58 (1998) 2925-2928), an anthracycline such as daunomycin or doxorubicin (see Kratz, F., et al., Current Med. Chem. 13 (2006) 477-523, Jeffrey, S. C., et al., Bioorg. Med. Chem. Letters 16 (2006) 358-362, Torgov, M. Y., et al., Bioconjug. Chem. 16 (2005) 717-721, Nagy, A., et al., Proc. Natl. Acad. Sci. USA 97 (2000) 829-834, Dubowchik, G. M., et al., Bioorg. Med. Chem. Lett. 12 (2002) 1529-1532, King, H. D., et al., J. Med. Chem. 45 (2002) 4336-4343, and U.S. Pat. No. 6,630,579), methotrexate, vindesine, a taxane such as docetaxel, paclitaxel, larotaxel, tesetaxel, and ortataxel, a trichothecene, and CC 1065.

In one embodiment the effector moiety is an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria*

*officinalis* inhibitor, gelonin, mitogellin, restrictocin, phenomycin, enomycin, and the tricothecenes.

In one embodiment the effector moiety is a radioactive atom. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu. When the radioconjugate is used for detection, it may comprise a radioactive atom for scintigraphic studies, for example $Tc^{99}m$ or $I^{123}$, or a spin label for nuclear magnetic resonance (NMR) imaging (also known as magnetic resonance imaging, MRI), such as $I^{123}$ again, $I^{131}$, $In^{111}$, $F^{19}$, $C^{13}$, $N^{15}$, $O^{17}$, gadolinium, manganese or iron.

The effector moiety can be conjugated to any component of the complex as reported herein using a variety of bifunctional protein coupling agents such as N-succinimidyl-3-(2-pyridyldithio) propionate (SPDP), succinimidyl-4-(N-maleiimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido components (such as bis (p-azidobenzoyl) hexane diamine), bis-diazonium derivatives (such as bis-(p-diazoniumbenzoyl)-ethylene diamine), diisocyanates (such as toluene 2,6-diisocyanate), and bis-active fluorine components (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine penta acetic acid (MX-DTPA) is an exemplary chelating agent for conjugation of radionucleotide to the complex (see WO 94/11026). The linker for conjugating the toxic moiety to the complex as reported herein can be a "cleavable linker" facilitating release of a cytotoxic drug in the cell. For example, an acid-labile linker, peptidase-sensitive linker, photolabile linker, dimethyl linker, or disulfide-containing linker (Chari, R. V., et al., Cancer Res. 52 (1992) 127-131, U.S. Pat. No. 5,208,020) can be used.

The effector moiety may be conjugated to a compound of the complex as reported herein, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Complex Dependent Enzyme Mediated Prodrug Therapy (CDEPT)

The complex as reported herein may also be used in CDEPT by using an effector moiety which is a prodrug-activating enzyme which converts a prodrug (e.g. a peptidyl chemotherapeutic agent, see WO 81/01145) to an active anti-cancer drug (see also, for example, WO 88/07378 and U.S. Pat. No. 4,975,278).

The enzyme component of the complex useful for CDEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs, arylsulfatase useful for converting sulfate containing prodrugs into free drugs, cytosine deaminase useful for converting non-toxic 5-fluorocytosine into the anti-cancer drug, 5-fluorouracil, proteases, such as *Serratia* protease, thermolysin, subtilisin, carboxypeptidases and cathepsins (such as cathepsins B and L), that are useful for converting peptide-containing prodrugs into free drugs, D-alanylcarboxypeptidases, useful for converting prodrugs that contain D-amino acid substituents, carbohydrate-cleaving enzymes such as β-galactosidase and neuraminidase useful for converting glycosylated prodrugs into free drugs, β-lactamase useful for converting drugs derivatized with β-lactams into free drugs, and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs as reported herein into free active drugs (see, e.g., Massey, R. J., Nature 328 (1987) 457-458). Complex-abzyme conjugates can be prepared as described herein for delivery of the abzyme to a tumor cell population. The enzymes can be non-covalently or covalently bound to the complex by techniques well known in the art such as the use of the heterobifunctional crosslinking reagents discussed above. Alternatively, fusion proteins comprising at least the antigen binding region of an antibody linked to at least a functionally active portion of an enzyme can be constructed using recombinant DNA techniques well known in the art (see, e.g., Neuberger, M. S., et al., Nature 312 (1984) 604-608.

Methods and Compositions for Diagnostics and Detection

In certain embodiments any of the complexes provided herein is useful for detecting the presence of a target specifically bound by the polypeptides in the complex in a biological sample. The term "detecting" as used herein encompasses quantitative or qualitative detection.

In one embodiment the complex is provided for use in a method of diagnosis or detection. In a further aspect, a method of detecting the presence of the target of the polypeptides of the complex as reported herein in a biological sample is provided. In certain embodiments, the method comprises contacting the biological sample with a complex as reported herein under conditions permissive for binding of the polypeptides to its target, and detecting whether a complex is formed between the complex and the target. Such method may be an in vitro or in vivo method.

In one embodiment the complex as reported herein is used to select subjects eligible for therapy with an isolated polypeptide comprised in the complex, e.g. where the target is a biomarker for selection of patients.

In certain embodiments a labeled complex is provided, i.e. a complex wherein the effector moiety is a label. Labels include, but are not limited to, labels that are detected directly (such as fluorescent, chromophoric, electron-dense, chemiluminescent, and radioactive labels), as well as labels, such as enzymes or ligands, that are detected indirectly, e.g., through an enzymatic reaction or molecular interaction. Exemplary labels include, but are not limited to, the radioisotopes $P^{32}$, $C^{14}$, $^{125}$, $H^{3}$, and $I^{131}$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of a complex as reported herein are prepared by mixing such complex having the desired degree of purity with one or more optional pharmaceutically acceptable carriers (Osol, A. (ed.), Remington's Pharmaceutical Sciences, 16th edition, Mack Publishing Company (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol), low molecular weight (less than about 10 residues) polypeptides, proteins, such as serum albumin, gelatin, or immunoglobulins, hydrophilic polymers such as poly vinylpyrrolidone, amino acids such as glycine, glutamine, asparagine, histidine, arginine, or lysine, monosaccharides, disaccharides, and other carbohydrates including glucose, mannose, or dextrins, chelating agents such as EDTA, sugars such as sucrose, mannitol, trehalose or sorbitol, salt-forming counter-ions such as sodium, metal complexes (e.g. Zn-protein complexes), and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, especially those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. (ed.), (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

Any of the complexes reported herein may be used in therapeutic methods.

In one aspect a complex as reported herein for use as a medicament is provided. In further aspects a complex for use in treating cancer is provided. In certain embodiments a complex for use in a method of treatment is provided. In certain embodiments the invention provides a complex for use in a method of treating an individual having cancer comprising administering to the individual an effective amount of the complex. In one such embodiment the method further comprises administering to the individual an effective amount of at least one additional therapeutic agent. In further embodiments the invention provides a complex as reported herein for use in inhibiting angiogenesis or inhibiting cell proliferation or depleting B-cells. In certain embodiments, the invention provides a complex for use in a method of inhibiting angiogenesis, or inhibiting cell proliferation, or depleting B-cells in an individual comprising administering to the individual an effective of the complex to inhibit angiogenesis, or inhibit cell proliferation, or deplete B-cells. An "individual" according to any of the above embodiments is especially a human.

In a further aspect herein is provided the use of a complex as reported herein in the manufacture or preparation of a medicament. In one embodiment the medicament is for treatment of cancer. In a further embodiment the medicament is for use in a method of treating cancer comprising administering to an individual having cancer an effective amount of the medicament. In a further embodiment the medicament is for inhibiting angiogenesis, or inhibiting cell proliferation, or depleting B-cells. In a further embodiment the medicament is for use in a method of inhibiting angiogenesis, or inhibiting cell proliferation, or depleting B-cells in an individual comprising administering to the individual an amount effective of the medicament to inhibit angiogenesis, or inhibit cell proliferation, or deplete B-cells. An "individual" according to any of the above embodiments may be a human.

In a further aspect as reported herein a method for treating cancer is provided. In one embodiment the method comprises administering to an individual having such cancer an effective amount of a complex as reported herein. An "individual" according to any of the above embodiments may be a human.

In a further aspect as reported herein a method for inhibiting angiogenesis, or inhibiting cell proliferation, or depleting B-cells in an individual is provided. In one embodiment the method comprises administering to the individual an effective amount of a complex as reported herein to inhibit angiogenesis, or inhibit cell proliferation, or deplete B-cells. In one embodiment an "individual" is a human.

In a further aspect as reported herein a pharmaceutical formulations comprising any of the complexes provided herein, e.g., for use in any of the above therapeutic methods is provided. In one embodiment a pharmaceutical formulation comprises any of the complexes provided herein and a pharmaceutically acceptable carrier. In another embodiment a pharmaceutical formulation comprises any of the complexes as reported herein and at least one additional therapeutic agent.

Complexes as reported herein can be used either alone or in combination with other agents in a therapy. For instance, a complex as reported herein may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Complexes as reported herein can also be used in combination with radiation therapy.

A complex as reported herein can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Complexes as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The complex need not be, but is optionally formulated with one or more agents currently used to prevent or treat the disorder in question. The effective amount of such other agents depends on the amount of complex present in the formulation, the type of disorder or treatment, and other factors discussed above. These are generally used in the same dosages and with administration routes as described herein, or about from 1% to 99% of the dosages described herein, or in any dosage and by any route that is empirically/clinically determined to be appropriate.

For the prevention or treatment of disease, the appropriate dosage of a complex as reported herein (when used alone or in combination with one or more other additional therapeutic agents) will depend on the type of disease to be treated, the type of complex, the severity and course of the disease, whether the complex is administered for preventive or therapeutic purposes, previous therapy, the patient's clinical history and response to the complex, and the discretion of the attending physician. The complex is suitably administered to the patient at one time or over a series of treatments. Depending on the type and severity of the disease, about 1 µg/kg to 15 mg/kg (e.g. 0.1 mg/kg-10 mg/kg) of complex can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the complex would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the complex). An initial higher loading dose, followed by one or more lower doses may be administered. The progress of this therapy can be easily monitored by conventional techniques and assays.

Articles of Manufacture

In one aspect as reported herein an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a complex as reported herein. The label or package insert indicates that the composition is used for treating the condition of choice. Moreover, the article of manufacture may comprise (a) a first container with a composition contained therein, wherein the composition comprises a complex as reported herein; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Assays

As mentioned above, the expression level of any cell surface target can be detected by an immunohistochemical method.

For example, methods for the detection of HER2 are well known in the art and corresponding commercial kits are easily available. Exemplary kits which may be used are, inter alia, HercepTest™ produced and distributed by the company Dako or the test called Ventana Pathway™. Suitably the level of HER2 protein expression is assessed by using the reagents provided with and following the protocol of the HercepTest™. A skilled person will be aware of further means and methods for determining the expression level of HER2 by immunohistochemical methods (see for example WO 2005/117553). Therefore, the expression level of HER2 can be easily and reproducibly determined by a person skilled in the art without undue burden. However, to ensure accurate and reproducible results, the testing must be performed in a specialized laboratory, which can ensure validation of the testing procedures.

Alternatively, further methods for the evaluation of the protein expression level of HER2 may be used, e.g. Western Blots, ELISA-based detection systems and so on. A normal expression level of HER2 protein can be determined by these techniques and a tissue sample of those patients classified as having a normal level of HER2 protein expression further analyzed for c-Myc gene amplification.

The expression level of HER2 may also be determined by the evaluation of mRNA expression by corresponding techniques, such as Northern Blot, real time PCR, RT PCT and the like. All these detection systems are well known in the art and can be deduced from standard text books, such as Lottspeich, F. and Zorbas, H., (Bioanalytik, Spektrum Akademischer Verlag (1998)) or Sambrook and Russell (Molecular Cloning: A Laboratory Manual, CSH Press, Cold Spring Harbor, N.Y., USA (2001)). A normal expression level of HER2 mRNA can be determined by these techniques and a tissue sample of those patients classified as having a normal level of HER2 mRNA expression further analyzed for c-Myc gene amplification.

Generally, i.e. not target specifically, the growth inhibitory characteristics of the complex as reported herein can be evaluated using the breast tumor cell line, SK-BR-3 (see Hudziak, R. M., et al., Mol. Cell. Biol. 9 (1989) 1165-1172). Briefly, SK-BR-3 cells can be detached by using 0.25% (vol/vol) trypsin and suspended in complete medium at a density of $4 \times 10^5$ cells per ml. Aliquots of 100 μl ($4 \times 10^4$ cells) can be plated into 96-well microdilution plates, the cells can be allowed to adhere, and 100 μl of media alone or media containing the complex (final concentration about 5 μg/ml) can be then added. After 72 hours, plates can be washed twice with PBS (pH 7.5), stained with crystal violet (0.5% in methanol), and analyzed for relative cell proliferation as described in Sugaman, B. J., et al., Science 230 (1985) 943-945.

Monoclonal antibodies 2C4 and 4D5 inhibited SK-BR-3 relative cell proliferation by about 20% and about 56%, respectively.

Generally, i.e. non-target specifically, the complex as reported herein can be evaluated for its ability to inhibit HRO-stimulated tyrosine phosphorylation of proteins in the MW 180,000 range from whole-cell lysates of MCF7 cells (Lewis, G. D., et al., Cancer Research 56 (1996) 1457-1465). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis.

However, these cells are ideal for HRG tyrosine phosphorylation assays because under the assay conditions used, in the absence of exogenously added HRG, they exhibit low to undetectable levels of tyrosine phosphorylation proteins in the MW 180,000 range.

For the assay MCF7 cells can be plated in 24-well plates and the complex as reported herein can be added to each well and incubated for 30 minutes at room temperature; then rHRGβ$1_{177-244}$ can be added to each well to a final concentration of 0.2 nM, and the incubation can be continued for 8 minutes. Media can be carefully aspirated from each well, and reactions can be stopped by the addition of 100 μl of SDS sample buffer (5% SDS, 25 mM DTT, and 25 mM Tris-HCl, pH 6.8). Each sample (25 μl) can be electrophoresed on a 4-12% gradient gel (Novex) and then electrophoretically transferred to poly vinylidene difluoride membrane. Anti-phosphotyrosine (4G 10, from UBI, used at 1 μg/ml) immunoblots can be developed, and the intensity of the predominant reactive band at Mr-180,000 can be quantified by reflectance densitometry, as described previously (Holmes, W. E., et al., Science 256 (1992) 1205-1210, Sliwkowski, M. X., et al., J. Biol. Chem. 269 (1994) 14661-14665).

Monoclonal antibodies 2C4, and 4D5, significantly inhibited the generation of a HRG-induced tyrosine phosphorylation signal at MW 180,000. In the absence of HRG, none of these antibodies were able to stimulate tyrosine phosphorylation of proteins in the MW 180,000 range. Also, these antibodies do not cross-react with EGFR (Fendly, B. M., et al., Cancer Research 50 (1990) 1550-1558), ErbB3, or ErbB4. Antibody 2C4 significantly inhibited HRG stimulation of p180 tyrosine phosphorylation to <25% of control. Monoclonal antibody 4D5 was able to block HRG stimulation of tyrosine phosphorylation by about 50%.

Inhibition of HRG binding to MCF7 breast tumor cell lines by the complex as reported herein can be performed with monolayer cultures on ice in a 24-well-plate format (Lewis, G. D., et al., Cancer Research 56 (1996) 1457-1465). The complex can be added to each well and incubated for 30 minutes. $I^{125}$-labeled rHRGβ$1_{177-224}$ (25 pm) can be added, and the incubation can be continued for 4 to 16 hours.

Analysis of the data yielded an $IC_{50}$ of 2.4±0.3 nM for 2C4 and a maximum inhibition of −74% for 2C4 in agreement with the tyrosine phosphorylation data.

The ability of ErbB3 to associate with ErbB2 can be tested in a co-immunoprecipitation experiment. $1.0 \times 10^6$ MCF7 or SK-BR-3 can be were seeded in six well tissue culture plates in 50:50 DMEM/Ham's F12 medium containing 10% fetal bovine serum (FBS) and 10 mM HEPES, pH 7.2 (growth medium), and allowed to attach overnight. The cells can be starved for two hours in growth medium without serum prior to beginning the experiment.

The cells can be washed briefly with phosphate buffered saline (PBS) and then incubated with either 100 nM of the complex diluted in 0.2% w/v bovine serum albumin (BSA), RPMI medium, with 10 mM HEPES, pH 7.2 (binding buffer), or with binding buffer alone (control). After one hour at room temperature, HRG can be added to a final concentration of 5 nM to half the wells (+). A similar volume of binding buffer can be added to the other wells (−). The incubation can be continued for approximately 10 minutes.

Supernatants can be removed by aspiration and the cells can be lysed in RPMI, 10 mM HEPES, pH 7.2, 1.0% (v/v) TRITON X-100™, 1.0% (w/v) CHAPS (lysis buffer), containing 0.2 mM PMSF, 10 μg/ml leupeptin, and 10 TU/ml aprotinin. The lysates can be cleared of insoluble material by centrifugation. ErbB2 can be immunoprecipitated using a monoclonal antibody covalently coupled to an affinity gel (Affi-Prep, Bio-Rad). This antibody (Ab-3, Oncogene Sciences) recognizes a cytoplasmic domain epitope. Immunoprecipitation can be performed by adding 10 μl of gel slurry containing approximately 8.5 μg of immobilized antibody to each lysate, and the samples can be allowed to mix at room temperature for two hours. The gels can then be collected by centrifugation. The gels can be washed batchwise three times with lysis buffer to remove unbound material. SDS sample buffer can then be added and the samples can be heated briefly in a boiling water bath.

Supernatants can be run on 4-12% polyacrylamide gels and electroblotted onto nitrocellulose membranes.

The presence of ErbB3 can be assessed by probing the blots with a polyclonal antibody against a cytoplasmic domain epitope thereof (c-17, Santa Cruz Biotech). The blots can be visualized using a chemiluminescent substrate (ECL, Amersham).

Generally, the ability of the complex to inhibit EGF, TGF-α or HRG activation of MAPK can be assessed in the following way: MCF7 cells ($10^5$ cells/well) can be plated in serum containing media in 12-well cell culture plates. The next day, the cell media can be removed and fresh media containing 0.1% serum can be added to each well. This procedure can be repeated the following day and prior to assay the media can be replaced with serum-free binding buffer (Jones, J. T., et al., J. Biol. Chem. 273 (1998) 11667-11674, and Schaefer, G., et al., J. Biol. Chem. 274 (1999) 859-866). Cells can be allowed to equilibrate to room temperature and then incubated for 30 minutes with 0.5 ml of 200 nM complex solution. Cells can then be treated with 1 nM EGF, 1 nM TGF-α or 0.2 nM HRG for 15 minutes. The reaction can be stopped by aspirating the cell medium and then adding 0.2 ml SDS-PAGE sample buffer containing 1% DTT. MAPK activation can be assessed by Western blotting using an anti-active MAPK antibody (Promega) as described previously (Jones, J. T., et al., J. Biol. Chem. 273 (1998) 11667-11674).

Generally, a xenograft model using the lung adenocarcinoma cell line, Calu-3, can be used to assess the efficacy of the complex as reported herein to suppress tumor growth. Female NCR nude mice can be inoculated subcutaneously with 20×10$^6$ cells in 0.1 ml. Tumor measurements can be taken twice per week and when tumor modules reached a volume of 100 mm$^3$, animals can be randomized to treatment groups. The treatment groups can be:
(a) control monoclonal antibody, e.g. mAb 1766;
(b) HERCEPTIN®, 10 mg/kg;
(c) monoclonal antibody 2C4, 10 mg/kg and/or monoclonal antibody 4D5, 10 mg/kg;
(d) HERCEPTIN® and 2C4, each at 10 mg/kg; and
(e) the complex as reported herein, 10 mg/kg.

Animals can be treated twice per week until day 24. Tumor volumes can be measured twice per week until day 38.

Human colorectal cell lines such as HCA-7, LS 174T or CaCo-2 can be implanted subcutaneously in athymic nude mice as described in Sheng, H., et al., J. Clin. Invest. 99 (1997) 2254-2259. Once tumors are established to about 100 mm$^3$ in volume, groups of animals can be treated with 10-50 mg/kg of the complex as reported herein administered twice weekly by injection in the intraperitoneal cavity.

The effect of the complex on human breast cancer cells which do not overexpress ErbB2 can be assessed in a 3 day Alamar Blue assay (Ahmed, S. A., J. Immunol. Methods 170 (1994) 211-224, Tommasi, S., et al., Int. J. Oncol. 5 (1994) 473-477). The cells used in this assay can be MDA-175 human breast cancer cells which express ErbB2 at a 1+ level.

Generally the efficacy of the complex against MCF7 xenografts which are estrogen receptor positive (ER+) and express low levels of ErbB2 can be assessed as follows: Female mice supplemented with estrogen can be used. The complex can be administered at a dose of 30 mg/kg every week.

The following examples, figures and sequences are provided to aid the understanding of the present invention, the true scope of which is set forth in the appended claims. It is understood that modifications can be made in the procedures set forth without departing from the spirit of the invention.

```
Sequences

SEQ ID NO: 01   VH (mAb 1.4.168)

SEQ ID NO: 02   VL (mAb 1.4.168)

SEQ ID NO: 03   VH (mAb 8.1.2)

SEQ ID NO: 04   VL (mAb 8.1.2)

SEQ ID NO: 05   17mer ss-DNA (covalently bound with 5' end to
                FAB' of anti-TroponinT MAB a and FAB' 1.4.168 to
                IGF-1R, respectively)

SEQ ID NO: 06   19mer ss-DNA (covalently bound with 3' end to
                FAB' of anti-TroponinT MAB b and FAB' 8.1.2 to
                phosphorylated IGF-1R, respectively)

SEQ ID NO: 07   complementary 19mer ss-DNA (used as part of a
                linker)

SEQ ID NO: 08   complementary 17mer ss-DNA (used as part of a
                linker)

SEQ ID NO: 09   Epitope "A" for anti-Troponin antibody a.

SEQ ID NO: 10   Epitope "B" for anti-Troponin antibody b.

SEQ ID NO: 11   IGF-1R (1340-1366)

SEQ ID NO: 12   hInsR (1355-1382)

SEQ ID NO: 13   35-mer L-DNA polynucleotide linker

SEQ ID NO: 14   75-mer L-DNA polynucleotide linker

SEQ ID NO: 15   95-mer L-DNA polynucleotide linker

SEQ ID NO: 16   4D5 FAB' heavy chain amino acid sequence

SEQ ID NO: 17   4D5 FAB' light chain amino acid sequence

SEQ ID NO: 18   2C4 FAB' heavy chain amino acid sequence

SEQ ID NO: 19   2C4 FAB' light chain amino acid sequence

SEQ ID NO: 20   Residues 22-645 within the extracellular domain
                (ECD) of ErbB2
```

| Sequences | |
|---|---|
| SEQ ID NO: 21 | 5'-AGT CTA TTA ATG CTT CTG C-XXX-Y-Z-3', wherein X = propylene-phosphate introduced via phosphoramidite C3 (3-(4,4'-dimethoxytrityloxy)propyl-1-[(2-cyanoethyl)-(N,N-diisopropyl)]-phosphoramidite (Glen Research), wherein Y = 5'-amino-modifier C6 introduced via (6-(4-monomethoxytritylamino)hexyl-(2-cyanoethyl)-(N,N-diisopropyl)-phosphoramidite (Glen Research), and wherein Z = 4[N-maleinimidomethyl]cyclohexane-1-carboxy introduced via sulfosuccinimidyl 4-[N-maleimidomethyl]cyclohexane-1-carboxylate (ThermoFischer). |
| SEQ ID NO: 22 | 5'-Y-Z-XXX-AGT TCT ATC GTC GTC CA-3', wherein X = propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y = 5'-Amino-Modifier C6 introduced via (6-(4-Monomethoxytritylamino)hexyl-(2-cyanoethyl)-(N,N-diisopropyl)-phosphoramidite (Glen Research), and wherein Z = 4[N-maleinimidomethyl]cyclohexane-1-carboxy introduced via Sulfosuccinimidyl 4-[N-maleimidomethyl]cyclohexane-1-carboxylate (ThermoFischer). |
| SEQ ID NO: 23 | 5'-GCA GAA GCA TTA ATA GAC T (Biotin-dT)-GG ACG ACG ATA GAA CT-3' |
| SEQ ID NO: 24 | 5'-GCA GAA GCA TTA ATA GAC T TTTTT-(Biotin-dT)-TTTTT GG ACG ACG ATA GAA CT-3' |
| SEQ ID NO: 25 | 5'-GCA GAA GCA TTA ATA GAC T TTTTTTTTTTTTTT-(Biotin-dT)-TTTTTTTTTTTTTT GG ACG ACG ATA GAA CT-3'. |
| SEQ ID NO: 26 | anti-HER2 antibody 4D5 heavy chain variable domain |
| SEQ ID NO: 27 | VH CDR1 |
| SEQ ID NO: 28 | VH CDR2 |
| SEQ ID NO: 29 | VH CDR3 |
| SEQ ID NO: 30 | anti-HER2 antibody 4D5 heavy light variable domain |
| SEQ ID NO: 31 | VL CDR1 |
| SEQ ID NO: 32 | VL CDR2 |
| SEQ ID NO: 33 | VL CDR3 |
| SEQ ID NO: 34 | anti-HER2 antibody 2C4 heavy chain variable domain |
| SEQ ID NO: 35 | VH CDR1 |
| SEQ ID NO: 36 | VH CDR2 |
| SEQ ID NO: 37 | VH CDR3 |
| SEQ ID NO: 38 | anti-HER2 antibody 2C4 light chain variable domain |
| SEQ ID NO: 39 | VL CDR1 |
| SEQ ID NO: 40 | VL CDR2 |
| SEQ ID NO: 41 | VL CDR3 |
| SEQ ID NO: 42 | 5'-X-AGT CTA TTA ATG CTT CTG C-ZZZ-Y-; X = Fluorescein Y = C7 Aminolinker Z = C3 spacer |

| Sequences |
| --- |
| SEQ ID NO: 43  5'-X AGT CTA TTA ATG CTT CTG C-ZZZ-Y-;<br>X = Cy5 Y = C7 Aminolinker Z = C3 spacer |
| SEQ ID NO: 44  5'-X-ZZZ-AGT TCT ATC GTC GTC CA-Y-3';<br>X = aminolinker Y = Fluorescein Z = C3 spacer |
| SEQ ID NO: 45  5'-X-(AGT CTA TTA ATG CTT CTG C)-(ZZZ)-y-;<br>X = Fluorescein Y = C7 Aminolinker Z = C3 spacer |
| SEQ ID NO: 46  5'-X-(ZZZ-(AGT TCT ATC GTC GTC CA)-Y-3';<br>X = aminolinker Y = Fluorescein Z = C3 spacer |
| SEQ ID NO: 47  5'-G CAG AAG CAT TAA TAG ACT-TGG ACG ACG ATA GAA CT-3' |
| SEQ ID NO: 48  5'-G CAG AAG CAT TAA TAG ACT-(T40)-TGG ACG ACG ATA GAA CT-3' |
| SEQ ID NO: 49  5'-[B-L]G CAG AAG CAT TAA TAG ACT-(Biotin-dT)-TGG ACG ACG ATA GAA CT-3' |
| SEQ ID NO: 50  5'[B-L]G CAG AAG CAT TAA TAG ACT-T5-(Biotin-dT)-T5-TGG ACG ACG ATA GAA CT-3' |
| SEQ ID NO: 51  5'-[B-L]G CAG AAG CAT TAA TAG ACT-T20-(Biotin-dT)-T20-TGG ACG ACG ATA GAA CT-3' |
| SEQ ID NO: 52  5'-[B-L] G CAG AAG CAT TAA TAG ACT-T30-(Biotin-dT)-T30-TGG ACG ACG ATA GAA CT-3' |
| SEQ ID NO: 53  5'-GCA GAA GCA TTA ATA GAC T T5-(Biotin-dT)-T5 TG GAC GAC GAT AGA ACT-3' |
| SEQ ID NO: 54  5'-GCA GAA GCA TTA ATA GAC T T10-(Biotin-dT)-T10 TGG ACG ACG ATA GAA CT-3' |
| SEQ ID NO: 55  5'-GCA GAA GCA TTA ATA GAC T T15-(Biotin-dT)-T15 TGG ACG ACG ATA GAA CT-3' |
| SEQ ID NO: 56  5'-GCA GAA GCA TTA ATA GAC T T20-(Biotin-dT)-T20 TGG ACG ACG ATA GAA CT-3' |
| SEQ ID NO: 57  5'-G CAG AAG CAT TAA TAG ACT-Spacer C18-(Biotin-dT)-Spacer C18-TGG ACG ACG ATA GAA CT-3' |
| SEQ ID NO: 58  5'-G CAG AAG CAT TAA TAG ACT-(Spacer C18)2-(Biotin-dT)-(Spacer C18)2-TGG ACG ACG ATA GAA CT-3' |
| SEQ ID NO: 59  5'-G CAG AAG CAT TAA TAG ACT-(Spacer C18)3-(Biotin-dT)-(Spacer C18)3-TGG ACG ACG ATA GAA CT-3' |
| SEQ ID NO: 60  5'-G CAG AAG CAT TAA TAG ACT-(Spacer C18)4-(Biotin-dT)-(Spacer C18)4-TGG ACG ACG ATA GAA CT-3' |
| SEQ ID NO: 61  5'-G CAG AAG CAT TAA TAG ACT-T20-(Dig-dT)-T20-TGG ACG ACG ATA GAA CT-3' |
| SEQ ID NO: 62  5'-G CAG AAG CAT TAA TAG ACT-(Dig-dT)-TGG ACG ACG ATA GAA CT-3' |
| SEQ ID NO: 63  5'-G CAG AAG CAT TAA TAG ACT-(Biotin-dT)-TGG ACG ACG ATA GAA CT-3' |
| SEQ ID NO: 64  YPYDVPDYA |
| SEQ ID NO: 65  GLNDIFEAQKIEWHE |
| SEQ ID NO: 66  SGGGS |
| SEQ ID NO: 67  f-Met-Leu-Phe (fMLP) |
| SEQ ID NO: 68  f-Met-Leu-Phe-o-methyl ester |

-continued

| Sequences | |
|---|---|
| SEQ ID NO: 69 | IgG1 constant domain |
| SEQ ID NO: 70 | IgG2 constant domain |
| SEQ ID NO: 71 | IgG4 constant domain |
| SEQ ID NO: 72 | Cy5-Y-ATG CGA-GTA CCT TAG AGT C-Z-Cy5 |
| SEQ ID NO: 73 | 5'-G CAG AAG CAT TAA TAG ACT-T20-GAC TCT AAG GTA CTC GCA T-T20-TGG ACG ACG ATA GAA CT-3' |

FIGURES

FIG. 1 Scheme of the BIAcore assay setup. ss-L-DNA-bi linkers were presented on a BIAcore SA sensor. Flow cell 1 served as a control (not shown).

Figure 2:
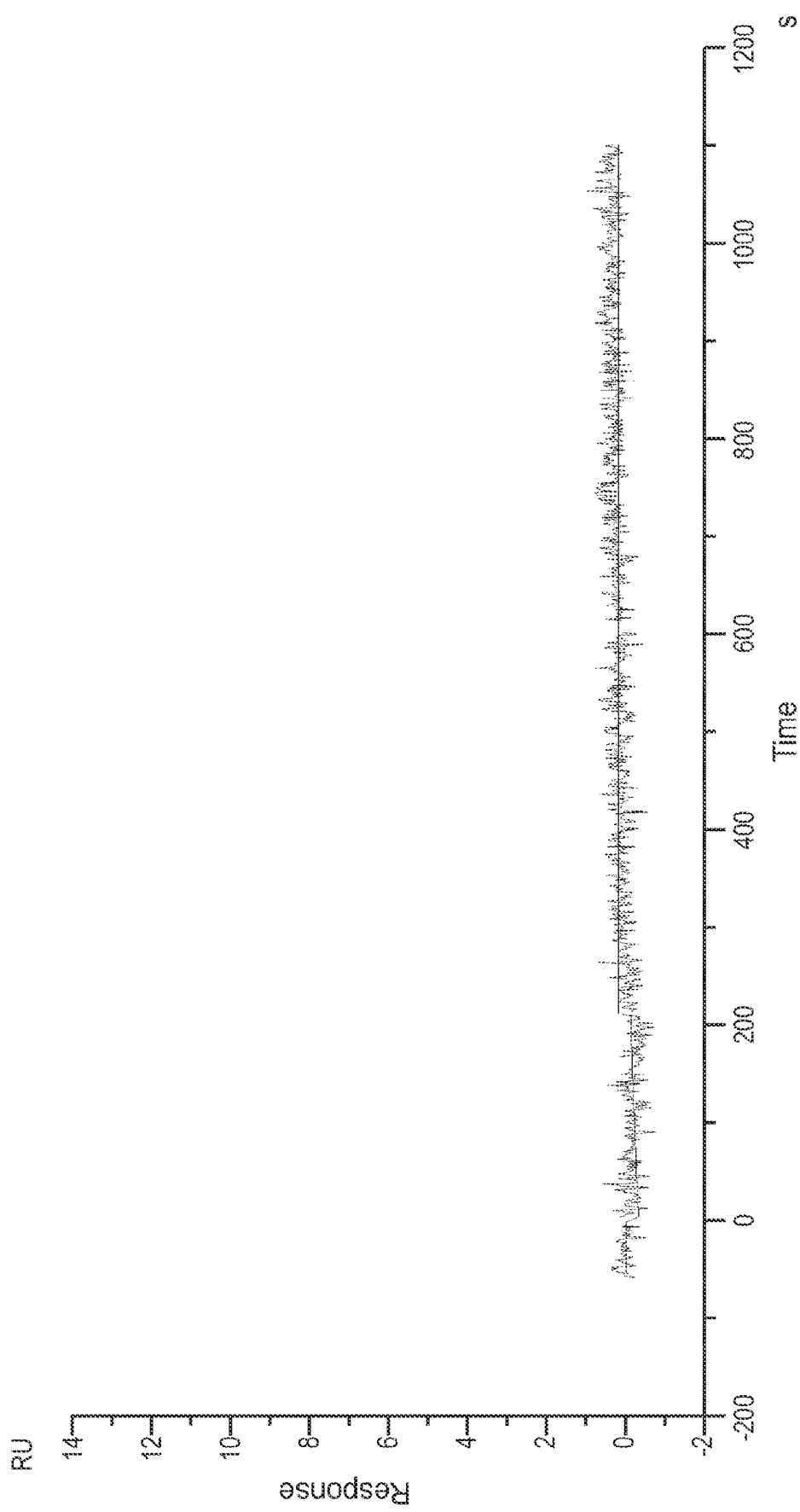

FIG. 2 BIAcore sensorgrams for the HER2-ECD interaction with ss-D-DNA labeled FAB fragments.

Figure 3:
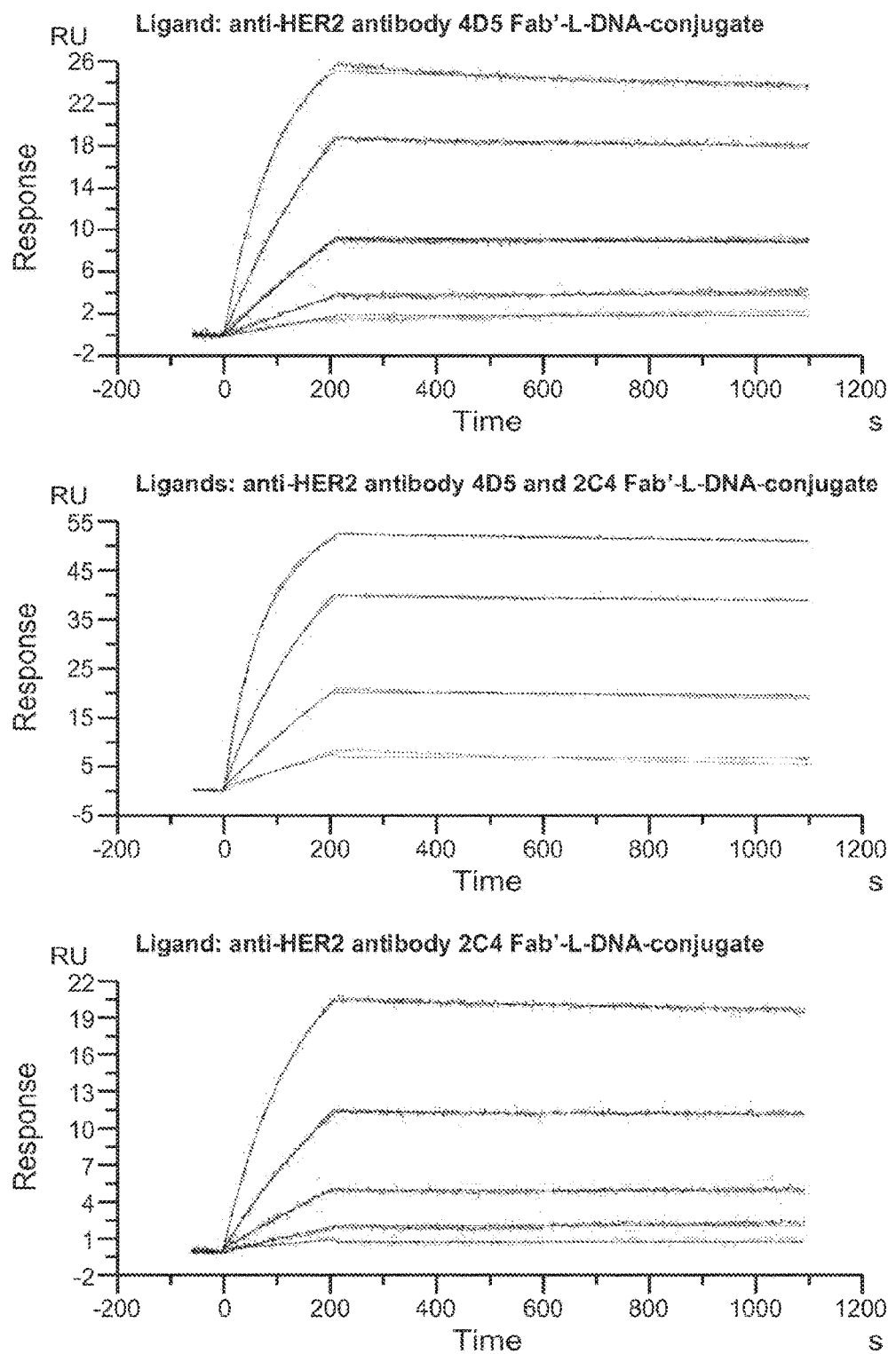

FIG. 3 BIAcore sensorgrams showing concentration dependent interaction measurements of the complex as reported herein comprising a 35-mer (=35 nucleotide length) as linker polynucleotide with HER2-ECD.

Figure 4:
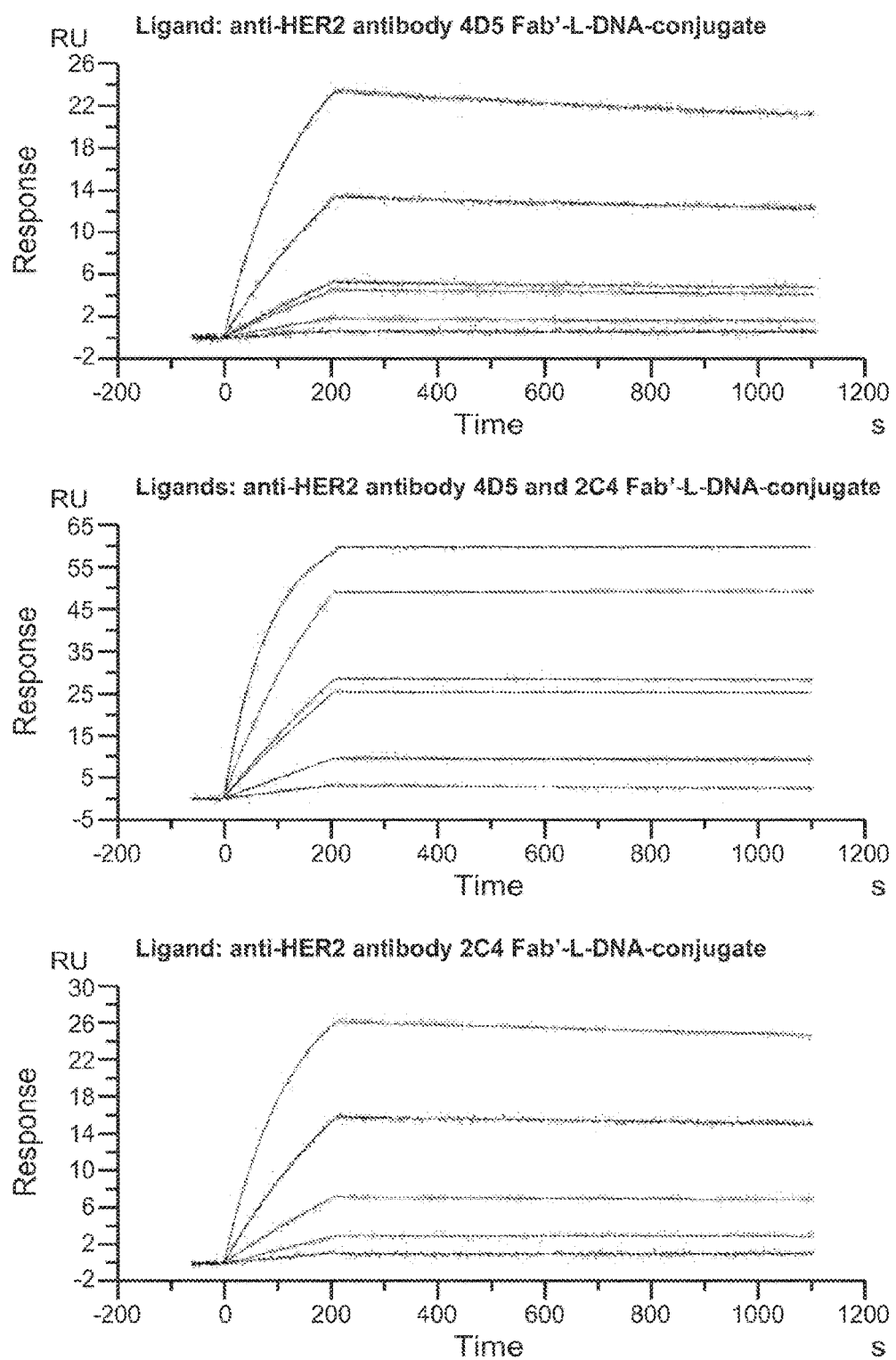

FIG. 4 BIAcore sensorgrams showing concentration dependent interaction measurements of the complex as reported herein comprising a 75-mer (=75 nucleotide length) as linker polynucleotide with HER2-ECD.

Figure 5:
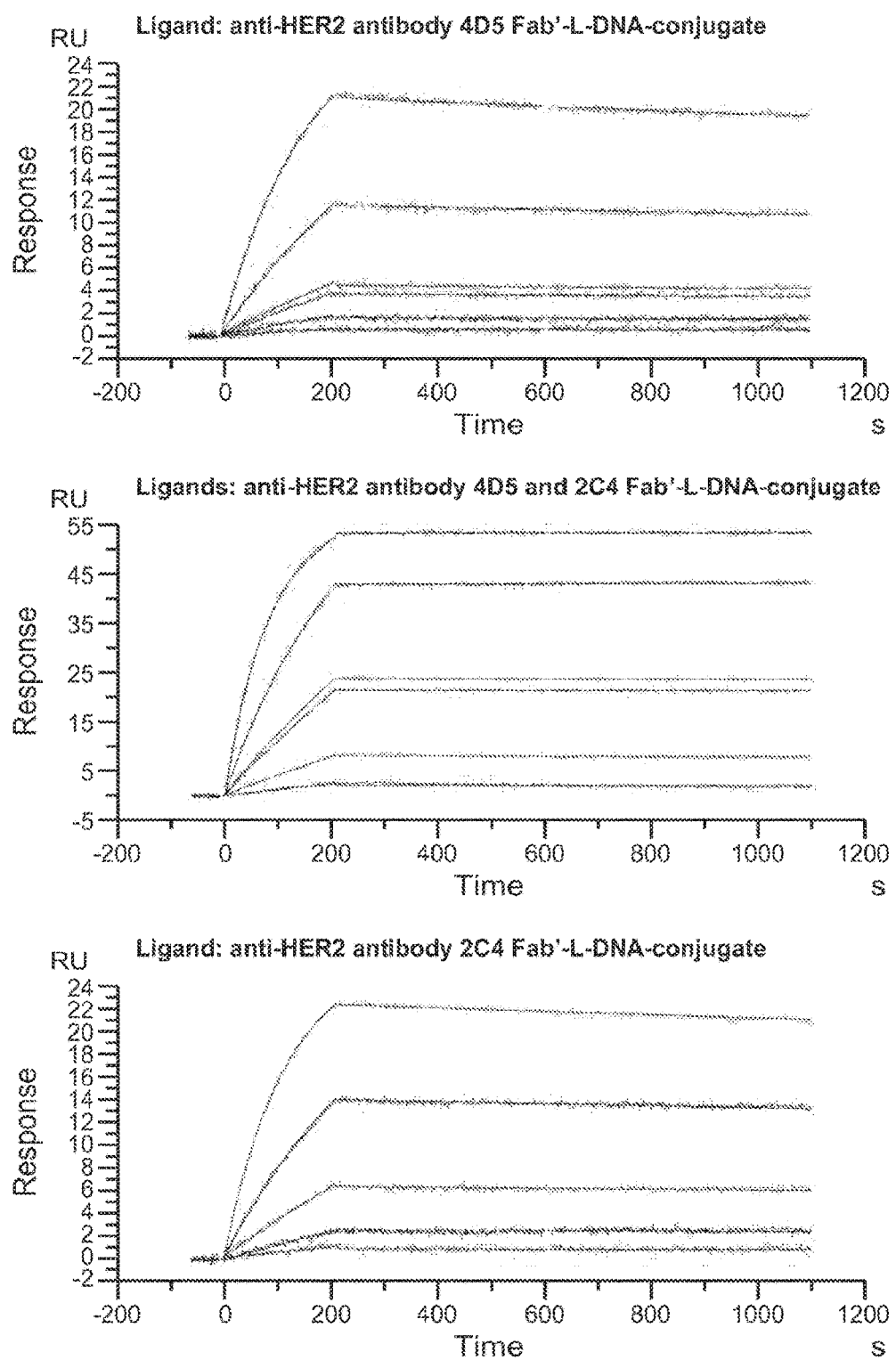

FIG. 5 BIAcore sensorgrams showing concentration dependent interaction measurements of the complex as reported herein comprising a 95-mer (=95 nucleotide length) as linker polynucleotide with HER2-ECD.

Figure 6:
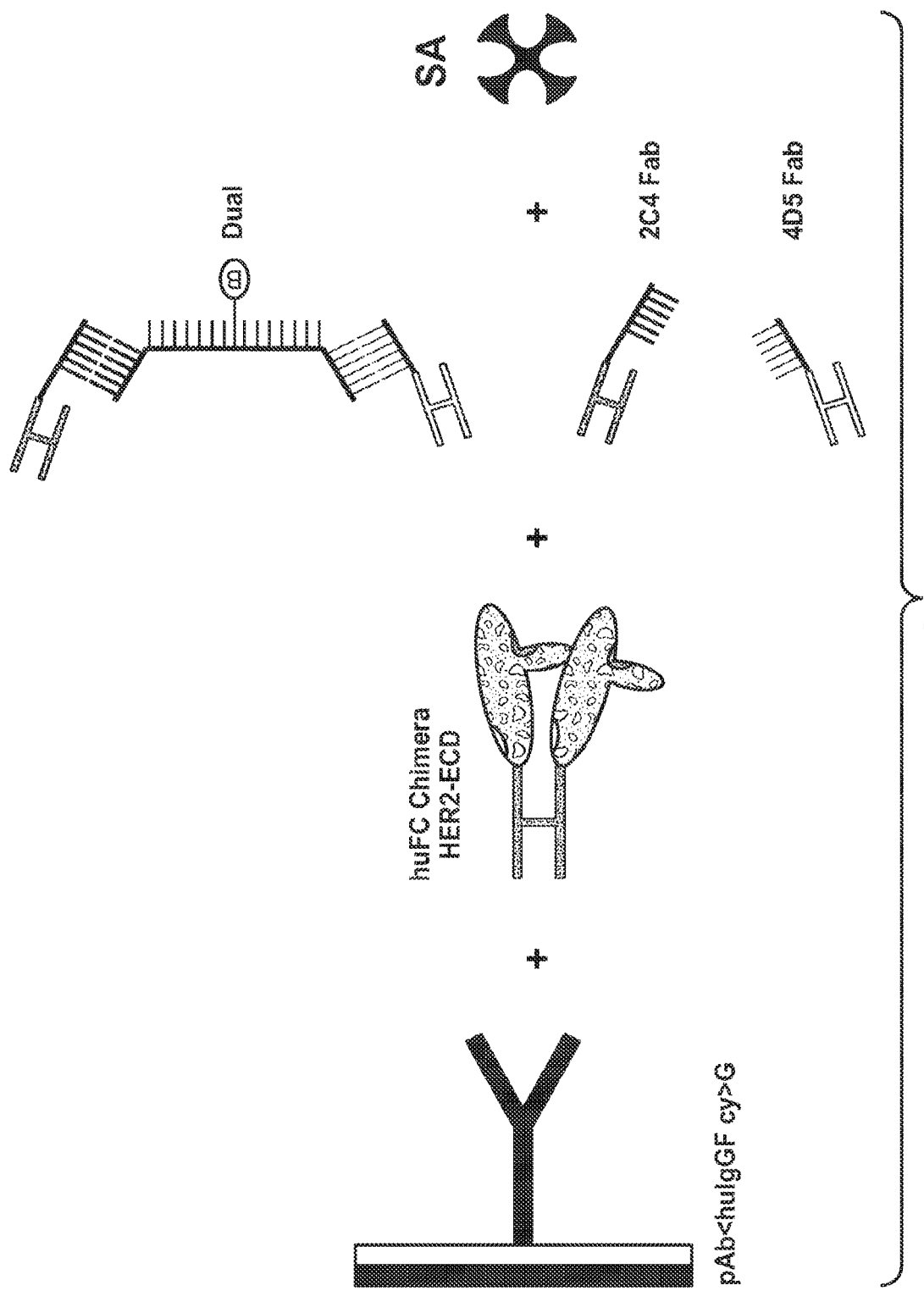

FIG. 6 Scheme of the BIAcore assay setup: polyclonal goat anti human IgG-Fc gamma antibody was presented on a BIAcore SA sensor. Flow cell 1 served as a control (not shown).

Figure 7:
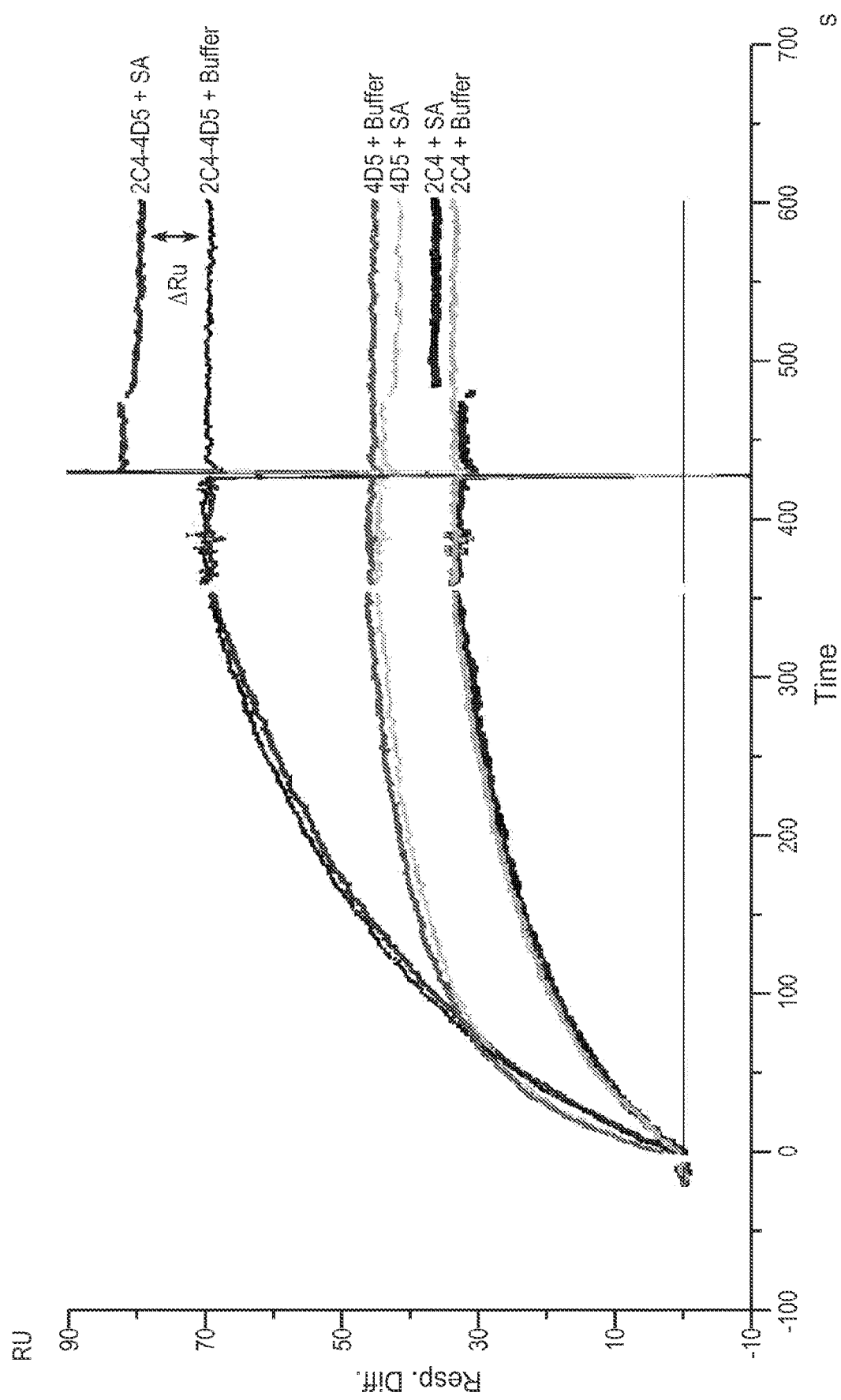

FIG. 7 The BIAcore sensorgram shows an overlay plot of interaction signals upon 50 nM injections of anti-HER2 antibody 2C4-FAB'-ss-L-DNA (2C4), anti-HER2 antibody 4D5-FAB'-ss-L-DNA (4D5) and fully established complex (2C4-75mer-4D5) connected by a 75mer ss-L-DNA linker.

Figure 8:
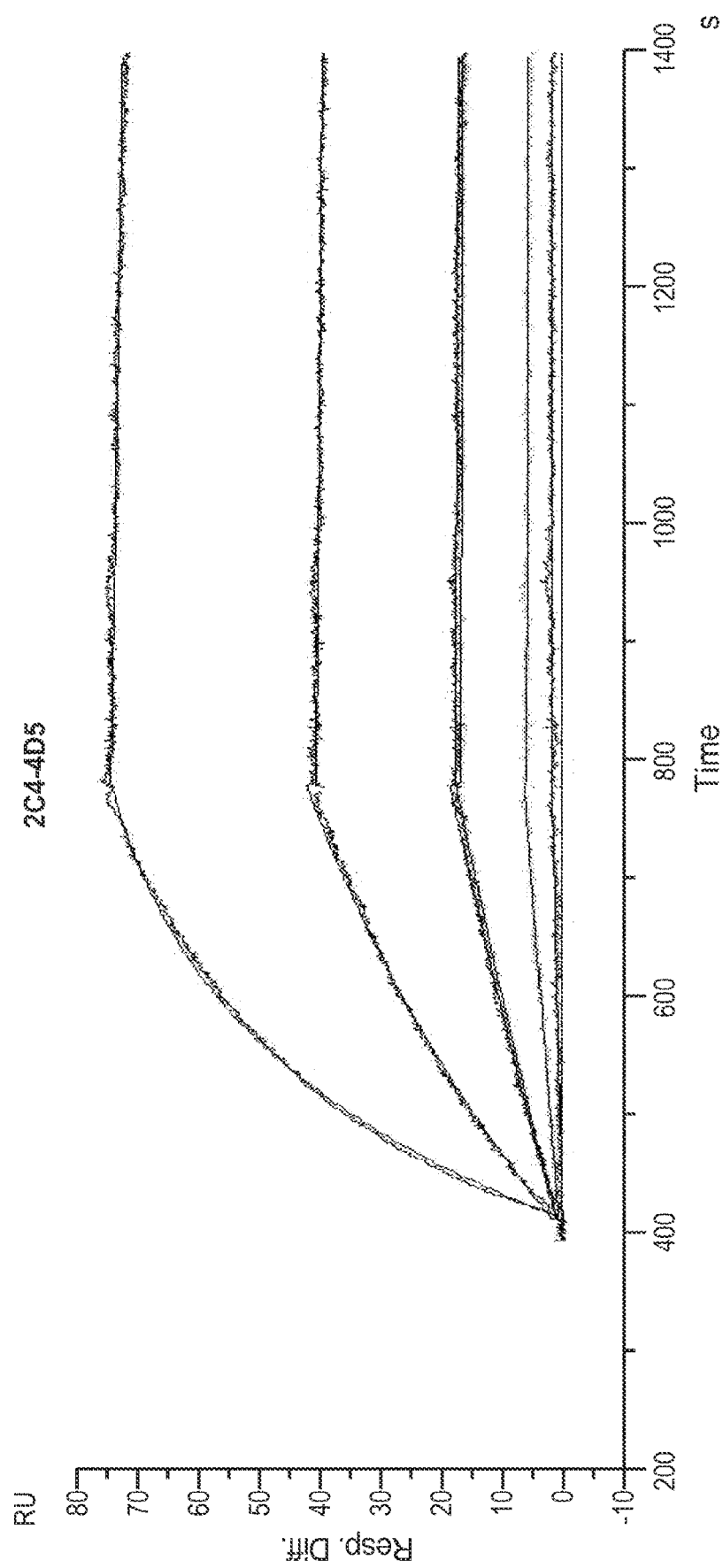
Figure 9:
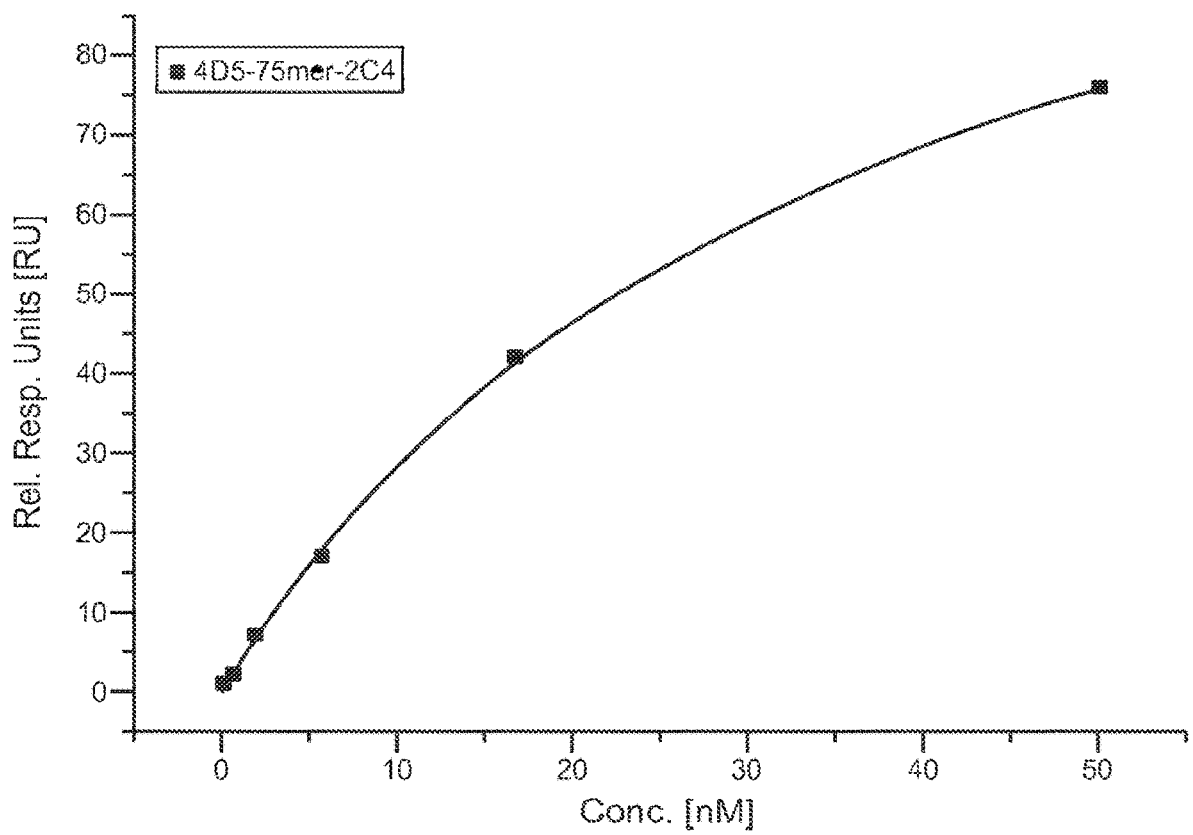

FIG. 8 BIAcore sensorgram showing an overlay plot of concentration-dependent measurements of the fully established 75-mer complex as analyte in solution interacting with the surface presented huFc chimera HER2 ECD FIG. 9 Plot of the response levels of FIG. 8 versus the analyte concentration of the fully established complex.

Figure 10A:
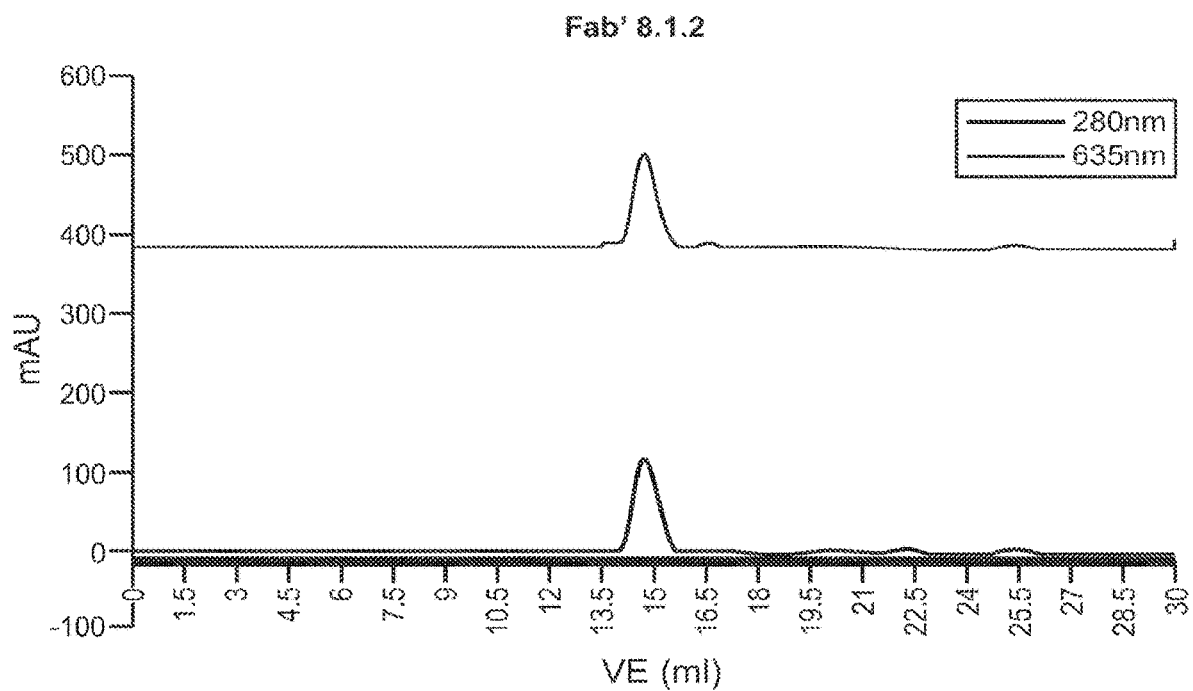
Figure 10B:
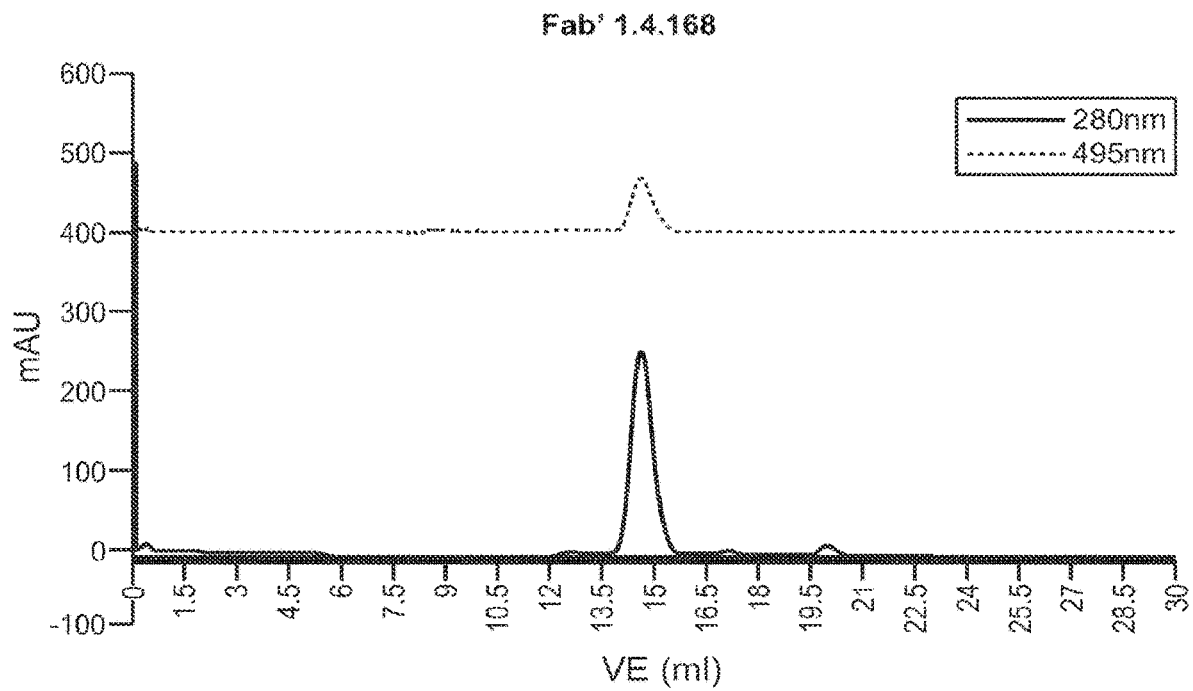
Figure 10C:
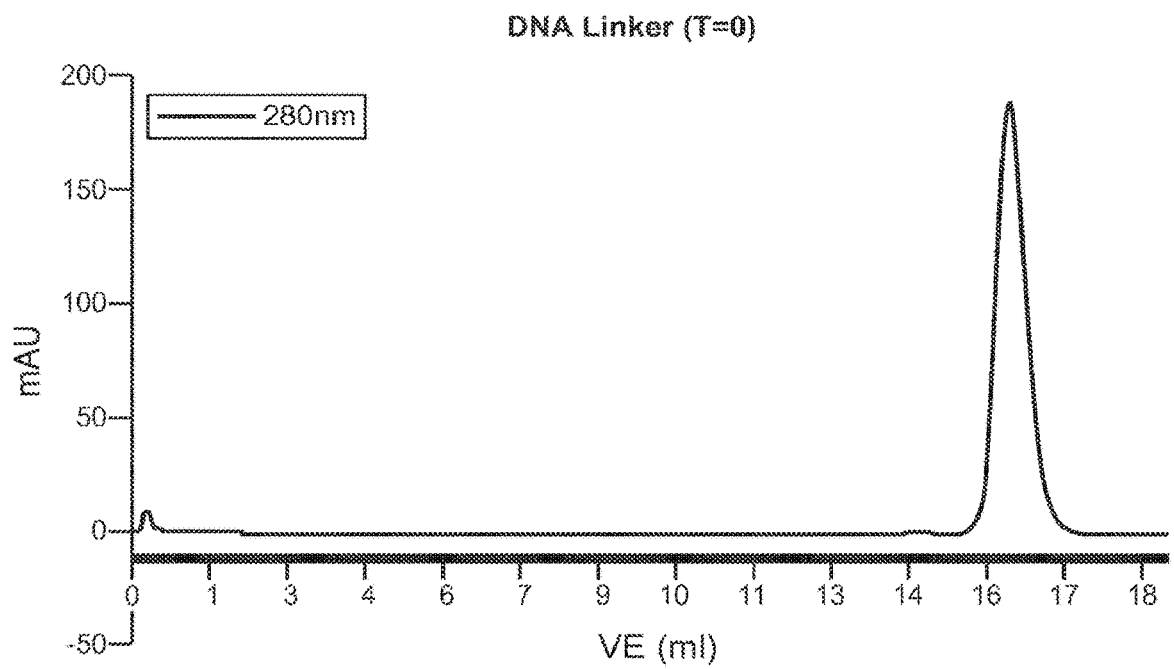
Figure 10D:
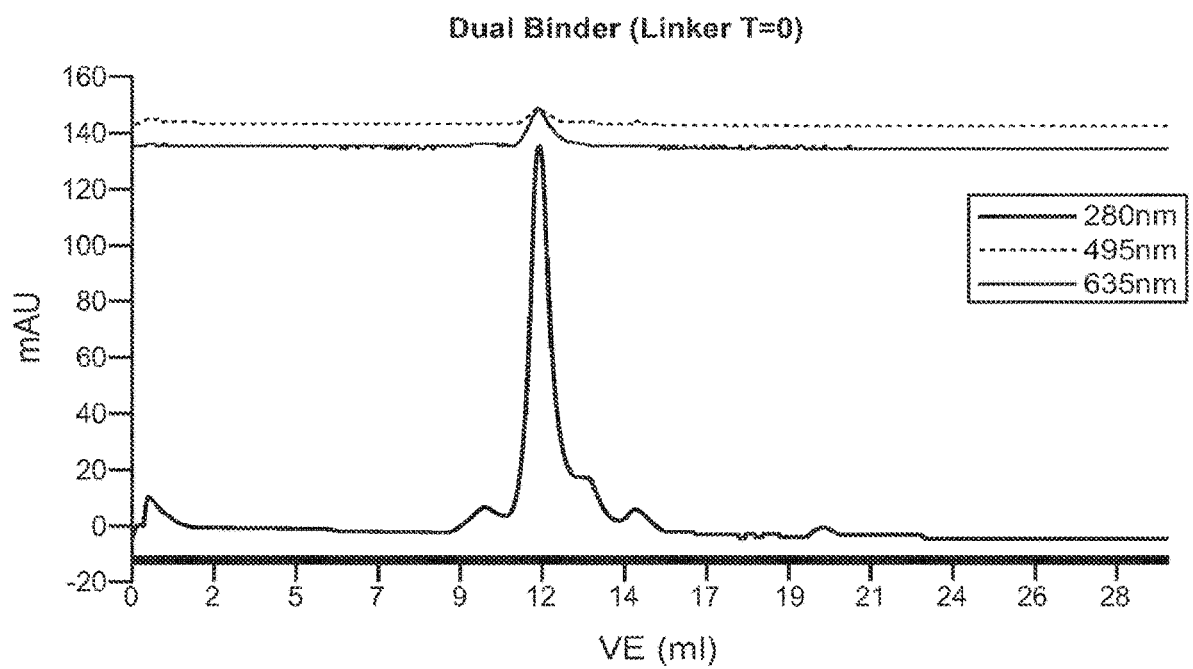

FIGS. 10A-10D Analytical gel filtration experiments assessing efficiency of the anti-pIGF1-R complex assembly. FIGS. 10A, 10B, and 10C show the elution profile of the individual complex components (fluorescein-ss-FAB' 1.4.168, Cy5-ssFab' 8.1.2 and Linker DNA (T=0)). FIG. 10D shows the elution profile after the 3 components needed to form the bivalent binding agent had been mixed in a 1:1:1 molar ratio. The thicker (bottom) curve represents absorbance measured at 280 nm indicating the presence of the ss-FAB' proteins or the linker DNA, respectively. The thinner top curve in FIGS. 10B and 10D (absorbance at 495 nm) indicates the presence of Cy5 and the thinner top curve in a) FIG. 10A and the middle curve in FIG. 10D (absorbance at 635 nm) indicates the presence of fluorescein. Comparison of the elution volumes of the single complex components ($VE_{ssFab'\ 1.4.168}$~15 ml; $VE_{ssFab'\ 8.1.2}$~15 ml; $VE_{linker}$~16 ml) with the elution volume of the reaction mix ($VE_{mix}$~12 ml) demonstrates that the complex assembly reaction was successful (rate of yield: ~90%). The major 280 nm peak that represents the eluted complex nicely overlaps with the major peaks in the 495 nm and 695 nm channel, proving the presence of both ss-FAB' 8.1.2 and ssFab'1.4.168 in the peak representing the bivalent binding agent.

Figure 11:
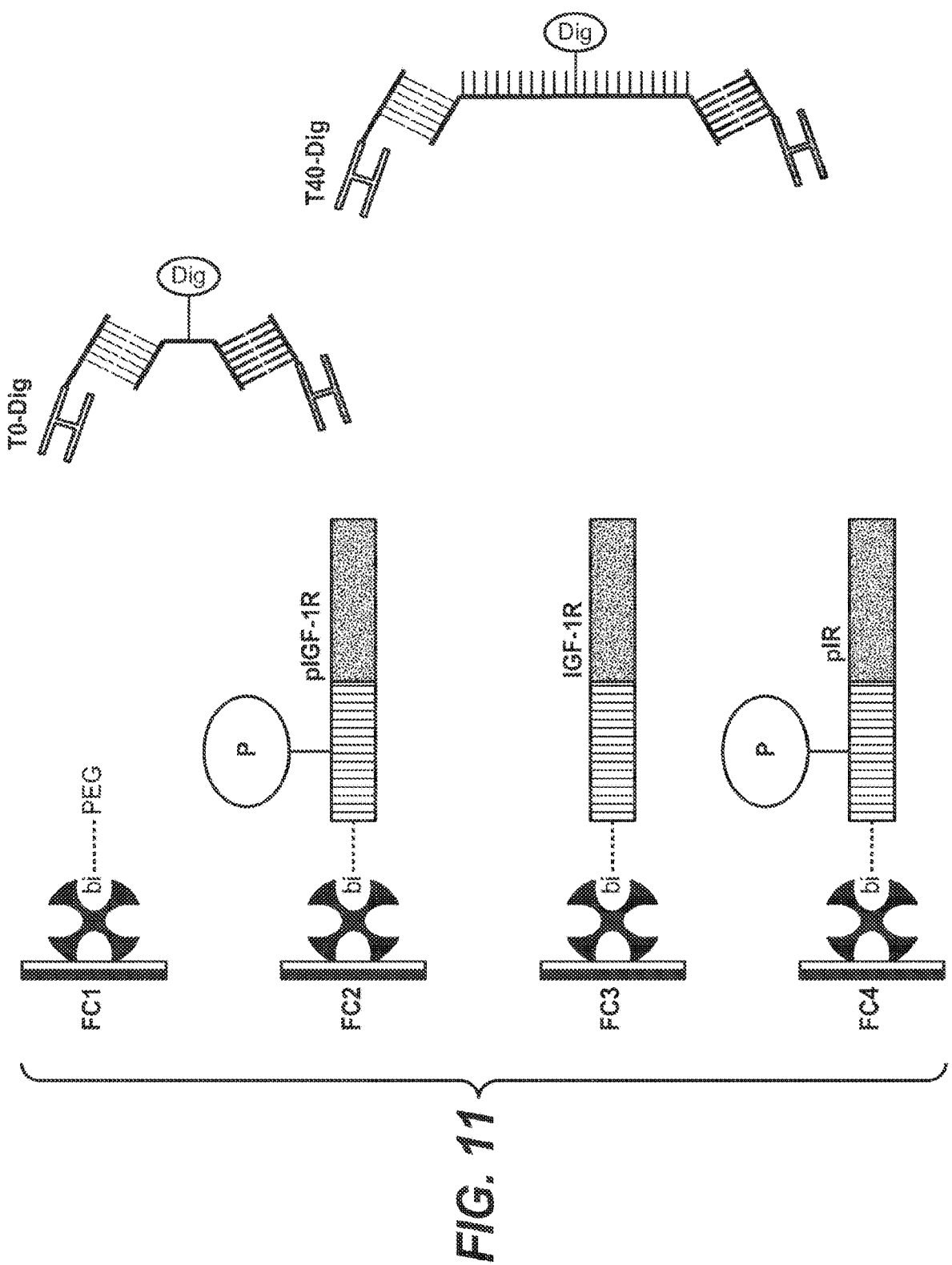

FIG. 11 Scheme of the BIAcore experiment: schematically and exemplarily, two binding molecules in solution are shown. The T=0-Dig, bivalent binding agent and the T=40-Dig, bivalent binding agent. Both these bivalent binding agents only differ in their linker-length (no additional T versus 40 additional Ts, separating the two hybridizing nucleic acid sequences). Furthermore, ss-FAB' fragments 8.1.2 and 1.4.168 were used.

Figure 12:
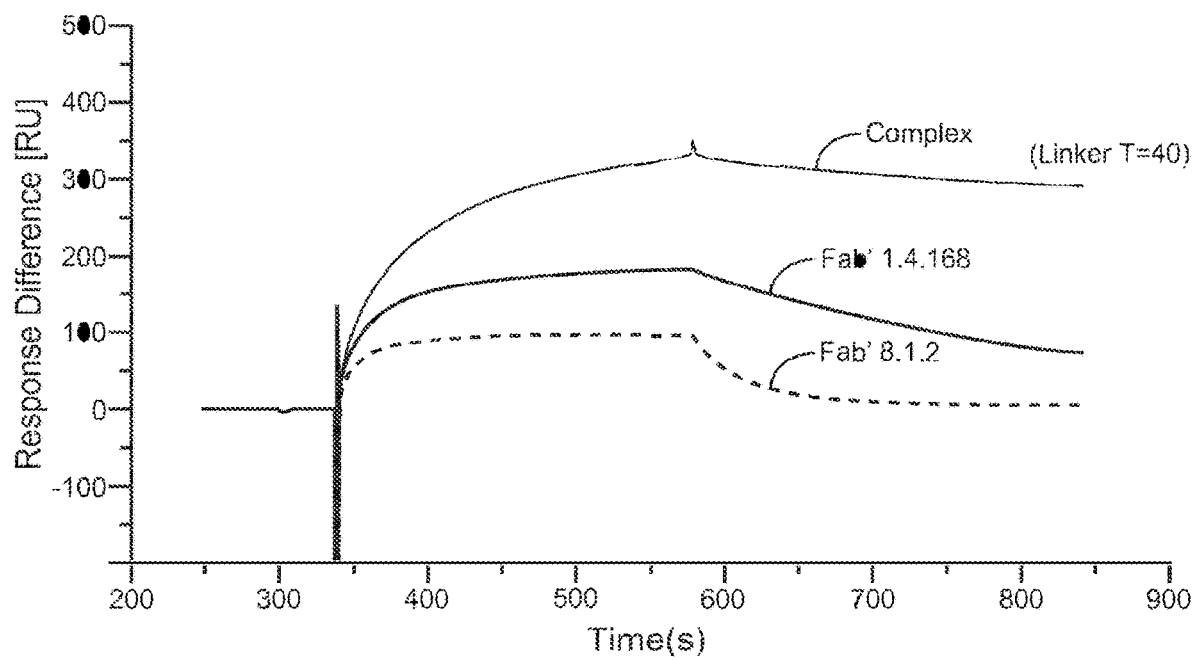

FIG. 12 BIAcore sensorgram with overlay plot of three kinetics showing the interaction of 100 nM bivalent binding agent (consisting of ss-FAB 8.1.2 and ss-FAB 1.4.168 hybridized on the T40-Dig ss-DNA-Linker) with the immobilized peptide pIGF-1R compared to the binding characteristics of 100 nM ss-FAB 1.4.168 or 100 nM ss-FAB 8.1.2 to the same peptide. Highest binding performance is only obtained with the complex construct, clearly showing, that the cooperative binding effect of the Complex increases affinity versus the target peptide pIGF-1R.

Figure 13:
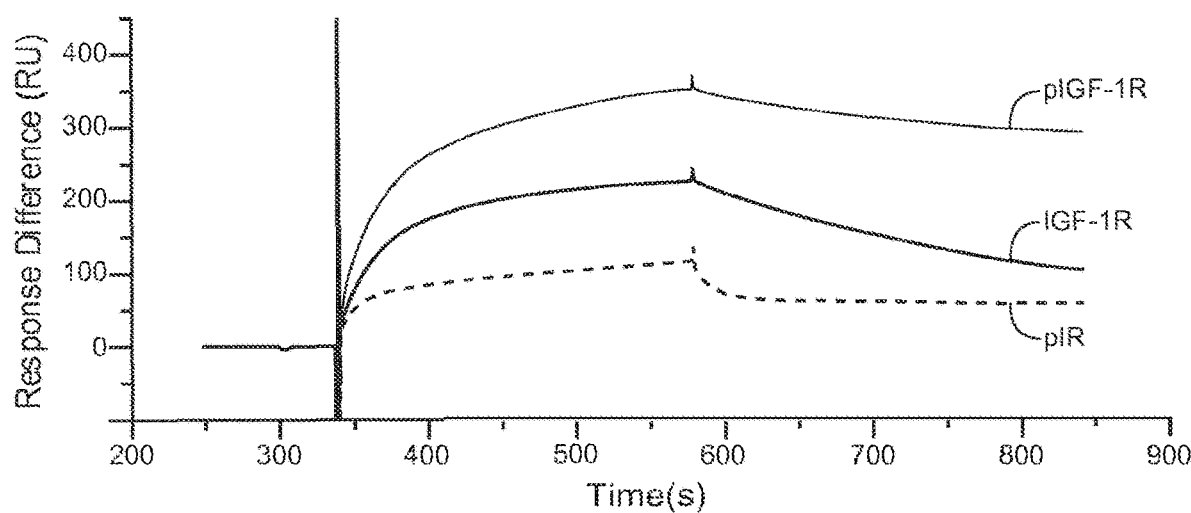

FIG. 13 BIAcore sensorgram with overlay plot of three kinetics showing the interactions of the bivalent binding agent consisting of ss-FAB 8.1.2 and ss-FAB 1.4.168 hybridized on the T40-Dig ss-DNA-Linker with immobilized peptides pIGF-1R (phosphorylated IGF-1R), IGF-1R or IR (phosphorylated insulin receptor). Highest binding performance is obtained with the pIGF-1R peptide, clearly showing, that the cooperative binding effect of the Complex increases specificity versus the target peptide pIGF-1R as compared to e.g. the phosphorylated insulin receptor peptide (IR).

Figure 14:
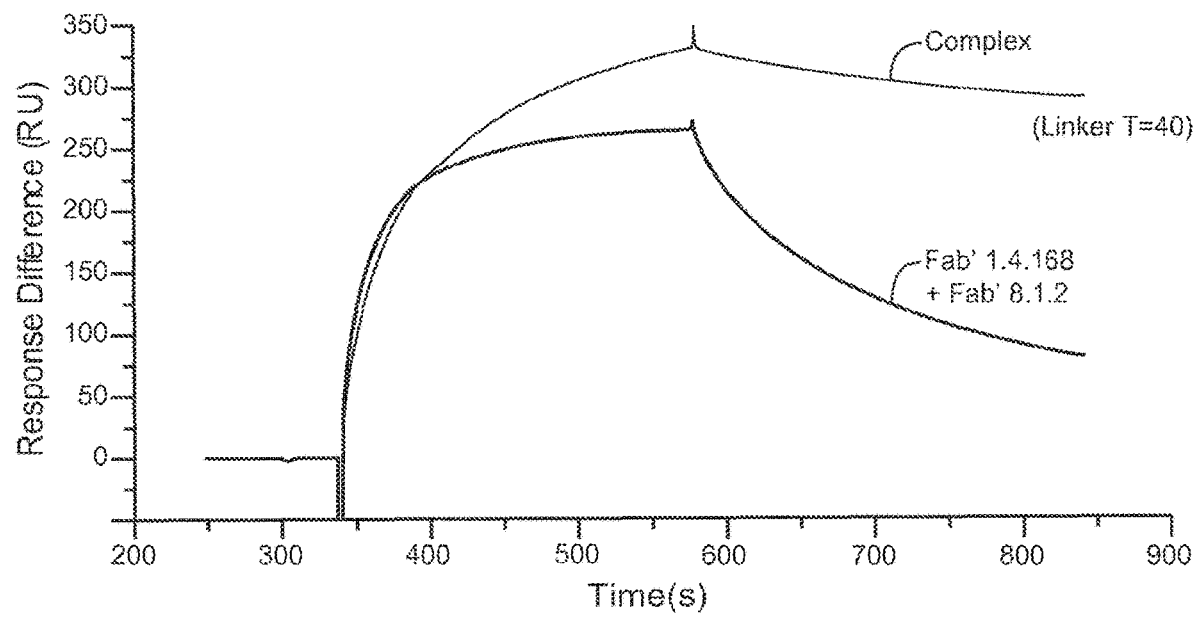

FIG. 14 BIAcore sensorgram with overlay plot of two kinetics showing the interactions of 100 nM bivalent binding agent consisting of ss-FAB' 8.1.2 and ss-FAB' 1.4.168 hybridized on the T=40-Dig ss-DNA-Linker and a mixture of 100 nM ss-FAB' 8.1.2 and 100 nM ss-FAB' 1.4.168 without linker DNA. Best binding performance is only obtained with the bivalent binding agent, whereas the mixture of the ss-FAB's without linker doesn't show an observable cooperative binding effect, despite the fact that the total concentration of these ss-FAB's had been at 200 nM.

Figure 15:
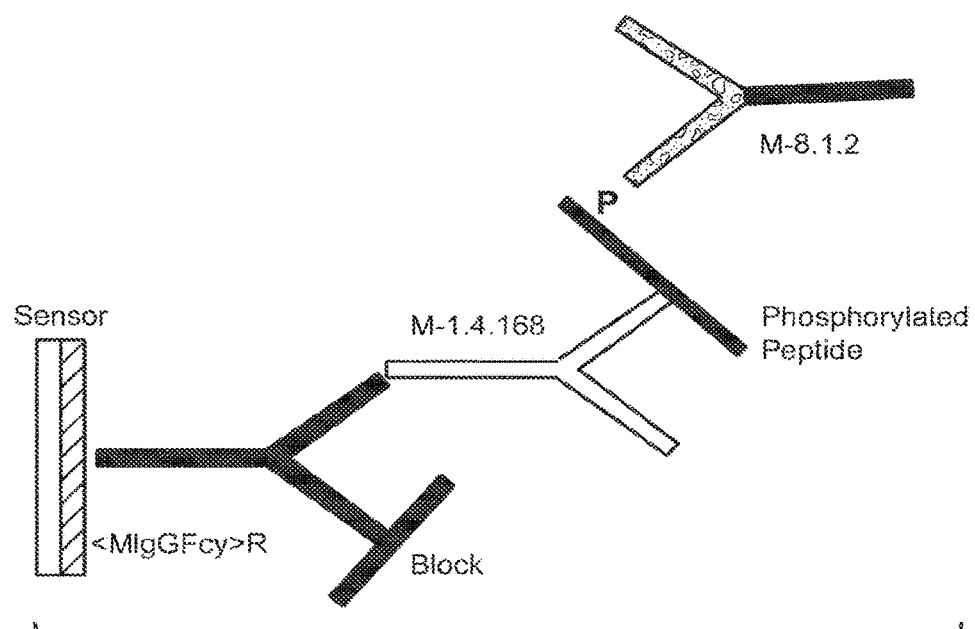

FIG. 15 Schematic drawing of a BIAcore sandwich assay. This assay has been used to investigate the epitope accessibility for both antibodies on the phosphorylated IGF-1R peptide. <MIgGFcy>R presents a rabbit anti-mouse antibody used to capture the murine antibody M-1.4.168. M-1.4.168 then is used to capture the pIGF-1R peptide. M-8.1.2 finally forms the sandwich consisting of M-1.4.168, the peptide and M-8.1.2.

Figure 16:
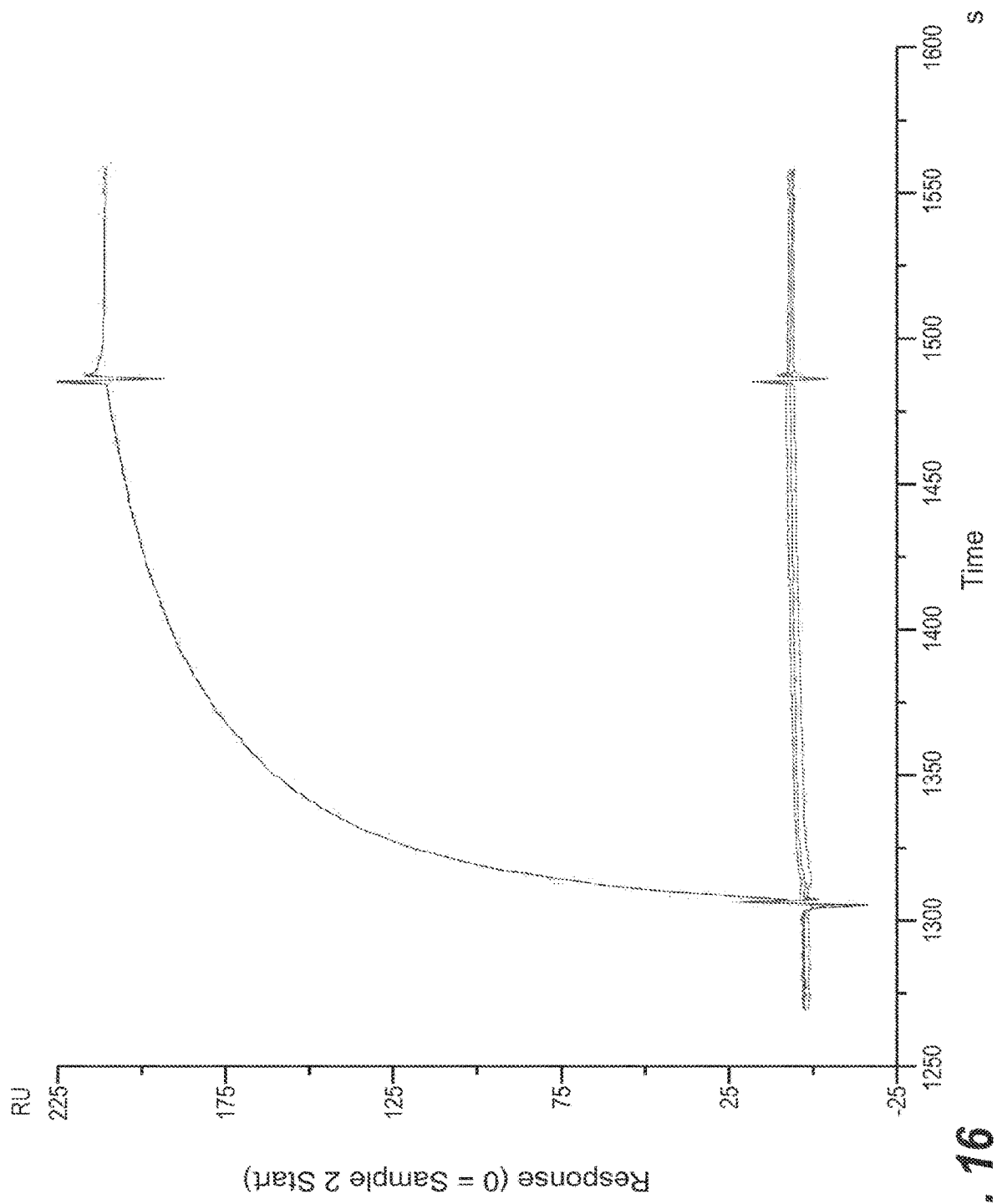

FIG. 16 BIAcore sensorgram showing the binding signal (thick line) of the secondary antibody 8.1.2. to the pIGF-1R peptide after this was captured by antibody 1.4.168 on the BIAcore chip. The other signals (thin lines) are control signals: given are the lines for a homologous control with 500 nM 1.4.168, 500 nM target unrelated antibody <CKMM>M-33-IgG; and 500 nM target unrelated control antibody <TSH>M-1.20-IgG, respectively. No binding event could be detected in any of these controls.

Figure 17:
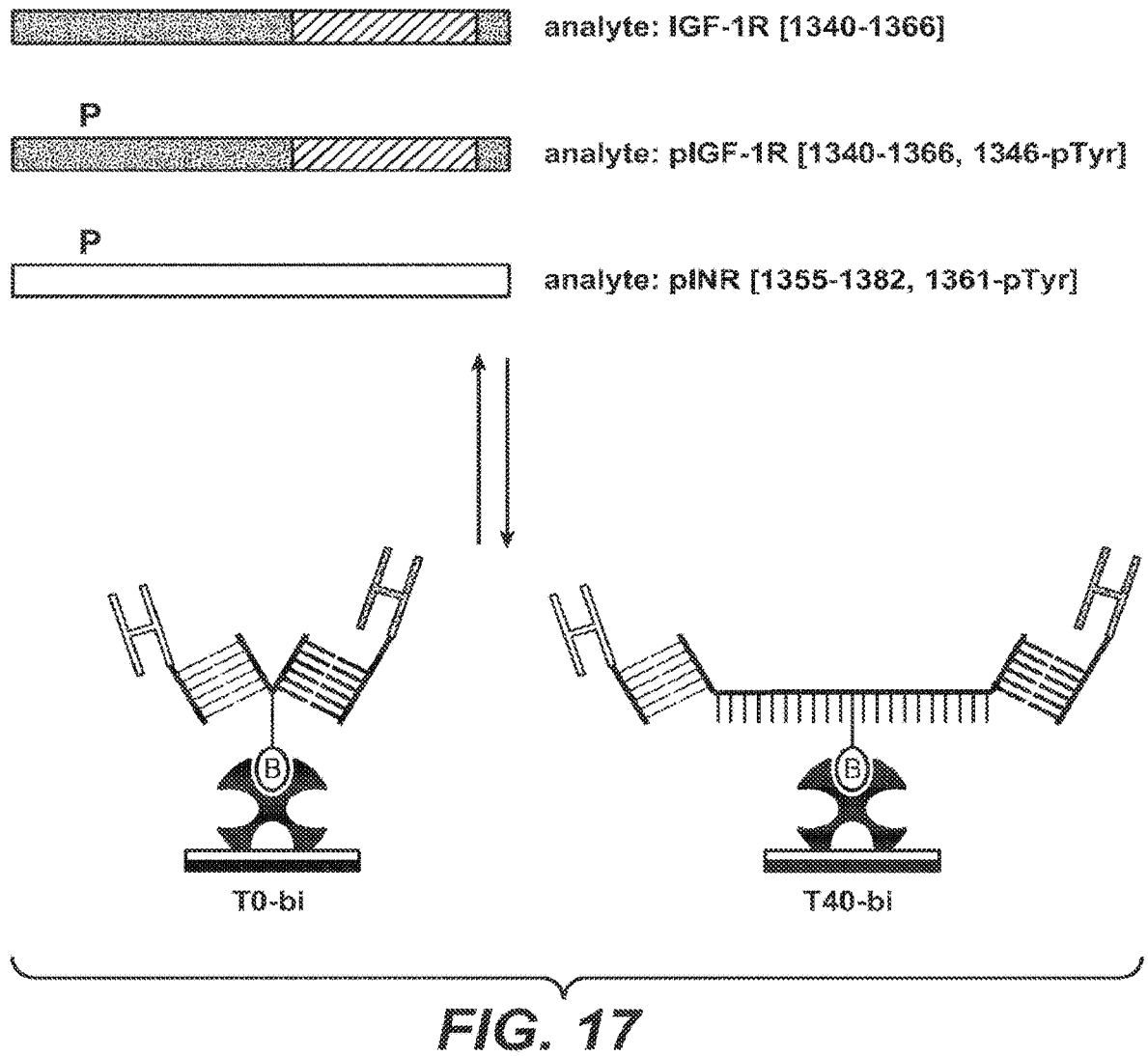

FIG. 17 Schematic drawing of the BIAcore assay, presenting the complex s on the sensor surface. On Flow Cell 1 (=FC1) (not shown) amino-PEO-biotin was captured. On FC2, FC3 and FC4 bivalent binding agents with increasing linker length were immobilized. Analyte 1: IGF-1R-peptide containing the M-1.4.168 ss-FAB epitope (thin line)—the M-8.1.2 ss-FAB phospho-epitope is not present, because this peptide is not phosphorylated; analyte 2: pIGF-1R peptide containing the M-8.1.2 ss-FAB phospho-epitope (P) and the M-1.4.168 ss-FAB epitope (thin line). Analyte 3: pINR peptide, containing the cross reacting M-8.1.2 ss-FAB phospho-epitope, but not the epitope for M-1.4.168.

FIG. 18 Kinetic data of the Complex experiment. T40-bi complex with ss-FAB 8.1.2 and ss-FAB 1.4.168 shows a 1300-fold lower off-rate (KD=2.79E-05/s) versus pIGF-1R when compared to pINR (KD=3.70E-02).

Figure 19:
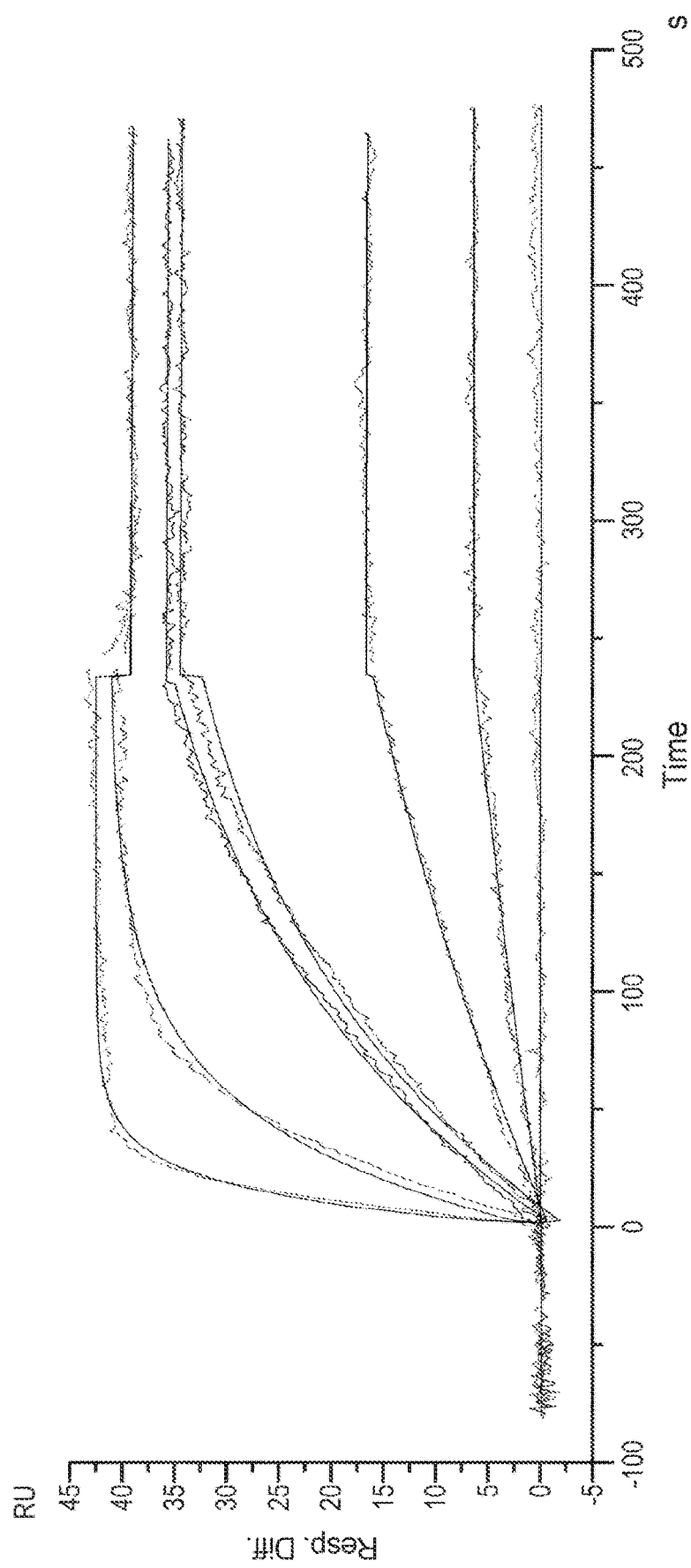

FIG. 19 BIAcore sensorgram, showing concentration dependent measurement of the T40-bi complex vs. the pIGF-1R peptide (the phosphorylated IGF-1R peptide).

Figure 20:
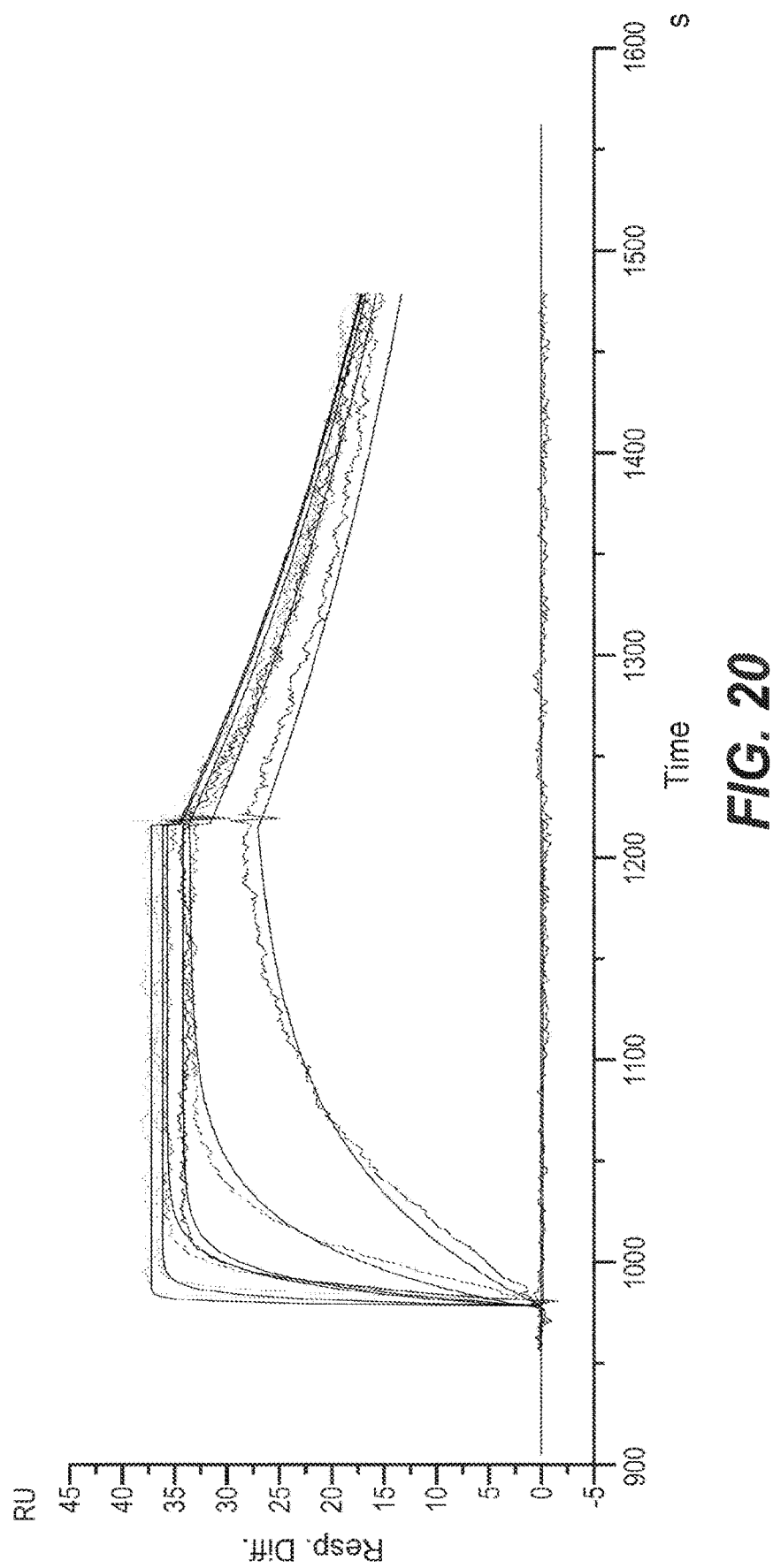

FIG. 20 BIAcore sensorgram, showing concentration dependent measurement of the T40-bi complex vs. the IGF-1R peptide (the non-phosphorylated IGF-1R peptide).

Figure 21:
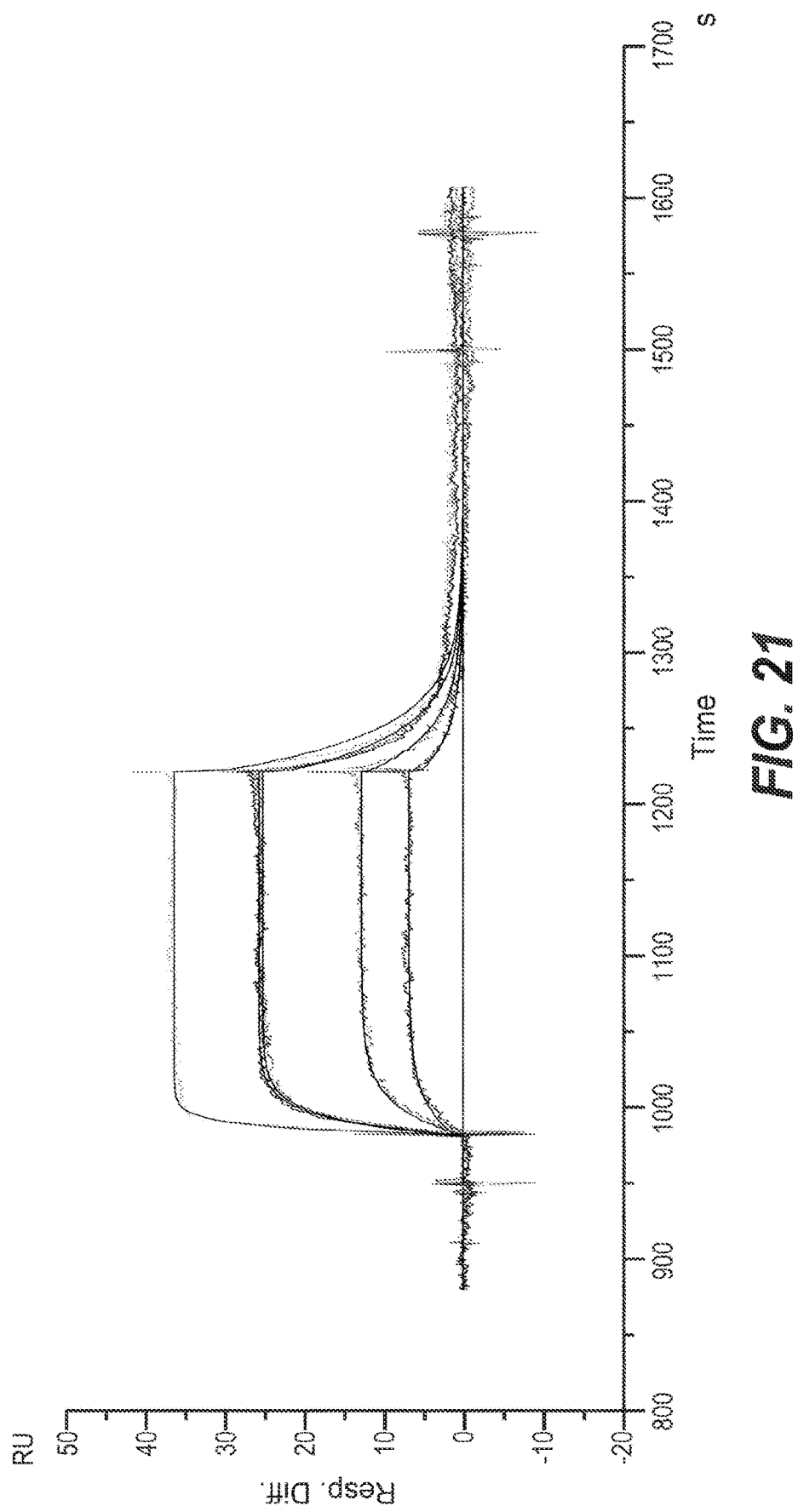

FIG. 21 BIAcore sensorgram, showing concentration dependent measurement of the T40-bi complex vs. the pINR peptide (the phosphorylated insulin receptor peptide).

FIG. 22 Staining of tumor cells with Cy5 labeled Xolair® and Herceptin®.

FIGS. 23A-23B NIRF imaging of KPL-4 cells.

FIG. 24 Ex vivo staining of KPL-4 xenografts.

Figure 25:
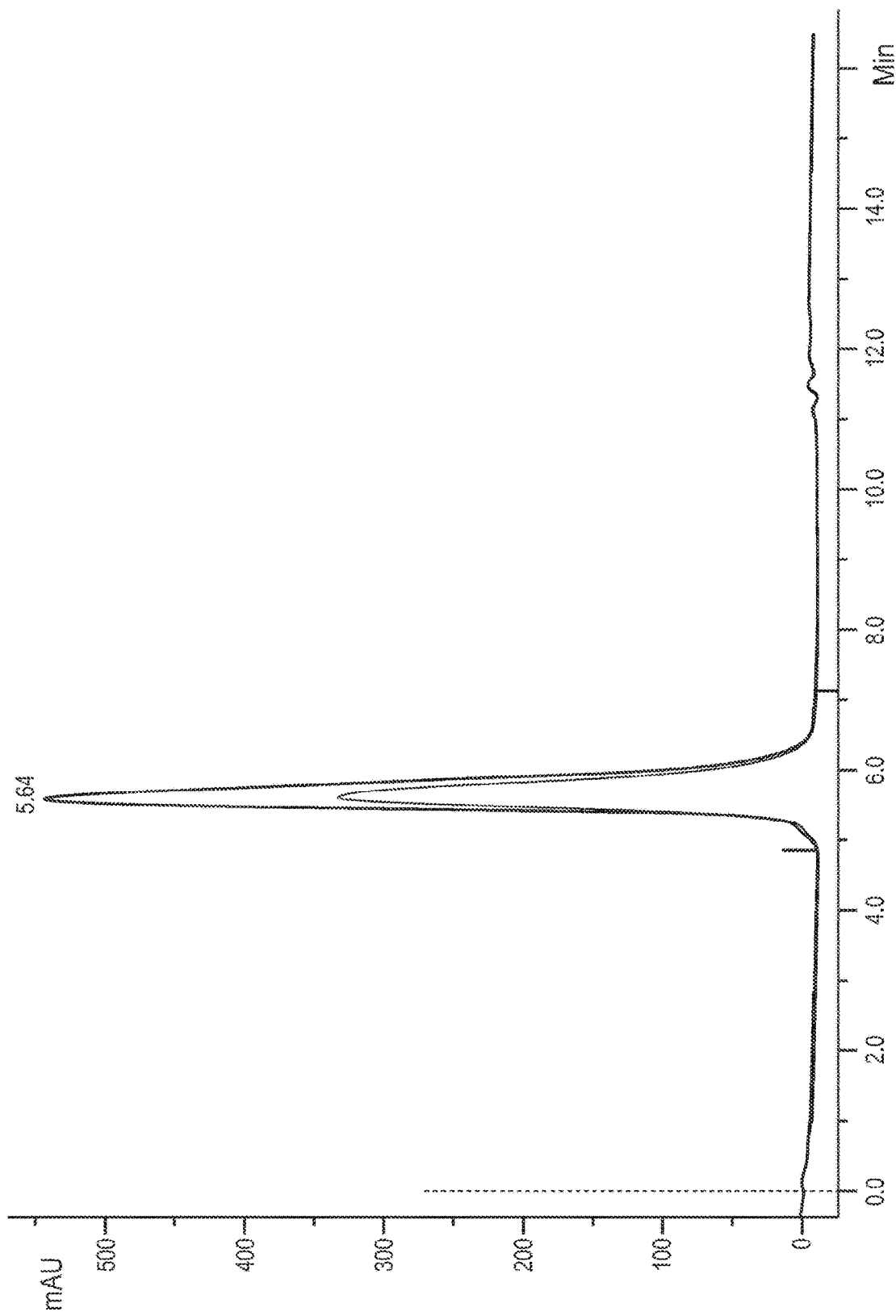

FIG. 25 Size exclusion profile of freshly prepared 4D5-95mer-2C4 complex. Upper signal: 260 nm signal, lower signal: 280 nm signal. No aggregates can be detected between start at 0.0 min and the elution peak at 5.64 min.

Figure 26:
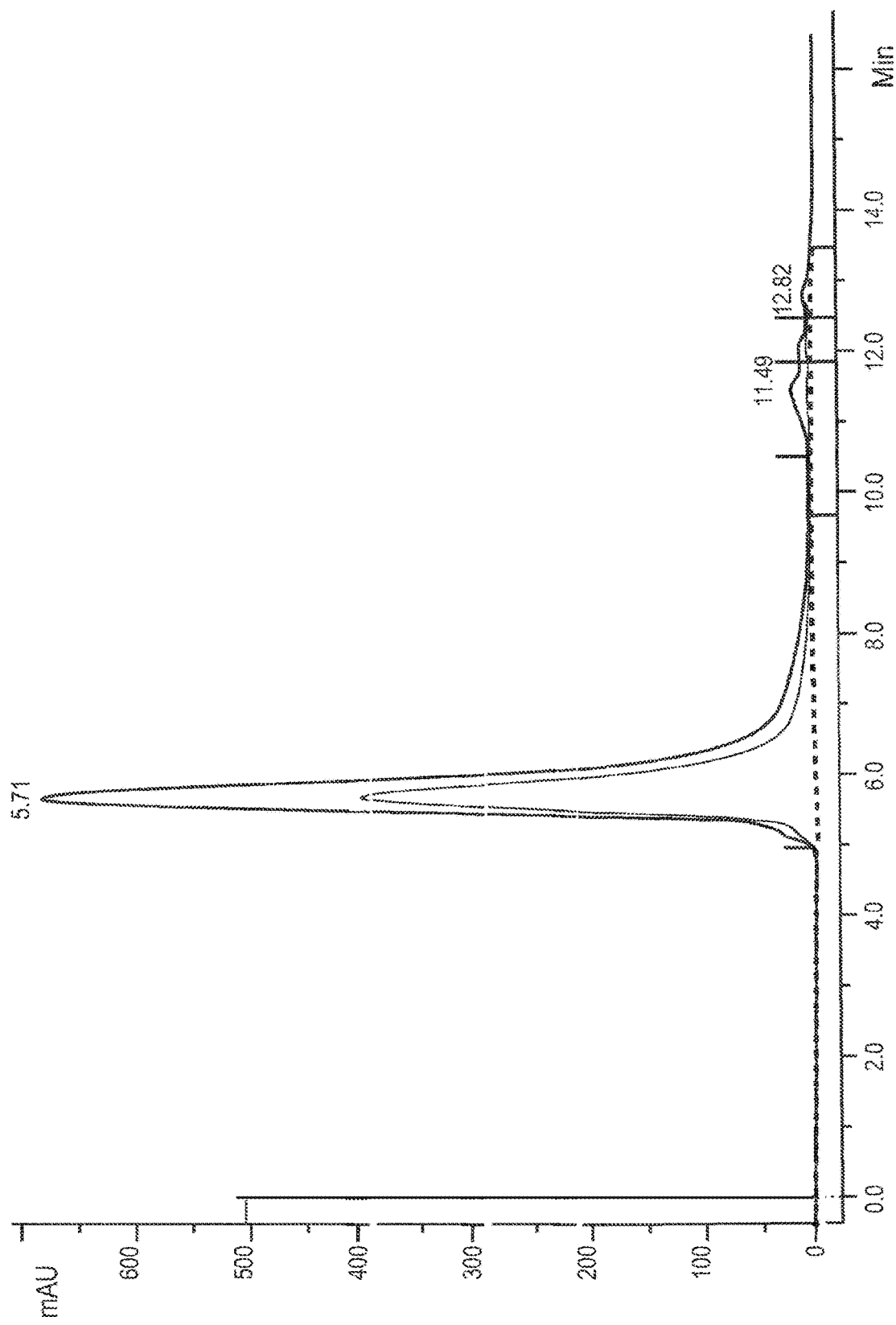

FIG. 26 Size exclusion profile of the 4D5-95mer-2C4 complex after a freezing and thawing cycle. Upper signal: 260 nm signal, lower signal: 280 nm signal. No aggregates can be detected between start at 0.0 min and the elution peak at 5.71 min.

EXAMPLE 1

Formation of FAB-ss-DNA-Conjugates

Two monoclonal antibodies binding to human cardiac Troponin T at different, non-overlapping epitopes, epitope a and epitope b, respectively, were used. Both these antibodies are used in the current Roche Elecsys™ Troponin T assay, wherein Troponin T is detected in a sandwich immunoassay format.

Purification of the monoclonal antibodies from culture supernatant was carried out using state of the art methods of protein chemistry.

The purified monoclonal antibodies are protease digested with either pre-activated papain (anti-epitope a MAb) or pepsin (anti-epitope b MAb) yielding F(ab')2 fragments that are subsequently reduced to FAB'-fragments with a low concentration of cysteamine at 37° C. The reaction is stopped by separating the cysteamine on a Sephadex G-25 column (GE Healthcare) from the polypeptide-containing part of the sample.

The FAB'-fragments are conjugated with the below described activated ss-DNAa and ss-DNAb oligonucleotides.

a) Anti-Troponin T (Epitope A) Antibody FAB-ss-DNA-Conjugate A

For preparation of the anti-Troponin T <epitope a> antibody FAB-ss-DNAa-conjugate A a derivative of SEQ ID NO: 05 is used, i.e. 5'-AGT CTA TTA ATG CTT CTG C(=SEQ ID NO:5)-XXX—Y-Z-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=3''-Amino-Modifier C6 introduced via 3'-Amino Modifier TFA Amino C-6 lcaa CPG (ChemGenes) and wherein Z=4[N-maleinimidomethyl]cyclohexane-1-carboxy introduced via Sulfosuccinimidyl 4-[N-maleimidomethyl]cyclohexane-1-carboxylate (ThermoFischer).

b) Anti-Troponin T (Epitope B) Antibody FAB-ss-DNA-Conjugate B

For the preparation of the anti-Troponin T <epitope b> antibody FAB-ss-DNAb-conjugate B a derivative of SEQ ID NO: 06 is used, i.e. 5'-Y—Z-XXX-AGT TCT ATC GTC GTC CA-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=5'-Amino-Modifier C6 introduced via (6-(4-Monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

The oligonucleotides of SEQ ID NO: 05 or 06, respectively, have been synthesized by state of the art oligonucleotide synthesis methods. The introduction of the maleinimido group was done via reaction of the amino group of Y with the succinimidyl group of Z which was incorporated during the solid phase oligonucleotide synthesis process.

The single-stranded DNA constructs shown above bear a thiol-reactive maleimido group that reacts with a cysteine of the FAB' hinge region generated by the cysteamine treatment. In order to obtain a high percentage of single-labeled FAB'-fragments the relative molar ratio of ss-DNA to FAB'-fragment is kept low. Purification of single-labeled FAB'-fragments (ss-DNA:FAB'=1:1) occurs via anion exchange chromatography (column: MonoQ, GE Healthcare). Verification of efficient labeling and purification is achieved by analytical gel filtration chromatography and SDS-PAGE.

EXAMPLE 2

Formation of Biotinylated Linker Molecules

The oligonucleotides used in the ss-DNA linkers L1, L2 and L3, respectively, have been synthesized by state of the art oligonucleotide synthesis methods and employing a biotinylated phosphoramidite reagent for biotinylation.

Linker 1 (=L$_1$), a biotinylated ss-DNA linker 1 with no spacer has the following composition:

5'-GCA GAA GCA TTA ATA GAC T (Biotin-dT)-GG ACG ACG ATA GAA CT-3'. It comprises ss-DNA oligonucleotides of SEQ ID NO: 7 and 8, respectively, and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyano-ethyl)-(N,N-diisopropyl)]-phosphoramidite (Glen Research).

Linker 2 (=$L_2$), a biotinylated ss-DNA linker 2 with a 10mer spacer has the following composition:

5'-GCA GAA GCA TTA ATA GAC T T5-(Biotin-dT)-T5 GG ACG ACG ATA GAA CT-3'. It comprises ss-DNA oligonucleotides of SEQ ID NO: 7 and 8, respectively, twice oligonucleotide stretches of five thymidines each and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyano-ethyl)-(N,N-diisopropyl)]-phosphoramidite (Glen Research).

Linker 3 (=$L_3$), a biotinylated ss-DNA linker 3 with a 30mer spacer has the following composition:

5'-GCA GAA GCA TTA ATA GAC T T15-(Biotin-dT)-T15 GG ACG ACG ATA GAA CT-3'. It comprises ss-DNA oligonucleotides of SEQ ID NO: 7 and 8, respectively, twice oligonucleotide stretches of fifteen thymidines each and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research).

EXAMPLE 3

Epitopes for Monovalent Troponin T Binders a and b, Respectively

Synthetic peptides have been construed that individually only have a moderate affinity to the corresponding FAB'-fragment derived from the anti-Troponin T antibodies a and b, respectively.

a) The Epitope "A" for Antibody a is Comprised in:

```
SEQ ID NO: 9 = ERAEQQRIRAEREKEUUSLKDRIEKRRRAERAE
amide, wherein U represents β-Alanine.
``` b) The Epitope "B" for Antibody b is Comprised in:

```
SEQ ID NO: 10 = SLKDRIERRRAERAEOOERAEQQRIRAEREKE
amide, wherein O represents Amino-trioxa-octanoic-
acid
```

As the skilled artisan will appreciate it is possible to combine these two epitope-containing peptides two ways and both variants have been designed and prepared by linear combining the epitopes "A" and "B". The sequences of both variants, the linear sequences of epitopes "A"-"B" (=TnT 1) and "B"-"A" (=TnT 2), respectively have been prepared by state of the art peptide synthesis methods.

The sequences for epitopes "A" and "B", respectively, had been modified compared to the original epitopes on the human cardiac Troponin T sequence (P45379/UniProtKB) in order to reduce the binding affinity for each of the FABs thereto. Under these circumstances the dynamics of the effect of hetero-bivalent binding is better visible, e.g. by analyzing binding affinity with the BIAcore Technology.

EXAMPLE 4

Biomolecular Interaction Analysis

For this experiment a BIAcore 3000 instrument (GE Healthcare) was used with a BIAcore SA sensor mounted into the system at T=25° C. Preconditioning was done at 100 µl/min with 3×1 min injection of 1 M NaCl in 50 mM NaOH and 1 min 10 mM HCl.

HBS-ET (10 mM HEPES pH 7.4, 150 mM NaC, 1 mM EDTA, 0.05% Tween® 20 was used as system buffer. The sample buffer was identical to the system buffer.

The BIAcore 3000 System was driven under the control software V1.1.1. Flow cell 1 was saturated with 7 RU D-biotin. On flow cell 2, 1063 RU biotinylated ss-DNA linker L1 was immobilized. On flow cell 3, 879 RU biotinylated ss-DNA linker L2 was immobilized. On flow cell 4, 674 RU biotinylated ss-DNA linker L3 was captured.

Thereafter, FAB fragment DNA conjugate A was injected at 600 nM. FAB fragment DNA conjugate B was injected into the system at 900 nM. The conjugates were injected for 3 min at a flow rate of 2 µl/min. The conjugates were consecutively injected to monitor the respective saturation signal of each FAB fragment DNA conjugate on its respective linker. FAB combinations were driven with a single FAB fragment DNA conjugate A, a single FAB fragment DNA conjugate B and both FAB fragment DNA conjugates A and B present on the respective linker. Stable baselines were generated after the linkers have been saturated by the FAB fragment DNA conjugates, which was a prerequisite for further kinetic measurements.

The peptidic analytes TnT1 and TnT2 were injected as analytes in solution into the system in order to interact with the surface presented FAB fragments.

TnT1 was injected at 500 nM, TnT2 was injected at 900 nM analyte concentration. Both peptides were injected at 50 µl/min for 4 min association time. The dissociation was monitored for 5 min. Regeneration was done by a 1 min injection at 50 µl/min of 50 mM NaOH over all flow cells.

Kinetic data was determined using the BIAevaluation software (V.4.1). The dissociation rate KD (1/s) of the TnT1 and TnT2 peptides from the respective surface presented FAB fragment combinations was determined according to a linear Langmuir 1:1 fitting model. The complex halftime in min were calculated according to the solution of the first order kinetic equation: ln(2)/(60*kD).

Results:

The experimental data given in Tables 5 and 6, respectively demonstrate an increase in complex stability between analyte (TnT1 or TnT2), respectively, and the various heterobivalent FAB-FAB conjugates A-B as compared to the monovalent dsDNA FAB A or B conjugate, respectively. This effect is seen in each Table in line 1 compared to lines 2 and 3.

TABLE 5

Analysis data using TnT1 with linkers of various length

| FAB fragment DNA conjugate A | FAB fragment DNA conjugate B | kD (1/s) | t½ diss (min) |
|---|---|---|---|
| a) Linker L1 | | | |
| x | x | 6.6E−03 | 1.7 |
| x | — | 3.2E−02 | 0.4 |
| — | x | 1.2E−01 | 0.1 |
| b) Linker L2 | | | |
| x | x | 4.85E−03 | 2.4 |
| x | — | 2.8E−02 | 0.4 |
| — | x | 1.3E−01 | 0.1 |
| c) Linker L3 | | | |
| x | x | 2.0E−03 | 5.7 |
| x | — | 1.57E−02 | 0.7 |
| — | x | 1.56E−02 | 0.7 |

TABLE 6

Analysis data using TnT2 with linkers of various length

| FAB fragment DNA conjugate A | FAB fragment DNA conjugate B | kD (/1/s) | t½ diss (min) |
|---|---|---|---|
| a) Linker L1 | | | |
| x | x | 1.4E−02 | 0.8 |
| x | — | 4.3E−02 | 0.3 |
| — | x | 1.4E−01 | 0.1 |
| b) Linker L2 | | | |
| x | x | 4.9E−03 | 2.3 |
| x | — | 3.5E−02 | 0.3 |
| — | x | 1.3E−01 | 0.1 |
| c) Linker L3 | | | |
| x | x | 8.0E−03 | 1.5 |
| x | — | 4.9E−02 | 0.2 |
| — | x | 3.2E−01 | 0.04 |

The avidity effect is further dependent on the length of the linker. In the sub-tables shown under Table 1 the 30mer linker $L_3$ shows the lowest dissociation rate or highest complex stability, in sub-tables shown under Table 2 the 10mer $L_2$ linker exhibits the lowest dissociation rate or highest complex stability. These data taken together demonstrate that the flexibility in linker length as inherent to the approach given in the present invention is of great utility and advantage.

EXAMPLE 5

Formation of FAB'-ss-DNA-Conjugates

Two monoclonal antibodies binding to human HER2 (ErbB2 or p185$^{neu}$) at different, non-overlapping epitopes A and B were used. The first antibody is anti-HER2 antibody 4D5 (huMAb4D5-8, rhuMab HER2, trastuzumab or HERCEPTIN®; see U.S. Pat. No. 5,821,337 incorporated herein by reference in its entirety). The second antibody is anti-HER2 antibody 2C4 (Pertuzumab).

Purification of the monoclonal antibodies from culture supernatant can be carried out using state of the art methods of protein chemistry.

The purified monoclonal antibodies are protease digested with either pre-activated papain or pepsin yielding F(ab')2 fragments. These are subsequently reduced to FAB'-fragments with a low concentration of cysteamine at 37° C. The reaction is stopped by separating the cysteamine on a Sephadex G-25 column (GE Healthcare) from the polypeptide-containing part of the sample.

The obtained FAB'-fragments are conjugated with the activated ss-DNA polynucleotides.

a) Anti-HER2 Antibody 4D5 FAB'-ss-DNA-Conjugate

For preparation of the anti-HER2 antibody 4D5 FAB'-ss-DNA-conjugate a derivative of SED ID NO: 05 is used, i.e. 5'-AGT CTA TTA ATG CTT CTG C(=SEQ ID NO: 05)-XXX-Y-Z-3', wherein X=propylene-phosphate introduced via phosphoramidite C3 (3-(4,4'-dimethoxytrityloxy)propyl-1-[(2-cyanoethyl)-(N,N-diisopropyl)]-phosphoramidite (Glen Research), wherein Y=5'-amino-modifier C6 introduced via (6-(4-monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

b) Anti-HER2 Antibody 2C4 FAB'-ss-DNA-Conjugate

For the preparation of the anti-HER2 antibody 2C4 FAB'-ss-DNA-conjugate B a derivative of SEQ ID NO: 06 is used, i.e. 5'-Y—Z-XXX-AGT TCT ATC GTC GTC CA-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=5'-Amino-Modifier C6 introduced via (6-(4-Monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

The polynucleotides of SEQ ID NO: 05 or SEQ ID NO: 06, respectively, have been synthesized by state of the art polynucleotide synthesis methods. The introduction of the maleinimido group was done via reaction of the amino group of Y which was incorporated during the solid phase polynucleotide synthesis process with the Sulfosuccinimidyl 4-[N-maleimidomethyl] cyclohexane-1-carboxylate (ThermoFischer).

The single-stranded DNA constructs bear a thiol-reactive maleimido group that reacts with a cysteine of the FAB' hinge region generated by the cysteamine treatment. In order to obtain a high percentage of single-labeled FAB'-fragments the relative molar ratio of ss-DNA to FAB'-fragment is kept low. Purification of single-labeled FAB'-fragments (ss-DNA:FAB'=1:1) occurs via anion exchange chromatography (column: MonoQ, GE Healthcare). Verification of efficient labeling and purification is achieved by analytical gel filtration chromatography and SDS-PAGE.

EXAMPLE 6

Biomolecular Interaction Analysis

For this experiment a BIAcore T100 instrument (GE Healthcare) was used with a BIAcore SA sensor mounted into the system at T=25° C. Preconditioning occurred at 100 µl/min with 3×1 min injection of 1 M NaCl in 50 mM NaOH, pH 8.0 followed by a 1 min injection of 10 mM HCl. The system buffer was HBS-EP (10 mM HEPES pH 7.4, 150 mM NaCl, 1 mM EDTA, 0.05% P 20). The sample buffer was the system buffer supplemented with 1 mg/ml CMD (carboxymethyldextrane).

Biotinylated ss-L-DNA linkers were captured on the SA surface in the respective flow cells. Flow cell 1 was saturated with amino-PEO-Biotin (PIERCE).

40 RU of the biotinylated 35mer oligonucleotide linker were captured on flow cell 2. 55 RU of the biotinylated 75mer oligonucleotide linker were captured on flow cell 3. 60 RU of biotinylated 95mer oligonucleotide linker were captured on flow cell 4.

250 nM anti-HER2 antibody 4D5-FAB'-ss-L-DNA was injected into the system for 3 min. 300 nM anti-HER2 antibody 2C4-FAB'-ss-L-DNA was injected into the system at 2 µl/min for 5 min. The DNA-labeled FAB fragments were injected alone or in combination.

As a control only 250 nM anti-HER2 antibody 4D5-FAB'-ss-D-DNA and 300 nM anti-HER2 antibody 2C4-FAB'-ss-D-DNA was injected into the system. As a further control, buffer was injected instead of the DNA-labeled FAB fragments. After hybridization of the ss-L-DNA-labeled FAB fragments on the respective ss-L-DNA bi-linkers, the analyte in solution hHER2-ECD was injected at different concentration series from 24 nM, 8 nM, 3 nM, 1 nM, 0.3 nM, 0 nM into the system for 3.5 min association phase at 100 µl/min. The dissociation phase was monitored at 100 µl/min for 15 min. The system was regenerated by a 30 sec injection at 20 µl/min of 100 mM glycine buffer (Glycine pH 11, 150 mM NaCl), followed by a second 1 min injection of water at 30 µl/min.

The signals were measured as analyte concentration-dependent, time resolved sensorgrams. The data was evaluated using the BIAcore BIAevaluation software 4.1. As a fitting model a standard Langmuir binary binding model was used.

Results:

No HER2-ECD interaction could be observed when ss-D-DNA labeled FAB fragments were injected into the system, because the ss-D-DNA-labeled FAB fragments didn't hybridize with spiegelmeric ss-L-DNA linkers presented on the sensor surface (FIG. 2).

Table 7: Kinetic results of the complexation experiment. Linker: Surface presented biotinylated ss-L-DNA polynucleotide linker, Oligo_35mer-Bi, Oligo_75mer-Bi and Oligo_95mer-Bi differing in linker length. ss-L-DNA-FAB: 2C4-ss-L-DNA: anti-HER2 antibody 2C4-FAB'-ss-L-DNA labeled with 19mer-Fluorescein. 4D5-ss-L-DNA: anti-HER2 antibody 4D5-FAB'-ss-L-DNA labeled with 17mer-Fluorescein. 4D5-+2C4-ss-L-DNA: surface presented combination of both fragments. LRU: mass in response units, which is hybridized on the sensor surface. Antigen: An 87 kDa HER2-ECD was used as analyte in solution. ka: association rate in (1/Ms). kD: dissociation rate in (1/s). t1/2 diss: antigen complex halftime calculated in hours according to the solution ln(2)/kD*3600 of a first order kinetic equation. kD: affinity in molar. kD: affinity calculated in picomolar. Rmax: Maximum analyte response signal at saturation in response units (RU). MR: Molar Ratio, indicating the stoichiometry of the interaction. Chi2, U-value: quality indicator of the measurements.

The BIAcore sensorgrams showing concentration dependent measurements of the 95-mer complex HER2-ECD interaction (FIG. 5). The 95-mer linker carries poly-T to increase the linker length compared to the 35-mer linker. The kinetic data indicates that the fully established complex shows a dramatic improvement of its kinetic performance. This is due to increased linker length and flexibility of the 95-mer.

The BIAcore assay setup comprised the following (see also FIG. 1): ss-L-DNA-bi linkers were presented on a BIAcore SA sensor. Flow cell 1 served as a control. As analyte in solution Her2-ECD was used. Anti-HER2 antibody 2C4-FAB'-ss-L-DNA and anti-HER2 antibody 2C4-FAB'-ss-L-DNA were hybridized to the surface presented linkers.

Here is shown, for the first time, a fully functional cooperative binding event between Herceptin-FAB and Pertuzumab-FAB linked together via a highly flexible ss-L-DNA linker. The data in Table 3 provides evidence for the presence of a cooperative binding event. Despite the Rmax values of the fully established complex s are roughly double the signal height of the singly FAB-armed constructs, the Molar Ratio values are exactly 1 (MR=1). This is a clear evidence for the presence of a simultaneous, cooperative binding event of both FAB fragments. The complex counts as a single molecule with a 1:1 Langmuir binding stoichiometry. Despite having 2 independently binding HER2 interfaces no inter molecule binding between one complex and two HER2 domains can be detected.

The avidity constants for synergizing pairs of monoclonal antibodies or for a chemically cross-linked bispecific F(ab')2 is generally only up to 15 times greater than the affinity constants for the individual monoclonal antibodies, which is

TABLE 7

| Linker | ss-L-DNA-Fab | LRU | Antigen | $k_a$ 1/Ms | $k_d$ 1/s | $t_{1/2}$-diss hours | $K_D$ M | $K_D$ pM | $R_{max}$ RU | MR | Chi$^2$ RU$^2$ |
|---|---|---|---|---|---|---|---|---|---|---|---|
| Oligo_35mer_Bi | 4D5- + 2C4-ss-L-DNA | 84 | Her2-ECD | 5.9E+05 | 6.7E−05 | 3 | 1.1E−10 | 100 | 59 | 0.9 | 0.2 |
| Oligo_35mer_Bi | 4D5-ss-L-DNA | 16 | Her2-ECD | 4.0E+05 | 3.4E−05 | 6 | 8.5E−11 | 100 | 29 | 1.2 | 0.1 |
| Oligo_35mer_Bi | 2C4-ss-L-DNA | 31 | Her2-ECD | 3.3E+05 | 3.6E−05 | 5 | 1.1E−10 | 100 | 26 | 0.6 | 0.03 |
| Oligo_75mer_Bi | 4D5- + 2C4-ss-L-DNA | 87 | Her2-ECD | 5.1E+05 | 4.6E−06 | 4164 | 9.1E−14 | 0.1 | 65 | 1.0 | 0.1 |
| Oligo_75mer_Bi | 4D5-ss-L-DNA | 16 | Her2-ECD | 2.9E+05 | 6.1E−05 | 3 | 2.1E−10 | 200 | 31 | 1.3 | 0.04 |
| Oligo_75mer_Bi | 2C4-ss-L-DNA | 29 | Her2-ECD | 3.8E+05 | 6.3E−05 | 3 | 1.6E−10 | 200 | 32 | 0.7 | 0.03 |
| Oligo_95mer_Bi | 4D5- + 2C4-ss-L-DNA | 76 | Her2-ECD | 5.0E+05 | 4.9E−08 | 3942 | 9.9E−14 | 0.1 | 58 | 1.0 | 0.1 |
| Oligo_95mer_Bi | 4D5-ss-L-DNA | 14 | Her2-ECD | 1.0E+05 | 9.5E−05 | 2 | 3.1E−10 | 300 | 28 | 1.3 | 0.03 |
| Oligo_95mer_Bi | 2C4-ss-L-DNA | 28 | Her2-ECD | 3.8E+05 | 6.8E−05 | 3 | 1.8E−10 | 300 | 27 | 0.6 | 0.03 |

The BIAcore sensorgrams show concentration dependent measurements of the 35-mer complex HER2-ECD interaction (FIG. 3). This linker is consisting of solely the hybridization motives sequences of the DNA labels. The kinetic data indicates that the fully established complex shows no improvement of the kinetic performance. This is due to the insufficient linker length and lacking flexibility of the 35-mer.

The BIAcore sensorgrams showing concentration dependent measurements of the 75-mer complex HER2-ECD interaction (FIG. 4). The 75-mer linker carries poly-T to increase the linker length compared to the 35-mer linker. The kinetic data indicates that the fully established complex shows a dramatic improvement of its kinetic performance. This is due to an optimal linker length and flexibility of the 75-mer.

significantly less than the theoretical avidity expected for ideal combination between the reactants (Cheong, H. S., et al., Biochem. Biophys. Res. Commun. 173 (1990) 795-800). Without being bound by this theory one reason for this might be that the individual epitope/paratope interactions involved in a synergistic binding (resulting in a high avidity) must be orientated in a particular way relative to each other for optimal synergy.

Furthermore, the data presented in Table 7 provides evidence, that the short 35-mer linker, which consists just from the ss-L-DNA hybridization motives doesn't show enough flexibility or/and linker length to produce the cooperative binding effect. The 35-mer linker is a rigid, double helix L-DNA construct. The hybridization generates a double L-DNA helix, which is shorter and less flexible than the ss-L-DNA sequence. The helix shows reduced degrees of freedom and can be seen as a rigid linker construct. Table 7 shows, that the 35-mer linker isn't able to generate a cooperative binding event.

Extending the linker length by a highly flexible poly-T ss-L-DNA to form a 75-mer and a 95-mer, respectively, provides for an increase in affinity and especially in antigen complex stability kD (1/s).

The chi2 values indicate a high quality of the measurements. All measurements show extremely small errors. The data can be fitted to a Langmuir 1:1 fitting model residuals deviate only +/−1 RU, small chi2 values and only 10 iterative calculations were necessary for obtaining the data.

A cooperative binding effect works according to the physical law, in that the free binding energies ΔG1 and ΔG2 summarize. The affinities multiply: KDcoop=KD1×KD2. Furthermore, the dissociation rates also multiply: KD coop=kd1×KD 2. This is exactly observable in the 75-mer and 95-mer linker experiment. This results in very long complex half-lives of 4146 hours (173 days) and 3942 hours (164 days), respectively. The affinities are in the range of 100 fmol/l. It is obvious, that a cooperative binding event occurs.

The association rates of all fully established complex s are faster, when compared to the singly hybridized constructs. Despite showing a higher molecular weight the association rate increases.

Here we could show, that trastuzumab and Pertuzumab linked together in a complex as reported herein simultaneously binds to the HER-2 extracellular domain (ECD). Both FAB fragments bind to genuine epitopes on the HER2-ECD (PDB 1 S78 and PDB 1N82). Additionally both FAB fragments strongly differ in their binding angles. By using the optimal 75-mer (30 nm) ss-L-DNA linker length and its beneficial flexibility and length properties a cooperative binding event could be shown.

The signals were measured as analyte concentration-dependent, time resolved sensorgrams. The data was evaluated using the BIAcore BIAevaluation software 4.1. As a fitting model a standard Langmuir binary binding model was used.

EXAMPLE 7

Additional Biomolecular Interaction Analysis

A BIAcore 3000 instrument was mounted with a CM-5 sensor chip. The sensor was preconditioned as recommended by the manufacturer (GE healthcare, Uppsala, Sweden). The system buffer was (10 mM HEPES pH 7.4, 150 mM NaCl, 1 mM EDTA, 0.05% Tween® 20). The system buffer was also used as the sample buffer. The system was operated at 25° C. under the control software 4.1.

30 μg/ml polyclonal goat anti human IgG-Fc gamma antibody (Jackson Laboratories, USA) in 10 mM acetate buffer pH 4.5 were immobilized by standard NHS/EDC chemistry at 13,952 RU on flow cell 1 and 15,047 RU on flow cell 2. The system was regenerated at 20 μl/min using a 20 sec. pulse of a 10 mM glycine pH 1.5 buffer, a 1 min pulse of 10 mM glycine pH 1.7 buffer, and a 30 sec. pulse of 10 mM glycine pH 1.5 buffer. On flow cell 1, 5 nM huIgG (Bayer Healthcare) were injected for 1 min at 10 μl/min as a reference.

On flow cell 2, 10 nM human HER2 extracellular receptor FC chimera (hHER2-ECDpresSFc) were injected for 1 min at 10 μl/min. Typically 100 response units of the prebuilt homodimeric hHER2-ECDpresSFc were captured via the human FC portion on flow cell 2 by a goat anti human IgG-Fc gamma antibody. Typically 130 response units of huIgG were captured via the human FC portion on flow cell 1.

The signal on flow cell 2 was referenced versus flow cell 1.

The ss-L-DNA labeled FAB fragments anti-HER2 antibody 4D5-FAB'-ss-L-DNA and anti-HER2 antibody 2C4-FAB'-ss-L-DNA were hybridized with the 75mer ss-L-DNA linker by a 1:1:1 molar stoichiometry. The fully established complex 2C4-75mer-4D5 was injected for three minutes at 50 nM into the system. As a control, the single FAB fragments were injected at 50 nM into the system.

Immediately after injection end 250 nM streptavidin or system buffer was injected into the system for 3 min at 10 μl/min. Since the 75mer linker contains a single biotin moiety in the center of its sequence, the SA should work as a probe to recognize the biotin within the linker, but not the presence of the FAB fragments.

In another experiment the fully established 4D5-75mer-2C4 complex was injected into the system at different concentration steps 0 nM, 0.6 nM, 1.9 nM, 2x 5.6 nM, 16.7 nM, 50 nM at 10 μl/min for 3 min. The concentration dependent response levels of the hHER2-ECDpresSFc analyte were monitored. The response levels were plotted over the concentration steps of the hHER2-ECDpresSFc. The data was visualized using the software Origin 7. The data was fitted using the Hill equation $y=V_{max}*x^n/(k^n+x^n)$ as provided by the Origin 7 software.

The BIAcore assay setup comprised the following (see also FIG. 6): A polyclonal goat anti human IgG-Fc gamma antibody was immobilized on the BIAcore CM5 sensor and serves as a capture system for the huFc chimera HER2 ECD. Anti-HER2 antibody 2C4-FAB'-ss-L-DNA (2C4 FAB), anti-HER2 antibody 4D5-FAB'-ss-L-DNA (4D5 FAB) and fully established complexes were injected, followed by the injection of streptavidin (SA). The aim of the experiment is to demonstrate the presence and accessibility of the biotin moiety within the 75mer ss-L-DNA linker.

Results of the experiment are depicted in FIG. 7. The BIAcore sensorgram shows an overlay plot of interaction signals upon 50 nM injections of anti-HER2 antibody 2C4-FAB'-ss-L-DNA (2C4), anti-HER2 antibody 4D5-FAB'-ss-L-DNA (4D5) and fully established complex (2C4-75mer-4D5) connected by a 75mer ss-L-DNA linker. The overlay plot shows that due to its higher mass of 137 kDa the fully established complex binder (2C4-75mer-4D5+ buffer) generates a higher signal response level, when compared to the FAB fragment injections (2C4+ buffer, 4D5+ buffer). The FAB fragments have a calculated molecular weight of 57 kDa, each. Immediately after injection end at 420 sec, 250 nM streptavidin or system buffer was injected. The double headed arrow marks the 14 RU signal shift (ARU) induced by the 250 nM streptavidin injection (2C4-75mer-4D5+SA) compared to the buffer injection (2C4-75mer-4D5+ buffer). The FAB fragments show no signal shift upon SA injection and remain at the buffer signal level ((2C4+SA), (2C4+ buffer), (4D5+SA), (4D5+ buffer)). Streptavidin is the effector moiety. It shows the accessibility of the ss-L-DNA linker.

BIAcore sensorgram showing an overlay plot of concentration-dependent measurements of the fully established 75-mer complex as analyte in solution interacting with the surface presented huFc chimera HER2 ECD is shown in FIG. 8. The black lines represent the 1:1 Langmuir fit on the data. Kinetic data, association rate ka=1.25*10$^5$ 1/Ms, dissociation rate KD=3.39*10$^{-5}$ 1/s, affinity constant 0.3 nM.

The response levels of FIG. 8 were plotted versus the analyte concentration of the fully established complex (FIG. 9). The data was fitted according to the hill equation and the hill factor was determined (Origin 7). Equation: $y=V_{max}*x^n/(k^n+x^n)$, Chi2/DoF=0.6653, R2=0.99973; n=1.00201+/−0.06143.

In Table 8 the kinetic data from the BIAcore assay format as depicted in FIG. 6 is shown. The cooperative binding effect can be produced with the complex in solution. The Molar Ratios show, that exactly a single complex recognizes a single HER2-ECD chimera. Kinetic data, association rate ka 1/Ms, dissociation rate kD 1/s, affinity constant KD (M) and in (nM), maximum binding response signal (Rmax), amount of captured huFc Chim Her2ECD Ligand (RU), Complex halftime according to Langmuir t1/2 diss. Molar Ratio MR, indicating the stoichiometry of the binding events. Error chi2. 4D5-2C4-75mer is the fully established complex. 4D5-75mer and 2C4-75mer are the FAB fragments, but hybridized to the ss-L-DNA 75mer linker.

TABLE 8

| Ligand | Ligand (RU) | Analyte | ka (1/Ms) | kd (1/s) | t½ diss (min) | KD (M) | KD (nM) | Rmax (RU) | MR | Chi2 |
|---|---|---|---|---|---|---|---|---|---|---|
| huFC | 106 | 4D5-2C4-75mer | 1.25E+05 | 3.39E−05 | 342 | 2.71E−10 | 0.3 | 83 | 1.1 | 0.28 |
| chim. HER2 ECD | 104 | 4D5-75mer | 8.54E+04 | 1.45E−04 | 80 | 1.69E−09 | 1.7 | 46 | 1.1 | 0.18 |
|  | 103 | 2C4-75mer | 8.87E+04 | 1.17E−04 | 99 | 1.32E−09 | 1.3 | 46 | 1.1 | 0.15 |

The data presented in Table 8 demonstrate, that the fully established complex, connected via a 75mer ss-L-DNA linker shows cooperative binding. The single FAB fragments show lower affinity, when compared to the fully established complex. The signal levels at Rmax shows the increased molecular mass of the complex versus the single FAB fragments. Despite a higher signal level, the Molar Ratios are exactly at 1.1. This shows that statistically each complex binds to a single huFc chimeric HER2 ECD molecule.

The amplification factor by cooperativity is not so high when compared to the previous assay format, wherein the complex was assembled on the sensor surface. KDcoop is triggered up to 6-fold. Without being bound by theory, this could be due to the nature of the homodimeric huFc chimeric HER2 ECD. Potentially the dual binder recognizes the two separated HER2 ECDs in the huFc HER2 chimera and cannot fully establish cooperativity.

The efficient delivery of an effector moiety in form of a dye could be shown by the FACS analysis (see next example) sing the phycoerythrin-labeled streptavidin probe on living cells. The streptavidin labeled probe could easily access the biotin moiety in the 75mer ss-L-DNA linker construct.

Data form the measurement as outlined above was used for the generation of the Hill Plot (FIG. 9). The Hill analysis of the complex shows, that the binding events of the FAB fragments are independent from each other and don't interfere with each other. No cooperative binding in terms of a structural disturbance of the HER2 molecule could be detected, the Hill coefficient (n=1.00201+/−0.06143) is exactly 1. Therefore, the linker chemistry, the nature of the ss-L-DNA linker and the oligo-labeled FAB fragment are not negatively interfering with the target molecule recognition.

EXAMPLE 8

Further Complexes—Synthesis and Characterization
Synthesis of Hybridizable Oligonucleotides The following amino modified precursors comprising the sequences given in SEQ ID NOs: 05 and 06, respectively, were synthesized according to standard methods. The below given oligonucleotides not only comprise the so-called aminolinker, but also a fluorescent dye. As the skilled artisan will readily appreciate, this fluorescent dye is very convenient to facilitate purification of the oligonucleotide as such, as well as of components comprising them.

a) 5'-Fluorescein-AGT CTA TTA ATG CTT CTG C-(Spacer C3)3-C7Aminolinker-;
b) 5'-Cy5 AGT CTA TTA ATG CTT CTG C-(Spacer C3)3-C7Aminolinker-;
c) 5'-Aminolinker-(Spacer C3)3-AGT TCT ATC GTC GTC CA-Fluorescein-3';
d) 5'-Fluorescein-(beta L AGT CTA TTA ATG CTT CTG C)-(Spacer C3)3-C7Aminolinker-; (beta L indicates that this is an L-DNA oligonucleotide); and
e) 5'-Aminolinker-(Spacer C3)3-(beta L-AGT TCT ATC GTC GTC CA)-Fluorescein-3' (beta L indicates that this is an L-DNA oligonucleotide).

Synthesis was performed on an ABI 394 synthesizer at a 10 μmol scale in the trityl on (for 5' amino modification) or trityl off mode (for 3' amino modification) using commercially available CPGs as solid supports and standard dA(bz), dT, dG (iBu) and dC(Bz) phosphoramidites (Sigma Aldrich).

The following amidites, amino modifiers and CPG supports were used to introduce the C3-spacer, a dye and amino moieties, respectively, during oligonucleotide synthesis:

spacer phosphoramidite C3 (3-(4,4'-Dimethoxytrityloxy) propyl-1-[(2-cyanoethyl)-(N,N-diisopropyl)]-phosphoramidite (Glen Research);

5' amino modifier is introduced by using 5'-Amino-Modifier C6 (6-(4-Monomethoxytritylamino) hexyl-(2-cyanoethyl)-(N,N-diisopropyl)-phosphoramidite (Glen Research);

5'-Fluorescein Phosphoramidite 6-(3',6'-dipivaloylfluoresceinyl-6-carboxamido)-hexyl-1-O-(2-cyanoethyl)-(N,N-diisopropyl)-phosphoramidite (Glen Research);

Cy5™ Phosphoramidite 1-[3-(4-monomethoxytrityloxy) propyl]-1'-[3-[(2-cyanoethyl)-(N,N-diisopropyl phosphoramidityl] propyl]-3,3,3',3'-tetramethylindodicarbocyanine chloride (Glen Research);

LightCycler Fluorescein CPG 500 A (Roche Applied Science); and

3'-Amino Modifier TFA Amino C-6 lcaa CPG 500 A (ChemGenes).

For Cy5 labeled oligonucleotides, dA(tac), dT, dG(tac), dC(tac) phosphoramidites, (Sigma Aldrich), were used and deprotection with 33% ammonia was performed for 2h at room temperature.

L-DNA oligonucleotides were synthesized by using beta-L-dA(bz), dT, dG (iBu) and dC(Bz) phosphoramidites (ChemGenes)

Purification of fluorescein modified hybridizable oligonucleotides was performed by a two-step procedure: First the oligonucleotides were purified on reversed-phase HPLC (Merck-Hitachi-HPLC; RP-18 column; gradient system [A: 0.1 M (Et₃NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The fractions (monitored by analytical RP HPLC) containing the desired product were combined and evaporated to dryness. (Oligonucleotides modified at the 5' end with monomethoxytrityl protected alkylamino group are detrylated by incubating with 20% acetic acid for 20 min). The oligomers containing fluorescein as label were purified again by IEX chromatography on a HPLC [Mono Q column: Buffer A: Sodium hydroxide (10 mmol/l; pH ~12) Buffer B 1 M Sodium chloride dissolved in Sodium hydroxide (10 mmol/l; pH ~12) gradient: in 30 minutes from 100% buffer A to 100% buffer B flow 1 ml/min detection at 260 nm]. The product was desalted via dialysis.

Cy5 labeled oligomers were used after the first purification on reversed-phase HPLC (Merck-Hitachi-HPLC; RP-18 column; gradient system [A: 0.1 M (Et₃NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The oligomers were desalted by dialysis and lyophilized on a Speed-Vac evaporator to yield solids which were frozen at −24° C.

Activation of Hybridizable Oligonucleotides

The amino modified oligonucleotides from Example 2 were dissolved in 0.1 M sodium borate buffer pH 8.5 buffer (c=600 µmol) and reacted with a 18-fold molar excess of Sulfo SMCC (Sulfosuccinimidyl 4-[N-maleimidomethyl] cyclohexane-1-carboxylate dissolved in DMF (c=3 mg/100 µl) from Thermo Scientific, The reaction product was thoroughly dialyzed against water in order to remove the hydrolysis product of sulfo-SMCC 4-[N-maleimidomethyl] cyclohexane-1-carboxylate.

The dialysate was concentrated by evaporation and directly used for conjugation with a monovalent binder comprising a thiol group.

Synthesis of Linker Oligonucleotides Comprising Hybridizable Oligonucleotides at Both Ends Oligonucleotides were synthesized by standard methods on an ABI 394 synthesizer at a 10 µmol scale in the trityl on mode using commercially available dT-CPG as solid supports and using standard dA(bz), dT, dG (iBu) and dC(Bz) phosphoramidites (Sigma Aldrich).

L-DNA oligonucleotides were synthesized by using commercially available beta L-dT-CPG as solid support and beta-L-dA(bz), dT, dG (iBu) and dC(Bz) phosphoramidites (ChemGenes)

Purification of the oligonucleotides was performed as described under Example 3 on a reversed-phase HPLC. The fractions (monitored by analytical RP HPLC) containing the desired product were combined and evaporated to dryness. Detrytilation was performed by incubating with 80% acetic acid for 15 min). The acetic acid was removed by evaporation. The reminder was dissolved in water and lyophilized The following amidites and CPG supports were used to introduce the C18 spacer, digoxigenin and biotin group during oligonucleotide synthesis:
  spacer phosphoramidite 18 (18-O-Dimethoxytritylhexaethyleneglycol, 1-[(2-cyanoethyl)-(N,N-diisopropyl)]-phosphoramidite (Glen Research);
  biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research);
  biotin Phosphoramidite 1-Dimethoxytrityloxy-2-(N-biotinyl-4-aminobutyl)-propyl-3-O-(2-cyanoethyl)-(N,N-diisopropyl)-phosphoramidite and
  5'-Dimethoxytrityl-5-[N-(trifluoroacetylaminohexyl)-3-acrylimido]-2'-deoxy uridine, 3'-[(2-cyanoethyl)-(N,N-diisopropyl)]-phosphoramidite for amino modification and postlabeling with Digoxigenin-N-Hydroxyl-succinimidyl ester.

The Following Bridging Constructs or Linkers were Synthesized:

Linker 1:
5'-G CAG AAG CAT TAA TAG ACT-TGG ACG ACG ATA GAA CT-3'

Linker 2:
5-G CAG AAG CAT TAA TAG ACT-(T40)-TGG ACG ACG ATA GAA CT-3'

Linker 3:
5'-[B-L] G CAG AAG CAT TAA TAG ACT-(Biotin-dT)-TGG ACG ACG ATA GAA CT-3'

Linker 4:
5'-[B-L] G CAG AAG CAT TAA TAG ACT-T5-(Biotin-dT)-T5-TGG ACG ACG ATA GAA CT-3'

Linker 5:
5'-[B-L] G CAG AAG CAT TAA TAG ACT-T20-(Biotin-dT)-T20-TGG ACG ACG ATA GAA CT-3'

Linker 6:
5'-[B-L] G CAG AAG CAT TAA TAG ACT-T30-(Biotin-dT)-T30-TGG ACG ACG ATA GAA CT-3'

Linker 7:
5'-GCA GAA GCA TTA ATA GAC T T5-(Biotin-dT)-T5 TG GAC GAC GAT AGA ACT-3'

Linker 8:
5'-GCA GAA GCA TTA ATA GAC T T10-(Biotin-dT)-T10 TGG ACG ACG ATA GAA CT-3'

Linker 9:
5'-GCA GAA GCA TTA ATA GAC T T15-(Biotin-dT)-T15 TGG ACG ACG ATA GAA CT-3'

Linker 10:
5'-GCA GAA GCA TTA ATA GAC T T20-(Biotin-dT)-T20 TGG ACG ACG ATA GAA CT-3'

Linker 11:
5-G CAG AAG CAT TAA TAG ACT-Spacer C18-(Biotin-dT)-Spacer C18-TGG ACG ACG ATA GAA CT-3'

Linker 12:
5'-G CAG AAG CAT TAA TAG ACT-(Spacer C18)2-(Biotin-dT)-(Spacer C18)2-TGG ACG ACG ATA GAA CT-3'

Linker 13:
5'-G CAG AAG CAT TAA TAG ACT-(Spacer C18)3-(Biotin-dT)-(Spacer C18)3-TGG ACG ACG ATA GAA CT-3'

Linker 14:
5'-G CAG AAG CAT TAA TAG ACT-(Spacer C18)4-(Biotin-dT)-(Spacer C18)4-TGG ACG ACG ATA GAA CT-3'

-continued

Linker 15:
5'-G CAG AAG CAT TAA TAG ACT-T20-(Dig-dT)-T20-
TGG ACG ACG ATA GAA CT-3'

Linker 16:
5'-G CAG AAG CAT TAA TAG ACT-(Dig-dT)-TGG ACG ACG
ATA GAA CT-3'

Linker 17:
5'-G CAG AAG CAT TAA TAG ACT-(Biotin-dT)-TGG ACG
ACG ATA GAA CT-3'

The above bridging construct examples comprise at least a first hybridizable oligonucleotide and a second hybridizable oligonucleotide. Linkers 3 to 18 in addition to the hybridizable nucleic acid stretches comprise a central biotinylated or digoxigenylated thymidine, respectively, or a spacer consisting of thymidine units of the length given above.

The 5'-hybridizable oligonucleotide corresponds to SEQ ID NO: 07 and the 3'-hybridizable oligonucleotide corresponds to SEQ ID NO: 08, respectively. The oligonucleotide of SEQ ID NO: 07 will readily hybridize with the oligonucleotide of SED ID NO: 06. The oligonucleotide of SEQ ID NO: 08 will readily hybridize with the oligonucleotide of SED ID NO: 05.

In the above bridging construct examples [B-L] indicates that an L-DNA oligonucleotide sequence is given; spacer C 18, Biotin and Biotin dT respectively, refer to the C18 spacer, the Biotin and the Biotin-dT as derived from the above given building blocks; and T with a number indicates the number of thymidine residues incorporated into the linker at the position given.

Assembly of the Complex

A) Cleavage of IgGs and Labeling of FAB' Fragments with ss-DNA

Purified monoclonal antibodies were cleaved with the help of pepsin protease yielding F(ab')$_2$ fragments that are subsequently reduced to FAB' fragments by treatment with low concentrations of cysteamine at 37° C. The reaction is stopped via separation of cysteamine on a PD 10 column. The FAB' fragments are labeled with an activated oligonucleotide as produced according to Example 3. This single-stranded DNA (=ss-DNA) bears a thiol-reactive maleimido group that reacts with the cysteines of the FAB' hinge region. In order to obtain high percentages of single-labeled FAB' fragments the relative molar ratio of ss-DNA to FAB'-fragment is kept low. Purification of single-labeled FAB' fragments (ss-DNA: FAB'=1:1) occurs via ion exchange chromatography (column: Source 15 Q PE 4.6/100, Pharmacia/GE). Verification of efficient purification is achieved by analytical gel filtration and SDS-PAGE.

B) Assembly of a Complex Comprising Two Polypeptides Specifically Binding to a Target The anti-pIGF-1R complex is based on two FAB' fragments that target different epitopes of the intracellular domain of IGF-1R: FAB' 8.1.2 detects a phosphorylation site (pTyr 1346) and FAB' 1.4.168 a non-phospho site of the target protein. The FAB' fragments have been covalently linked to single-stranded DNA (ss-DNA): FAB' 1.4.168 to a 17mer ss-DNA comprising SEQ ID NO: 05 and containing fluorescein as a fluorescent marker and FAB' 8.1.2 to a 19mer ss-DNA comprising SEQ ID NO: 06 and containing Cy5 as fluorescent marker. In the following, these FAB's with covalently bound 17mer or 19mer ss-DNA are named ss-FAB' 1.4.168 and ss-FAB' 8.1.2 respectively. Complex assembly is mediated by a linker (i.e. a bridging construct comprising two complementary ss-DNA oligonucleotides (SEQ ID NOs: 7 and 8, respectively) that hybridize to the corresponding ss-DNAs of the ss-FAB' fragments. The distance between the two ss-FAB' fragments of the complex can be modified by using spacers, e.g. C18-spacer or DNAs of different length, respectively.

For assembly evaluation the complex components ss-FAB' 8.1.2, ss-FAB' 1.4.168 and the linker constructs (1) (=linker 17 of example 2.4) 5'-G CAG AAG CAT TAA TAG ACT T(-Bi)-TGG ACG ACG ATA GAA CT-3' and (2) (=linker 10 of example 2.4) 5'-G CAG AAG CAT TAA TAG ACT-T(20)-T(-Bi)-(T20)-TGG ACG ACG ATA GAA CT-3' were mixed in equimolar quantities at room temperature. After a 1 minute incubation step the reaction mix was analyzed on an analytical gel filtration column (Superdex™ 200, 10/300 GL, GE Healthcare). Comparison of the elution volumes ($V_E$) of the single complex components with the $V_E$ of the reaction mix demonstrates that the complex has been formed successfully (FIG. 10).

BIAcore Experiment Assessing Binding of Anti-pIGF-1R Complex to Immobilized IGF-1R and IR Peptides For this experiment a BIAcore 2000 instrument (GE Healthcare) was used with a BIAcore SA sensor mounted into the system at T=25° C. Preconditioning occurred at 100 µl/min with 3×1 min injection of 1 M NaCl in 50 mM NaOH and 1 min 10 mM HCl.

HBS-ET (10 mM HEPES pH 7.4, 150 mM NaCl, 1 mM EDTA, 0.05% Tween® 20 was used as system buffer. The sample buffer was identical with the system buffer. The BIAcore 2000 System was driven under the control software V. 1.1.

Subsequently biotinylated peptides were captured on the SA surface in the respective flow cells. 16 RU of IGF-1R (1340-1366)[1346-pTyr; Glu(Bi-PEG-1340]amid (i.e. the— 1346 tyrosine phosphorylated—peptide of SEQ ID NO:11 comprising a PEG-linker bound via glutamic acid corresponding to position 1340 and being biotinylated at the other end of the linker) was captured on flow cell 2. 18 RU of IGF-1R(1340-1366); Glu(Bi-PEG-1340]amid (i.e. the— 1346 tyrosine non-phosphorylated—peptide of SEQ ID NO: 11 comprising a PEG-linker bound via glutamic acid corresponding to position 1340 and being biotinylated at the other end of the linker) was captured on flow cell 3. 20 RU of hInsR(1355-1382)[1361-pTyr; Glu(Bi-PEG-1355]amid (i.e. the—1361 tyrosine phosphorylated—peptide of SEQ ID NO: 12 comprising a PEG-linker bound via glutamic acid corresponding to position 1355 of human insulin receptor and being biotinylated at the other end of the linker) was captured on flow cell 4. Finally all flow cells were saturated with d-biotin.

For the complex formation the assembly protocol as described above was used. When individual runs with only one of the two ss-FAB's were performed, the absence or presence of linker DNA did not affect the association or dissociation curves.

100 nM of analyte (i.e. in these experiments a bivalent dual binding agent) in solution was injected at 50 µl/min for 240 sec association time and dissociation was monitored for 500 sec. Efficient regeneration was achieved by using a 1 min injection step at 50 µl/min with 80 mM NaOH. Flow cell 1 served as a reference. A blank buffer injection was used instead of an antigen injection to double reference the data by buffer signal subtraction.

In each measurement cycle one of the following analytes in solution was injected over all 4 flow cells: 100 nM ss-FAB' 8.1.2, 100 nM ss-FAB' 1.4.168, a mixture of 100 nM ss-FAB' 8.1.2 and 100 nM ss-FAB', 100 nM bivalent binding agent consisting of ss-FAB' 8.1.2 and ss-FAB' 1.4.168 hybridized on linker (3) (5'-G CAG AAG CAT TAA TAG ACT-T(20)-T(-Dig)-(T20)-TGG ACG ACG ATA GAA CT-3'(=linker 15)), and 100 nM bivalent binding agent consisting of ss-FAB' 8.1.2 and ss-FAB' 1.4.168 hybridized on linker (1) (5'-G CAG AAG CAT TAA TAG ACT-T(-Dig) -TGG ACG ACG ATA GAA CT-3'(=linker 16)), respectively.

The signals were monitored as time-dependent BIAcore sensorgrams.

Report points were set at the end of the analyte association phase (Binding Late, BL) and at the end of the analyte dissociation phase (Stability Late, SL) to monitor the response unit signal heights of each interaction. The dissociation rates kD (1/s) were calculated according to a linear 1:1 Langmuir fit using the BIAcore evaluation software 4.1. The complex halftimes in minutes were calculated upon the formula ln(2)/(60*kD).

The sensorgrams (FIG. 11 to FIG. 14) show a gain in both specificity and complex stability in pIGF-1R binding when ss-FAB' 1.4.168 and ss-FAB' 1.4.168 are used in form of a complex (=bivalent binding agent), probably due to the underlying cooperative binding effect. FAB' 1.4.168 alone shows no cross reactivity for the pIR peptide but does not discriminate between the phosphorylated and non-phosphorylated form of IGF-1R (T1/2 dis=3 min in both cases). FAB' 8.1.2, however, binds only to the phosphorylated version of the IGF1-R peptide but exhibits some undesired cross reactivity with phosphorylated Insulin Receptor. The complex discriminates well between the pIGF-1R peptide and both other peptides (see FIG. 13) and thus helps to overcome issues of unspecific binding. Note that the gain in specificity is lost when both FAB's are applied without linker DNA (FIG. 14). The gain in affinity of the Complex towards the pIGF-1R peptide manifests in increased dissociation half times compared to individual FAB's and the FAB' mix omitting the linker DNA (FIG. 12 and FIG. 14). Although the tested Complex s with two different DNA linker share an overall positive effect on target binding specificity and affinity, the longer linker (with T40-Dig as a spacer) (i.e. linker 15) seems to be advantageous with respect to both criteria.

BIAcore Assay Sandwich of M-1.4.168-IgG and M-8.1.2

A BIAcore T100 instrument (GE Healthcare) was used with a BIAcore CM5 sensor mounted into the system. The sensor was preconditioned by a 1 min injection at 100 µl/min of 0.1% SDS, 50 mM NaOH, 10 mM HCl and 100 mM H3PO4.

The system buffer was HBS-ET (10 mM HEPES pH 7.4, 150 mM NaCl, 1 mM EDTA, 0.05% Tween® 20). The sample buffer was the system buffer.

The BIAcore T100 System was driven under the control software V1.1.1. Polyclonal rabbit IgG antibody <IgGFCγM>R (Jackson ImmunoResearch Laboratories Inc.) at 30 µg/ml in 10 mM Na-Acetate pH 4.5 was immobilized at 10 000 RU on the flow cells 1, 2, 3, and 4, respectively, via EDC/NHS chemistry according to the manufacturer's instructions. Finally, the sensor surface was blocked with 1M ethanolamine. The complete experiment was driven at 13° C.

500 nM primary mAb M-1.004.168-IgG was captured for 1 min at 10 µl/min on the <IgGFCγM>R surface. 3 µM of an IgG fragment mixture (of IgG classes IgG1, IgG2a, IgG2b, IgG3) containing blocking solution was injected at 30 µl/min for 5 min. The peptide IGF-1R(1340-1366)[1346-pTyr; Glu (Bi-PEG-1340]amid was injected at 300 nM for 3 min at 30 µl/min. 300 nM secondary antibody M-8.1.2-IgG was injected at 30 µl min. The sensor was regenerated using 10 mM Glycine-HCl pH 1.7 at 50 µl/min for 3 min.

In FIG. 15 the assay setup is presented. In FIG. 18 the measurement results are given. The measurements clearly indicate that both monoclonal antibodies are able to simultaneously bind two distinct, unrelated epitopes on their respective target peptide. This is a prerequisite to any latter experiments with the goal to generate cooperative binding events.

BIAcore Assay Complex on Sensor Surface

A BIAcore 3000 instrument (GE Healthcare) was used with a BIAcore SA sensor mounted into the system at T=25° C. The system was preconditioned at 100 µl/min with 3×1 min injection of 1 M NaCl in 50 mM NaOH and 1 min 10 mM HCl.

The system buffer was HBS-ET (10 mM HEPES pH 7.4, 150 mM NaCl, 1 mM EDTA, 0.05% Tween® 20). The sample buffer was the system buffer.

The BIAcore 3000 System was driven under the control software V4.1.

124 RU amino-PEO-biotin were captured on the reference flow cell 1. 1595 RU biotinylated 14.6 kDa TO-Bi 37-mer ss-DNA-Linker (1) (5'-G CAG AAG CAT TAA TAG ACT-T(-Bi)-TGG ACG ACG ATA GAA CT-3') (=linker 17 of example 2.4) and 1042 RU biotinylated 23.7 kDa T40-Bi 77-mer ss-DNA-Linker (2) (5'-G CAG AAG CAT TAA TAG ACT-T(20)- (Biotin-dT)-(T20)-TGG ACG ACG ATA GAA CT-3'=linker 10) were captured on different flow cells. 300 nM ss-FAB 8.1.2 and 300 nM ss-FAB 1.004.168 were injected into the system at 50 µl/min for 3 min. As a control only 300 nM ss-FAB 8.1.2 or 300 nM ss-FAB 1.004.168 was injected to test the kinetic contribution of each ss-FAB. As a control, buffer was injected instead of the ss-Fabs. The peptides IGF-1R(1340-1366)[1346-pTyr]amid, INR(1355-1382)[1361-pTyr]amid IGF-1R(1340-1366)amid and were injected into system at 50 µl/min for 4 min, free in solution, in concentration steps of 0 nM, 4 nM, 11 nM, 33 nM (twice), 100 nM and 300 nM. In another embodiment to measure the affinities versus peptides IGF-1R(1340-1366)[1346-pTyr] amid the concentration steps of 0 nM, 0.4 nM, 1.1 nM, 3.3 nM (twice), 10 nM and 30 nM.

The dissociation was monitored at 50 µl/min for 5.3 min. The system was regenerated after each concentration step with a 12 sec pulse of 250 mM NaOH and was reloaded with ss-FAB ligand.

FIG. 17 schematically describes the assay setup on the BIAcore instrument. The tables given in FIG. 18 show the quantification results from this approach. FIG. 19, FIG. 20 and FIG. 21 depict exemplary BIAcore results from this assay setup.

The table in FIG. 18 demonstrates the benefits of the complex concept. The T40 dual binding agent (a dual binding agent with linker 10 of example 2.4, i.e. a linker with a spacer of T20-Biotin-dT-T20) results in a 2-fold improved antigen complex halftime (414 min) and a 3-fold improved affinity (10 pM) as compared to the TO dual binding agent (i.e. a dual binding agent with linker 16) with 192 min and 30 pM, respectively. This underlines the necessity to optimize the linker length to generate the optimal cooperative binding effect.

The T40 dual binding agent (i.e. the dual binding agent comprising the T40-Bi linker (linker 10)) exhibits a 10 pM affinity versus the phosphorylated IGF-1R peptide (table in FIG. 18, FIG. 19). This is a 2400-fold affinity improvement versus the phosphorylated insulin receptor peptide (24 nM) and a 100-fold improvement versus the non-phosphorylated IGF-1R peptide.

Therefore, the goal to increase specificity and affinity by the combination of two distinct and separated binding events is achieved.

The cooperative binding effect especially becomes obvious from the dissociation rates against the phosphorylated IGF-1R peptide, where the complex shows 414 min antigen complex halftime, versus 0.5 min with the monovalent binder 8.1.2 alone and versus 3 min with the monovalent binder 1.4.168 alone, respectively.

Furthermore, the fully assembled construct roughly multiplies its dissociation rates kD (1/s), when compared to the singly FAB hybridized constructs (FIG. 21, FIG. 20, FIG. 21 and table in FIG. 18). Interestingly, also the association rate ka (1/Ms) slightly increases when compared to the single FAB interaction events, this may be due to an increase of the construct's molecular flexibility.

EXAMPLE 9

Binding Assays—In Vitro and Ex Vivo
Detection Oligonucleotide Probe-Cy5
The ss-L-DNA detection oligonucleotide Probe-Cy5 5' Cy5-Y-ATG CGA-GTA CCT TAG AGT C-Z-Cy5 3' (SEQ ID NO: 72), has been synthesized by state of the art oligonucleotide synthesis methods. The introduction of the Cy5 dye was done via reaction of the amino groups with Cy5 monoreactive NHS ester. (GE Healthcare Lifescience, STADT, LAND). For the nucleotides L-DNA amidites (ChemGenes, STADT, LAND) were used. The 5' and 3' amino groups were introduced during the solid phase oligonucleotide synthesis process wherein Y=5'-Amino-Modifier C6 introduced via (6-(4-Monomethoxytritylamino) hexyl-(2-cyanoethyl)-(N,N-diisopropyl)-phosphoramidite (Glen Research), and Z=3'-Aminomodifier C6 introduced via 3'Aminomodifier TFA Amino C6 long chain aminoalkyl Controlled Pore Glass 1000 A (ChemGenes).

Dual Binder Linker Oligonucleotide
The ss-L-DNA oligonucleotide linker SEQ ID NO: 73 5'-G CAG AAG CAT TAA TAG ACT-T20-GAC TCT AAG GTA CTC GCA T-T20-TGG ACG ACG ATA GAA CT-3' has been synthesized by state of the art oligonucleotide synthesis methods.

Assembly of the Complex
The complex was assembled by hybridizing the anti-HER2 antibody 2C4-FAB'-ss-L-DNA labeled with FITC and the anti-HER2 antibody 4D5-FAB'-ss-L-DNA labeled with FITC in equimolar stoichiometry with the ss-L-DNA linker of SEQ ID NO: 73. In order to verify the correct assembly of the complex, the complex was subjected to an SEC chromatography step and was filtered through a sterile filter.

In Vitro Binding Assay
Human breast cancer KPL-4 cells were seeded with a concentration of $2 \times 10^6$ cells/ml in a volume of 30 μl into μ-slides VI (ibidi, Germany). Three hours thereafter, 70 μl medium (RPMI 1640, 2 mM L-glutamine, 10% FCS) was added to allow the cells to adhere.

After an incubation of 24 hours at 37° C. and 5% $CO_2$ in a water saturated atmosphere (effective for all following incubations), the supernatant was removed and cells were washed once with 100 μl PBS to remove residual medium.

For the sequential application, 50 μl of the complex 4D5-2C4 as prepared above labeled with FITC solution (c=2.5 μg/ml) was added and incubated for 45 minutes, followed by one washing step with 100 μl PBS and a further incubation with 50 μl of the DNA-probe (SEQ ID NO: 72) at an equimolar amount (0.13 μg/ml).

The pre-mixed procedure was performed by first mixing the complex and the detection Probe. Thereafter it was added to the cells (concentrations see above) followed by incubation for 45 minutes.

Xolair®, a humanized IgG1 monoclonal antibody targeting human IgE immunoglobulin was used as a negative control and Herceptin® labeled with Cy5 targeting human HER-2 receptor was used as a positive control. Both antibodies were applied at the same concentration (2.5 μg/ml).

Subsequently, the supernatant was removed and cells were washed once with 100 μl PBS. Cell nuclei were afterwards stained with DAPI by adding 50 μl of a HOECHST33342 solution (c=10 μg/ml) and incubated for 15 minutes. To remove the cell staining dye, cells were washed twice with 100 μl PBS after removal of the supernatant. Another 120 μl PBS were added to keep the cells moist to ensure viability. All dilutions were made with medium (without L-Glutamine and FCS) to ensure viability of the cells and to avoid detachment of the cells. After this procedure, slides were imaged by multispectral fluorescence analysis using the NUANCE System (CRi, Cambridge, USA). Images were normalized for comparability of the fluorescence intensities.

Ex Vivo Analysis
Immunodeficient SCID beige mice with established KPL-4 tumors (orthotopically implanted) were injected i.v. with 50 μg complex in 100 μl PBS and 18 hours thereafter the Cy5-labeled DNA-probe was injected at an equimolar concentration (2.63 μg per mouse). Tumors were explanted 48 hours thereafter and examined by multispectral fluorescence analysis using the MAESTRO system (CRi, Cambridge, USA).

Results
In Vitro Binding Assay
The complex is doubly FITC labeled via each of its FAB'-ss-L-DNA components.

The detection probe is a doubly Cy5 labeled ss-L-DNA 20-mer oligonucleotide probe, which can be hybridized to the 95mer ss-L-DNA linker of the complex.

In contrast to Xolair-Cy5 (no fluorescence signal, negative control) Herceptin-Cy5 specifically stained the tumor cells (FIG. 22). The FITC labeled 4D5-2C4-95mer complex specifically binds to KPL-4 tumor cells as can be seen by sequential incubation with the detection Probe (measured in the Cy5 fluorescence channel) which is co-localized with the complex to the tumor cells indicating the hybridization of the detection oligonucleotide Probe-Cy5 to the complex. In the sequential incubation mode as well as in the pre-mixed setting specific staining of the tumor cells to the Her-2 antigen could be demonstrated (FIG. 2).

In FIG. 22 the near infrared image of the cancer cells incubated with the complex and the detection probe is shown (NIRF imaging). In the top right of the Figure a sketch of the fully assembled 4D5-2C4-95mer complex hybridized to the Cy5 labeled detection oligonucleotide is shown. In the middle right of the Figure a cartoon of Cy5 labeled Herceptin is shown. In the bottom right of the Figure the signal intensity bar is shown.

In the top left of FIG. 22 the binding of Cy5 labeled Herceptin® to the cancer cells is shown (positive control). The KPL-4 cell membranes appear as bright lighting rings surrounding the DAPI-stained cell nuclei. In the bottom left the incubation of Cy5 labeled Xolair® is shown (negative control). No membrane staining but the DAPI stain of the cell nuclei can be detected. In the bottom middle of the Figure the binding of the 4D5-2C4-FITC complex is shown. The fluorescein signal of the membrane bound complex appears as lighting rings surrounding the DAPI stained cell nuclei. In the top middle of the Figure the binding of the 4D5-2C4-FITC complex and the Cy5 labeled detection probe is shown. The detection of the complex via the Cy5 labeled ss-L-DNA detection probe, which was sequentially hybridized, can be seen. The Cy5 signal of the detection oligonucleotide appears as membrane staining, showing bright lighting rings surrounding the DAPI stained cell nuclei.

In FIG. 23 the near infrared (NIRF) imaging of KPL-4 cells is shown. In FIG. 23 A the results of the sequential application of FITC labeled 4D5-2C4 complex and the Cy5 labeled detection probe is shown. In FIG. 23 B the results of the incubation of KPL-4 cells with premixed FITC labeled 4D5-2C4 complex and Cy5 labeled detection probe is shown. Both images show membrane-located signals. As a control, cells were stained with DAPI.

The experiment demonstrates that the complex as reported herein can first be applied in order to specifically target HER-2 positive cells. In a second step, the labeled detection probe can be applied in order to hybridize to the target bound complex. The fluorescence labeled detection probe is thereby a proof of concept for the time delayed, sequential application and specific targeting of an oligonucleotide-based effector moiety. In this case the payload is a fluorescent dye for the purpose of in vitro cell imaging.

Ex Vivo Binding Assay

As depicted in FIG. 24 (left image) a strong fluorescence signal is detectable in the experimental setting where the sample was incubated first with the complex and thereafter with the Cy5 labeled detection probe. In contrast (right image), no fluorescence signal could be detected in the tumors previously injected in the KPL-4 xenograft with the Cy5 labeled detection probe alone.

FIG. 24 shows explanted KPL-4 tumors subjected to NIRF Imaging. In the first image Cy5 fluorescence signals obtained from three KPL-4 tumors explanted from mice, which were sequentially treated with the first the 4D5-2C4 complex and thereafter the detection probe is shown. In the right image it is shown that no fluorescence signal was obtained from three KPL-4 tumors, when three mice where treated with detection probe alone, omitting the 4D5-2C4 complex.

EXAMPLE 10

Inhibition of Cell Proliferation in MDA-MB-175 Breast Cancer Cell Line $2 \times 10^4$ MDA-MB-175 breast cancer cells cultured in DMEM/F12 medium supplemented with 10% fetal calve serum, 2 mM Glutamin and Penicillin/Streptomycine were seeded in 96-well plates. Antibodies and complex, respectively, were added in the indicated concentrations the next day (40 to 0.0063 µg/ml). Alter 6 day incubation Alamar Blue was added and plates were incubated for 3-4 h in a tissue culture incubator. Fluorescence was measured (excitation 530 nm/emission 590) and percentage inhibition was calculated using untreated cells as reference.

Results

The anti-HER2 antibody 2C4 (Pertuzumab) showed a maximum inhibition of 44%. The anti-HER2 antibody Herceptin showed a maximum inhibition of 9%. The complex as reported herein comprising the FAB fragments of Pertuzumab and Herceptin® shows a maximum inhibition of 46%.

It has to be pointed out that Petuzumab was tested as full length IgG antibody with two HER2 binding sites, whereas the complex comprises a single Pertuzumab Fab fragment with a single HER2 binding site.

EXAMPLE 11

Freeze-Thaw-Stability of the Complex

The complex was assembled by hybridizing the anti-HER2 antibody 2C4-FAB'-ss-L-DNA labeled with FITC and the anti-HER2 antibody 4D5-FAB'-ss-L-DNA labeled with FITC in equimolar stoichiometry with the ss-L-DNA linker of SEQ ID NO: 73. In order to verify the correct assembly of the complex, the complex was subjected to a SEC chromatography step and was filtered through a sterile filter.

Fifty µl of the complex (1.5 mg/ml) were analyzed by analytical SEC using a TSK3000 column (GE). The running buffer was 0.1 M $KH_2PO_4$ pH 6.8. The flow rate was 1 ml/min. The chromatogram is shown in FIG. 25.

After freezing and thawing, the complex was re-chromatographed. Fifty µl of the complex (1.5 mg/ml) were analyzed by analytical SEC using a TSK3000 column (GE). The running buffer was 0.1 M $KH_2PO_4$ pH 6.8. The flow rate was 1 ml/min. The chromatogram is shown in FIG. 26.

The invention claimed is:

1. A method of producing a complex comprising the components
   a) a first polypeptide that specifically binds to a first target and that is conjugated to a first member of a first binding pair,
   b) a second polypeptide that specifically binds to a second target and that is conjugated to a first member of a second binding pair, and
   c) a polynucleotide linker conjugated to the second member of the first binding pair and conjugated to the second member of the second binding pair, wherein the polynucleotide linker comprises ss-L-DNA,
   comprising the steps of:
   i) synthesizing the first polypeptide specifically binding to the first target which is conjugated to the first member of the first binding pair, and synthesizing the second polypeptide specifically binding to the second target which is conjugated to the first member of a second binding pair, respectively,
   ii) synthesizing the polynucleotide linker conjugated at its first terminus to the second member of the first binding pair and conjugated at its second terminus to the second member of the second binding pair, and
   iii) forming the complex by hybridizing the synthesized components,
   wherein the first and second member of the first binding pair comprise the nucleic acid sequences of SEQ ID NO: 5 and SEQ ID NO: 8 or
   wherein the first and second member of the second binding pair comprise the nucleic acid sequences of SEQ ID NO: 6 and SEQ ID NO: 7.

2. The method according to claim 1, wherein the complex further comprises an effector moiety conjugated to a polynucleotide that is complementary to at least a part of the polynucleotide linker ss-L-DNA.

3. The method of claim 2, wherein the effector moiety is selected from the group consisting of a binding moiety, a labeling moiety and a biologically active moiety.

4. The method according to claim 1, wherein the first polypeptide is a monovalent antibody or monovalent antibody fragment.

5. The method of claim 1, wherein the first and second polypeptides bind to the same target and to non-overlapping epitopes on the same target.

6. The method of claim 5, wherein the polynucleotide linker has an optimal length for synergistic binding of the first and second polypeptides to the non-overlapping epitopes on the same target.

7. The method of claim 1, wherein the members of the first and second binding pairs are ss-LDNA.

8. The method of claim 1, wherein the members of the first and second binding pairs are ss-LDNA of 10 to 50 nucleotides in length.

9. The method of claim 1, wherein the polynucleotide linker has a length of at least 70 nucleotides.

10. The method of claim 1, wherein the complex is a non-covalent complex.

11. The method of claim 1,
    wherein the first polypeptide is a FAB' fragment of the anti-HER2 antibody 2C4 comprising an HVR-H1 comprising the amino acid sequence of SEQ ID NO: 35, an HVR-H2 comprising the amino acid sequence of SEQ ID NO: 36, an HVR-H3 comprising the amino acid sequence of SEQ ID NO: 37, an HVR-L1 comprising the amino acid sequence of SEQ ID NO: 39, an HVR-L2 comprising the amino acid sequence of SEQ ID NO: 40, and an HVR-L3 comprising the amino acid sequence of SEQ ID NO: 41;
    the second polypeptide is a FAB' fragment of the anti-HER2 antibody 4D5 comprising an HVR-H1 comprising the amino acid sequence of SEQ ID NO: 27, an HVR-H2 comprising the amino acid sequence of SEQ ID NO: 28, an HVR-H3 comprising the amino acid sequence of SEQ ID NO: 29, an HVR-L1 comprising the amino acid sequence of SEQ ID NO: 31, a HVR-L2 comprising the amino acid sequence of SEQ ID NO: 32, and an HVR-L3 comprising the amino acid sequence of SEQ ID NO: 33;
    the members of the first and the second binding pairs are hybridizing nucleic acids; and
    the ss-L-DNA-linker comprises 60 to 100 L-DNA nucleotides.

* * * * *